(12) United States Patent
Singh et al.

(10) Patent No.: US 8,575,377 B2
(45) Date of Patent: *Nov. 5, 2013

(54) SYNTHESIS OF LONG-CHAIN POLYUNSATURATED FATTY ACIDS BY RECOMBINANT CELL

(71) Applicants: Surinder Pal Singh, Downer (AU); Stanley Suresh Robert, Oyster Cove (AU); Peter David Nichols, West Hobart (AU); Susan Irene Ellis Blackburn, Battery Point (AU); Xue-Rong Zhou, Evatt (AU); James Robertson Petrie, Bywong (AU); Allan Graham Green, Braddon (AU)

(72) Inventors: Surinder Pal Singh, Downer (AU); Stanley Suresh Robert, Oyster Cove (AU); Peter David Nichols, West Hobart (AU); Susan Irene Ellis Blackburn, Battery Point (AU); Xue-Rong Zhou, Evatt (AU); James Robertson Petrie, Bywong (AU); Allan Graham Green, Braddon (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/651,275

(22) Filed: Oct. 12, 2012

(65) Prior Publication Data

US 2013/0060053 A1    Mar. 7, 2013

Related U.S. Application Data

(63) Continuation of application No. 13/243,747, filed on Sep. 23, 2011, now Pat. No. 8,288,572, which is a continuation of application No. 12/661,978, filed on Mar. 26, 2010, now Pat. No. 8,106,226, which is a continuation of application No. 11/112,882, filed on Apr. 22, 2005, now Pat. No. 7,807,849.

(60) Provisional application No. 60/668,705, filed on Apr. 5, 2005, provisional application No. 60/613,861, filed on Sep. 27, 2004, provisional application No. 60/564,627, filed on Apr. 22, 2004.

(30) Foreign Application Priority Data

Apr. 5, 2005   (AU) .............................. 2005901673

(51) Int. Cl.
  *C11B 5/00*   (2006.01)
(52) U.S. Cl.
  USPC .......................................................... 554/9
(58) Field of Classification Search
  USPC ............................................................ 554/9
  See application file for complete search history.

(56) References Cited

U.S. PATENT DOCUMENTS 5,552,306 A   9/1996  Thomas et al.
5,614,393 A   3/1997  Thomas et al.
(Continued)

FOREIGN PATENT DOCUMENTS

AU   200059710   12/2000
AU   200065607    1/2001
(Continued)

OTHER PUBLICATIONS

Nov. 21, 2011 Examination Report issued in connection with corresponding Canadian Patent Application No. 2,563,875 (Commonwealth Scientific and Industrial Research Organisation).

(Continued)

*Primary Examiner* — Deborah D Carr
(74) *Attorney, Agent, or Firm* — John P. White; Gary J. Gershik; Cooper & Dunham LLP

(57) ABSTRACT

The present invention relates to methods of synthesizing long-chain polyunsaturated fatty acids, especially eicosapentaenoic acid, docosapentaenoic acid and docosahexaenoic acid, in recombinant cells such as yeast or plant cells. Also provided are recombinant cells or plants which produce long-chain polyunsaturated fatty acids. Furthermore, the present invention relates to a group of new enzymes which possess desaturase or elongase activity that can be used in methods of synthesizing long-chain polyunsaturated fatty acids.

20 Claims, 15 Drawing Sheets

(56) References Cited

U.S. PATENT DOCUMENTS

Figure 1:
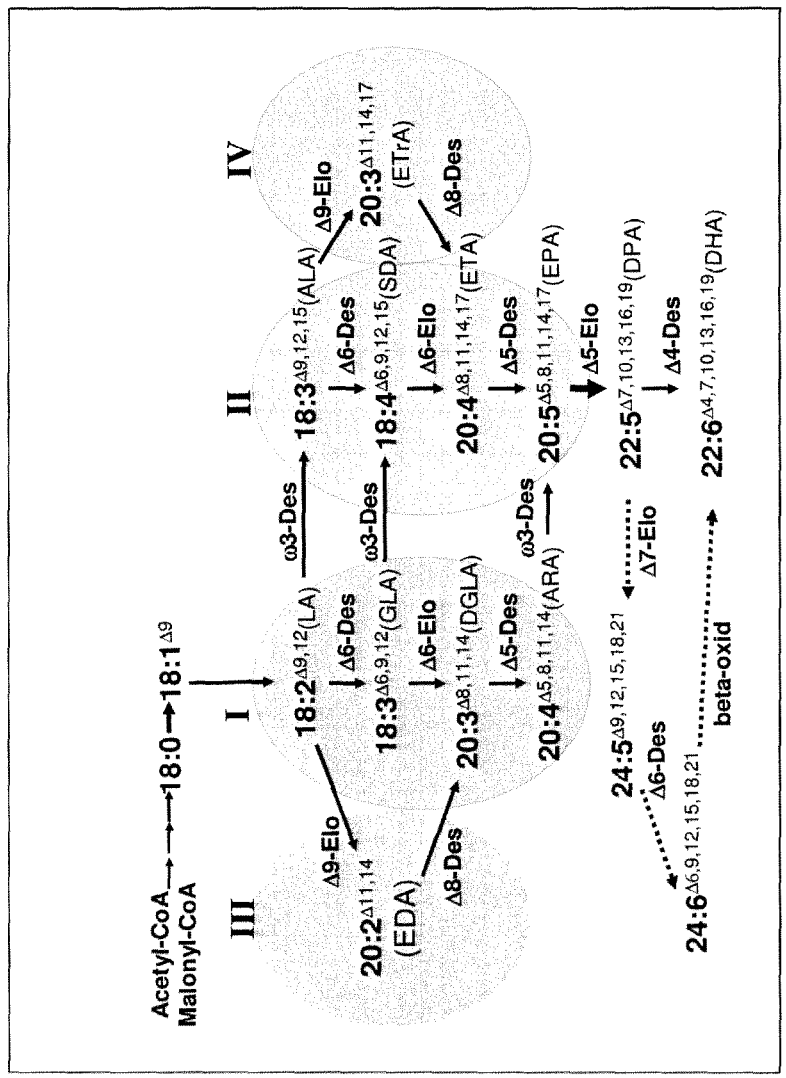

| Patent No. | | Date | Inventor |
|---|---|---|---|
| 5,663,068 | A | 9/1997 | Thomas et al. |
| 5,668,299 | A | 9/1997 | Debonte et al. |
| 5,683,898 | A | 11/1997 | Yazawa et al. |
| 5,689,050 | A | 11/1997 | Thomas et al. |
| 5,789,220 | A | 8/1998 | Thomas et al. |
| 5,798,259 | A | 8/1998 | Yazawa et al. |
| 5,952,544 | A | 9/1999 | Browse et al. |
| 5,968,809 | A | 10/1999 | Knutzon et al. |
| 5,972,664 | A | 10/1999 | Knutzon et al. |
| 6,051,754 | A | 4/2000 | Knutzon et al. |
| 6,075,183 | A | 6/2000 | Knutzon et al. |
| 6,136,574 | A | 10/2000 | Knutzon et al. |
| 6,140,486 | A | 10/2000 | Facciotti et al. |
| 6,194,167 | B1 | 2/2001 | Browse et al. |
| 6,342,658 | B1 | 1/2002 | DeBonte et al. |
| 6,355,861 | B1 | 3/2002 | Thomas et al. |
| 6,372,965 | B1 | 4/2002 | Lightner et al. |
| 6,403,349 | B1 | 6/2002 | Mukerji et al. |
| 6,410,288 | B1 | 6/2002 | Knutzon et al. |
| 6,428,990 | B1 | 8/2002 | Mukerji et al. |
| 6,432,684 | B1 | 8/2002 | Mukerji et al. |
| 6,459,018 | B1 | 10/2002 | Knutzon et al. |
| 6,492,108 | B1 | 12/2002 | Hillman et al. |
| 6,566,583 | B1 | 5/2003 | Facciotti et al. |
| 6,589,767 | B1 | 7/2003 | Knutzon et al. |
| 6,635,451 | B2 | 10/2003 | Mukerji et al. |
| 6,677,145 | B2 | 1/2004 | Mukerji et al. |
| 6,683,232 | B1 | 1/2004 | Thomas et al. |
| 6,686,185 | B1 | 2/2004 | Logan et al. |
| 6,825,017 | B1 | 11/2004 | Browse et al. |
| 6,825,335 | B1 | 11/2004 | Marin et al. |
| 6,838,594 | B1 | 1/2005 | Kinney et al. |
| 6,858,416 | B2 | 2/2005 | Mukerji et al. |
| 6,864,077 | B1 | 3/2005 | Cahoon et al. |
| 6,875,595 | B2 | 4/2005 | Kloek et al. |
| 6,884,921 | B2 | 4/2005 | Browse et al. |
| 6,897,050 | B1 | 5/2005 | Napier et al. |
| 6,913,916 | B1 | 7/2005 | Mukerji et al. |
| 6,958,229 | B2 | 10/2005 | Suzuki et al. |
| 6,967,243 | B2 | 11/2005 | Debonte et al. |
| 7,001,772 | B2 | 2/2006 | Roessler et al. |
| 7,045,683 | B2 | 5/2006 | Mukerji et al. |
| 7,067,285 | B2 | 6/2006 | Mukerji et al. |
| 7,067,722 | B2 | 6/2006 | Fillatti et al. |
| 7,070,970 | B2 | 7/2006 | Mukerji et al. |
| 7,081,356 | B2 | 7/2006 | Putten et al. |
| 7,087,432 | B2 | 8/2006 | Qiu et al. |
| 7,091,005 | B2 | 8/2006 | Petrushkin et al. |
| 7,135,614 | B1 | 11/2006 | DeBonte et al. |
| 7,135,623 | B1 | 11/2006 | Rusing et al. |
| 7,148,336 | B2 | 12/2006 | Fillatti et al. |
| 7,179,620 | B2 | 2/2007 | Petrukhin et al. |
| 7,179,647 | B2 | 2/2007 | Lerchl et al. |
| 7,189,559 | B2 | 3/2007 | Damude et al. |
| 7,192,762 | B2 | 3/2007 | Macool et al. |
| 7,198,937 | B2 | 4/2007 | Xue et al. |
| 7,208,297 | B2 | 4/2007 | Mukerji et al. |
| 7,211,418 | B2 | 5/2007 | Metz et al. |
| 7,211,656 | B2 | 5/2007 | Mukerji et |
| 7,214,853 | B2 | 5/2007 | Facciotti et al. |
| 7,217,856 | B2 | 5/2007 | Weaver et al. |
| 7,220,897 | B2 | 5/2007 | Mukerji et al. |
| 7,241,619 | B2 | 7/2007 | Mukerji et al. |
| 7,244,563 | B2 | 7/2007 | Cahoon et al. |
| 7,247,461 | B2 | 7/2007 | Metz et al. |
| 7,256,022 | B2 | 8/2007 | Metz et al. |
| 7,256,023 | B2 | 8/2007 | Metz et al. |
| 7,256,033 | B2 | 8/2007 | Damude et al. |
| 7,256,329 | B2 | 8/2007 | Fillatti |
| 7,259,295 | B2 | 8/2007 | Metz et al. |
| 7,262,343 | B1 | 8/2007 | DeBonte et al. |
| 7,271,315 | B2 | 9/2007 | Metz et al. |
| 7,273,746 | B2 | 9/2007 | Yadav et al. |
| 7,282,623 | B2 | 10/2007 | Thomas |
| 7,297,523 | B2 | 11/2007 | Winther et al. |
| 7,375,205 | B2 | 5/2008 | Mukerji et al. |
| 7,402,735 | B2 | 7/2008 | Browse et al. |
| 7,411,054 | B2 | 8/2008 | Meyers et al. |
| 7,476,522 | B2 | 1/2009 | Putten et al. |
| 7,495,149 | B2 | 2/2009 | Cahoon et al. |
| 7,504,259 | B2 | 3/2009 | Yadav et al. |
| 7,531,718 | B2 | 5/2009 | Fillatti et al. |
| 7,537,920 | B2 | 5/2009 | Renz et al. |
| 7,541,519 | B2 | 6/2009 | Debonte et al. |
| 7,544,859 | B2 | 6/2009 | Heinz et al. |
| 7,550,286 | B2 | 6/2009 | Damude et al. |
| 7,550,651 | B2 | 6/2009 | Damude et al. |
| 7,554,008 | B2 | 6/2009 | Napier et al. |
| 7,563,949 | B2 | 7/2009 | Fillatti |
| 7,589,253 | B2 | 9/2009 | Green et al. |
| 7,601,889 | B2 | 10/2009 | Napier et al. |
| 7,615,679 | B2 | 11/2009 | Lerchl et al. |
| 7,622,632 | B2 | 11/2009 | Ursin et al. |
| 7,629,503 | B2 | 12/2009 | Cirpus et al. |
| 7,659,120 | B2 | 2/2010 | Yadav et al. |
| 7,671,252 | B2 | 3/2010 | Qiu et al. |
| 7,709,239 | B2 | 5/2010 | Damude et al. |
| 7,714,185 | B2 | 5/2010 | Napier et al. |
| 7,736,884 | B2 | 6/2010 | Gunnarsson et al. |
| 7,777,098 | B2 | 8/2010 | Cirpus et al. |
| 7,807,846 | B2 * | 10/2010 | Kozawa et al. ............... 548/531 |
| 7,807,849 | B2 | 10/2010 | Singh et al. |
| 7,834,248 | B2 | 11/2010 | Green et al. |
| 7,834,250 | B2 | 11/2010 | Singh et al. |
| 7,838,651 | B2 | 11/2010 | Picataggio et al. |
| 7,842,852 | B2 | 11/2010 | Cirpus et al. |
| 7,855,321 | B2 | 12/2010 | Renz et al. |
| 7,871,804 | B2 | 1/2011 | Cirpus et al. |
| 7,901,928 | B2 | 3/2011 | Yadav et al. |
| 7,932,438 | B2 | 4/2011 | Singh et al. |
| 8,071,341 | B2 | 12/2011 | Singh et al. |
| 8,084,074 | B2 | 12/2011 | Kinney et al. |
| 8,106,226 | B2 * | 1/2012 | Singh et al. ....................... 554/9 |
| 8,158,392 | B1 | 4/2012 | Singh et al. |
| 8,288,572 | B2 * | 10/2012 | Singh et al. ....................... 554/9 |
| 2001/0023259 | A1 | 9/2001 | Slabas et al. |
| 2002/0009779 | A1 | 1/2002 | Meyers et al. |
| 2002/0042933 | A1 | 4/2002 | Browse et al. |
| 2002/0065406 | A1 | 5/2002 | Meyers et al. |
| 2002/0076786 | A1 | 6/2002 | Curtis et al. |
| 2002/0107373 | A1 | 8/2002 | Curtis et al. |
| 2002/0108147 | A1 | 8/2002 | Thomas et al. |
| 2002/0111307 | A1 | 8/2002 | Glucksmann et al. |
| 2002/0115178 | A1 | 8/2002 | Meyers et al. |
| 2002/0138874 | A1 | 9/2002 | Mukerji et al. |
| 2002/0146784 | A1 | 10/2002 | Suzuki et al. |
| 2002/0156254 | A1 | 10/2002 | Qiu et al. |
| 2002/0170090 | A1 | 11/2002 | Browse et al. |
| 2002/0194641 | A1 | 12/2002 | Metz et al. |
| 2003/0077747 | A1 | 4/2003 | Hillman et al. |
| 2003/0079250 | A1 | 4/2003 | Fillatti et al. |
| 2003/0082754 | A1 | 5/2003 | Mukerji et al. |
| 2003/0084480 | A1 | 5/2003 | Fillatti et al. |
| 2003/0101486 | A1 | 5/2003 | Facciotti et al. |
| 2003/0104596 | A1 | 6/2003 | Mukerji et al. |
| 2003/0131379 | A1 | 7/2003 | Debonte et al. |
| 2003/0134400 | A1 | 7/2003 | Mukerji et al. |
| 2003/0152983 | A1 | 8/2003 | Napier et al. |
| 2003/0157144 | A1 | 8/2003 | Mukerji et al. |
| 2003/0159164 | A1 | 8/2003 | Kopchick et al. |
| 2003/0163845 | A1 | 8/2003 | Mukerji et al. |
| 2003/0166207 | A1 | 9/2003 | Roessler et al. |
| 2003/0167525 | A1 | 9/2003 | Mukerji et al. |
| 2003/0172398 | A1 | 9/2003 | Browse et al. |
| 2003/0172399 | A1 | 9/2003 | Fillatti et al. |
| 2003/0177508 | A1 | 9/2003 | Mukerji et al. |
| 2003/0190733 | A1 | 10/2003 | Mukerji et al. |
| 2003/0196217 | A1 | 10/2003 | Mukerji et al. |
| 2004/0009501 | A1 | 1/2004 | Curtis et al. |
| 2004/0049805 | A1 | 3/2004 | Lerchl et al. |
| 2004/0053234 | A1 | 3/2004 | Winther et al. |
| 2004/0053379 | A1 | 3/2004 | Lerchl et al. |
| 2004/0066899 | A1 | 4/2004 | Winther et al. |
| 2004/0067226 | A1 | 4/2004 | Petrukhin et al. |

(56) References Cited

U.S. PATENT DOCUMENTS

| | | |
|---|---|---|
| 2004/0078845 A1 | 4/2004 | Thomas et al. |
| 2004/0098762 A1 | 5/2004 | Fillatti et al. |
| 2004/0111763 A1 | 6/2004 | Heinz et al. |
| 2004/0157221 A9 | 8/2004 | Curtis et al. |
| 2004/0172682 A1 | 9/2004 | Kinney et al. |
| 2004/0180414 A1 | 9/2004 | Putten et al. |
| 2004/0195512 A1 | 10/2004 | Crosetto et al. |
| 2004/0224413 A1 | 11/2004 | Cahoon et al. |
| 2004/0235127 A1 | 11/2004 | Metz et al. |
| 2005/0003442 A1 | 1/2005 | Mukerji et al. |
| 2005/0005328 A1 | 1/2005 | Mukerji et al. |
| 2005/0005329 A1 | 1/2005 | Mukerji et al. |
| 2005/0009140 A1 | 1/2005 | Mukerji et al. |
| 2005/0089865 A1 | 4/2005 | Napier et al. |
| 2005/0089879 A1 | 4/2005 | Feussner et al. |
| 2005/0089981 A1 | 4/2005 | Napier et al. |
| 2005/0100995 A1 | 5/2005 | Weaver et al. |
| 2005/0112719 A1 | 5/2005 | Roessler et al. |
| 2005/0164192 A1 | 7/2005 | Graham et al. |
| 2005/0166271 A1 | 7/2005 | Feubner et al. |
| 2005/0214761 A1 | 9/2005 | Lerchl et al. |
| 2005/0262588 A1 | 11/2005 | Dehesh et al. |
| 2005/0262589 A1 | 11/2005 | Fillatti et al. |
| 2005/0262591 A1 | 11/2005 | Debonte et al. |
| 2005/0266440 A1 | 12/2005 | Metz et al. |
| 2005/0273883 A1 | 12/2005 | Metz et al. |
| 2005/0273884 A1 | 12/2005 | Metz et al. |
| 2005/0273885 A1 | 12/2005 | Singh et al. |
| 2006/0014268 A1 | 1/2006 | Suzuki et al. |
| 2006/0078973 A1 | 4/2006 | Renz et al. |
| 2006/0094088 A1 | 5/2006 | Picataggio et al. |
| 2006/0094092 A1 | 5/2006 | Damude et al. |
| 2006/0094102 A1 | 5/2006 | Xue et al. |
| 2006/0110806 A1 | 5/2006 | Damude et al. |
| 2006/0115881 A1 | 6/2006 | Damude et al. |
| 2006/0117414 A1 | 6/2006 | Qiu et al. |
| 2006/0156435 A1 | 7/2006 | Ursin et al. |
| 2006/0168687 A1 | 7/2006 | Renz et al. |
| 2006/0174376 A1 | 8/2006 | Renz et al. |
| 2006/0191042 A1 | 8/2006 | Fillatti et al. |
| 2006/0195939 A1 | 8/2006 | Damude et al. |
| 2006/0205047 A1 | 9/2006 | Putten et al. |
| 2006/0206961 A1 | 9/2006 | Cirpus et al. |
| 2006/0218668 A1 | 9/2006 | Cirpus et al. |
| 2006/0246556 A1 | 11/2006 | Napier et al. |
| 2007/0028326 A1 | 2/2007 | Cirpus et al. |
| 2007/0059730 A1 | 3/2007 | Curtis et al. |
| 2007/0061921 A1 | 3/2007 | Graham et al. |
| 2007/0118929 A1 | 5/2007 | Damude et al. |
| 2007/0163002 A1 | 7/2007 | DeBonte et al. |
| 2007/0220634 A1 | 9/2007 | Metz |
| 2007/0224661 A1 | 9/2007 | Cirpus et al. |
| 2007/0244192 A1 | 10/2007 | Metz et al. |
| 2007/0245431 A1 | 10/2007 | Metz et al. |
| 2007/0259355 A1 | 11/2007 | Luy et al. |
| 2007/0261138 A1 | 11/2007 | Graham et al. |
| 2007/0270494 A1 | 11/2007 | Metz et al. |
| 2007/0294790 A1 | 12/2007 | Graham et al. |
| 2008/0005811 A1 | 1/2008 | Metz et al. |
| 2008/0022422 A1 | 1/2008 | Weaver et al. |
| 2008/0057495 A1 | 3/2008 | Ohyama et al. |
| 2008/0063691 A1 | 3/2008 | Ursin et al. |
| 2008/0076166 A1 | 3/2008 | Cirpus et al. |
| 2008/0155705 A1 | 6/2008 | Zank et al. |
| 2008/0160054 A1 | 7/2008 | Heinz et al. |
| 2008/0214667 A1 | 9/2008 | Das et al. |
| 2008/0220143 A1 | 9/2008 | Kinney et al. |
| 2008/0220500 A1 | 9/2008 | Winther et al. |
| 2008/0241133 A1 | 10/2008 | Curtis et al. |
| 2008/0254191 A1 | 10/2008 | Damude et al. |
| 2008/0254195 A1 | 10/2008 | Damude et al. |
| 2008/0260929 A1 | 10/2008 | Ursin et al. |
| 2008/0268539 A1 | 10/2008 | Singh et al. |
| 2009/0093033 A1 | 4/2009 | Luy et al. |
| 2009/0158462 A1 | 6/2009 | Cirpus et al. |
| 2009/0222951 A1 | 9/2009 | Cirpus et al. |
| 2009/0253188 A1 | 10/2009 | Zhu et al. |
| 2009/0320161 A1 | 12/2009 | McGonigle et al. |
| 2010/0088776 A1 | 4/2010 | Bauer et al. |
| 2010/0092640 A1 | 4/2010 | Ursin et al. |
| 2010/0189868 A1 | 7/2010 | Damude et al. |
| 2010/0227924 A1 | 9/2010 | Cirpus et al. |
| 2011/0015415 A1 | 1/2011 | Singh et al. |
| 2011/0016585 A1 | 1/2011 | Pereira et al. |
| 2011/0054198 A1 | 3/2011 | Singh et al. |
| 2011/0059204 A1 | 3/2011 | Jackson et al. |
| 2011/0059496 A1 | 3/2011 | Zhu et al. |
| 2011/0190521 A1 | 8/2011 | Damcevski et al. |
| 2011/0201065 A1 | 8/2011 | Singh et al. |
| 2011/0269983 A1 | 11/2011 | Kinney et al. |
| 2012/0041218 A1 | 2/2012 | Singh et al. |
| 2012/0083615 A1 | 4/2012 | Singh et al. |
| 2012/0215018 A1 | 8/2012 | Singh et al. |

FOREIGN PATENT DOCUMENTS

| | | |
|---|---|---|
| AU | 776477 | 9/2004 |
| AU | 2007/276257 | 1/2008 |
| JP | 200021782 | 8/2000 |
| JP | 2001095588 | 4/2001 |
| JP | 2001145490 | 5/2001 |
| JP | 2001169780 | 7/2001 |
| JP | 2003116566 | 4/2003 |
| WO | WO 93/06712 | 4/1993 |
| WO | WO 93/23545 | 11/1993 |
| WO | WO 96/21022 | 7/1996 |
| WO | WO 97/21340 | 6/1997 |
| WO | WO 98/01565 | 1/1998 |
| WO | WO 98/18952 | 5/1998 |
| WO | WO 98/46763 | 10/1998 |
| WO | WO 98/46764 | 10/1998 |
| WO | WO 98/46765 | 10/1998 |
| WO | WO 98/39468 | 11/1998 |
| WO | WO 98/55625 | 12/1998 |
| WO | WO 98/56239 | 12/1998 |
| WO | WO 99/33958 | 7/1999 |
| WO | WO 99/49050 | 9/1999 |
| WO | WO 99/61602 | 12/1999 |
| WO | WO 99/64614 | 12/1999 |
| WO | WO 99/64616 | 12/1999 |
| WO | WO 00/12720 | 3/2000 |
| WO | WO 00/20602 | 4/2000 |
| WO | WO 00/20603 | 4/2000 |
| WO | WO 00/21557 | 4/2000 |
| WO | WO 00/40705 | 7/2000 |
| WO | WO 00/42195 | 7/2000 |
| WO | WO 00/52183 | 9/2000 |
| WO | WO 00/53770 | 9/2000 |
| WO | WO 00/55330 | 9/2000 |
| WO | WO 00/75341 | 12/2000 |
| WO | WO 01/02591 | 1/2001 |
| WO | WO 01/04636 | 1/2001 |
| WO | WO 01/14538 | 3/2001 |
| WO | WO 01/20001 | 3/2001 |
| WO | WO 01/38484 | 5/2001 |
| WO | WO 01/38512 | 5/2001 |
| WO | WO 01/44485 | 6/2001 |
| WO | WO 01/66758 | 9/2001 |
| WO | WO 01/75069 | 10/2001 |
| WO | WO 01/92489 | 12/2001 |
| WO | WO 02/08401 | 1/2002 |
| WO | WO 02/26946 | 4/2002 |
| WO | WO 02/081668 | 10/2002 |
| WO | WO 02/081702 | 10/2002 |
| WO | WO 02/083869 | 10/2002 |
| WO | WO 02/083870 | 10/2002 |
| WO | WO 02/090493 | 11/2002 |
| WO | WO 02/092540 | 11/2002 |
| WO | WO 03/064596 | 8/2003 |
| WO | WO 03/093482 | 11/2003 |
| WO | WO 03/102138 | 12/2003 |
| WO | WO 2004/005442 | 1/2004 |
| WO | WO 2004/057001 | 7/2004 |
| WO | WO 2004/071467 | 8/2004 |

(56) References Cited

FOREIGN PATENT DOCUMENTS

| WO | WO 2004/087180 | 10/2004 |
|---|---|---|
| WO | WO 2005/007845 | 1/2005 |
| WO | WO 2005/012316 | 2/2005 |
| WO | WO 2005/083053 | 9/2005 |
| WO | WO 2005/083093 | 9/2005 |
| WO | WO 2005/097982 | 10/2005 |
| WO | WO 2005/098033 | 10/2005 |
| WO | WO 2005/118814 | 12/2005 |
| WO | WO 2006/064317 | 6/2006 |
| WO | WO 2006/069936 | 7/2006 |
| WO | WO 2005/080578 | 9/2006 |
| WO | WO 2007/005882 | 1/2007 |
| WO | WO 2007/092460 | 8/2007 |
| WO | WO 2007/127381 | 11/2007 |
| WO | WO 2008/009600 | 1/2008 |
| WO | WO 2008/025068 | 6/2008 |
| WO | WO 2009/129582 | 10/2009 |
| WO | WO 2010/009500 | 1/2010 |
| WO | WO 2010/023202 | 3/2010 |

OTHER PUBLICATIONS

Nov. 30, 2011 Request for Re-Examination filed in connection to corresponding Chinese Patent Application No. CN200580020696.
English language translation of claims submitted with Nov. 30, 2011 Request for Re-Examination filed in connection to corresponding Chinese Patent Application No. CN200580020696.
Sayanova et al., The role of Δ6-desaturase acyl-carrier specificity in the efficient synthesis of long-chain polyunsaturated fatty acids in transgenic plants. Plant Biotechnology Journal, (2012) 10:195-206.
Response to Office Action, filed Mar. 22, 2012 in connection with U.S. Appl. No. 13/044,984.
Final Office Action, issued May 17, 2012 in connection with U.S. Appl. No. 13/044,984.
May 22, 2012 Response to Examination Report, filed in connection with Canadian Patent Application No. 2,563,875.
File History of U.S. Patent No. 8,158,392, Singh et al., issued Apr. 17, 2012 (U.S. Appl. No. 13/311,240, filed Sep. 23, 2011).
File History of U.S. Patent Application No. 2012-0015144, Singh et al., Jan. 19, 2012 (U.S. Appl. No. 13/129,940, filed Sep. 30, 2011).
Australian Examination Report, issued Mar. 14, 2011 in connection with Australian Patent Application No. 2005235627.
Response to Australian Examination Report, filed Apr. 19, 2011 in connection with Australian Patent Application No. 2005235627.
Australian Examination Report, issued May 16, 2011 in connection with Australian Patent Application No. 2005235627.
Response to Australian Examination Report, filed Jun. 14, 2011 in connection with Australian Patent Application No. 2005235627.
Examination Report issued Mar. 14, 2012 in connection with corresponding European Patent Application No. 05733657.0.
Extended European Search Report and Opinion issued Feb. 10, 2012 in connection with corresponding European Divisional Patent Application No. 11155266.7.
Rule 69 EPC Communication issued Mar. 19, 2012 in connection with European Divisional Patent Application No. 11155266.7.
Brazilian Technical Opinion issued Mar. 1, 2012 in connection with corresponding Brazilian Patent Application No. PI 0510132-8.
Response filed to Brazilian Technical Opinion filed Mar. 29, 2012 in connection with corresponding Brazilian Patent Application No. PI 0510132-8.
File History of U.S. Patent Application Publication No. 2012-0041218, Singh et al., published Feb. 16, 2012, (U.S. Appl. No. 13/243,747, filed Sep. 23, 2011).
U.S. Appl. No. 13/011,773, filed Jan. 21, 2011, Liu et al.
U.S. Appl. No. 13/011,779, filed Jan. 21, 2011, Liu et al.
U.S. Appl. No. 12/989,405, filed May 16, 2011, Zhou et al.
U.S. Appl. No. 13/171,032, filed Jun. 28, 2011, Petrie et al.
International Preliminary Report on Patentability, issued May 24, 2011 in connection with PCT International Application Publication No. PCT/AU2009/001488.

Written Opinion of the International Search Authority, issued Apr. 1, 2010 in connection with PCT International Application Publication No. PCT/AU2009/001488.
International Search Report, issued Apr. 1, 2010 in connection with PCT International Application Publication No. PCT/AU2009/001488.
PCT International Preliminary Report on Patentability issued Oct. 25, 2006 for PCT International Application Publication No. WO 2005/103253.
Dafny-Yelin et al., Delivery of Multiple Transgenes to Plant Cells, Plant Physiology, Dec. 2007, vol. 145, pp. 1118-1128 Robert et al., Metabolic engineering of *Arabidopsis* to produce nutritionally important DHA in seed oil, Functional Plant Biology, 2005, vol. 32, p. 473-479 (Abstract Only).
Halpin, Gene stacking in transgenic plants—the challenge for 21st century plant biotechnology, Plant Biotechnology Journal 2005, 3, pp. 141-155.
Robert et al., Metabolic engineering of *Arabidopsis* to produce nutritionally important DHA in seed oil, Functional Plant Biology, 2005, vol. 32, p. 473-479 (Abstract Only).
Slater et al., Metabolic engineering of *Arabidopsis* and Brassica for poly(3-hydroxybutyrate-co-3-hydroxyvalerate) copolymer production, Nature Biotechnology, Oct. 1999, vol. 12, 1011-1016.
Meyer et al. (2003) GenBank Accession No. AY278558, NCBI, pp. 1-2.
Tonon et al. (2003) GenBank Accession No. AY332747, NCBI, pp. 1-2.
Thurmond et al. (2001) GenBank Accession No. AF391543, NCBI, pp. 1-2.
Cho et al. (1999) GenBank Accession No. AF199596, NCBI, pp. 1-2.
Australian Examination Report, issued Nov. 16, 2009 in connection with Australian Patent Application No. 2005235627.
Response to Australian Examination Report, filed Feb. 25, 2011 in connection with Australian Patent Application No. 2005235627.
Chinese Examination Report, issued Apr. 10, 2009 in connection with Chinese Patent Application No. 200580020696.3.
Response to Chinese Examination Report, filed Jul. 21, 2009 in connection with Chinese Patent Application No. 200580020696.3.
Chinese Examination Report, issued Apr. 30, 2010 in connection with Chinese Patent Application No. 200580020696.3.
Response to Chinese Examination Report, filed Sep. 15, 2010 in connection with Chinese Patent Application No. 200580020696.3.
Aug. 18, 2011 Decision of Rejection issued by the Chinese Patent Office in connection with corresponding Chinese Patent Application No. 200580020696.3, including an English language translation.
Oct. 25, 2011 Partial European Search Report issued by the European Patent Office in connection with counterpart European Patent Application No. 11155266.7.
Oct. 25, 2011 Extended European Search Report issued by the European Patent Office in connection with counterpart European Patent Application No. 11155282.4.
Oct. 25, 2011 Extended European Search Report issued by the European Patent Office in connection with counterpart European Patent Application No. 11155364.0.
Oct. 17, 2011 Response to Apr. 6, 2011 Communication from the Examining Division, filed in connection with counterpart European Patent Application No. EP 05733657.0.
Requirement for Restriction/Election issued Mar. 5, 2007 in connection with U.S. Appl. No. 11/112,882.
Response to Requirement for Restriction/Election filed May 7, 2007 in connection with U.S. Appl. No. 11/112,882.
Non Final Office Action issued Oct. 11, 2007 in connection with U.S. Appl. No. 11/112,882.
Response to Non Final Office Action filed Oct. 31, 2007 in connection with U.S. Appl. No. 11/112,882.
Notice of Informal or Non-Responsive Amendment issued Feb. 26, 2008 in connection with U.S. Appl. No. 11/112,882.
Response to Office Action filed Mar. 11, 2008 in connection with U.S. Appl. No. 11/112,882.
Non-Final Office Action issued Jun. 17, 2008 in connection with U.S. Appl. No. 11/112,882.
Response to Non-Final Office Action filed Oct. 17, 2008 in connection with U.S. Appl. No. 11/112,882.

(56) References Cited

OTHER PUBLICATIONS

Final Office Action issued Apr. 1, 2009 in connection with U.S. Appl. No. 11/112,882.
Response to Final Office Action filed Jul. 1, 2009 in connection with U.S. Appl. No. 11/112,882.
Notice of Allowance issued Aug. 21, 2009 in connection with U.S. Appl. No. 11/112,882.
Restriction Requirement issued Apr. 30, 2009 in connection with U.S. Appl. No. 11/587,092.
Response to Restriction Requirement filed Jun. 30, 2009 in connection with U.S. Appl. No. 11/587,092.
Non-Final Office Action issued Nov. 17, 2009 in connection with U.S. Appl. No. 11/587,092.
Examiner Interview Summary Record Feb. 22, 2010 in connection with U.S. Appl. No. 11/587,092.
Response to Non-Final Office Action, filed Mar. 17, 2010 in connection with U.S. Appl. No. 11/587,092.
Jul. 2, 2010 Notice of Allowance in connection with U.S. Appl. No. 11/587,092.
Office Action issued by the U.S. Patent Office on Dec. 28, 2010 in connection with U.S. Appl. No. 12/661,978.
Response to Office Action, filed Jan. 25, 2011 in connection with U.S. Appl. No. 12/661,978.
Final Office Action, issued Apr. 18, 2011 in connection with U.S. Appl. No. 12/661,978.
Interview Summary Record, issued May 24, 2011 in connection with U.S. Appl. No. 12/661,978.
Response to Final Office Action, filed Jun. 16, 2011 in connection with U.S. Appl. No. 12/661,978.
Notice of Allowance, issued Sep. 1, 2011 in connection with U.S. Appl. No. 12/661,978.
Non-Final Office Action issued Jan. 5, 2011 in connection with U.S. Appl. No. 12/945,708.
Response to Non-Final Office Action filed Jan. 10, 2011 in connection with U.S. Appl. No. 12/945,708.
Notice of Allowance, issued Feb. 11, 2011 in connection with U.S. Appl. No. 12/945,708.
Accelerated Examination Support Document, filed Apr. 25, 2011 in connection with U.S. Appl. No. 13/093,252.
Pre-Examination Search Document, filed Apr. 25, 2011 in connection with U.S. Appl. No. 13/093,252.
Non-Final Office Action, issued Aug. 30, 2011 in connection with U.S. Appl. No. 13/093,252.
Examiner Interview Summary, issued Sep. 13, 2011 in connection with U.S. Appl. No. 13/093,252.
Amendment in Response to Office Action and Summary of Examiner Interview, filed Sep. 16, 2011 in connection with U.S. Appl. No. 13/093,252.
Notice of Allowance, issued Oct. 7, 2011 in connection with U.S. Appl. No. 13/093,252.
Dec. 5, 2011 Accelerated Examination Support Document, filed in connection with U.S. Appl. No. 13/311,240.
Dec. 5, 2011 Pre-Examination Search Document, filed in connection with U.S. Appl. No. 13/311,240.
Feb. 6, 2012 Communication, filed in connection with U.S. Appl. No. 13/311,240.
Feb. 17, 2012 Notice of Allowance, issued in connection with U.S. Appl. No. 13/311,240.
Feb. 1, 2012 Non-Final Office Action, issued in connection with U.S. Appl. No. 13/243,747.
May 1, 2012 Amendment, filed in connection with U.S. Appl. No. 13/243,747.
Jul. 6, 2012 Notice of Allowance, issued in connection with U.S. Appl. No. 13/243,747.
Certik M. and Shimizu S., Biosynthesis and regulation of microbial polyunsaturated fatty acid production. J. Biosci Bioeng, 1999; 87(1):1-14.
Damude et al., (2007) "Engineering Oilseed Plants for a Sustainable, Land-Based Source of Long Chain Polyunsaturated Fatty Acids" Lipids, 42:179-185.
Domergue et al., (2003), Acyl Carriers Used as Substrates by the Desaturases and Elongases Involved in Very Long-chian Polyunsaturated Fatty Acids Biosynthesis Reconstituted in Yeast, J. Biol. Chem. 278; 35115-35126.
Hoffmann et al., (2008) "Metabolic Engineering of ω3-Very Long Chain Polyunsaturated Fatty Acid Production by an Exclusively Acyl-CoA-dependent Pathway" The Journal of Biological Chemistry, 283:22352-22362.
Kajikawa M. et al., Isolation and characterization of delta(6)-desaturase, an ELO-like enzyme and delta(5)-desaturase from liverword Marchantia polymorpha and production of arachidonic and eicosapentaenoic acids in the methylotrophic yeast Pichia pastoris. Plant Mol Biol, 2004; 54(3):335-52.
Marquardt et al., (2000) "cDNA cloning, genomic structure, and chromosomal localization of three members of the human fatty acid desaturase family" Genomics, 66(2):175-83.
Parker-Barnes, J.M., et al., (2000) "Identification and Characterization of an Enzyme Involved in the Elongation of n-6 and n-3 Polyunsaturated Fatty Acids," Proceedings of the National Academy of Sciences of The United States of America, 97(15): 8284-8289.
Qi et al., (2004) "Production of very long chain polyunsatured omega-3 and omega-6 fatty acids in plants" Nature Biotechnology 22:739-745 (published online May 16, 2004).
Qiu et al. (2001) GenBank Accession No. AF489589, NCBI p. 1.
Qiu, X., et al., (2001) "Identification of a Δ4 Fatty Acid Desaturase from *Thraustochytrium* sp. Involved in the Biosynthesis of Docosahexanoic Acid by Heterologous Expression in *Saccharomyces cerevisiae* and *Brassica juncea*," The Journal of Biological Chemistry, 276(34):31561-31566.
Sayanova O.V. and Napier J.A., Eicosapentaenoic acid: biosynthetic routes and the potential for synthesis in transgenic plants. Phytochemistry, 2004; 65(2):147-58.
Truksa et al., (2006) "Metabolic Engineering of Plants to Produce Very Long-Chain Polyunsaturated Fatty Acids", Transgenic Research, 15:131-137.
Sep. 24, 2012 Response to Mar. 14, 2012 Communication from the Examining Division, filed in connection with European Patent Application No. 05733657.0.
Communication from the Examining Division issued by the European Patent Office on Nov. 9, 2012 in connection with European Patent Application No. 05733657.0.
Sep. 7, 2012 Amendment after receipt of European Search Report, filed in connection with European Patent Application No. 11155282.4.
Sep. 10, 2012 Amendment after receipt of European Search Report, filed in connection with European Patent Application No. 11155364.0.
Examination Report, issued by the Australian Patent Office on Sep. 6, 2012 in connection with Australian Patent Application No. 2011232757.
Response to Notification of Re-Examination filed on Oct. 18, 2012 in connection with Chinese Patent Application No. 200580020696.3, including English language the filed claims.
May 9, 2013 Notice of Allowance, issued in connection with U.S. Appl. No. 13/448,107.
Mar. 12, 2013 Office Action, issued in connection with U.S. Appl. No. 12/310,645.
Apr. 5, 2013 Response filed in connection with European Patent Application No. 10184533.7.
Mar. 11, 2013 Office Action, issued in connection with European Patent Application No. 11155282.4.
Feb. 13, 2013 Office Action issued in connection with European Patent Application No. 11155364.0.
Jan. 3, 2013 Response filed in connection with European Patent Application No. 11155266.7.
Oct. 18, 2012 Request for Reexamination filed in connection with Chinese Patent Application No. 200580020696.3, including English Language claims.
Jan. 29, 2013 Office Action issued in connection with Chinese Patent Application No. 201210006139.8, including English Language Translation.
Nov. 23, 2012 Office Action issued in connection with Canadian Patent Application No. 2,563,875.

(56) References Cited

OTHER PUBLICATIONS

Tsevegsuren et al., (2003) "Isomers of hexadecenoic and hexadecadienoic acids in Androspace septentrionalis (Primulaceae) seed oil" Lipids 38(11):1173-1178.

International Search Report issued on Jun. 23, 2005, in connection with PCT International Application No. PCT/AU05/000571, filed Apr. 22, 2005.

Supplementary European Search Report dated Apr. 1, 2008 issued by the European Patent Office in connection with related International Application No. PCT/AU2005/000571.

Notification of European publication number issued Jan. 31, 2007 in connection with European Patent Application No. 05733657.0.

Supplementary European Search Report issued Apr. 1, 2008 in connection with European Patent Application No. 05733657.0.

Communication Pursuant to Article 94(3) EPC issued Feb. 2, 2009 in connection with European Patent Application No. 05733657.0.

Amendment in Response to Feb. 2, 2009 Communication Pursuant to Article 94(3) EPC issued in connection with European Patent Application No. 05733657.0.

Abbadi, A., et al., (2001) "Transgenic Oilseeds As Sustainable Source of Nutritionally Relevant C20 and C22 Polyunsaturated Fatty Acids?" European Journal of Lipid Science and Technology, 103(2): 106-113.

Abbadi, A., et al., (2004) "Biosynthesis of Very-Long-Chain Polyunsaturated Fatty Acids in Transgenic Oilseeds: Constraints on Their Accumulation," The Plant Cell, 16(10): 2734-3748.

The *C. elegans* Sequencing Consortium, (1998) "Genome Sequence of the Nematode *C. elegans*: A Platform for Investigating Biology," Science, 282(5396): 2012-2018.

Agaba, M., et al., (2004) "Zebrafish cDNA Encoding Multifunctional Fatty Acid Elongase Involved in Production of Eicosapentaenoic (20:5n-3) and Docosahexaenoic (22:6n-3) Acids," Marine Biotechnology, 6(3): 251-261.

Akiyama, H., et al., (1998) "A Novel Plasmid Recombination Mechanism of the Marine *Cyanobacterium synechococcus* sp. PCC7002," DNA Research, 5(6): 327-334.

Akiyama, H., et al., (1998) "Nucleotide Sequence of Plasmid pAQ1 of Marine *Cyanobacterium synechococcus* sp. PCC7002," DNA Research, 5(2): 127-129.

Bäumlein, H., et al., (1992) "Cis-Analysis of a Seed Protein Gene Promoter: The Conservative RY Repeat CATGCATC Within the Legumin Box is Essential for Tissue-Specific Expression of a Legumin Gene," The Plant Journal, 2(2): 233-239.

Bäumlein, H., et al., (1991) "A Novel Seed Protein Gene From Vicia faba is Developmentally Regulated in Transgenic Tobacco and *Arabidopsis* Plants," Molecular and General Genetics, 225(3): 459-467.

Beaudoin, F., et al., (2000) "Heterologous Reconstitution in Yeast of the Polyunsaturated Fatty Acid Biosynthetic Pathway," Proceedings of the National Academy of Sciences of The United States of America, 97(12): 6421-6426.

Berberich, T., et al., (1998) "Two Maize Genes Encoding Omega-3 Fatty Acid Desaturase and Their Differential Expression to Temperature," Plant Molecular Biology, 36(2): 297-306.

Bolch, C.J.S., et al., (1999) "Genetic, Morphological, and Toxicological Variation Among Globally Distributed Strains of Nodularia (Cyanobacteria)," Journal of Phycology, 35(2): 339-355.

Bolch, C.J.S., et al., (1999) "Genetic Variation Among Strains of the Toxic Dinoflagellate Gymnodinium Catenatum (Dinophyceae)," Journal of Phycology, 35: 356-367.

Broun, P., et al., (1998) "A Bifunctional oleate 12-Hydroxylase: Desaturase From *Lesquerella fendleri*," The Plant Journal, 13(2): 201-210.

Brown, M.R., et al., (1997) "Nutritional Properties of Microalgae for Mariculture," Aquaculture, 151(1): 315-331.

Browse, J.A. and Slack, C.R., (1981) "Catalase Stimulates Linoleate Desaturase Activity in Microsomes From Developing Linseed Cotyledons," Federation of European Biochemical Societies Letters, 131(1): 111-114.

Chinain, M., et al., "Intraspecific Variation in the Dinoflagellate Gambierdiscus Toxicus (Dinophyceae). I. Isozyme Analysis," Journal of Phycology, 33: 36-43.

Cho, H.P., et al., (1999) "Cloning, Expression, and Nutritional Regulation of the Mammalian Δ-6 Desaturase," The Journal of Biological Chemistry, 274(1): 471-477.

Cho, H.P., et al., (1999) "Cloning, Expression, and Fatty Acid Regulation of the Human Δ-5 Desaturase," The Journal of Biological Chemistry, 274(52): 37335-37339.

Clough, S.J. and Bent, A.F., (1998) "Floral Dip: A Simplified Method for Agrobacterium-Mediated Transformation of *Arabidopsis thaliana*," 16(6); 735-743.

Coleman, A.W., (1977) "Sexual and Genetic Isolation in the Cosmopolitan Algal Species Pandorina Morum," American Journal of Botany, 64(3): 361-368.

Domergue, F., et al., (2002) "Cloning and Functional Characterization of *Phaeodactylum tricornutum* Front-End Desaturases Involved in Eicosapentaenoic Acid Biosynthesis," European Journal of Biochemistry, 269(16): 4105-4113.

Domergue, F., et al., (2003) "Acyl Carriers Used As Substrates by the Desaturases and Elongases Involved in Very Long-Chain Polyunsaturated Fatty Acids Biosynthesis Reconstituted in Yeast," The Journal of Biological Chemistry, 278(37): 35115-35126.

Domergue, F., et al., (2003) "New Insight Into *Phaeodactylum tricornutum* Fatty Acid Metabolism. Cloning and Functional Characterization of Plastidial and Microsomal Δ12-Fatty Acid Desaturases," Plant Physiology, 131(4): 1648-1660.

Drexler, H., et al., (2003) "Metabolic Engineering of Fatty Acids for Breeding of New Oilseed Crops: Strategies, Problems and First Results," Journal of Plant Physiology, 160(7): 779-802.

Dunstan, G.A., et al., (1994) "Essential Polyunsaturated Fatty Acids From 14 Species of Diatom (*Bacillariophyceae*)," Phytochemistry, 35(1): 155-161.

Gallagher, J.C., (1980) "Population Genetics of Skeletonema Costatum (*Bacillariophyceae*) In Narragansett Bay," Journal of Phycology, (16)3: 464-474.

Garcia-Maroto, F., et al., (2002) "Cloning and Molecular Characterization of the Δ6-Desaturase From Two Echium Plant Species: Production of GLA by Heterologous Expression in Yeast and Tobacco," Lipids, 37(4): 417-426.

Girke, T., et al., (1998) "Identification of a Novel Δ6-Acyl-Group Desaturase by Targeted Gene Disruption in *Physcomitrella patens*," The Plant Journal, 15(1): 39-48.

Guil-Guerrero, J.L., et al., (2000) "Occurrence and Characterization of Oils Rich in γ-Linolenic Acid Part I: Echium Seeds From Macaronesia," Phytochemistry, 53(4): 451-456.

Haseloff, J. and Gerlach, W.L., (1988) "Simple RNA Enzymes With New and Highly Specific Endoribonuclease Activities," Nature, 334: 585-591.

Hastings, N., et al., (2001) "A Vertebrate Fatty Acid Desaturase With Δ5 and Δ6 Activities," Proceedings of the National Academy of Sciences of The United States of America, 98(25): 14304-14309.

Hong, H., et al., (2002) "Isolation and Characterization of a Δ5 FA Desaturase From Pythium irregulare by Heterologous Expression in *Saccaromyces cerevisiae* and Oilseed Crops," Lipids, 37(9): 863-868.

Horiguchi, G., et al., (1998) "Developmental Regulation of Genes for Microsome and Plastid Omega-3 Fatty Acid Desaturases In Wheat (*Triticum aestivum* L.)," Plant and Cell Physiology, 39(5): 540-544.

Huang, Y., et al., (1999) "Cloning of Δ12-And Δ6-Desaturases From Mortierella alpine and Recombinant Production of γ-Linolenic Acid in *Saccharomyces cerevisiae*," Lipids, 34(7): 649-659.

Ikeda, K., et al., (2002) "Transformation of the Fresh Water *Cyanobacterium synechococcus* PCC7942 With the Shuttle-Vector pAQ-EX1 Developed for the Marine *Cyanobacterium synechococcus* PCC7002," World Journal of Microbiology & Biotechnology, 18(1): 55-56.

Inagaki, K., et al., (2002) "Identification and Expression of a Rat Fatty Acid Elongase Involved in the Biosynthesis of C18 Fatty Acids," Bioscience, Biotechnology, and Biochemistry, 66(3): 613-621.

(56) References Cited

OTHER PUBLICATIONS

Jones, A.V.M. and Harwood, J.L., (1980) "Desaturation of Linoleic Acid From Exogenous Lipids by Isolated Chloroplasts," The Biochemical Journal, 190(3): 851-854.
Knutzon, D.S., et el., (1998) "Identification of Δ5-Desaturase From *Mortierella alpina* by Heterologous Expression in Bakers' Yeast and Canola," The Journal of Biological Chemistry, 273(45): 29360-29366.
Lee, M., et al., (1998) "Identification of Non-Heme Diiron Proteins That Catalyze Triple Bond and Epoxy Group Formation," Science, 280(5365): 915-918.
Leonard, A.E., et al., (2000) "cDNA Cloning and Characterization of Human Δ5-Desaturase Involved in the Biosynthesis of Arachidonic Acid," The Biochemical Journal, 347(Pt 3): 719-724.
Leonard, A.E., et al., (2000) "Cloning of a Human cDNA Encoding a Novel Enzyme Involved in the Elongation of Long-Chain Polyunsaturated Fatty Acids," The Biochemical Journal, 350(Pt 3): 765-770.
Leonard, A.E., et al., (2002) "Identification and Expression of Mammalian Long-Chain PUFA Elongation Enzymes," Lipids, 37(8): 733-740.
Lo, J., et al., (2003) "15,000 Unique Zebrafish EST Clusters and Their Future Use in Microarray for Profiling Gene Expression Patterns During Embryogenesis," Genome Research Letter, 13(3): 455-466.
Mansour, M.P., et al., (1999) "The Fatty Acid and Sterol Composition of Five Marine Dinoflagellates," Journal of Phycology, 35(4): 710-720.
Medlin, L.K., et al., (1996) "Genetic Characterization of *Emiliania huxleyi* (Haptophyta)," Journal of Marine Systems, 9: 13-31.
Metz, J.G., et al., (2001) "Production of Polyunsaturated Fatty Acids by Polyketide Synthases in Both Prokaryotes and Eukaryotes," Science, 293(5528) : 290-293.
Meyer, A., et al., (2003) "Biosynthesis of Docosahexaenoic Acid in *Euglena gracilis*: Biochemical and Molecular Evidence for the Involvement of a Δ4-Fatty Acyl Group Desaturase," Biochemistry, 42(32): 9779-9788.
Meyer, A., et al., (2004) "Novel Fatty Acid Elongases and Their Use for the Reconstitution of Docosahexaenoic Acid Biosynthesis," Journal of Lipid Research, 45(10): 1899-1909.
Michaelson, L.V., et al., (1998) "Isolation of a Δ5-Fatty Acid Desaturase Gene From *Mortirella alpina*," The Journal of Biological Chemistry, 273(30): 19055-19059.
Michaelson, L.V., et al., (1998) "Functional Identification of a Fatty Acid Δ5 Desaturase Gene From *Caenorhabditis elegans*," Federation of European Biochemical Societies Letters, 439(3): 215-218.
Mitchell, A.G. and Martin, C., (1995) "A Novel Cytochrome b5-Like Domain Is Linked to the Carboxyl Terminus of the *Saccharomyces cerevisiae* Δ-9 Fatty Acid Desaturase," The Journal of Biological Chemistry, 270(50): 29766-29772.
Morita, N., et al., (2000) "Biosynthesis of Fatty Acids in the Docosahexaenoic Acid-Producing Bacterium Moritella marina Strain MP-1" Biochemical Society Transactions, 28(6): 943-945.
Napier, J.A., et al., (1998) "Identification of a *Caenorhabditis elegans* Δ6-Fatty-Acid-Desaturase by Heterologous Expression in *Saccharomyces cerevisiae*," The Biochemical Journal, 330(Pt 2): 611-614.
Napier, J.A., et al., (1999) "A Growing Family of Cytochrome b5-Domain Fusion Proteins," Trends in Plant Science, 4(1): 2-4.
Napier, J.A., at al., (1999) "Plant Desaturases: Harvesting the Fat of the Land," Current Opinion in Plant Biology, 2(2): 123-127.
Pereira, S.L., et al., (2004) "A Novel omega3-Fatty Acid Desaturase Involved in the Biosynthesis of Eicosapentaenoic Acid," The Biochemical Journal, 378 (Pt 2): 665-671.
Perriman, R., et al., (1992) "Extended Target-Site Specificity for a Hammerhead Ribozyme," Gene, 113(2): 157-163.
Qi, B., et al., (2002) "Identification of a cDNA Encoding a Novel C18-Δ9 Polyunsaturated Fatty Acid-Specific Elongating Activity From the Docosahexaenoic Acid(DHA)—Producing Microalga, *Isochrysis galbana*," Federation of European Biochemical Societies Letters, 510(3): 159-165.

Qui, X., et al., (2001) "Identification of a Δ4 Fatty Acid Desaturase From *Thraustochytrium* sp. Involved in the Biosynthesis of Docosahexanoic Acid by Heterologous Expression In *Saccharomyces cerveisiae* and *Brassica juncea*," The Journal of Biological Chemistry, 276(34): 31561-31566.
Reddy, A.S., et al., (1993) "Isolation of a Δ6 -Desaturase Gene From the *Cyanobacterium synechocystis* sp. Strain PCC6803 by Gain-of-Function Expression in *Anabaena* sp. Strain PCC7120," Plant Molecular Biology, 27: 293-300.
Saito, T., et al., (2008) "A Second Functional Δ5 Fatty Acid Desaturase in the Cellular Slime Mould *Dictyostelium discoideum*," European Journal of Biochemistry, 267(6): 1813-1818.
Sakuradani, E., et al., (1999) "Δ6-Fatty Acid Desaturase From an Arachidonic Acid-Producing Mortierella Fungus. Gene Cloning and Its Heterologous Expression in a Fungus, *Aspergillus*," Gene, 238(2): 445-453.
Sayanova, O.V., et al., (1997) "Expression of a Borage Desaturase cDNA Containing an N-Terminal Cytochrome b5 Domain Results in the Accumulation of High Levels of Δ6-Desaturated Fatty Acids in Transgenic Tobacco," Proceedings of the National Academy of Sciences of The United States of America, 94(8): 4211-4216.
Sayanova, O.V., et al., (1999) "Histidine-41 of the Cytochrome b5 Domain of the Borage Δ6 Fatty Acid Desaturase Is Essential for Enzyme Activity," Plant Physiology, 121(2): 641-646.
Sayancva, O.V., at al., (2003) "Identification of Primula Fatty Acid Δ6-Desaturases with n-3 Substrate Preferences," Federation of European Biochemical Societies, 542: 100-104.
Sayanova, O.V. and Napier, J.A., (2004) "Eicosapentaenoic Acid: Biosynthetic Routes and the Potential for Synthesis in Transgenic Plants," Phytochemistry, 65(2): 147-158.
Shippy, R., et al., (1999) "The Hairpin Ribozyme—Discovery, Mechanism, and Development for Gene Therapy," Molecular Biotechnology, 12(1): 117-129.
Simopoulos, A.P., (2000) "Symposium: Role of Poultry Products in Enriching the Human Diet With N-3 PUFA," Poultry Science, 79: 961-970.
Singh, S., et al., (2001) "Transgenic Expression of a Δ12-Epoxygenase Gene in *Arabidopsis* Seeds Inhibits Accumulation of Linoleic Acid," Planta, 212: 872-879.
Smith, N.A., et al., (2000) "Total Silencing by Intron-Spliced Hairpin RNAs," Nature, 407(6802): 319-320.
Sperling, P., et al., (2000) "A Bifunctional Δ6-Fatty Acyl Acetylenase/Desaturase From the Moss Ceratodon purpureus," European Journal of Biochemistry, 267(12): 3801-3811.
Sperling, P. and Heinz, E., (2001) "Desaturases Fused to Their Electron Donor," European Journal of Lipid Science and Technology, 103(3): 158-180.
Sprecher, H., et al., (1995) "Reevaluation of the Pathways for the Biosynthesis of Polyunsaturated Fatty Acids," Journal of Lipid Research, 36(12): 2471-2477.
Spychalla, J.P., et al., (1997) "Identification of an animal omega-3 Fatty Acid Desaturase by Heterologous Expression in *Arabidopsis*," Proceedings of the National Academy of Sciences of The United States of America, 94(4): 1142-1147.
Stålberg, K., et al., (1993) "Deletion Analysis of a 2S Seed Storage Protein Promoter of *Brassica napus* in Transgenic Tobacco," Plant Molecular Biology, 23(4): 671-683.
Takeyama, H., et al., (1997) "Expression of the Eicosapentaenoic Acid Synthesis Gene Cluster From Shewanella sp. in a Transgenic Marine Cyanobacterium, *Synechococcus* sp.," Microbiology, 143(Pt 8): 2725-2731.
Tanaka, M., et al., (1999) "Isolation of Clustered Genes That Are Notably Homologous to the Eicosapentaenoic Acid Biosynthesis Gene Cluster From the Docosaehexaenoic Acid-Producing Bacterium Vibrio marinus Strain MP-1," Biotechnology Letters, 21(11): 939-945.
Tonon, T., et al., (2003) "Identification of a Very Long Chain Polyunsaturated Fatty Acid Δ4-Desaturase From the Microalga *Pavlova lutheri*," Federation of European biochemical Societies, 553(3): 440-444.
Trautwein, E.A., (2001) "n-3 Fatty Acids—Physiological and Technical Aspects for Their Use in Food," European Journal of Lipid Science and Technology, 103(1): 45-55.

(56) References Cited

OTHER PUBLICATIONS

Tvrdik, P., et al., (2000) "Role of a New Mammalian Gene Family in the Biosynthesis of Very Long Chain Fatty Acids and Sphingolipids," The Journal of Cell Biology, 149(3): 707-717.

Valvekens, D., et al., (1988) "*Agrobacterium tumefaciens*—Mediated Transformation of *Arabidopsis thaliana* Root Explants by Using Kanamycin Selection," Proceedings of the National Academy of Sciences of the United States of America, 85(15) 5536-5540.

Volkman, J.K., et al., (1989) "Fatty Acid and Lipid Composition of 10 Species of Microalgae Used in Mariculture," Journal of Experimental Marine Biology and Ecology, 128(3): 219-240.

Wallis, J.G. and Browse, J., (1999) "The Δ8-Desaturase of *Euglena gracilis*: An Alternate Pathway for Synthesis of 20-Carbon Polyunsaturated Fatty Acids," Archives of Biochemistry and Biophysics, 365(2): 307-316.

Wang, M.B., et al., (1997) "Intron-Mediated Improvement of a Selectable Marker Gene for Plant Transformation Using *Agrobacterium tumefaciens*," Journal of Genetics & Breeding, 51: 325-334.

Waterbury, J.B. and Willey, J.M., (1988) "Isolation and Growth of Marine Planktonic Cyanobacteria," Methods of Enzymology, 167: 100-105.

Waterhouse, P.M., et al., (1998) "Virus Resistance and Gene Silencing in Plants Can Be Induced by Simultaneous Expression of Sense and Antisense RNA," Proceedings of the National Academy of Sciences of The United States of America, 95(23): 13959-13964.

Watts, J.L. and Browse, J., (1999) "Isolation and Characterization of a Δ5-Fatty Acid Desaturase From *Caenorhabditis elegans*," Archives of Biochemistry and Biophysics, 362(1): 175-182.

Williams, J.G.K. and Szalay, A.A., (1983) "Stable Integration of Foreign DNA Into the Chromosome of the *Cyanobacterium synechococcus* R2," Gene, 24(1): 37-51.

Whitney, H., et al., (2003) "Functional Characterization of Two Cytochrome b5-Fusion Desaturases From Anemone leveillei: The Unexpected Identification of a Fatty Acid Δ6-Desaturase," Planta, 217(6): 983-992.

Wolf, R. L., et al., (1999) "Arachidonic Eicosapentaenoic, and Biosynthetically Related Fatty Acids in the Seed Lipids from a Primitive Gymnosperm, *Agathis robusta*" Lipids, 34(10):1083-1097.

Yazawa, K., (1996) "Production of Eicosapentaenoic Acid From Marine Bacteria," Lipids, Lipids, 31: S297-300.

Yu, R., et al., (2000) "Production of Eicosapentaenoic Acid by a Recombinant Marine Cyanobacterium, *Synechococcus* sp.," Lipids, 35(10): 1061-1064.

Zank, T.K., et al., (2002) "Cloning and Functional Characterization of an Enzyme Involved in the Elongation of Δ6-Polyunsaturated Fatty Acids From the Moss *Physcomitrella patens*," The Plant Journal, 31(3): 255-268.

Zhang, Q., et al., (2004) "Identification and Characterization of a Novel Δ6-Fatty Acid Desaturase Gene From *Rhizopus arrhizus*," Federation of European Biochemical Societies Letters, 556(1-3): 81-85.

Zhou, X. and Christie, P.J., (1997) "Suppression of Mutant Phenotypes of the *Agrobacterium tumefaciens* VirB11 ATPase by Overproduction of VirB Proteins," Journal of Bacteriology, 179(18): 5835-5842.

Sanger Institute. (2003) GenBank Accession No. NM_069350, NCBI, pp. 1-4.

Knutzon et al. (1998) GenBank Accession No. AF067654, NCBI, pp. 1-2.

Hong et al. (2001) GenBank Accession No. AF419297, NCBI, pp. 1-2.

Saito et al. (1999) GenBank Accession No. AB022097, NCBI, pp. 1-2.

Domergue et al. (2002) GenBank Accession No. AY082392, NCBI, pp. 1-2.

Qiu et al. (2003) GenBank Accession No. AF489588, NCBI, pp. 1-2.

Kajikawa et al. (2004) GenBank Accession No. AY583465, NCBI, pp. 1-2.

GenBank Accession No. NM_013402, NCBI, pp. 1-6.

GenBank Accession No. NM_019699, NCBI, pp. 1-3.

Swinburne et al. (1998) GenBank Accession No. Z70271, NCBI, pp. 1-11.

Sayanova et al. (1996) GenBank Accession No. U79010, NCBI, pp. 1-2.

Maroto et al. (2001) GenBank Accession No. AY055117, NCBI, pp. 1-2.

Maroto et al. (2001) GenBank Accession No. AY055118, NCBI, pp. 1-2.

Sayanova et al. (2003) GenBank Accession No. AY234127, NCBI, pp. 1-2.

Sayanova et al. (2003) GenBank Accession No. AF536525, NCBI, pp. 1-2.

Sperling et al. (1999) GenBank Accession No. AJ250735, NCBI, pp. 1-2.

Kajikawa et al. (2004) GenBank Accession No. AY583463, NCBI, pp. 1-2.

Knutzon et al. (1998) GenBank Accession No. AF110510, NCBI, pp. 1-2.

Kobayashi et al. (1998) GenBank Accession No. AB020032, NCBI, pp. 1-2.

Qui et al. (2001) GenBank Accession No. AF419296, NCBI, pp. 1-2.

Aki et al. (2000) GenBank Accession No. AB052086, NCBI, pp. 1-2.

Zhang et al. (2003) GenBank Accession No. AY320288, NCBI, pp. 1-2.

Domergue et al. (2002) GenBank Accession No. AY082393, NCBI, pp. 1-2.

Reddy et al. (1993) GenBank Accession No. L11421, NCBI, pp. 1-2.

Hastings et al. (2000) GenBank Accession No. AF309556, NCBI, pp. 1-2.

Wallis et al. (1991) GenBank Accession No. AF139720, NCBI, pp. 1-2.

Libisch et al. (1999) GenBank Accession No. AF133728, NCBI, pp. 1-2.

(2003) GenBank Accession No. NM 069288, NCBI, pp. 1-3.

Zank et al. (2002) GenBank Accession No. AF428243, NCBI, pp. 1-2.

Kajikawa et al. (2004) GenBank Accession No. AY583464, NCBI, pp. 1-2.

Chaung et al. (1999) GenBank Accession No. AF206662, NCBI, pp. 1-2.

Cirpues et al. (2003) GenBank Accession No. AX951565, NCBI, p. 1.

Heinz et al. (2001) GenBank Accession No. AX214454, NCBI, p. 1.

Leonard et al. (2000) GenBank Accession No. AF231981, NCBI, pp. 1-2.

Aki et al. (2001) GenBank Accession No. AB071985, NCBI, pp. 1-2.

Aki et al. (2001) GenBank Accession No. AB071986, NCBI, pp. 1-2.

Tvrdik et al. (1999) GenBank Accession No. AF170907, NCBI, pp. 1-2.

Tvrdik et al. (1999) GenBank Accession No. AF170908, NCBI, pp. 1-2.

Agaba et al. (2004) GenBank Accession No. AF532782, NCBI, pp. 1-2.

Lo et al. (2003) GenBank Accession No. NM_199532, NCBI, pp. 1-2.

Wilkinson et al. (1996) GenBank Accession No. 268749, NCBI, pp. 1-8.

Qi et al. (2001) GenBank Accession No. AX464802, NCBI, pp. 1.

Meyer et al. (2003) GenBank Accession No. AF390174, NCBI, pp. 1-2.

Jan. 15, 2013 Office Action, issued in connection with U.S. Appl. No. 13/448,107.

Apr. 15, 2013 Response, filed in connection with U.S. Appl. No. 13/448,107.

(56) References Cited

OTHER PUBLICATIONS

Dec. 7, 2012 Office Action, issued in connection with U.S. Appl. No. 13/448,107.
Jan. 7, 2013 Response, filed in connection with U.S. Appl. No. 13/448,107.
Mar. 11, 2013 Office Action issued in connection with European Patent Application No. 11155282.4.
May 23, 2013 Response filed in connection with Canadian Patent Application No. 2,563,875.
May 16, 2013 Response filed in connection with European Patent Application No. 05733657.0.

* cited by examiner

Figure 10

SYNTHESIS OF LONG-CHAIN POLYUNSATURATED FATTY ACIDS BY RECOMBINANT CELL

This application is a continuation of U.S. Ser. No. 13/243,747, filed Sep. 23, 2011, a continuation of U.S. Ser. No. 12/661,978, filed Mar. 26, 2010, now U.S. Pat. No. 8,106,226, issued Jan. 31, 2012, a continuation of U.S. Ser. No. 11/112,882, filed Apr. 22, 2005, now U.S. Pat. No. 7,807,849, issued Oct. 5, 2010 which claims the benefit of U.S. Provisional Application Nos. 60/668,705, filed Apr. 5, 2005; 60/613,861, filed Sep. 27, 2004; and 60/564,627, filed Apr. 22, 2004; and claims priority of Australian Provisional Application No. 2005901673, filed Apr. 5, 2005, the content of all of which are hereby incorporated by reference into the subject application.

FIELD OF THE INVENTION

The present invention relates to methods of synthesizing long-chain polyunsaturated fatty acids, especially eicosapentaenoic acid, docosapentaenoic acid and docosahexaenoic acid, in recombinant cells such as yeast or plant cells. Also provided are recombinant cells or plants which produce long-chain polyunsaturated fatty acids. Furthermore, the present invention relates to a group of new enzymes which possess desaturase or elongase activity that can be used in methods of synthesizing long-chain polyunsaturated fatty acids.

BACKGROUND OF THE INVENTION

Omega-3 long-chain polyunsaturated fatty acid(s) (LC-PUFA) are now widely recognized as important compounds for human and animal health. These fatty acids may be obtained from dietary sources or by conversion of linoleic (LA, omega-6) or α-linolenic (ALA, omega-3) fatty acids, both of which are regarded as essential fatty acids in the human diet. While humans and many other vertebrate animals are able to convert LA or ALA, obtained from plant sources, to LC-PUFA, they carry out this conversion at a very low rate. Moreover, most modern societies have imbalanced diets in which at least 90% of polyunsaturated fatty acid(s) (PUFA) consist of omega-6 fatty acids, instead of the 4:1 ratio or less for omega-6:omega-3 fatty acids that is regarded as ideal (Trautwein, 2001). The immediate dietary source of LC-PUFA such as eicosapentaenoic acid (EPA, 20:5) and docosahexaenoic acid (DHA, 22:6) for humans is mostly from fish or fish oil. Health professionals have therefore recommended the regular inclusion of fish containing significant levels of LC-PUFA into the human diet. Increasingly, fish-derived LC-PUFA oils are being incorporated into food products and in infant formula. However, due to a decline in global and national fisheries, alternative sources of these beneficial health-enhancing oils are needed.

Inclusion of omega-3 LC-PUFA such as EPA and DHA in the human diet has been linked with numerous health-related benefits. These include prevention or reduction of coronary heart disease, hypertension, type-2 diabetes, renal disease, rheumatoid arthritis, ulcerative colitis and chronic obstructive pulmonary disease, and aiding brain development and growth (Simopoulos, 2000). More recently, a number of studies have also indicated that omega-3 PUFA may be beneficial in infant nutrition and development and against various mental disorders such as schizophrenia, attention deficit hyperactive disorder and Alzheimer's disease.

Higher plants, in contrast to animals, lack the capacity to synthesise polyunsaturated fatty acids with chain lengths longer than 18 carbons. In particular, crop and horticultural plants along with other angiosperms do not have the enzymes needed to synthesize the longer chain omega-3 fatty acids such as EPA, DPA and DHA that are derived from ALA. An important goal in plant biotechnology is therefore the engineering of crop plants, particularly oilseed crops, that produce substantial quantities of LC-PUFA, thus providing an alternative source of these compounds.

Pathways of LC-PUFA Synthesis

Biosynthesis of LC-PUFA from linoleic and α-linolenic fatty acids in organisms such as microalgae, mosses and fungi may occur by a series of alternating oxygen-dependent desaturations and elongation reactions as shown schematically in FIG. 1. In one pathway (FIG. 1, II), the desaturation reactions are catalysed by Δ6, Δ5, and Δ4 desaturases, each of which adds an additional double bond into the fatty acid carbon chain, while each of a Δ6 and a Δ5 elongase reaction adds a two-carbon unit to lengthen the chain. The conversion of ALA to DHA in these organisms therefore requires three desaturations and two elongations. Genes encoding the enzymes required for the production of DHA in this aerobic pathway have been cloned from various microorganisms and lower plants including microalgae, mosses, fungi. Genes encoding some of the enzymes including one that catalyses the fifth step, the Δ5 elongase, have been isolated from vertebrate animals including mammals (reviewed in Sayanova and Napier, 2004). However, the Δ5 elongase isolated from human cells is not specific for the EPA to DPA reaction, having a wide specificity for fatty acid substrates (Leonard et al., 2002).

Alternative routes have been shown to exist for two sections of the ALA to DHA pathway in some groups of organisms. The conversion of ALA to ETA may be carried out by a combination of a Δ9 elongase and a Δ8 desaturase (the so-called Δ8 desaturation route, see FIG. 1, IV) in certain protists and thraustochytrids, as evidenced by the isolated of genes encoding such enzymes (Wallis and Browse, 1999; Qi et al., 2002). In mammals, the so-called "Sprecher" pathway converts DPA to DHA by three reactions, independent of a Δ4 desaturase (Sprecher et al., 1995).

Besides these desaturase/elongase systems, EPA and DHA can also be synthesized through an anaerobic pathway in a number of organisms such as *Shewanella*, *Mortiella* and *Schizhochytrium* (Abbadi et al., 2001). The operons encoding these polyketide synthase (PKS) enzyme complexes have been cloned from some bacteria (Morita et al., 2000; Metz et al., 2001; Tanaka et al. 1999; Yazawa, 1996; Yu et al., 2000; WO 00/42195). The EPA PKS operon isolated from *Shewanella* spp has been expressed in *Synechococcus* allowing it to synthesize EPA (Takeyama et al., 1997). The genes encoding these enzymes are arranged in relatively large operons, and their expression in transgenic plants has not been reported. Therefore it remains to be seen if the anaerobic PKS-like system is a possible alternative to the more classic aerobic desaturase/elongase for the transgenic synthesis of LC-PUFA.

Desaturases

The desaturase enzymes that have been shown to participate in LC-PUFA biosynthesis all belong to the group of so-called "front-end" desaturases which are characterised by the presence of a cytochrome $b_5$ domain at the N-terminus of each protein. The cyt $b_5$ domain presumably acts as a receptor of electrons required for desaturation (Napier et al., 1999; Sperling and Heinz, 2001).

The enzyme Δ5 desaturase catalyses the further desaturation of C20 LC-PUFA leading to arachidonic acid (ARA, 20:40ω6) and EPA (20:5ω3). Genes encoding this enzyme have been isolated from a number of organisms, including algae (*Thraustochytrium* sp. Qiu et al., 2001), fungi (*M. alpine, Pythium irregulare*, Michaelson et al., 1998; Hong et al., 2002), *Caenorhabditis elegans* and mammals. A gene encoding a bifunctional Δ5-/Δ6-desaturase has also been identified from zebrafish (Hasting et al., 2001). The gene encoding this enzyme might represent an ancestral form of the "front-end desaturase" which later duplicated and evolved distinct functions. The last desaturation step to produce DHA is catalysed by a Δ4 desaturase and a gene encoding this enzyme has been isolated from the freshwater protist species *Euglena gracilis* and the marine species *Thraustochytrium* sp. (Qiu et al., 2001; Meyer et al., 2003).

Elongases

Several genes encoding PUFA-elongation enzymes have also been isolated (Sayanova and Napier, 2004). The members of this gene family were unrelated to the elongase genes present in higher plants, such as FAE1 of *Arabidopsis*, that are involved in the extension of saturated and monounsaturated fatty acids. An example of the latter is erucic acid (22:1) in *Brassicas*. In some protist species, LC-PUFA are synthesized by elongation of linoleic or α-linolenic acid with a C2 unit, before desaturation with Δ8 desaturase (FIG. 1 part IV; "Δ8-desaturation" pathway). Δ6 desaturase and Δ6 elongase activities were not detected in these species. Instead, a Δ9-elongase activity would be expected in such organisms, and in support of this, a C18 Δ9-elongase gene has recently been isolated from *Isochrysis galbana* (Qi et al., 2002).

Engineered Production of LC-PUFA

Transgenic oilseed crops that are engineered to produce major LC-PUFA by the insertion of these genes have been suggested as a sustainable source of nutritionally important fatty acids. However, the requirement for coordinate expression and activity of five new enzymes encoded by genes from possibly diverse sources has made this goal difficult to achieve and the proposal remained speculative until now.

The LC-PUFA oxygen-dependent biosynthetic pathway to form EPA (FIG. 1) has been successfully constituted in yeast by the co-expression of a Δ6-elongase with Δ6- and Δ5 fatty acid desaturases, resulting in small but significant accumulation of ARA and EPA from exogenously supplied linoleic and α-linolenic acids (Beaudoin et al., 2000; Zank et al., 2000). This demonstrated the ability of the genes belonging to the LC-PUFA synthesis pathway to function in heterologous organisms. However, the efficiency of producing EPA was very low. For example, three genes obtained from *C. elegans, Borago officinalis* and *Mortierella alpina* were expressed in yeast (Beaudoin et al., 2000). When the transformed yeast were supplied with 18:2ω-3 (LA) or 18:3ω-3 (ALA), there was slight production of 20:4ω-6 or 20:5ω-3, at conversion efficiencies of 0.65% and 0.3%, respectively. Other workers similarly obtained very low efficiency production of EPA by using genes expressing two desaturases and one elongase in yeast (Domergue et al., 2003a; Zank et al., 2002). There remains, therefore, a need to improve the efficiency of production of EPA in organisms such as yeast, let alone the production of the C22 PUFA which requires the provision of additional enzymatic steps.

Some progress has been made in the quest for introducing the aerobic LC-PUFA biosynthetic pathway into higher plants including oilseed crops (reviewed by Sayanova and Napier, 2004; Drexler et al., 2003; Abbadi et al., 2001). A gene encoding a Δ6-fatty acid desaturase isolated from borage (*Borago officinalis*) was expressed in transgenic tobacco and *Arabidopsis*, resulting in the production of GLA (18:3ω6) and SDA (18:4ω3), the direct precursors for LC-PUFA, in the transgenic plants (Sayanova et al., 1997; 1999). However, this provides only a single, first step.

Domergue et al. (2003a) used a combination of three genes, encoding Δ6- and Δ5 fatty acid desaturases and a Δ6-elongase in both yeast and transgenic linseed. The desaturase genes were obtained from the diatom *Phaeodactylum tricornutum* and the elongase gene from the moss *Physcomitrella patens*. Low elongation yields were obtained for endogenously produced Δ6-fatty acids in yeast cells (i.e. combining the first and second enzymatic steps), and the main C20 PUFA product formed was $20:2^{\Delta 11,14}$, representing an unwanted side reaction. Domergue et al. (2003a) also state, without presenting data, that the combination of the three genes were expressed in transgenic linseed which consequently produced ARA and EPA, but that production was inefficient. They commented that the same problem as had been observed in yeast existed in the seeds of higher plants and that the "bottleneck" needed to be circumvented for production of LC-PUFA in oil seed crops.

WO 2004/071467 (DuPont) reported the expression of various desaturases and elongases in soybean cells but did not show the synthesis of DHA in regenerated plants or in seeds.

Abbadi et al. (2004) described attempts to express combinations of desaturases and elongases in transgenic linseed, but achieved only low levels of synthesis of EPA. Abbadi et al. (2004) indicated that their low levels of EPA production were also due to an unknown "bottleneck".

Qi et al. (2004) achieved synthesis in leaves but did not report results in seeds. This is an important issue as the nature of LC-PUFA synthesis can vary between leaves and seeds. In particular, oilseeds store lipid in seeds mostly as TAG while leaves synthesize the lipid mostly as phosphatidyl lipids. Furthermore, Qi et al. (2004) only produced AA and EPA.

As a result, there is a need for further methods of producing long-chain polyunsaturated, particularly EPA, DPA and DHA, in recombinant cells.

SUMMARY OF THE INVENTION

In a first aspect, the present invention provides a recombinant cell which is capable of synthesising a long chain polyunsaturated fatty acid(s) (LC-PUFA), comprising one or more polynucleotides which encode at least two enzymes each of which is a Δ5/Δ6 bifunctional desaturase, Δ5 desaturase, Δ6 desaturase, Δ5/Δ6 bifunctional elongase, Δ5 elongase, Δ6 elongase, Δ4 desaturase, Δ9 elongase, or Δ8 desaturase, wherein the one or more polynucleotides are operably linked to one or more promoters that are capable of directing expression of said polynucleotides in the cell, wherein said recombinant cell is derived from a cell that is not capable of synthesising said LC-PUFA.

In a second aspect, the present invention provides a recombinant cell with an enhanced capacity to synthesize a LC-PUFA relative to an isogenic non-recombinant cell, comprising one or more polynucleotides which encode at least two enzymes each of which is a Δ5/Δ6 bifunctional desaturase, Δ5 desaturase, 46 desaturase, Δ5/Δ6 bifunctional elongase, Δ5 elongase, Δ6 elongase, Δ4 desaturase, Δ9 elongase, or Δ8 desaturase, wherein the one or more polynucleotides are operably linked to one or more promoters that are capable of expressing said polynucleotides in said recombinant cell.

In one embodiment, at least one of the enzymes is a Δ5 elongase.

The present inventors are the first to identify an enzyme which has greater Δ5 elongase activity than Δ6 elongase activity. As a result, this enzyme provides an efficient means of producing DPA in a recombinant cell as the Δ5 elongation of EPA is favoured over the Δ6 elongation of SDA. Thus, in an embodiment, the Δ5 elongase is relatively specific, that is, where the Δ5 elongase also has Δ6 elongase activity the elongase is more efficient at synthesizing DPA from EPA than it is at synthesizing ETA from SDA.

In another embodiment, the Δ5 elongase comprises i) an amino acid sequence as provided in SEQ ID NO:2, ii) an amino acid sequence which is at least 50%, more preferably at least 80%, even more preferably at least 90%, identical to SEQ ID NO:2, or iii) a biologically active fragment of i) or ii).

In another embodiment, the Δ5 elongase can be purified from algae.

In another embodiment, at least one of the enzymes is a Δ9 elongase.

The present inventors are the first to identify an enzyme which has both Δ9 elongase activity and Δ6 elongase activity. When expressed in a cell with a Δ6 desaturase and a Δ8 desaturase this enzyme can use the two available pathways to produce ETA from ALA. DGLA from LA, or both (see FIG. 1), thus increasing the efficiency of ETA and/or DGLA production. Thus, in an embodiment, the Δ9 elongase also has Δ6 elongase activity. Preferably, the Δ9 elongase is more efficient at synthesizing ETrA from ALA than it is at synthesizing ETA from SDA. Furthermore, in another embodiment the Δ9 elongase is able to elongate SDA to ETA, GLA to DGLA, or both, in a yeast cell.

In a further embodiment, the Δ9 elongase comprises i) an amino acid sequence as provided in SEQ ID NO:3, SEQ ID NO:85 or SEQ ID NO:86, ii) an amino acid sequence which is at least 50%, more preferably at least 80%, even more preferably at least 90%, identical to SEQ ID NO:3, SEQ ID NO:85 or SEQ ID NO:86, or iii) a biologically active fragment of i) or ii).

Preferably, the Δ9 elongase can be purified from algae or fungi.

It is well known in the art that the greater the number of transgenes in an organism, the greater the likelihood that at least one fitness parameter of the organism, such as expression level of at least one of the transgenes, growth rate, oil production, reproductive capacity etc, will be compromised. Accordingly, it is desirable to minimize the number of transgenes in a recombinant cell. To this end, the present inventors have devised numerous strategies for producing LC-PUFA's in a cell which avoid the need for a gene to each step in the relevant pathway.

Thus, in another embodiment, at least one of the enzymes is a Δ5/Δ6 bifunctional desaturase or a Δ5/Δ6 bifunctional elongase. The Δ5/Δ6 bifunctional desaturase may be naturally produced by a freshwater species of fish.

In a particular embodiment, the Δ5/Δ6 bifunctional desaturase comprises i) an amino acid sequence as provided in SEQ ID NO:15, ii) an amino acid sequence which is at least 50%, more preferably at least 80%, even more preferably at least 90%, identical to SEQ ID NO:15, or iii) a biologically active fragment of i) or ii).

Preferably, the Δ5/Δ6 bifunctional desaturase is naturally produced by a freshwater species of fish.

Preferably, the Δ5/Δ6 bifunctional elongase comprises i) an amino acid sequence as provided in SEQ ID NO:2 or SEQ ID NO:14, ii) an amino acid sequence which is at least 50%, more preferably at least 80%, even more preferably at least 90%, identical to SEQ ID NO:2 or SEQ ID NO:14, or iii) a biologically active fragment of i) or ii).

In another embodiment, at least one of the enzymes is a Δ5 desaturase.

In a further embodiment, at least one of the enzymes is a Δ8 desaturase.

In another embodiment, the LC-PUFA is docosahexaenoic acid (DHA).

Preferably, the introduced polynucleotide(s) encode three or four enzymes each of which is a Δ5/Δ6 bifunctional desaturase, Δ5 desaturase, Δ6 desaturase, Δ5/Δ6 bifunctional elongase, Δ5 elongase, Δ6 elongase, or Δ4 desaturase. More preferably, the enzymes are any one of the following combinations;

i) a Δ5/Δ6 bifunctional desaturase, a Δ5/Δ6 bifunctional elongase, and a Δ4 desaturase, ii) a Δ5/Δ6 bifunctional desaturase, a Δ5 elongase, a Δ6 elongase, and a Δ4 desaturase, or iii) a Δ5 desaturase, a Δ6 desaturase, a Δ5/Δ6 bifunctional elongase, and a Δ4 desaturase.

In another embodiment, the LC-PUFA is DHA and the introduced polynucleotide(s) encode five enzymes wherein the enzymes are any one of the following combinations;

i) a Δ4 desaturase, a Δ5 desaturase, a Δ6 desaturase, a Δ5 elongase and a Δ6 elongase, or ii) a Δ4 desaturase, a Δ5 desaturase, a Δ8 desaturase, a Δ5 elongase and a Δ9 elongase.

In a further embodiment, the cell is of an organism suitable for fermentation, and the enzymes are at least a Δ5/Δ6 bifunctional desaturase, a Δ5 elongase, a Δ6 elongase, and a Δ4 desaturase.

In another embodiment, the LC-PUFA is docosapentaenoic acid (DPA). Preferably, the introduced polynucleotide(s) encode two or three enzymes each of which is a Δ5/Δ6 bifunctional desaturase, Δ5 desaturase, Δ6 desaturase, Δ5/Δ6 bifunctional elongase. Δ5 elongase, or Δ6 elongase. More preferably, the enzymes are any one of the following combinations;

i) a Δ5/Δ6 bifunctional desaturase and a Δ5/Δ6 bifunctional elongase, ii) a Δ5/Δ6 bifunctional desaturase, a Δ5/Δ6 elongase, and a Δ6 elongase, or iii) a Δ5 desaturase, a Δ6 desaturase, and a Δ5/Δ6 bifunctional elongase.

In a further embodiment, the LC-PUFA is DPA and the introduced polynucleotide(s) encode four enzymes wherein the enzymes are any one of the following combinations:

i) a Δ5 desaturase, a Δ6 desaturase, a Δ5 elongase and a Δ6 elongase, or ii) a Δ5 desaturase, a Δ8 desaturase, a Δ5 elongase and a Δ9 elongase.

In another embodiment, the cell is of an organism suitable for fermentation, and the enzymes are at least a Δ5/Δ6 bifunctional desaturase, a Δ5 elongase, and a Δ6 elongase.

In a further embodiment, the LC-PUFA is eicosapentaenoic acid (EPA).

Preferably, the introduced polynucleotide(s) encode a Δ5/Δ6 bifunctional desaturase and a Δ5/Δ6 bifunctional elongase.

In another embodiment, the introduced polynucleotide(s) encode three enzymes wherein the enzymes are any one of the following combinations;

i) a Δ5 desaturase, a Δ6 desaturase, and a Δ6 elongase, or ii) a Δ5 desaturase, a Δ8 desaturase, and a Δ9 elongase.

Evidence to date suggests that desaturases expressed in at least some recombinant cells, particularly yeast, have relatively low activity. However, the present inventors have identified that this may be a function of the capacity of the desaturase to use acyl-CoA as a substrate in LC-PUFA synthesis. In this regard, it has also been determined that desaturase of vertebrate origin are particularly useful for the production of LC-PUFA in recombinant cells, for example, plant cells, seeds, or yeast. Thus, in another preferred embodiment, the recombinant cell comprises either i) at least one Δ5 elongase catalyses the conversion of EPA to DPA in the cell, ii) at least one desaturase which is able to act on an acyl-CoA substrate, iii) at least one desaturase from a vertebrate or a variant desaturase thereof, or iv) any combination of i), ii) or iii).

In a particular embodiment, the Δ5 elongase comprises i) an amino acid sequence as provided in SEQ ID NO:2, ii) an amino acid sequence which is at least 50% identical to SEQ ID NO:2, or iii) a biologically active fragment of i) or ii).

The desaturase able to act on an acyl-CoA substrate or from a vertebrate may be a Δ5 desaturase, a Δ6 desaturase, or both. In a particular embodiment, the desaturase comprises i) an amino acid sequence as provided in SEQ ID NO:16, SEQ ID NO:21 or SEQ ID NO:22, ii) an amino acid sequence which is at least 50% identical to SEQ ID NO:16, SEQ ID NO:21 or SEQ ID NO:22, or iii) a biologically active fragment of i) or ii).

Preferably, the at least one desaturase is naturally produced by a vertebrate.

Alternatively, when the cell is a yeast cell, the LC-PUFA is DHA, and the enzymes are at least a Δ5/Δ6 bifunctional desaturase, a Δ5 elongase, a Δ6 elongase, and a Δ4 desaturase.

In a further alternative, when the cell is a yeast cell, the LC-PUFA is DPA, and the enzymes are at least a Δ5/Δ6 bifunctional desaturase, a Δ5 elongase, and a Δ6 elongase.

Although the cell may be any cell type, preferably, said cell is capable of producing said LC-PUFA from endogenously produced linoleic acid (LA), α-linolenic acid (ALA), or both. More preferably, the ratio of the endogenously produced ALA to LA is at least 1:1 or at least 2:1.

In one embodiment, the cell is a plant cell, a plant cell from an angiosperm, an oilseed plant cell, or a cell in a seed. Preferably, at least one promoter is a seed specific promoter.

In another embodiment, the cell is of a unicellular microorganism. Preferably, the unicellular microorganism is suitable for fermentation. Preferably, the microorganism is a yeast.

In a further embodiment, the cell is a non-human animal cell or a human cell in vitro.

In a further embodiment, the recombinant cell produces a LC-PUFA which is incorporated into triacylglycerols in said cell. More preferably, at least 50% of the LC-PUFA that is produced in said cell is incorporated into triacylglycerols.

In another embodiment, at least the protein coding region of one, two or more of the polynucleotides is obtained from an algal gene. Preferably, the algal gene is from the genus *Pavlova* such as from the species *Pavlova salina*.

In another aspect, the present invention provides a recombinant cell that is capable of producing DHA from a fatty acid which is ALA, LA, GLA, ARA, SDA, ETA, EPA, or any combination or mixture of these, wherein said recombinant cell is derived from a cell that is not capable of synthesising DHA.

In a further aspect, the present invention provides a recombinant cell that is capable of producing DPA from a fatty acid which is ALA, LA, GLA, ARA, SDA, ETA, EPA, or any combination or mixture of these, wherein said recombinant cell is derived from a cell that is not capable of synthesising DPA.

In yet a further aspect, the present invention provides a recombinant cell that is capable of producing EPA from a fatty acid which is ALA, LA, GLA, SDA, ETA or any combination or mixture of these, wherein said recombinant cell is derived from a cell that is not capable of synthesising EPA.

In another aspect, the present invention provides a recombinant cell that is capable of producing both ETrA from ALA and ETA from SDA, and which produces EPA from a fatty acid which is ALA, LA, GLA, SDA, ETA, or any combination or mixture of these, wherein said recombinant cell is derived from a cell that is not capable of synthesising ETrA, ETA or both.

In a further aspect, the present invention provides a recombinant cell of an organism useful in fermentation processes, wherein the cell is capable of producing DPA from LA. ALA, arachidonic acid (ARA), eicosatetraenoic acid (ETA), or any combination or mixture of these, wherein said recombinant cell is derived from a cell that is not capable of synthesising DPA.

In another aspect, the present invention provides a recombinant plant cell capable of producing DPA from LA, ALA, EPA, or any combination or mixture of these, wherein the plant cell is from an angiosperm.

In an embodiment, the plant cell is also capable of producing DHA.

In yet another aspect, the present invention provides a recombinant cell which is capable of synthesising DGLA, comprising a polynucleotide(s) encoding one or both of:

a) a polypeptide which is an Δ9 elongase, wherein the Δ9 elongase is selected from the group consisting of:

i) a polypeptide comprising an amino acid sequence as provided in SEQ ID NO:3, SEQ ID NO:85 or SEQ ID NO:86, ii) a polypeptide comprising an amino acid sequence which is at least 40% identical to SEQ ID NO:3, SEQ ID NO:85 or SEQ ID NO:86, and iii) a biologically active fragment of i) or ii), and/or b) a polypeptide which is an Δ8 desaturase, wherein the Δ8 desaturase is selected from the group consisting of:

i) a polypeptide comprising an amino acid sequence as provided in SEQ ID NO:1, ii) a polypeptide comprising an amino acid sequence which is at least 40% identical to SEQ ID NO:1, and iii) a biologically active fragment of i) or ii), wherein the polynucleotide(s) is operably linked to one or more promoters that are capable of directing expression of said polynucleotide(s) in the cell, and wherein said recombinant cell is derived from a cell that is not capable of synthesising DGLA.

In an embodiment, the cell is capable of converting DGLA to ARA.

In another embodiment, the cell further comprises a polynucleotide which encodes a Δ5 desaturase, wherein the polynucleotide encoding the Δ5 desaturase is operably linked to one or more promoters that are capable of directing expression of said polynucleotide in the cell, and wherein the cell is capable of producing ARA.

In a particular embodiment, the cell lacks ω3 desaturase activity and is not capable of producing ALA. Such cells may be naturally occurring, or produced by reducing the ω3 desaturase activity of the cell using techniques well known in the art.

Preferably, the cell is a plant cell or a cell of an organism suitable for fermentation.

In a further embodiment, a recombinant cell of the invention also possesses the enzyme required to perform the "Sprecher" pathway of converting EPA to DHA. These enzymes may be native to the cell or produced recombinantly. Such enzymes at least include a Δ7 elongase, Δ6 desaturase and enzymes required for the peroxisomal β-oxidation of tetracosahexaenoic acid to produce DHA.

The present inventors have also identified a group of new desaturases and elongases. As a result, further aspects of the invention relate to these enzymes, as well as homologs/variants/derivatives thereof.

The polypeptide may be a fusion protein further comprising at least one other polypeptide sequence.

The at least one other polypeptide may be a polypeptide that enhances the stability of a polypeptide of the present invention, or a polypeptide that assists in the purification of the fusion protein.

Also provided are isolated polynucleotides which, inter alia, encode polypeptides of the invention.

In a further aspect, the present invention provides a vector comprising or encoding a polynucleotide according to the invention. Preferably, the polynucleotide is operably linked to a seed specific promoter.

In another aspect, the present invention provides a recombinant cell comprising an isolated polynucleotide according to the invention.

In a further aspect, the present invention provides a method of producing a cell capable of synthesising one or more LC-PUFA, the method comprising introducing into the cell one or more polynucleotides which encode at least two enzymes each of which is a Δ5/Δ6 bifunctional desaturase, Δ5 desaturase, Δ6 desaturase, Δ5/Δ6 bifunctional elongase, Δ5 elongase, Δ6 elongase, Δ4 desaturase, Δ9 elongase, or Δ8 desaturase, wherein the one or more polynucleotides are operably linked to one or more promoters that are capable of directing expression of said polynucleotides in the cell.

In another aspect, the present invention provides a method of producing a recombinant cell with an enhanced capacity to synthesize one or more LC-PUFA, the method comprising introducing into a first cell one or more polynucleotides which encode at least two enzymes each of which is a Δ5/Δ6 bifunctional desaturase, Δ5 desaturase, Δ6 desaturase, Δ5/Δ6 bifunctional elongase, Δ5 elongase, Δ6 elongase, Δ4 desaturase, Δ9 elongase, or Δ8 desaturase, wherein the one or more polynucleotides are operably linked to one or more promoters that are capable of directing expression of said polynucleotides in the recombinant cell, and wherein said recombinant cell has an enhanced capacity to synthesize said one or more LC-PUFA relative to said first cell.

Naturally, it will be appreciated that each of the embodiments described herein in relation to the recombinant cells of the invention will equally apply to methods for the production of said cells.

In a further aspect, the present invention provides a cell produced by a method of the invention.

In another aspect, the present invention provides a transgenic plant comprising at least one recombinant cell according to the invention.

Preferably, the plant is an angiosperm. More preferably, the plant is an oilseed plant.

In a further embodiment, the transgenic plant, or part thereof including a transgenic seed, does not comprise a transgene which encodes an enzyme which preferentially converts an ω6 LC-PUFA into an ω3 LC-PUFA.

In yet a further embodiment, the transgenic plant, or part thereof including a transgenic seed, comprises a transgene encoding a Δ8 desaturase and/or a Δ9 elongase.

In a further aspect, the present invention provides a method of producing an oilseed, the method comprising
i) growing a transgenic oilseed plant according to the invention under suitable conditions, and
ii) harvesting the seed of the plant.

In a further aspect, the invention provides a part of the transgenic plant of the invention, wherein said part comprises an increased level of LC-PUFA in its fatty acid relative to the corresponding part from an isogenic non-transformed plant.

Preferably, said plant part is selected from, but not limited to, the group consisting of: a seed, leaf, stem, flower, pollen, roots or specialised storage organ (such as a tuber).

Previously, it has not been shown that LC-PUFA can be produced in plant seeds, nor that these LC-PUFA can be incorporated into plant oils such as triacylglycerol.

Thus, in another aspect the present invention provides a transgenic seed comprising a LC-PUFA.

Preferably, the LC-PUFA is selected from the group consisting of:
i) EPA,
ii) DPA,
iii) DHA,
iv) EPA and DPA, and
v) EPA. DHA, and DPA.

More preferably, the LC-PUFA is selected from the group consisting of:
i) DPA,
ii) DHA, or
iii) DHA and DPA.

Even more preferably, the LC-PUFA is EPA, DHA, and DPA.

Preferably, the seed is derived from an isogenic non-transgenic seed which produces LA and/or ALA. More preferably, the isogenic non-transgenic seed comprises a higher concentration of ALA than LA in its fatty acids. Even more preferably, the isogenic non-transgenic seed comprises at least about 13% ALA or at least about 27% ALA or at least about 50% ALA in its fatty acid.

Preferably, the total fatty acid in the oil of the seed comprises at least 9% C20 fatty acids.

Preferably, the seed is derived from an oilseed plant. More preferably, the oilseed plant is oilseed rape (*Brassica napus*), maize (*Zea mays*), sunflower (*Helianthus annuus*), soybean (*Glycine max*), sorghum (*Sorghum bicolor*), flax (*Linum usitatissimum*), sugar (*Saccharum officinarum*), beet (*Beta vulgaris*), cotton (*Gossypium hirsutum*), peanut (*Arachis hypogaea*), poppy (*Papaver somniferum*), mustard (*Sinapis alba*), castor bean (*Ricinus communis*), sesame (*Sesamum indicum*), or safflower (*Carthamus tinctorius*).

It is preferred that the seed has a germination rate which is substantially the same as that of the isogenic non-transgenic seed.

It is further preferred that the timing of germination of the seed is substantially the same as that of the isogenic non-transgenic seed.

Preferably, at least 25%, or at least 50%, or at least 75% of the LC-PUFA in the seed form part of triacylglycerols.

Surprisingly, the present inventors have found that transgenic seeds produced using the methods of the invention have levels of ALA and LA which are substantially the same as those of an isogenic non-transgenic seed. As a result, it is preferred that the transgenic seed has levels of ALA and LA which are substantially the same as those of an isogenic non-transgenic seed. Furthermore, it was surprising to note that the levels of monounsaturated fatty acids were decreased in transgenic seeds produced using the methods of the invention. Accordingly, in a further preferred embodiment, the transgenic seed has decreased levels of monounsaturated fatty acids when compared to an isogenic non-transgenic seed.

In another aspect, the present invention provides a method of producing a transgenic seed according to the invention, the method comprising i) introducing into a progenitor cell of a seed one or more polynucleotides which encode at least two enzymes each of which is a Δ5/Δ6 bifunctional desaturase, Δ5 desaturase, Δ6 desaturase, Δ5/Δ6 bifunctional elongase, Δ5 elongase, Δ6 elongase, Δ4 desaturase, Δ9 elongase, or Δ8 desaturase, wherein the one or more polynucleotides are operably linked to one or more promoters that are capable of directing expression of said polynucleotides in the cell, thereby producing a recombinant progenitor cell, ii) culturing said recombinant progenitor cell to produce a plant which comprises said transgenic seed, and iii) recovering the seed from the plant so produced.

In yet a further aspect, the present invention provides a method of producing a transgenic seed comprising cultivating a transgenic plant which produces the transgenic seed of the invention, and harvesting said transgenic seed from the plant.

In a further aspect, the invention provides an extract from the transgenic plant of the invention, or a plant part of the invention, or a seed of the invention, wherein said extract comprises an increased level of LC-PUFA in its fatty acid relative to a corresponding extract from an isogenic non-transformed plant.

Preferably, the extract is substantially purified oil comprising at least 50% triacylglycerols.

In a further aspect, the present invention provides a non-human transgenic animal comprising at least one recombinant cell according to the invention.

Also provided is a method of producing a LC-PUFA, the method comprising culturing, under suitable conditions, a recombinant cell according to the invention.

In one embodiment, the cell is of an organism suitable for fermentation and the method further comprises exposing the cell to at least one LC-PUFA precursor. Preferably, the LC-PUFA precursor is at least one of linoleic acid or α-linolenic acid. In a particular embodiment, the LC-PUFA precursor is provided in a vegetable oil.

In another embodiment, the cell is an algal cell and the method further comprises growing the algal cell under suitable conditions for production of said LC-PUFA.

In a further aspect, the present invention provides a method of producing one or more LC-PUFA, the method comprising cultivating, under suitable conditions, a transgenic plant of the invention.

In another aspect, the present invention provides a method of producing oil comprising at least one LC-PUFA, comprising obtaining the transgenic plant of the invention, or the plant part of the invention, or the seed of the invention, and extracting oil from said plant, plant part or seed.

Preferably, said oil is extracted from the seed by crushing said seed.

In another aspect, the present invention provides a method of producing DPA from EPA, the method comprising exposing EPA to a polypeptide of the invention and a fatty acid precursor, under suitable conditions.

In an embodiment, the method occurs in a cell which uses the polyketide-like system to produce EPA.

In yet another aspect, the present invention provides a fermentation process comprising the steps of:

i) providing a vessel containing a liquid composition comprising a cell of the invention and constituents required for fermentation and fatty acid biosynthesis; and ii) providing conditions conducive to the fermentation of the liquid composition contained in said vessel.

Preferably, a constituent required for fermentation and fatty acid biosynthesis is LA.

Preferably, the cell is a yeast cell.

In another aspect, the present invention provides a composition comprising a cell of the invention, or an extract or portion thereof comprising LC-PUFA, and a suitable carrier.

In another aspect, the present invention provides a composition comprising the transgenic plant of the invention, or the plant part of the invention, or the seed of the invention, or an extract or portion thereof comprising LC-PUFA, and a suitable carrier.

In yet another aspect, the present invention provides a feedstuff comprising a cell of the invention, a plant of the invention, the plant part of the invention, the seed of the invention, an extract of the invention, the product of the method of the invention, the product of the fermentation process of the invention, or a composition of the invention.

Preferably, the feedstuff at least comprises DPA, wherein at least one enzymatic reaction in the production of DPA was performed by a recombinant enzyme in a cell.

Furthermore, it is preferred that the feedstuff comprises at least comprises DHA, wherein at least one enzymatic reaction in the production of DHA was performed by a recombinant enzyme in a cell.

In a further aspect, the present invention provides a method of preparing a feedstuff, the method comprising admixing a cell of the invention, a plant of the invention, the plant part of the invention, the seed of the invention, an extract of the invention, the product of the method of the invention, the product of the fermentation process of the invention, or a composition of the invention, with a suitable carrier. Preferably, the feedstuff is for consumption by a mammal or a fish.

In a further aspect, the present invention provides a method of increasing the levels of a LC-PUFA in an organism, the method comprising administering to the organism a cell of the invention, a plant of the invention, the plant part of the invention, the seed of the invention, an extract of the invention, the product of the method of the invention, the product of the fermentation process of the invention, or a composition of the invention, or a feedstuff of the invention.

Preferably, the administration route is oral.

Preferably, the organism is a vertebrate. More preferably, the vertebrate is a human, fish, companion animal or livestock animal.

In a further aspect, the present invention provides a method of treating or preventing a condition which would benefit from a LC-PUFA, the method comprising administering to a subject a cell of the invention, a plant of the invention, the plant part of the invention, the seed of the invention, an extract of the invention, the product of the method of the invention, the product of the fermentation process of the invention, or a composition of the invention, or a feedstuff of the invention.

Preferably, the condition is arrhythmia's, angioplasty, inflammation, asthma, psoriasis, osteoporosis, kidney stones. AIDS, multiple sclerosis, rheumatoid arthritis, Crohn's disease, schizophrenia, cancer, foetal alcohol syndrome, attention deficient hyperactivity disorder, cystic fibrosis, phenylketonuria, unipolar depression, aggressive hostility, adrenoleukodystophy, coronary heart disease, hypertension, diabetes, obesity. Alzheimer's disease, chronic obstructive pulmonary disease, ulcerative colitis, restenosis after angioplasty, eczema, high blood pressure, platelet aggregation, gastrointestinal bleeding, endometriosis, premenstrual syndrome, myalgic encephalomyelitis, chronic fatigue after viral infections or ocular disease.

Whilst providing the subject with any amount of LC-PUFA will be beneficial to the subject, it is preferred that an effective amount to treat the condition is administered.

In another aspect, the present invention provides for the use of a cell of the invention, a plant of the invention, the plant part of the invention, the seed of the invention, an extract of the invention, the product of the method of the invention, the product of the fermentation process of the invention, or a composition of the invention, or a feedstuff of the invention, for the manufacture of a medicament for treating or preventing a condition which would benefit from a LC-PUFA.

The *Caenorhabditis elegans* Δ6 elongase has previously been expressed in yeast and been shown to convert octadecatetraenoic acid to eicosatetraenoic acid. However, the present inventors have surprisingly found that this enzyme also possesses Δ5 elongase activity, being able to convert eicosapentaenoic acid to docosapentaenoic acid.

In a further aspect, the present invention provides a method of producing an unbranched LC-PUFA comprising 22 carbon atoms, the method comprising incubating an unbranched 20 carbon atom LC-PUFA with a polypeptide selected from the group consisting of:

i) a polypeptide comprising an amino acid sequence as provided in SEQ ID NO:2 or SEQ ID NO:14, ii) a polypeptide comprising an amino acid sequence which is at least 50% identical to SEQ ID NO:2 or SEQ ID NO:14, and iii) a biologically active fragment of i) or ii), wherein the polypeptide also has Δ6 elongase activity.

Preferably, the unbranched LC-PUFA comprising 22 carbon atoms is DPA, and the unbranched 20 carbon atom LC-PUFA is EPA.

Preferably, the method is performed within a recombinant cell which produces the polypeptide and EPA.

In yet a further aspect, the present invention provides a substantially purified antibody, or fragment thereof, that specifically binds a polypeptide of the invention.

In another aspect, the present invention provides a method of identifying a recombinant cell, tissue or organism capable of synthesising one or more LC-PUFA, the method comprising detecting the presence in said cell, tissue or organism of one or more polynucleotides which encode at least two enzymes each of which is a Δ5/Δ6 bifunctional desaturase, Δ5 desaturase, Δ6 desaturase, Δ5/Δ6 bifunctional elongase, Δ5 elongase, Δ6 elongase, Δ4 desaturase, Δ9 elongase, or Δ8 desaturase, wherein the one or more polynucleotides are operably linked to one or more promoters that are capable of directing expression of said polynucleotides in the cell, tissue or organism.

Preferably, the method comprises a nucleic acid amplification step, a nucleic acid hybridisation step, a step of detecting the presence of a transgene in the cell, tissue or organism, or a step of determining the fatty acid content or composition of the cell, tissue or organism, Preferably, the organism is an animal, plant, angiosperm plant or microorganism.

In another aspect, the present invention provides a method of producing DPA from EPA, the method comprising exposing EPA to a Δ5 elongase of the invention and a fatty acid precursor, under suitable conditions.

Preferably, the method occurs in a cell which uses the polyketide-like system to produce EPA.

Naturally, recombinant (transgenic) cells, plants, non-human animals comprising a new polynucleotide provided herein may also produce other elongase and/or desaturases such as those defined herein.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Possible pathways of ω3 and ω6 LC-PUFA synthesis. The sectors labelled I, II, III, and IV correspond to the ω6 (Δ6), ω3 (Δ6), ω6 (Δ8), and ω3 (Δ) pathways, respectively. Compounds in sectors I and III are ω6 compounds, while those in sectors II and IV are ω3 compounds. "Des" refers to desaturase steps in the pathway catalysed by desaturases as indicated, while "Elo" refers to elongase steps catalysed by elongases as indicated. The thickened arrow indicates the Δ5 elongase step. The dashed arrows indicate the steps in the "Sprecher" pathway that operates in mammalian cells for the production of DHA from DPA.

Figure 2:
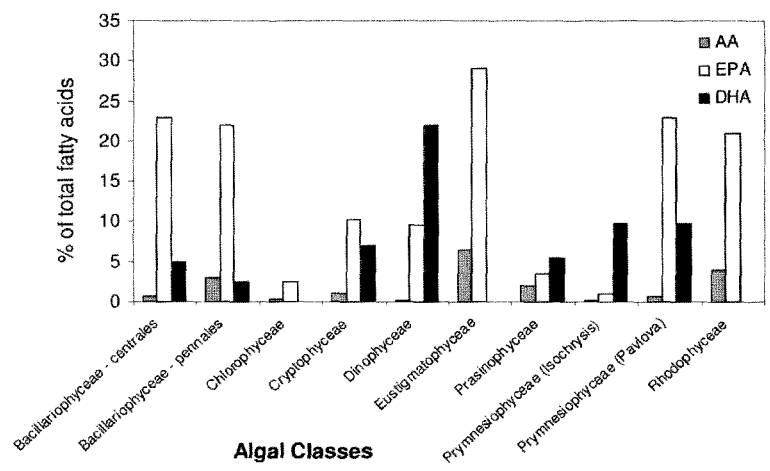

FIG. 2. Distribution of LC-PUFA in microalgal classes. Chlorophyceae and Prasinophyceae are described as "green algae", Eustigmatophyceae as "yellow-green algaae", Rhodophyceae as "red algae", and Bacillariophyceae and Prymnesiophyceae as diatoms and golden brown algae.

Figure 3:
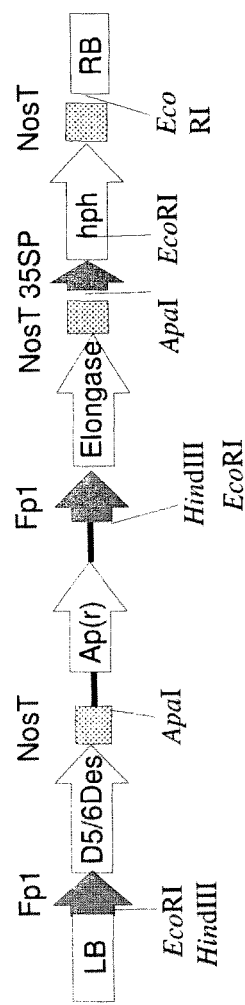

FIG. 3. Genetic construct for expression of LC-PUFA biosynthesis genes in plant cells.

Figure 4:
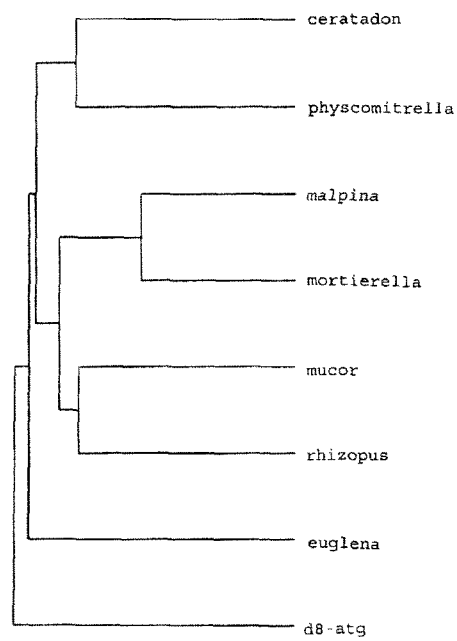

FIG. 4. PILEUP of desaturase enzymes. d8-atg—*Pavlova salina* Δ8 desaturase; euglena—AAD45877 (Δ8 desaturase, *Euglena gracilis*); rhizopus—AAP83964 (Δ6 desaturase, *Rhizopus* sp. NK030037); mucor—BAB69055 (Δ6 desaturase, *Mucor circinelloides*); mortierella—AAL73948 (Δ6 desaturase, *Mortierella isabellina*); malpina—BAA85588 (Δ6 desaturase, *Mortierella alpina*); physcomitrella—CAA11032 (Δ6 acyl-lipid desaturase, *Physcomitrella patens*); ceratadon—CAB94992 (Δ6 fatty acid acetylenase, *Ceratodon purpureus*).

Figure 5:
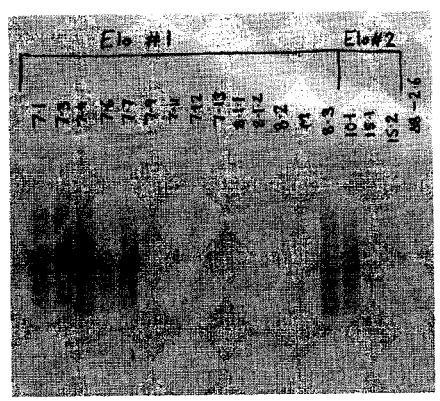

FIG. 5. Southern blot of PCR products, hybridized to Elo1 or Elo2 probes.

Figure 6:
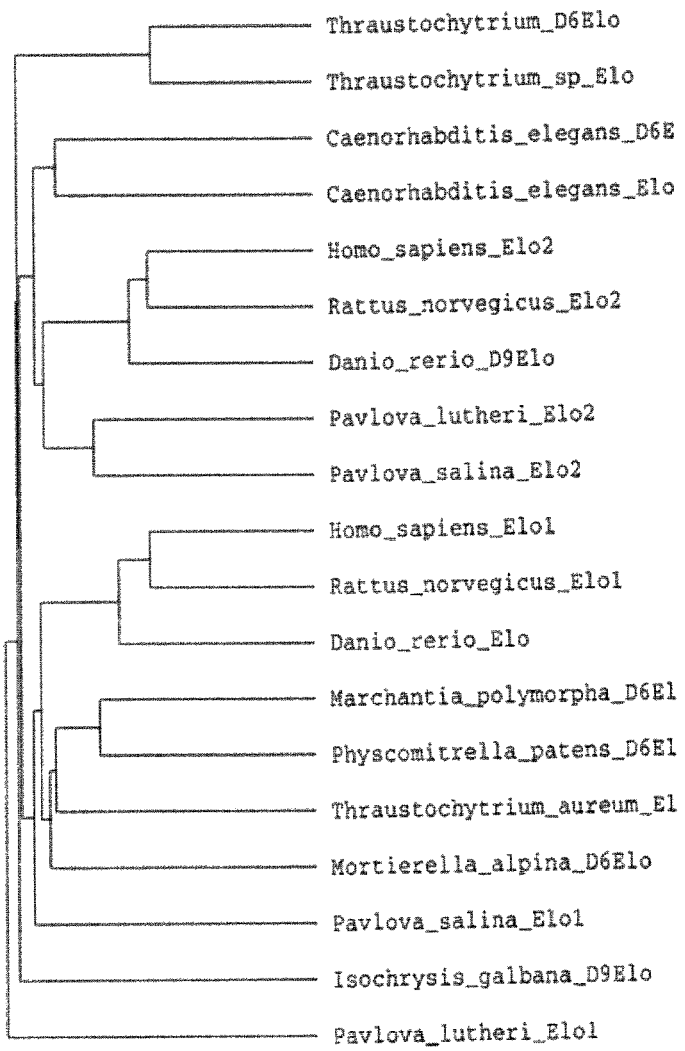

FIG. 6. PILEUP of elongase enzymes.

Figure 7A:
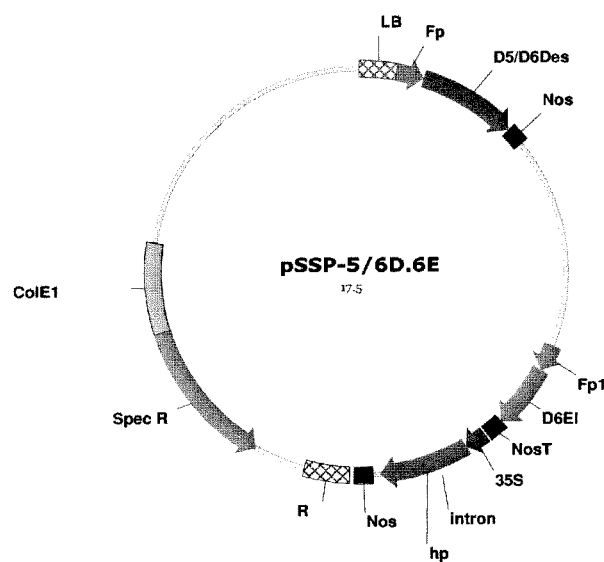
Figure 7B:
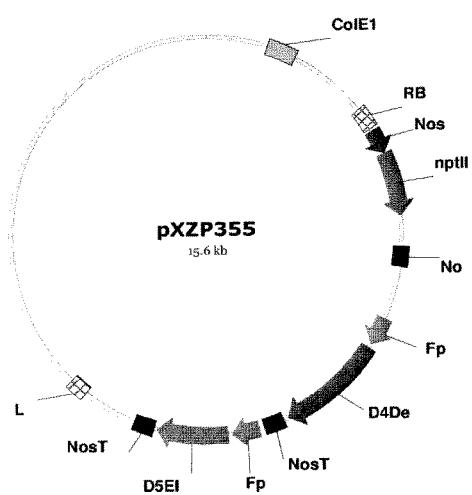

FIG. 7. Transgene constructs used to express genes encoding LC-PUFA biosynthetic enzymes in *Arabidopsis*. The "EPA construct" pSSP-5/6D.6E (also called pZebdesatCeloPWvec8 in Example 5) (FIG. 7A) contained the zebra-fish dual function Δ5/Δ6-desaturase (D5/D6Des) and the nematode Δ6-elongase (D6Elo) both driven by the truncated napin promoter (Fp1), and the hygromycin resistance selectable marker gene (hph) driven by the CaMV-35S (35SP) promoter. The "DHA construct" pXZP355 (FIG. 7B) comprised the *Pavlova salina* Δ4-desaturase (D4Des) and Δ5-elongase (D5Elo) genes both driven by the truncated napin promoter (Fp1), and the kanamycin resistance selectable marker gene (nptII) driven by the nopaline synthase promoter (NosP). All genes were flanked at the 3' end by the nopaline synthase terminator (NosT).

Figure 8:
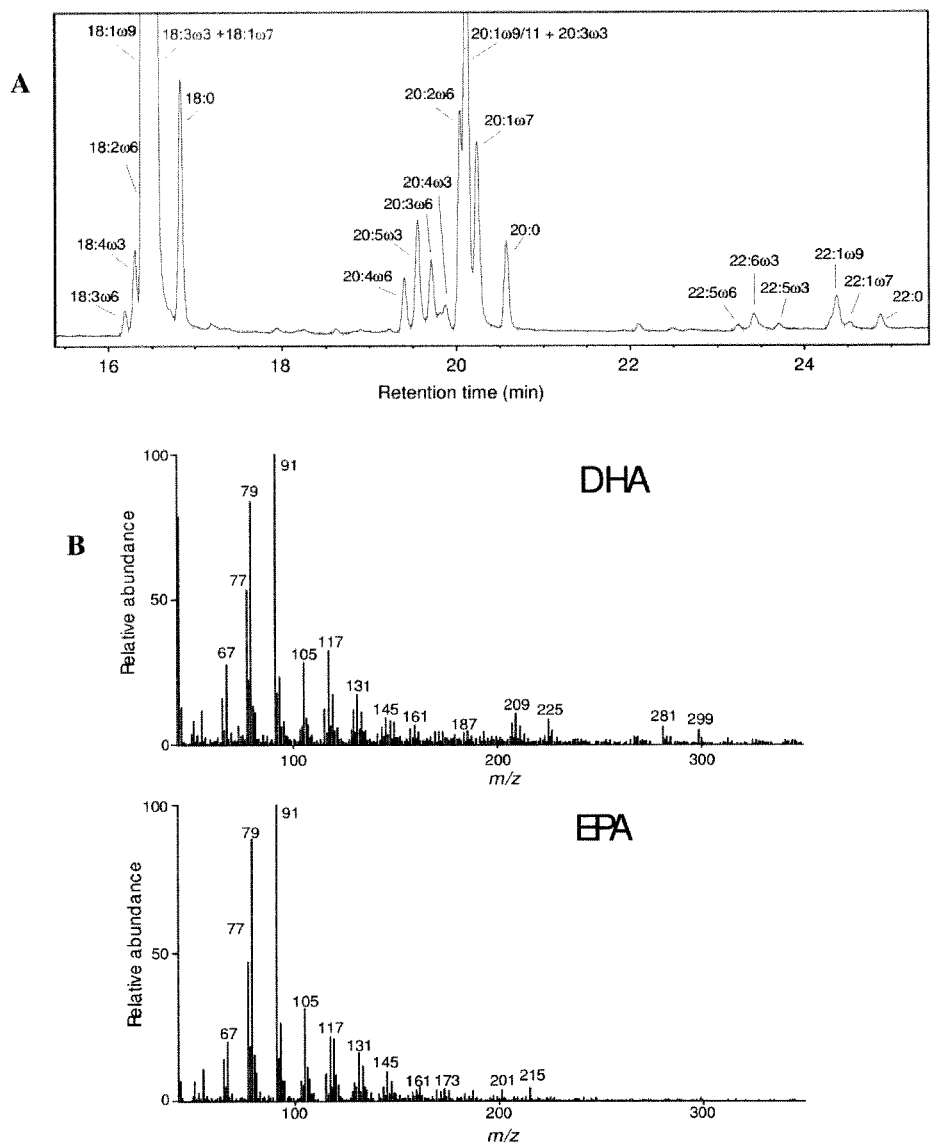

FIG. 8. A. Gas chromatogram (GLC) showing fatty acid profile for *Arabidopsis thaliana* line DO11 carrying EPA and DHA gene constructs. B. Mass spectra for EPA and DHA obtained from *Arabidopsis thaliana* line DO11.

Figure 9:
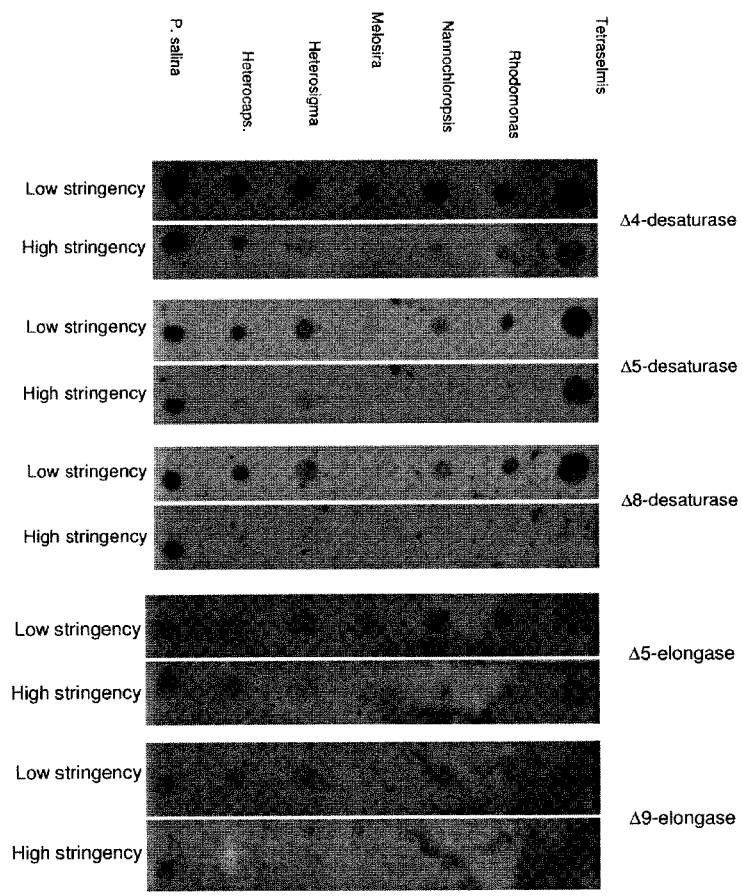

FIG. 9. Autoradiograms of dot-blot hybridisations carried out under low stringency or high stringency conditions, as described in Example 12, to DNA from various microalgal species indicated at the top, using radiolabelled probes consisting of *P. salina* LC-PUFA gene coding regions as indicated on the right.

Figure 10:
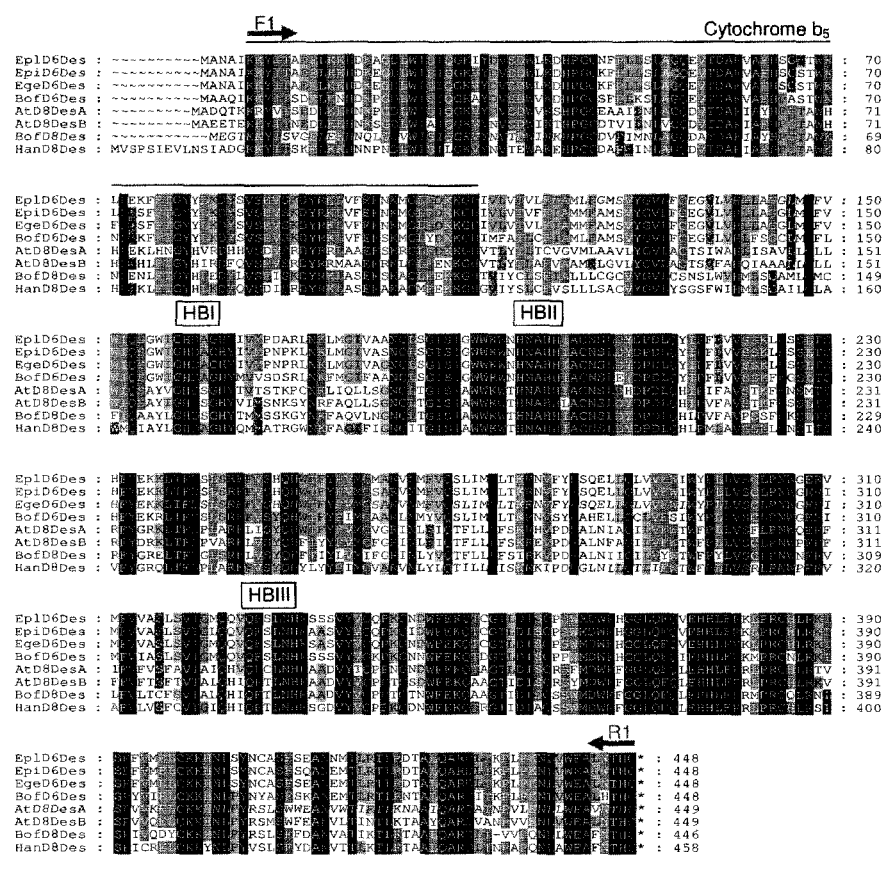

FIG. 10. Amino acid sequence alignment of Δ6- and Δ8-desaturases from higher plants. The amino acid sequences of Δ6-desaturases from *E. plantagineum* (EplD6Des) (SEQ ID NO:64), *E. gentianoides* (EgeD6Des, accession number AY055117) (SEQ ID NO:65), *E. pitardii* (EpiD6Des, AY055118) (SEQ ID NO:66), *Borago officinalis* (BofD6Des, U79010) (SEQ ID NO:67) and Δ8-desaturases from *B. officinalis* (BofD8Des, AF133728) (SEQ ID NO:68), *Helianthus annus* (HanD8Des, S68358) (SEQ ID NO:69), and *Arabidopsis thaliana* (AtD8DesA. AAC62885.1; and AtD8DesB, CAB71088.1) (SEQ ID NO:70 and SEQ ID NO:71 respectively) were aligned by PILEUP (GCG, Wisconsin, USA). HBI, HBII, HBIII are three conserved histidine boxes. F1 and R1 are the corresponding regions for the degenerate primers EpD6Des-F1 and EpD6Des-R1 used to amplify the cDNA. Them-terminal cytochrome $b_5$ domain with conserved HPGG motif is also indicated.

Figure 11:
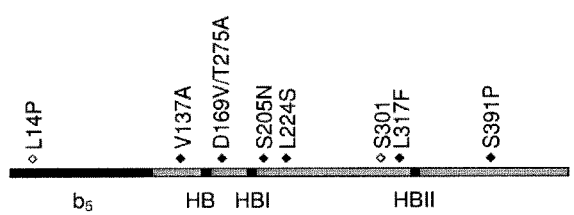
Figure 11:
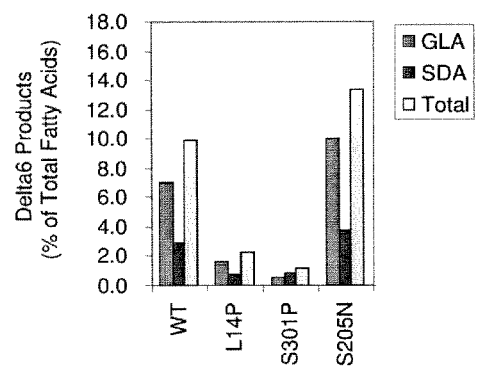

FIG. 11. Variant EplD6Des enzymes isolated and representative enzyme activities. EplD6Des with cytochrome b5, histidine boxes I, II, and III are shown as b5, HBI, HBII, HBIII respectively. Variants isolated are shown in panel A in the format: wild-type amino acid—position number—variant amino acid. Empty diamonds indicate mutants with significant reduction of enzyme activity, while solid diamonds indicate the variants with no significant effect on enzyme activity. Panel B shows the comparison of GLA and SDA production in transgenic tobacco leaves from two variants with that of wild-type enzyme.

Figure 12:
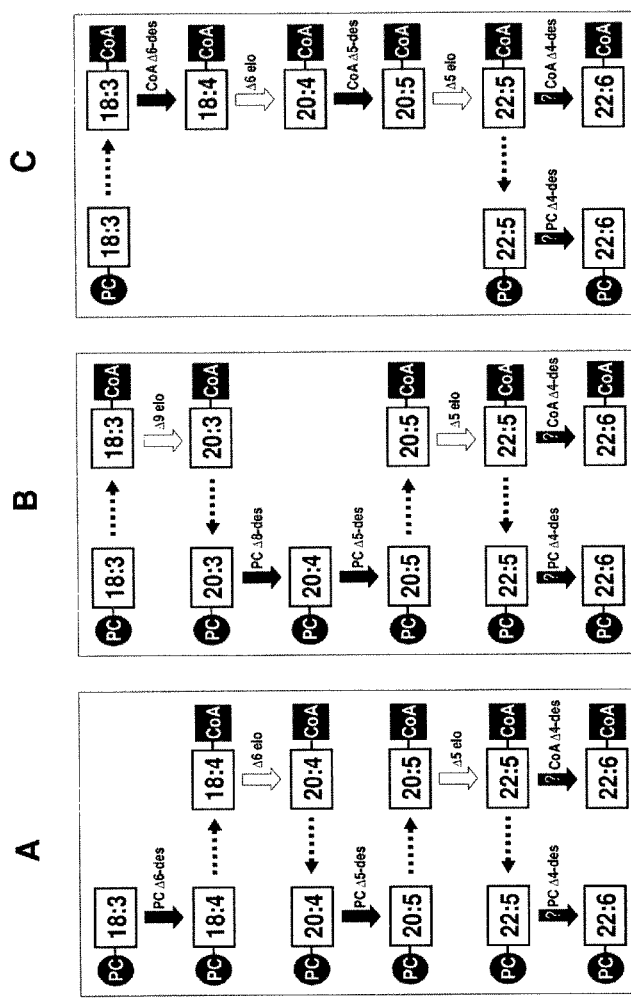

FIG. 12. Alternative pathways for synthesis of the ω3 LC-PUFA SDA (18:4), EPA (20:5) and DHA (22:6) from ALA (18:3). Desaturases, elongases and acyltransferases are shown as solid, open and dashed arrows respectively. Chain elongation occurs only on acyl-CoA substrates, whereas desaturation can occur on either acyl-PC [A&B] or acyl-CoA substrates [C]. The acyl-PC or acyl-CoA substrate preference of the final Δ4-desaturase step has not yet been determined. Pathways involving acyl-PC desaturases require acyltransferase-mediated shuttling of acyl groups between the PC and CoA substrates. Panels A and B show the "Δ6 pathway" and "Δ8 pathway" variants of the acyl-PC desaturase pathway respectively. Panel C shows the pathway expressed in the current study in which the acyl-CoA Δ6 and Δ5 desaturase activities were encoded by the zebra-fish Δ6/Δ5 dual-function desaturase. Synthesis of ω6 LC-PUFA such as ARA (20:4) occurs by the same set of reactions but commencing with LA (18:2) as the initial substrate.

Figure 13:
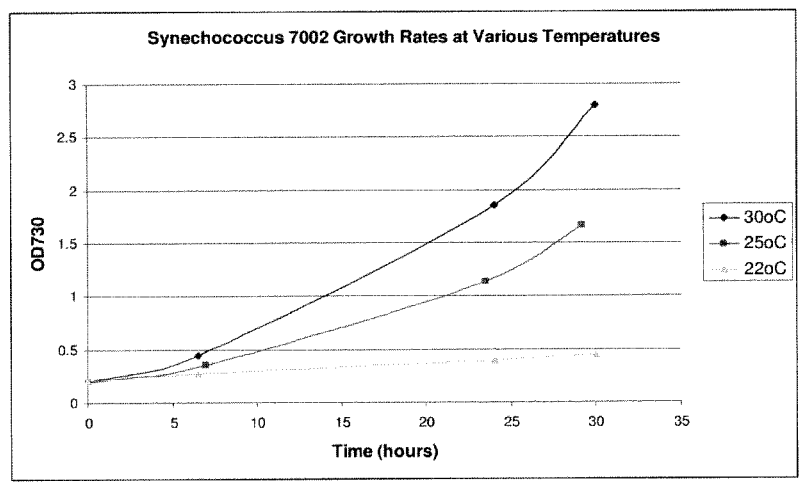

FIG. 13. Growth rates of *Synechococcus* 7002 at 22° C., 25° C., 30° C.

Figure 14:
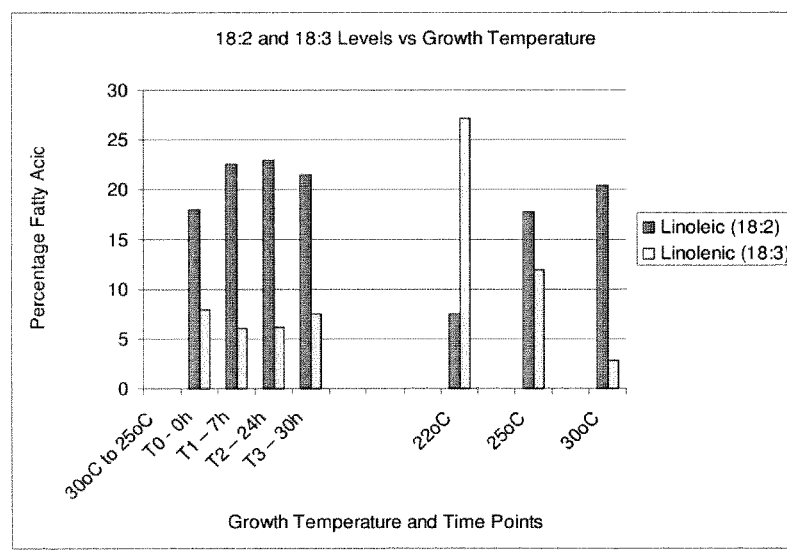

FIG. 14. *Synechococcus* 7002 linoleic and linolenic acid levels at various growth temperatures.

KEY TO THE SEQUENCE LISTING

SEQ ID NO:1—Δ8 desaturase from *Pavlova salina*.
SEQ ID NO:2—Δ5 elongase from *Pavlova salina*.
SEQ ID NO:3—Δ9 elongase from *Pavlova salina*.
SEQ ID NO:4—Δ4 desaturase from *Pavlova salina*.
SEQ ID NO:5—cDNA encoding open reading frame of Δ8 desaturase from *Pavlova salina*.
SEQ ID NO:6—Full length cDNA encoding of Δ8 desaturase from *Pavlova salina*.
SEQ ID NO:7—cDNA encoding open reading frame of Δ5 elongase from *Pavlova salina*.
SEQ ID NO:8—Full length cDNA encoding of Δ5 elongase from *Pavlova salina*.
SEQ ID NO:9—cDNA encoding open reading frame of Δ9 elongase from *Pavlova salina*.
SEQ ID NO:10—Full length cDNA encoding of Δ9 elongase from *Pavlova salina*.
SEQ ID NO:11—Partial cDNA encoding N-terminal portion of Δ4 desaturase from *Pavlova salina*.
SEQ ID NO:12—cDNA encoding open reading frame of Δ4 desaturase from *Pavlova salina*.
SEQ ID NO:13—Full length cDNA encoding Δ4 desaturase from *Pavlova salina*.
SEQ ID NO:14—Δ5/Δ6 bifunctional elongase from *Caenorhabditis elegans*.
SEQ ID NO:15—Δ5/Δ6 bifunctional desaturase from *Danio rerio* (zebrafish).
SEQ ID NO: 16—Δ5 desaturase from humans (Genbank Accession No: AAF29378),
SEQ ID NO:17—Δ5 desaturase from *Pythium irregulare* (Genbank Accession No: AAL13311).
SEQ ID NO:18—Δ5 desaturase from *Thraustochytrium* sp. (Genbank Accession No: AAM09687).
SEQ ID NO:19—Δ5 desaturase from *Mortierella alpina* (Genbank Accession No: O74212).
SEQ ID NO:20—Δ5 desaturase from *Caenorhabditis elegans* (Genbank Accession No: T43319).
SEQ ID NO:21—Δ6 desaturase from humans (Genbank Accession No: AAD20018).
SEQ ID NO:22—Δ6 desaturase from mouse (Genbank Accession No: NP_062673).
SEQ ID NO:23—Δ6 desaturase from *Pythium irregulare* (Genbank Accession No: AAL13310).
SEQ ID NO:24—Δ6 desaturase from *Borago officinalis* (Genbank Accession No: AAD01410).
SEQ ID NO:25—Δ6 desaturase from *Anemone leveillei* (Genbank Accession No: AAQ10731),
SEQ ID NO:26—Δ6 desaturase from *Ceratodon purpureus* (Genbank Accession No: CAB94993).
SEQ ID NO:27—Δ6 desaturase from *Physcomitrella patens* (Genbank Accession No: CAA11033).
SEQ ID NO:28—Δ6 desaturase from *Mortierella alpina* (Genbank Accession No: BAC82361).
SEQ ID NO:29—Δ6 desaturase from *Caenorhabditis elegans* (Genbank Accession No: AAC15586).
SEQ ID NO:30—Δ5 elongase from humans (Genbank Accession No: NP_068586).
SEQ ID NO:31—Δ6 elongase from *Physcomitrella patens* (Genbank Accession No: AAL84174).
SEQ ID NO:32—Δ6 elongase from *Mortierella alpina* (Genbank Accession No: AAF70417).
SEQ ID NO:33—Δ4 desaturase from *Thraustochytrium* sp. (Genbank Accession No: AAM09688).
SEQ ID NO:34—Δ4 desaturase from *Euglena gracilis* (Genbank Accession No: AAQ19605).
SEQ ID NO:35—Δ9 elongase from *Isochrysis galbana* (Genbank Accession No: AAL37626).
SEQ ID NO:36—Δ8 desaturase from *Euglena gracilis* (Genbank Accession No: AAD45877).
SEQ ID NO:37—cDNA encoding Δ5/Δ6 bifunctional elongase from *Caenorhabditis elegans*.

SEQ ID NO:38—cDNA encoding Δ5/Δ6 bifunctional desaturase from *Danio rerio* (zebrafish).

SEQ ID NO's:39 to 42, 46, 47, 50, 51, 53, 54, 56, 57, 81, 82, 83, 84 and 87—Oligonucleotide primers.

SEQ ID NO's:43 to 45, 48, 49 and 52—Conserved motifs of various desaturases/elongases.

SEQ ID NO:55—Partial cDNA encoding *Pavlova salina* FAE-like elongase.

SEQ ID NO:58—Full length cDNA encoding Δ5 desaturase from *Pavlova salina*.

SEQ ID NO:59—cDNA encoding open reading frame of Δ5 desaturase from *Pavlova salina*.

SEQ ID NO:60—Δ5 desaturase from *Pavlova salina*.

SEQ ID NO's 61 and 62—Fragments of *Echium pitardii* Δ6 desaturase.

SEQ ID NO:63—cDNA encoding open reading frame of Δ6 desaturase from *Echium plantagineum*.

SEQ ID NO:64—Δ6 desaturase from *Echium plantagineum*.

SEQ ID NO:65—Δ6 desaturase from *Echium gentianoides* (Genbank Accession No: AY055117).

SEQ ID NO:66—Δ6 desaturase from *Echium pitardii* (Genbank Accession No: AY055118).

SEQ ID NO:67—Δ6 desaturase from *Borago officinalis* (Genbank Accession No: U79010).

SEQ ID NO:68—Δ8 desaturase from *Borago officinalis* (Genbank Accession No: AF133728).

SEQ ID NO:69—Δ8 desaturase from *Helianthus annus* (Genbank Accession No: S68358).

SEQ ID NO:70—Δ8 desaturaseA from *Arabiposis thaliana* (Genbank Accession No: AAC62885.1).

SEQ ID NO:71—Δ8 desaturaseB from *Arabiposis thaliana* (Genbank Accession No: CAB71088.1).

SEQ ID NO:72 and 73—Conserved motifs of Δ6- and Δ8-desaturases.

SEQ ID NO:74—Δ6 elongase from *Thraustochytrium* sp. (Genbank Accession No: AX951565).

SEQ ID NO:75—Δ9 elongase from *Danio rerio* (Genbank Accession No: NM_199532).

SEQ ID NO:76—Δ9 elongase from *Pavlova lutheri*.

SEQ ID NO:77—Δ5 elongase from *Danio rerio* (Genbank Accession No: AF532782).

SEQ ID NO:78—Δ5 elongase from *Pavlova lutheri*.

SEQ ID NO:79—Partial gene sequence from *Heterocapsa niei* encoding an elongase.

SEQ ID NO:80—Protein encoded by SEQ ID NO:79, presence of stop codon suggests an intron in SEQ ID NO:79.

SEQ ID NO:85—Δ9 elongase from *Pavlova salina*, encoded by alternate start codon at position 31 of SEQ ID NO:9.

SEQ ID NO:86—Δ9 elongase from *Pavlova salina*, encoded by alternate start codon at position 85 of SEQ ID NO:9.

SEQ ID NO:88—Partial elongase amino acid sequence from *Melosira* sp.

SEQ ID NO:89—cDNA sequence encoding partial elongase from *Melosira* sp.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, plant biology, molecular genetics, immunology, immunohistochemistry, protein chemistry, fatty acid synthesis, and biochemistry).

Unless otherwise indicated, the recombinant nucleic acid, recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the terms "long-chain polyunsaturated fatty acid", "LC-PUFA" or "C20+ polyunsaturated fatty acid" refer to a fatty acid which comprises at least 20 carbon atoms in its carbon chain and at least three carbon-carbon double bonds. As used herein, the term "very long-chain polyunsaturated fatty acid", "VLC-PUFA" or "C22+ polyunsaturated fatty acid" refers to a fatty acid which comprises at least 22 carbon atoms in its carbon chain and at least three carbon-carbon double bonds. Ordinarily, the number of carbon atoms in the carbon chain of the fatty acids refers to an unbranched carbon chain. If the carbon chain is branched, the number of carbon atoms excludes those in sidegroups. In one embodiment, the long-chain polyunsaturated fatty acid is an ω3 fatty acid, that is, having a desaturation (carbon-carbon double bond) in the third carbon-carbon bond from the methyl end of the fatty acid. In another embodiment, the long-chain polyunsaturated fatty acid is an ω6 fatty acid, that is, having a desaturation (carbon-carbon double bond) in the sixth carbon-carbon bond from the methyl end of the fatty acid. In a further embodiment, the long-chain polyunsaturated fatty acid is selected from the group consisting of; arachidonic acid (ARA, 20:4Δ5,8,11,14; ω6), eicosatetraenoic acid (ETA, 20:4Δ8,11,14,17, ω3) eicosapentaenoic acid (EPA, 20:5Δ5,8,11,14,17; ω3), docosapentaenoic acid (DPA, 22:5Δ7,10,13,16,19, ω3), or docosahexaenoic acid (DHA, 22:6Δ4,7,10,13,16,19, ω3). The LC-PUFA may also be dihomo-γ-linoleic acid (DGLA) or eicosatrienoic acid (ETrA, 20:3Δ11,14,17, ω3). It would readily be apparent that the LC-PUFA that is produced according to the invention may be a mixture of any or all of the above and may include other LC-PUFA or derivatives of any of these LC-PUFA. In a preferred embodiment, the ω3 fatty acid is EPA, DPA, or DHA, or even more preferably DPA or DHA.

Furthermore, as used herein the terms "long-chain polyunsaturated fatty acid" or "very long-chain polyunsaturated fatty acid" refer to the fatty acid being in a free state (non-esterified) or in an esterified form such as part of a triglyceride, diacylglyceride, monoacylglyceride, acyl-CoA bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms. Thus, the LC-PUFA may be present as a mixture of forms in the lipid of a cell or a purified oil or lipid extracted from cells, tissues or organisms. In preferred embodiments, the invention provides oil comprising at least 75% or 85% triacylglycerols, with the remainder present as other forms of lipid such as those mentioned, with at least said triacylglycerols comprising the LC-PUFA. The oil may be further purified or treated, for example by hydrolysis with a strong base to release the free fatty acid, or by fractionation, distillation or the like.

As used herein, the abbreviations "LC-PUFA" and "VLC-PUFA" can refer to a single type of fatty acid, or to multiple types of fatty acids. For example, a transgenic plant of the invention which produces LC-PUFA may produce EPA, DPA and DHA.

The desaturase and elongase proteins and genes encoding them that may be used in the invention are any of those known in the art or homologues or derivatives thereof. Examples of such genes and the encoded protein sizes are listed in Table 1. The desaturase enzymes that have been shown to participate in LC-PUFA biosynthesis all belong to the group of so-called "front-end" desaturases which are characterised by the presence of a cytochrome $b_5$-like domain at the N-terminus of each protein. The

TABLE 1

Cloned genes involved in LC-PUFA biosynthesis.

| Enzyme | Type of organism | Species | Accession Nos. | Protein size (aa's) | References |
|---|---|---|---|---|---|
| Δ4-desaturase | Algae | *Euglena gracilis* | AY278558 | 541 | Meyer et al., 2003 |
| | | *Pavlova lutherii* | AY332747 | 445 | Tonon et al., 2003 |
| | | *Thraustochytrium sp.* | AF489589 | 519 | Qiu et al., 2001 |
| | | *Thraustochytrium aureum* | AF391543-5 | 515 | (NCBI) |
| Δ5-desaturase | Mammals | *Homo sapiens* | AF199596 | 444 | Cho et al., 1999b Leonard et al., 2000b |
| | Nematode | *Caenorhabditis elegans* | AF11440, NM_069350 | 447 | Michaelson et al., 1998b; Watts and Browse, 1999b |
| | Fungi | *Mortierella alpina* | AF067654 | 446 | Michaelson et al., 1998a; Knutzon et al., 1998 |
| | | *Pythium irregulare* | AF419297 | 456 | Hong et al., 2002a |
| | | *Dictyostelium discoideum* | AB022097 | 467 | Saito et al., 2000 |
| | | *Saprolegnia diclina* | | 470 | WO02081668 |
| | Diatom | *Phaeodactylum tricornutum* | AY082392 | 469 | Domergue et al., 2002 |
| | Algae | *Thraustochytrium sp* | AF489588 | 439 | Qiu et al., 2001 |
| | | *Thraustochytrium aureum* | | 439 | WO02081668 |
| | | *Isochrysis galbana* | | 442 | WO02081668 |
| | Moss | *Marchantia polymorpha* | AY583465 | 484 | Kajikawa et al., 2004 |
| Δ6-desaturase | Mammals | *Homo sapiens* | NM_013402 | 444 | Cho et al., 1999a; Leonard et al., 2000 |
| | | *Mus musculus* | NM_019699 | 444 | Cho et al., 1999a |
| | Nematode | *Caenorhabditis elegans* | Z70271 | 443 | Napier et al., 1998 |
| | Plants | *Borago officinales* | U79010 | 448 | Sayanova et al., 1997 |
| | | *Echium* | AY055117 AY055118 | | Garcia-Maroto et al., 2002 |
| | | *Primula vialii* | AY234127 | 453 | Sayanova et al., 2003 |
| | | *Anemone leveillei* | AF536525 | 446 | Whitney et al., 2003 |
| | Mosses | *Ceratodon purpureus* | AJ250735 | 520 | Sperling et al., 2000 |
| | | *Marchantia polymorpha* | AY583463 | 481 | Kajikawa et al., 2004 |
| | | *Physcomitrella patens* | | | Girke et al., 1998 |
| | Fungi | *Mortierella alpina* | AF110510 AB020032 | 457 | Huang et al., 1999; Sakuradani et al., 1999 |
| | | *Pythium irregulare* | AF419296 | 459 | Hong et al., 2002a |
| | | *Mucor circinelloides* | AB052086 | 467 | NCBI* |
| | | *Rhizopus sp.* | AY320288 | 458 | Zhang et al., 2004 |

TABLE 1-continued

Cloned genes involved in LC-PUFA biosynthesis.

| Enzyme | Type of organism | Species | Accession Nos. | Protein size (aa's) | References |
|---|---|---|---|---|---|
| | | Saprolegnia diclina | | 453 | WO02081668 |
| | Diatom | Phaeodactylum tricornutum | AY082393 | 477 | Domergue et al., 2002 |
| | Bacteria | Synechocystis | L11421 | 359 | Reddy et al., 1993 |
| | Algae | Thraustochytrium aureum | | 456 | WO02081668 |
| Bifunctional Δ5/Δ6 desaturase | Fish | Danio rerio | AF309556 | 444 | Hastings et al., 2001 |
| C20 Δ8-desaturase | Algae | Euglena gracilis | AF139720 | 419 | Wallis and Browse, 1999 |
| | Plants | Borago officinales | AF133728 | | |
| Δ6-elongase | Nematode | Caenorhabditis elegans | NM_069288 | 288 | Beaudoin et al., 2000 |
| | Mosses | Physcomitrella patens | AF428243 | 290 | Zank et al., 2002 |
| | | Marchantia polymorpha | AY583464 | 290 | Kajikawa et al., 2004 |
| | Fungi | Mortierella alpina | AF206662 | 318 | Parker-Barnes et al., 2000 |
| | Algae | Pavlova lutheri** | | 501 | WO 03078639 |
| | | Thraustochytrium | AX951565 | 271 | WO 03093482 |
| | | Thraustochytrium sp** | AX214454 | 271 | WO 0159128 |
| PUFA-elongase | Mammals | Homo sapiens | AF231981 | 299 | Leonard et al., 2000b; Leonard et al., 2002 |
| | | Rattus norvegicus | AB071985 | 299 | Inagaki et al., 2002 |
| | | Rattus norvegicus** | AB071986 | 267 | Inagaki et al., 2002 |
| | | Mus musculus | AF170907 | 279 | Tvrdik et al., 2000 |
| | | Mus musculus | AF170908 | 292 | Tvrdik et al., 2000 |
| | Fish | Danio rerio | AF532782 | 291 (282) | Agaba et al., 2004 |
| | | Danio rerio** | NM_199532 | 266 | Lo et al., 2003 |
| | Worm | Caenorhabditis elegans | Z68749 | 309 | Abbott et al 1998 Beaudoin et al 2000 |
| | Algae | Thraustochytrium aureum** | AX464802 | 272 | WO 0208401-A2 |
| | | Pavlova lutheri** | | ? | WO 03078639 |
| Δ9-elongase | Algae | Isochrysis galbana | AF390174 | 263 | Qi et al., 2002 |

*http://www.ncbi.nlm.nih.gov/
**Function not proven/not demonstrated cytochrome $b_5$-like domain presumably acts as a receptor of electrons required for desaturation (Napier et al., 1999; Sperling and Heinz, 2001).

Activity of any of the elongases or desaturases for use in the invention may be tested by expressing a gene encoding the enzyme in a cell such as, for example, a yeast cell or a plant cell, and determining whether the cell has an increased capacity to produce LC-PUFA compared to a comparable cell in which the enzyme is not expressed.

Unless stated to the contrary, embodiments of the present invention which relate to cells, plants, seeds, etc, and methods for the production thereof, and that refer to at least "two enzymes" (or at least "three enzymes" etc) of the list that is provided means that the polynucleotides encode at least two "different" enzymes from the list provided and not two identical (or very similar with only a few differences as to not substantially alter the activity of the encoded enzyme) open reading frames encoding essentially the same enzyme.

As used herein, unless stated to the contrary, the term "substantially the same", or variations thereof, means that two samples being analysed, for example two seeds from different sources, are substantially the same if they only vary about +/−10% in the trait being investigated.

As used herein, the term "an enzyme which preferentially converts an ω6 LC-PUFA into an ω3 LC-PUFA" means that the enzyme is more efficient at performing said conversion than it is at performing a desaturation reaction outlined in pathways II or III of FIG. 1.

Whilst certain enzymes are specifically described herein as "bifunctional", the absence of such a term does not necessarily imply that a particular enzyme does not possess an activity other than that specifically defined.

Desaturases

As used herein, a "Δ5/Δ6 bifunctional desaturase" or "Δ5/Δ6 desaturase" is at least capable of i) converting α-linolenic acid to octadecatetraenoic acid, and ii) converting eicosatetraenoic acid to eicosapentaenoic acid. That is, a Δ5/Δ6 bifunctional desaturase is both a Δ5 desaturase and a Δ6 desaturase, and Δ5/Δ6 bifunctional desaturases may be considered a sub-class of each of these. A gene encoding a bifunctional Δ5-/Δ6-desaturase has been identified from zebrafish (Hasting et al., 2001). The gene encoding this enzyme might represent an ancestral form of the "front-end desaturase" which later duplicated and the copies evolved distinct Δ5- and Δ6-desaturase functions. In one embodiment, the Δ5/Δ6 bifunctional desaturase is naturally produced by a freshwater species of fish. In a particular embodiment, the Δ5/Δ6 bifunctional desaturase comprises i) an amino acid sequence as provided in SEQ ID NO:15,
    ii) an amino acid sequence which is at least 50% identical to SEQ ID NO:15, or
    iii) a biologically active fragment of i) or ii).

As used herein, a "Δ5 desaturase" is at least capable of converting eicosatetraenoic acid to eicosapentaenoic acid. In one embodiment, the enzyme Δ5 desaturase catalyses the desaturation of C20 LC-PUFA, converting DGLA to arachidonic acid (ARA, 20:4ω6) and ETA to EPA (20:5ω3). Genes encoding this enzyme have been isolated from a number of organisms, including algae (*Thraustochytrium* sp. Qiu et al., 2001), fungi (*M. alpine, Pythium irregulare. P. tricornutum, Dictyostelium*), *Caenorhabditis elegans* and mammals (Table 1). In another embodiment, the Δ5 desaturase comprises (i) an amino acid sequence as provided in SEQ ID NO:16, SEQ ID NO:17, SEQ ID NO:18, SEQ ID NO:19, SEQ ID NO:20 or SEQ ID NO:60, (ii) an amino acid sequence which is at least 50% identical to any one of SEQ ID NO:16, SEQ ID NO:17, SEQ ID NO:18, SEQ ID NO:19, SEQ ID NO:20 or SEQ ID NO:60, or (iii) a biologically active fragment of i) or ii). In a further embodiment, the Δ5 desaturase comprises (i) an amino acid sequence as provided in SEQ ID NO:16, SEQ ID NO:17, SEQ ID NO:18, SEQ ID NO:20 or SEQ ID NO:60, (ii) an amino acid sequence which is at least 90% identical to any one of SEQ ID NO:16, SEQ ID NO:17, SEQ ID NO:18, SEQ ID NO:20 or SEQ ID NO:60, or (iii) a biologically active fragment of i) or ii). In a further embodiment, the Δ5 desaturase is encoded by the protein coding region of one of the Δ5 desaturase genes listed in Table 1 or gene substantially identical thereto.

As used herein, a "Δ6 desaturase" is at least capable of converting α-linolenic acid to octadecatetraenoic acid. In one embodiment, the enzyme Δ6 desaturase catalyses the desaturation of C18 LC-PUFA, converting LA to GLA and ALA to SDA. In another embodiment, the Δ6 desaturase comprises (i) an amino acid sequence as provided in SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:64 SEQ ID NO:65, SEQ ID NO:66 or SEQ ID NO:67, (ii) an amino acid sequence which is at least 50% identical to any one of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:64 SEQ ID NO:65, SEQ ID NO:66 or SEQ ID NO:67, or (iii) a biologically active fragment of i) or ii). In a further embodiment, the Δ6 desaturase comprises an amino acid sequence which is at least 90% identical to any one of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:64 SEQ ID NO:65, SEQ ID NO:66 or SEQ ID NO:67. In a further embodiment, the Δ6 desaturase is encoded by the protein coding region of one of the Δ6 desaturase genes listed in Table 1 or gene substantially identical thereto As used herein, a "Δ4 desaturase" is at least capable of converting docosapentaenoic acid to docosahexaenoic acid. The desaturation step to produce DHA from DPA is catalysed by a Δ4 desaturase in organisms other than mammals, and a gene encoding this enzyme has been isolated from the freshwater protist species *Euglena gracilis* and the marine species *Thraustochyrrium* sp. (Qiu et al., 2001; Meyer et al., 2003). In one embodiment, the Δ4 desaturase comprises (i) an amino acid sequence as provided in SEQ ID NO:4, SEQ ID NO:33 or SEQ ID NO:34, (ii) an amino acid sequence which is at least 50% identical to SEQ ID NO:4, SEQ ID NO:33 or SEQ ID NO:34, or (iii) a biologically active fragment of i) or ii). In a further embodiment, the Δ4 desaturase is encoded by the protein coding region of one of the Δ4 desaturase genes listed in Table 1 or gene substantially identical thereto.

As used herein, a "Δ8 desaturase" is at least capable of converting $20:3^{\Delta 11,14,17}\omega 3$ to eicosatetraenoic acid. In one embodiment, the Δ8 desaturase is relatively specific for Δ8 substrates. That is, it has greater activity in desaturating Δ8 substrates than other substrates, in particular Δ6 desaturated substrates. In a preferred embodiment, the Δ8 desaturase has little or no Δ6 desaturase activity when expressed in yeast cells. In another embodiment, the Δ8 desaturase comprises (i) an amino acid sequence as provided in SEQ ID NO:1, SEQ ID NO:36, SEQ ID NO:68, SEQ ID NO:69, SEQ ID NO:70 or SEQ ID NO:71, (ii) an amino acid sequence which is at least 50% identical to SEQ ID NO:1, SEQ ID NO:36, SEQ ID NO:68, SEQ ID NO:69, SEQ ID NO:70 or SEQ ID NO:71, or (iii) a biologically active fragment of i) or ii). In further embodiment, the Δ8 desaturase comprises (i) an amino acid sequence as provided in SEQ ID NO:1, (ii) an amino acid sequence which is at least 90% identical to SEQ ID NO:1, or (iii) a biologically active fragment of i) or ii).

As used herein, an "ω3 desaturase" is at least capable of converting LA to ALA and/or GLA to SDA and/or ARA to EPA. Examples of ω3 desaturase include those described by Pereira et al. (2004), Horiguchi et al. (1998), Berberich et al. (1998) and Spychalla et al. (1997). In one embodiment, a cell of the invention is a plant cell which lacks ω3 desaturase activity. Such cells can be produced using gene knockout technology well known in the art. These cells can be used to specifically produce large quantities of ω6 LC-PUFA such as DGLA.

Elongases

Biochemical evidence suggests that the fatty acid elongation consists of 4 steps: condensation, reduction, dehydration and a second reduction. In the context of this invention, an "elongase" refers to the polypeptide that catalyses the condensing step in the presence of the other members of the elongation complex, under suitable physiological conditions. It has been shown that heterologous or homologous expression in a cell of only the condensing component ("elongase") of the elongation protein complex is required for the elongation of the respective acyl chain. Thus the introduced elongase is able to successfully recruit the reduction and dehydration activities from the transgenic host to carry out successful acyl elongations. The specificity of the elongation reaction with respect to chain length and the degree of desaturation of fatty acid substrates is thought to reside in the condensing component. This component is also thought to be rate limiting in the elongation reaction.

Two groups of condensing enzymes have been identified so far. The first are involved in the extension of saturated and monounsaturated fatty acids (C18-22) such as, for example, the FAE1 gene of *Arabidopsis*. An example of a product formed is erucic acid (22:1) in *Brassicas*. This group are designated the FAE-like enzymes and do not appear to have a role in LC-PUFA biosynthesis. The other identified class of fatty acid elongases, designated the ELO family of elongases, are named after the ELO genes whose activities are required for the synthesis of the very long-chain fatty acids of sphingolipids in yeast. Apparent paralogs of the ELO-type elongases isolated from LC-PUFA synthesizing organisms like algae, mosses, fungi and nematodes have been shown to be involved in the elongation and synthesis of LC-PUFA. Several genes encoding such PUFA-elongation enzymes have also been isolated (Table 1). Such genes are unrelated in nucleotide or amino acid sequence to the FAE-like elongase genes present in higher plants.

As used herein, a "Δ5/Δ6 bifunctional elongase" or "Δ5/Δ6 elongase" is at least capable of i) converting octadecatetraenoic acid to eicosatetraenoic acid, and ii) converting eicosapentaenoic acid to docosapentaenoic acid. That is, a Δ5/Δ6 bifunctional elongase is both a Δ5 elongase and a Δ6 elongase, and Δ5/Δ6 bifunctional elongases may be considered a sub-class of each of these. In one embodiment, the Δ5/Δ6 bifunctional elongase is able to catalyse the elongation of EPA to form DPA in a plant cell such as, for example, a higher plant cell, when that cell is provided with a source of EPA. The EPA may be provided exogenously or preferably endogenously. A gene encoding such an elongase has been isolated from an invertebrate. $C.$ $elegans$ (Beaudoin et al., 2000) although it was not previously known to catalyse the Δ5-elongation step. In one embodiment, the Δ5/Δ6 bifunctional elongase comprises (i) an amino acid sequence as provided in SEQ ID NO:2 or SEQ ID NO:14, (ii) an amino acid sequence which is at least 50% identical to SEQ ID NO:2 or SEQ ID NO:14, or (iii) a biologically active fragment of i) or ii).

As used herein, a "Δ5 elongase" is at least capable of converting eicosapentaenoic acid to docosapentaenoic acid. In one embodiment, the Δ5 elongase is from a non-vertebrate source such as, for example, an algal or fungal source. Such elongases can have advantages in terms of the specificity of the elongation reactions carried out (for example the Δ5 elongase provided as SEQ ID NO:2). In a preferred embodiment, the Δ5 elongase is relatively specific for C20 substrates over C22 substrates. For example, it may have at least 10-fold lower activity toward C22 substrates (elongated to C24 fatty acids) relative to the activity toward a corresponding C20 substrate when expressed in yeast cells. It is preferred that the activity when using C20 Δ5 desaturated substrates is high, such as for example, providing an efficiency for the conversion of 20:5ω3 into 22:5ω3 of at least 7% when expressed in yeast cells. In another embodiment, the Δ5 elongase is relatively specific for Δ5 desaturated substrates over Δ6 desaturated substrates. For example, it may have at least 10-fold lower activity toward Δ6 desaturated C18 substrates relative to Δ5 desaturated C20 substrates when expressed in yeast cells. In a further embodiment, the Δ5 elongase comprises (i) an amino acid sequence as provided in SEQ ID NO:2, SEQ ID NO:30, SEQ ID NO:77 or SEQ ID NO:78, (ii) an amino acid sequence which is at least 50% identical to SEQ ID NO:2, SEQ ID NO:30, SEQ ID NO:77 or SEQ ID NO:78, or (iii) a biologically active fragment of i) or ii). In another embodiment, the Δ5 elongase comprises (i) an amino acid sequence as provided in SEQ ID NO:2, (ii) an amino acid sequence which is at least 90% identical to SEQ ID NO:2, or (iii) a biologically active fragment of i) or ii). In a further embodiment, the Δ5 elongase is encoded by the protein coding region of one of the Δ5 elongase genes listed in Table 1 or gene substantially identical thereto.

As used herein, a "Δ6 elongase" is at least capable of converting octadecatetraenoic acid to eicosatetraenoic acid. In one embodiment, the Δ6 elongase comprises (i) an amino acid sequence as provided in SEQ ID NO:2, SEQ ID NO:3, SEQ ID NO:31, SEQ ID NO:32, SEQ ID NO:74, SEQ ID NO:85, SEQ ID NO:86 or SEQ ID NO:88, (ii) an amino acid sequence which is at least 50% identical to SEQ ID NO:2, SEQ ID NO:3, SEQ ID NO:31, SEQ ID NO:32, SEQ ID NO:74, SEQ ID NO:85, SEQ ID NO:86 or SEQ ID NO:88, or (iii) a biologically active fragment of i) or ii). In another embodiment, the Δ6 elongase comprises (i) an amino acid sequence as provided in SEQ ID NO:2, SEQ ID NO:3 or SEQ ID NO:32, SEQ ID NO:85, SEQ ID NO:86 or SEQ ID NO:88, (ii) an amino acid sequence which is at least 90% identical to SEQ ID NO:2, SEQ ID NO:3, SEQ ID NO:32, SEQ ID NO:85, SEQ ID NO:86 or SEQ ID NO:88, or (iii) a biologically active fragment of i) or ii). In a further embodiment, the Δ6 elongase is encoded by the protein coding region of one of the Δ6 elongase genes listed in Table 1 or gene substantially identical thereto.

In some protist species, LC-PUFA are synthesized by elongation of linoleic or α-linolenic acid with a C2 unit, before desaturation with Δ8 desaturase (FIG. 1 part IV; "Δ8-desaturation" pathway). Δ6 desaturase and Δ6 elongase activities were not detected in these species. Instead, a Δ9-elongase activity would be expected in such organisms, and in support of this, a C18 Δ9-elongase gene has recently been isolated from $Isochrysis$ $galbana$ (Qi et al., 2002). As used herein, a "Δ9 elongase" is at least capable of converting α-linolenic acid to $20:3^{\Delta 11,14,17}\omega 3$. In one embodiment, the Δ9 elongase comprises (i) an amino acid sequence as provided in SEQ ID NO:3, SEQ ID NO:35, SEQ ID NO:75, SEQ ID NO:76. SEQ ID NO:85 or SEQ ID NO:86, (ii) an amino acid sequence which is at least 50% identical to SEQ ID NO:3, SEQ ID NO:35, SEQ ID NO:75, SEQ ID NO:76, SEQ ID NO:85 or SEQ ID NO:86, or (iii) a biologically active fragment of i) or ii). In another embodiment, the Δ9 elongase comprises (i) an amino acid sequence as provided in SEQ ID NO:3, SEQ ID NO:85 or SEQ ID NO:86, (ii) an amino acid sequence which is at least 90% identical to SEQ ID NO:3, SEQ ID NO:85 or SEQ ID NO:86, or (iii) a biologically active fragment of i) or ii). In a further embodiment, the Δ9 elongase is encoded by the protein coding region of the Δ9 elongase gene listed in Table 1 or gene substantially identical thereto. In another embodiment, the Δ9 elongase also has Δ6 elongase activity. The elongase in this embodiment is able to convert SDA to ETA and/or GLA to DGLA (Δ6 elongase activity) in addition to converting ALA to ETrA (Δ9 elongase). In a preferred embodiment, such an elongase is from an algal or fungal source such as, for example, the genus $Pavlova$.

As used herein, a "Δ4 elongase" is at least capable of converting docosahexaenoic acid to $24:6^{\Delta 6,9,12,15,18,21}\omega 3$.

Cells

Suitable cells of the invention include any cell that can be transformed with a polynucleotide encoding a polypeptide/enzyme described herein, and which is thereby capable of being used for producing LC-PUFA. Host cells into which the polynucleotide(s) are introduced can be either untransformed cells or cells that are already transformed with at least one nucleic acid molecule. Such nucleic acid molecule may related to LC-PUFA synthesis, or unrelated. Host cells of the present invention either can be endogenously (i.e., naturally) capable of producing proteins of the present invention or can be capable of producing such proteins only after being transformed with at least one nucleic acid molecule.

As used herein, the term "cell with an enhanced capacity to synthesize a long chain polyunsaturated fatty acid" is a relative term where the recombinant cell of the invention is compared to the native cell, with the recombinant cell producing more long chain polyunsaturated fatty acids, or a greater concentration of LC-PUFA such as EPA, DPA or DHA (relative to other fatty acids), than the native cell.

The cells may be prokaryotic or eukaryotic. Host cells of the present invention can be any cell capable of producing at least one protein described herein, and include bacterial, fungal (including yeast), parasite, arthropod, animal and plant cells. Preferred host cells are yeast and plant cells. In a preferred embodiment, the plant cells are seed cells.

In one embodiment, the cell is an animal cell or an algal cell. The animal cell may be of any type of animal such as, for example, a non-human animal cell, a non-human vertebrate cell, a non-human mammalian cell, or cells of aquatic animals such as fish or crustacea, invertebrates, insects, etc.

An example of a bacterial cell useful as a host cell of the present invention is *Synechococcus* spp. (also known as *Synechocystis* spp.), for example *Synechococcus elongatus*.

The cells may be of an organism suitable for fermentation. As used herein, the term the "fermentation process" refers to any fermentation process or any process comprising a fermentation step. A fermentation process includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, beta-carotene); and hormones. Fermentation processes also include fermentation processes used in the consumable alcohol industry (e.g., beer and wine), dairy industry (e.g., fermented dairy products), leather industry and tobacco industry. Preferred fermentation processes include alcohol fermentation processes, as are well known in the art. Preferred fermentation processes are anaerobic fermentation processes, as are well known in the art.

Suitable fermenting cells, typically microorganisms are able to ferment, i.e., convert, sugars, such as glucose or maltose, directly or indirectly into the desired fermentation product. Examples of fermenting microorganisms include fungal organisms, such as yeast. As used herein, "yeast" includes *Saccharomyces* spp., *Saccharomyces cerevisiae*, *Saccharomyces carlbergensis*, *Candida* spp., *Kluveromyces* spp., *Pichia* spp., *Hansenula* spp., *Trichoderma* spp., *Lipomyces starkey*, and *Yarrowia lipolytica*. Preferred yeast include strains of the *Saccharomyces* spp., and in particular, *Saccharomyces cerevisiae*. Commercially available yeast include, e.g., Red Star/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Evidence to date suggests that some desaturases expressed heterologously in yeast have relatively low activity in combination with some elongases. However, the present inventors have identified that this may be alleviated by providing a desaturase with the capacity of to use an acyl-CoA form of the fatty acid as a substrate in LC-PUFA synthesis, and this is thought to be advantageous in recombinant cells other than yeast as well. In this regard, it has also been determined that desaturases of vertebrate origin are particularly useful for the production of LC-PUFA. Thus in embodiments of the invention, either (i) at least one of the enzymes is a Δ5 elongase that catalyses the conversion of EPA to DPA in the cell, (ii) at least one of the desaturases is able to act on an acyl-CoA substrate, (iii) at least one desaturase is from vertebrate or is a variant thereof, or (iv) a combination of ii) and iii).

In a particularly preferred embodiment, the host cell is a plant cell, such as those described in further detail herein.

As used herein, a "progenitor cell of a seed" is a cell that divides and/or differentiates into a cell of a transgenic seed of the invention, and/or a cell that divides and/or differentiates into a transgenic plant that produces a transgenic seed of the invention.

Levels of LC-PUFA Produced

The levels of the LC-PUFA that are produced in the recombinant cell are of importance. The levels may be expressed as a composition (in percent) of the total fatty acid that is a particular LC-PUFA or group of related LC-PUFA, for example the ω3 LC-PUFA or the ω6 LC-PUFA, or the C22+ PUFA, or other which may be determined by methods known in the art. The level may also be expressed as a LC-PUFA content, such as for example the percentage of LC-PUFA in the dry weight of material comprising the recombinant cells, for example the percentage of the dry weight of seed that is LC-PUFA. It will be appreciated that the LC-PUFA that is produced in an oilseed may be considerably higher in terms of LC-PUFA content than in a vegetable or a grain that is not grown for oil production, yet both may have similar LC-PUFA compositions, and both may be used as sources of LC-PUFA for human or animal consumption.

The levels of LC-PUFA may be determined by any of the methods known in the art. For example, total lipid may be extracted from the cells, tissues or organisms and the fatty acid converted to methyl esters before analysis by gas chromatography (GC). Such techniques are described in Example 1. The peak position in the chromatogram may be used to identify each particular fatty acid, and the area under each peak integrated to determine the amount. As used herein, unless stated to the contrary, the percentage of particular fatty acid in a sample is determined as the area under the peak for that fatty acid as a percentage of the total area for fatty acids in the chromatogram. This corresponds essentially to a weight percentage (w/w). The identity of fatty acids may be confirmed by GC-MS, as described in Example 1.

In certain embodiments, where the recombinant cell is useful in a fermentation process such as, for example, a yeast cell, the level of EPA that is produced may be at least 0.21% of the total fatty acid in the cell, preferably at least 0.82% or at least 2% and even more preferably at least 5%.

In other embodiments, the total fatty acid of the recombinant cell may comprise at least 1.5% EPA, preferably at least 2.1% EPA, and more preferably at least 2.5%, at least 3.1%, at least 4% or at least 5.1% EPA.

In further embodiments, where the recombinant cell is useful in a fermentation process or is a plant cell and DPA is produced, the total fatty acid in the cell may comprise at least 0.1% DPA, preferably at least 0.13% or at least 0.15% and more preferably at least 0.5% or at least 1% DPA.

In further embodiments, the total fatty acid of the cell may comprise at least 2% C20 LC-PUFA, preferably at least 3% or at least 4% C20 LC-PUFA, more preferably at least 4.7% or at least 7.9% C20 LC-PUFA and most preferably at least 10.2% C20 LC-PUFA.

In further embodiments, the total fatty acid of the cell may comprise at least 2.5% C20 ω3 LC-PUFA, preferably at least 4.1% or more preferably at least 5% C20 ω3 LC-PUFA.

In other embodiments, where both EPA and DPA are synthesized in a cell, the level of EPA reached is at least 1.5%, at least 2.1% or at least 2.5% and the level of DPA at least 0.13%, at least 0.5% or at least 1.0%.

In each of these embodiments, the recombinant cell may be a cell of an organism that is suitable for fermentation such as, for example, a unicellular microorganism which may be a prokaryote or a eukaryote such as yeast, or a plant cell. In a preferred embodiment, the cell is a cell of an angiosperm (higher plant). In a further preferred embodiment, the cell is a cell in a seed such as, for example, an oilseed or a grain or cereal.

The level of production of LC-PUFA in the recombinant cell may also be expressed as a conversion ratio, i.e. the amount of the LC-PUFA formed as a percentage of one or more substrate PUFA or LC-PUFA. With regard to EPA, for example, this may be expressed as the ratio of the level of EPA (as a percentage in the total fatty acid) to the level of a substrate fatty acid (ALA, SDA, ETA or ETrA). In a preferred embodiment, the conversion efficiency is for ALA to EPA. In particular embodiments, the conversion ratio for production of EPA in a recombinant cell may be at least 0.5%, at least 1%, or at least 2%. In another embodiment, the conversion efficiency for ALA to EPA is at least 14.6%. In further embodiments, the conversion ratio for production of DPA from EPA in a recombinant cell is at least 5%, at least 7%, or at least 10%. In other embodiments, the total ω3 fatty acids produced that are products of Δ6 desaturation (i.e. downstream of 18:3ω3 (ALA), calculated as the sum of the percentages for 18:4ω3 (SDA), 20:4ω3 (ETA), 20:5ω3 (EPA) and 22:5ω3 (DPA)) is at least 4.2%. In a particular embodiment, the conversion efficiency of ALA to ω3 products through a Δ6 desaturation step and/or an Δ9 elongation step in a recombinant cell, preferably a plant cell, more preferably a seed cell, is at least 22% or at least 24%. Stated otherwise, in this embodiment the ratio of products derived from ALA to ALA (products:ALA) in the cell is at least 1:3.6.

The content of the LC-PUFA in the recombinant cell may be maximized if the parental cell used for introduction of the genes is chosen such that the level of fatty acid substrate that is produced or provided exogenously is optimal. In particular embodiments, the cell produces ALA endogenously at levels of at least 30%, at least 50%, or at least 66% of the total fatty acid. The level of LC-PUFA may also be maximized by growing or incubating the cells under optimal conditions, for example at a slightly lower temperature than the standard temperature for that cell, which is thought to favour accumulation of polyunsaturated fatty acid.

There are advantages to maximizing production of a desired LC-PUFA while minimizing the extent of side-reactions. In a particular embodiment, there is little or no ETrA detected (less than 0.1%) while the level of EPA is at least 2.1%.

Turning to transgenic plants of the invention, in one embodiment, at least one plant part synthesizes EPA, wherein the total fatty acid of the plant part comprises at least 1.5%, at least 2.1%, or at least 2.5% EPA.

In another embodiment, at least one plant part synthesizes DPA, wherein the total fatty acid of the plant part comprises at least 0.1%, at least 0.13%, or at least 0.5% DPA.

In a further embodiment, at least one plant part synthesizes DHA.

In another embodiment, at least one plant part synthesizes DHA, wherein the total fatty acid of the plant part comprises at least 0.1%, at least 0.2%, or at least 0.5% DHA.

In another embodiment, at least one plant part synthesizes at least one ω3 C20 LC-PUFA, wherein the total fatty acid of the plant part comprises at least 2.5%, or at least 4.1% ω3 C20 LC-PUFA.

In yet another embodiment, at least one plant part synthesizes EPA, wherein the efficiency of conversion of ALA to EPA in the plant part is at least 2% or at least 14.6%.

In a further embodiment, at least one plant part synthesizes ω3 polyunsaturated fatty acids that are the products of Δ6-desaturation of ALA and/or the products of Δ9 elongation of ALA, wherein the efficiency of conversion of ALA to said products in the plant part is at least 22% or at least 24%.

In yet another embodiment, at least one plant part synthesizes DPA from EPA, wherein the efficiency of conversion of EPA to DPA in the plant part is at least 5% or at least 7%.

With regard to transgenic seeds of the invention, in one embodiment EPA is synthesized in the seed and the total fatty acid of the seed comprises at least 1.5%, at least 2.1%, or at least 2.5% EPA.

In another embodiment, DPA is synthesized in the seed and the total fatty acid of the seed comprises at least 0.1%, at least 0.13%, or at least 0.5% DPA.

In a further embodiment, DHA is synthesized in the seed.

In another embodiment, DHA is synthesized in the seed and the total fatty acid of the seed comprises at least 0.1%, at least 0.2%, or at least 0.5% DHA.

In yet a further embodiment, at least one ω3 C20 LC-PUFA is synthesized in the seed and the total fatty acid of the seed comprises at least 2.5%, or at least 4.1% ω3 C20 LC-PUFA.

In a further embodiment. EPA is synthesized in the seed and the efficiency of conversion of ALA to EPA in the seed is at least 2% or at least 14.6%.

In another embodiment, ω3 polyunsaturated fatty acids that are the products of Δ6-desaturation of ALA and/or the products of Δ9 elongation of ALA, are synthesized in the seed, and the efficiency of conversion of ALA to said products in the seed is at least 22% or at least 24%.

In a further embodiment, DPA is synthesized from EPA in the seed and the efficiency of conversion of EPA to DPA in the seed is at least 5% or at least 7%.

Referring to extracts of the invention, in one embodiment, the total fatty acid content of the extract comprises at least 1.5%, at least 2.1%, or at least 2.5% EPA.

In another embodiment, the total fatty acid content of the extract comprises at least 0.1%, at least 0.13%, or at least 0.5% DPA.

In a further embodiment, the extract comprises DHA.

In another embodiment, the total fatty acid content of the extract comprises at east 0.1%, at least 0.2%, or at least 0.5% DHA.

In another embodiment, the total fatty acid content of the extract comprises at least 2.5%, or at least 4.1% ω3 C20 LC-PUFA.

In yet a further embodiment, the extract comprises ARA, EPA, DPA, DHA, or any mixture of these in the triacylglycerols.

With regard to methods of the invention for producing a LC-PUFA, in on embodiment, the cell comprises at least one C20 LC-PUFA, and the total fatty acid of the cell comprises at least 2%, at least 4.7%, or at least 7.9% C20 LC-PUFA.

In another embodiment, the cell comprises at least one ω3 C20 LC-PUFA, and the total fatty acid of the cell comprises at least 2.5%, or at least 4.1% ω3 C20 LC-PUFA.

In a further embodiment, the cell comprises ω3 polyunsaturated fatty acids that are the products of Δ6-desaturation of ALA and/or the products of Δ9 elongation of ALA, and the efficiency of conversion of ALA to said products in the cell is at least 22% or at least 24%.

In yet another embodiment, the cell comprises DPA, and the total fatty acid of the cell comprises at least 0.1%, at least 0.13%, or at least 0.5% DPA.

In a further embodiment, the cell comprises DPA, and the efficiency of conversion of EPA to DPA in the cell is at least 5% or at least 7%.

In another embodiment, the cell comprises EPA, and wherein the total fatty acid of the cell comprises at least 1.5%, at least 2.1%, or at least 2.5% EPA.

In a further embodiment, the cell comprises EPA, and the efficiency of conversion of ALA to EPA in the cell is at least 2% or at least 14.6%.

Polypeptides

In one aspect, the present invention provides a substantially purified polypeptide selected from the group consisting of:
i) a polypeptide comprising an amino acid sequence as provided in SEQ ID NO:1,
ii) a polypeptide comprising an amino acid sequence which is at least 40% identical to SEQ ID NO:1, and
iii) a biologically active fragment of i) or ii),
wherein the polypeptide has Δ8 desaturase activity.

Preferably, the Δ8 desaturase does not also have Δ6 desaturase activity.

In another aspect, the present invention provides a substantially purified polypeptide selected from the group consisting of:
i) a polypeptide comprising an amino acid sequence as provided in SEQ ID NO:2,
ii) a polypeptide comprising an amino acid sequence which is at least 60% identical to SEQ ID NO:2, and
iii) a biologically active fragment of i) or ii),
wherein the polypeptide has Δ5 elongase and/or Δ6 elongase activity.

Preferably, the polypeptide has Δ5 elongase and Δ6 elongase activity, and wherein the polypeptide is more efficient at synthesizing DPA from EPA than it is at synthesizing ETA from SDA. More preferably, the polypeptide can be purified from algae. Furthermore, when expressed in yeast cells, is more efficient at elongating C20 LC-PUFA than C22 LC-PUFA.

In another aspect, the invention provides a substantially purified polypeptide selected from the group consisting of:
i) a polypeptide comprising an amino acid sequence as provided in SEQ ID NO:3, SEQ ID NO:85 or SEQ ID NO:86,
ii) a polypeptide comprising an amino acid sequence which is at least 40% identical to SEQ ID NO:3, SEQ ID NO:85 or SEQ ID NO:86, and
iii) a biologically active fragment of i) or ii),
wherein the polypeptide has Δ9 elongase and/or Δ6 elongase activity.

Preferably, the polypeptide has Δ9 elongase and Δ6 elongase activity. Preferably, the polypeptide is more efficient at synthesizing ETrA from ALA than it is at synthesizing ETA from SDA. Further, it is preferred that the polypeptide can be purified from algae or fungi.

In yet another aspect, the present invention provides a substantially purified polypeptide selected from the group consisting of:
i) a polypeptide comprising an amino acid sequence as provided in SEQ ID NO:4,
ii) a polypeptide comprising an amino acid sequence which is at least 70% identical to SEQ ID NO:4, and
iii) a biologically active fragment of i) or ii),
wherein the polypeptide has Δ4 desaturase activity.

In a further aspect, the present invention provides a substantially purified polypeptide selected from the group consisting of:
i) a polypeptide comprising an amino acid sequence as provided in SEQ ID NO:60,
ii) a polypeptide comprising an amino acid sequence which is at least 55% identical to SEQ ID NO:60, and
iii) a biologically active fragment of i) or ii),
wherein the polypeptide has Δ5 desaturase activity.

In yet another aspect, the present invention provides a substantially purified polypeptide selected from the group consisting of:
i) a polypeptide comprising an amino acid sequence as provided in SEQ ID NO:64,
ii) a polypeptide comprising an amino acid sequence which is at least 90% identical to SEQ ID NO:64, and
iii) a biologically active fragment of i) or ii),
wherein the polypeptide has Δ6 desaturase activity.

In yet another aspect, the present invention provides a substantially purified polypeptide selected from the group consisting of:
i) a polypeptide comprising an amino acid sequence as provided in SEQ ID NO:88,
ii) a polypeptide comprising an amino acid sequence which is at least 76% identical to SEQ ID NO:88, and
iii) a biologically active fragment of i) or ii),
wherein the polypeptide has Δ6 elongase activity.

Preferably, in relation to any one of the above aspects, it is preferred that the polypeptide can be isolated from a species selected from the group consisting of *Pavlova* and *Melosira*.

By "substantially purified polypeptide" we mean a polypeptide that has been at least partially separated from the lipids, nucleic acids, other polypeptides, and other contaminating molecules with which it is associated in its native state. Preferably, the substantially purified polypeptide is at least 60% free, preferably at least 75% free, and most preferably at least 90% free from other components with which they are naturally associated. Furthermore, the term "polypeptide" is used interchangeably herein with the term "protein".

The % identity of a polypeptide is determined by GAP (Needleman and Wunsch, 1970) analysis (GCG program) with a gap creation penalty=5, and a gap extension penalty=0.3. Unless stated otherwise, the query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. Even more preferably, the query sequence is at least 100 amino acids in length and the GAP analysis aligns the two sequences over a region of at least 100 amino acids.

With regard to the defined polypeptides/enzymes, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polypeptides which are substantially identical to those specifically described herein. As used herein, with reference to a polypeptide the term "substantially identical" means the deletion, insertion and/or substitution of one or a few (for example 2, 3, or 4) amino acids whilst maintaining at least one activity of the native protein.

As used herein, the term "biologically active fragment" refers to a portion of the defined polypeptide/enzyme which still maintains desaturase or elongase activity (whichever is relevant). Such biologically active fragments can readily be determined by serial deletions of the full length protein, and testing the activity of the resulting fragment.

Amino acid sequence mutants/variants of the polypeptides/enzymes defined herein can be prepared by introducing appropriate nucleotide changes into a nucleic acid encoding the polypeptide, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 30 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active or binding site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 2.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

TABLE 2

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Polypeptides of the present invention can be produced in a variety of ways, including production and recovery of natural proteins, production and recovery of recombinant proteins, and chemical synthesis of the proteins. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides

In one aspect, the present invention provides an isolated polynucleotide comprising a sequence of nucleotides selected from the group consisting of:

i) a sequence of nucleotides as provided in SEQ ID NO:5 or SEQ ID NO:6;

ii) a sequence encoding a polypeptide of the invention;

iii) a sequence of nucleotides which is at least 50% identical to SEQ ID NO:5 or SEQ ID NO:6; and iv) a sequence which hybridizes to any one of i) to iii) under high stringency conditions.

In another aspect, the present invention provides an isolated polynucleotide comprising a sequence of nucleotides selected from the group consisting of:

i) a sequence of nucleotides as provided in SEQ ID NO:7 or SEQ ID NO:8;

ii) a sequence encoding a polypeptide of the invention;

iii) a sequence of nucleotides which is at least 51% identical to SEQ ID NO:7 or SEQ ID NO:8; and iv) a sequence which hybridizes to any one of i) to iii) under high stringency conditions.

In yet another aspect, the present invention provides an isolated polynucleotide comprising a sequence of nucleotides selected from the group consisting of:
  i) a sequence of nucleotides as provided in SEQ ID NO:9 or SEQ ID NO:10;
  ii) a sequence encoding a polypeptide of the invention;
  iii) a sequence of nucleotides which is at least 51% identical to SEQ ID NO:9 or SEQ ID NO:10; and
  iv) a sequence which hybridizes to any one of i) to iii) under high stringency conditions.

In a preferred embodiment, the sequence encoding a polypeptide of the invention is nucleotides 31 to 915 or SEQ ID NO:9 or nucleotides 85 to 915 of SEQ ID NO:9.

In a further aspect, the present invention provides an isolated polynucleotide comprising a sequence of nucleotides selected from the group consisting of:
  i) a sequence of nucleotides as provided in SEQ ID NO:11, SEQ ID NO:12 or SEQ ID NO:13;
  ii) a sequence encoding a polypeptide of the invention;
  iii) a sequence of nucleotides which is at least 70% identical to SEQ ID NO: 11, SEQ ID NO:12 or SEQ ID NO:13; and
  iv) a sequence which hybridizes to any one of i) to iii) under high stringency conditions.

In another aspect, the present invention provides an isolated polynucleotide comprising a sequence of nucleotides selected from the group consisting of:
  i) a sequence of nucleotides as provided in SEQ ID NO:58 or SEQ ID NO:59;
  ii) a sequence encoding a polypeptide of the invention;
  iii) a sequence of nucleotides which is at least 55% identical to SEQ ID NO:58 or SEQ ID NO:59; and
  iv) a sequence which hybridizes to any one of i) to iii) under high stringency conditions.

In another aspect, the present invention provides an isolated polynucleotide comprising a sequence of nucleotides selected from the group consisting of:
  i) a sequence of nucleotides as provided in SEQ ID NO:63;
  ii) a sequence encoding a polypeptide of the invention;
  iii) a sequence of nucleotides which is at least 90% identical to SEQ ID NO:63; and
  iv) a sequence which hybridizes to any one of i) to iii) under high stringency conditions.

In another aspect, the present invention provides an isolated polynucleotide comprising a sequence of nucleotides selected from the group consisting of:
  i) a sequence of nucleotides as provided in SEQ ID NO:89;
  ii) a sequence encoding a polypeptide of the invention;
  iii) a sequence of nucleotides which is at least 76% identical to SEQ ID NO:89; and
  iv) a sequence which hybridizes to any one of i) to iii) under high stringency conditions.

The present inventors are also the first to isolate polynucleotide encoding a keto-acyl synthase-like fatty acid elongase from a non-higher plant.

Accordingly, in a further aspect the present invention provides an isolated polynucleotide comprising a sequence of nucleotides selected from the group consisting of:
  i) a sequence of nucleotides as provided in SEQ ID NO:55;
  ii) a sequence of nucleotides which is at least 40% identical to SEQ ID NO:55; and
  iii) a sequence which hybridizes to i) or ii) under high stringency conditions.

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid molecule".

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides.

With regard to the defined polynucleotides, it will be appreciated that % identity figures higher than those provided above will encompass preferred embodiments. Thus, where applicable, in light of the minimum % identity figures, it is preferred that the polynucleotide comprises a nucleotide sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polynucleotides which are substantially identical to those specifically described herein. As used herein, with reference to a polynucleotide the term "substantially identical" means the substitution of one or a few (for example 2, 3, or 4) nucleotides whilst maintaining at least one activity of the native protein encoded by the polynucleotide. In addition, this term includes the addition or deletion of nucleotides which results in the increase or decrease in size of the encoded native protein by one or a few (for example 2, 3, or 4) amino acids whilst maintaining at least one activity of the native protein encoded by the polynucleotide.

Oligonucleotides of the present invention can be RNA. DNA, or derivatives of either. The minimum size of such oligonucleotides is the size required for the formation of a stable hybrid between an oligonucleotide and a complementary sequence on a nucleic acid molecule of the present invention. Preferably, the oligonucleotides are at least 15 nucleotides, more preferably at least 18 nucleotides, more preferably at least 19 nucleotides, more preferably at least 20 nucleotides, even more preferably at least 25 nucleotides in length. The present invention includes oligonucleotides that can be used as, for example, probes to identify nucleic acid molecules, or primers to produce nucleic acid molecules.

Oligonucleotide of the present invention used as a probe are typically conjugated with a label such as a radioisotope, an enzyme, biotin, a fluorescent molecule or a chemiluminescent molecule.

Polynucleotides and oligonucleotides of the present invention include those which hybridize under stringent conditions to a sequence provided as SEQ ID NO's: 5 to 13. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) form amide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Also provided are antisense and/or catalytic nucleic acids (such as ribozymes) which hybridize to a polynucleotide of the invention, and hence inhibit the production of an encoded protein. Furthermore, provided are dsRNA molecules, particularly small dsRNA molecules with a double stranded region of about 21 nucleotides, which can be used in RNA interference to inhibit the production of a polypeptide of the invention in a cell. Such inhibitory molecules can be used to alter the types of fatty acids produced by a cell, such an animal cell, moss, or algael cell. The production of such antisense, catalytic nucleic acids and dsRNA molecules is well with the capacity of the skilled person (see for example, G. Hartmann and S. Endres, Manual of Antisense Methodology, Kluwer (1999); Haseloff and Gerlach, 1988; Perriman et al., 1992; Shippy et al., 1999; Waterhouse et al. (1998); Smith et al. (2000); WO 99/32619, WO 99/53050, WO 99/49029, and WO 01/34815).

Gene Constructs and Vectors

One embodiment of the present invention includes a recombinant vector, which includes at least one isolated polynucleotide molecule encoding a polypeptide/enzyme defined herein, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

One type of recombinant vector comprises a nucleic acid molecule of the present invention operatively linked to an expression vector. As indicated above, the phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and effecting expression of a specified nucleic acid molecule. Preferably, the expression vector is also capable of replicating within the host cell.

Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, other animal, and plant cells. Preferred expression vectors of the present invention can direct gene expression in yeast, animal or plant cells.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules can remain extrachromosomal or can integrate into one or more sites within a chromosome of the transformed (i.e., recombinant) cell in such a manner that their ability to be expressed is retained.

Transgenic Plants and Parts Thereof

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. The plants may be vegetables or ornamental plants. The plants of the invention may be: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolour, Sorghum vulgar*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, or barley.

In one embodiment, the plant is an oilseed plant, preferably an oilseed crop plant. As used herein, an "oilseed plant" is a plant species used for the commercial production of oils from the seeds of the plant. The oilseed plant may be oil-seed rape (such as canola), maize, sunflower, soybean, sorghum, flax (linseed) or sugar beet. Furthermore, the oilseed plant may be other *Brassicas*, cotton, peanut, poppy, mustard, castor bean, sesame, safflower, or nut producing plants. The plant may produce high levels of oil in its fruit, such as olive, oil palm or coconut. Horticultural plants to which the present invention may be applied are lettuce, endive, or vegetable brassicas including cabbage, broccoli, or cauliflower. The present invention may be applied in tobacco, cucurbits, carrot, strawberry, tomato, or pepper.

When the production of ω3 LC-PUFA is desired it is preferable that the plant species which is to be transformed has an endogenous ratio of ALA to LA which is at least 1:1, more preferably at least 2:1. Examples include most, if not all, oilseeds such as linseed. This maximizes the amount of ALA substrate available for the production of SDA, ETA, ETrA, EPA, DPA and DHA.

The plants produced using the methods of the invention may already be transgenic, and/or transformed with additional genes to those described in detail herein. In one embodiment, the transgenic plants of the invention also produce a recombinant ω3 desaturase. The presence of a recombinant ω3 desaturase increases the ratio of ALA to LA in the plants which, as outlined in the previous paragraph, maximizes the production of LC-PUFA such as SDA, ETA, ETrA, EPA, DPA and DHA.

Grain plants that provide seeds of interest include oil-seed plants and leguminous plants. Seeds of interest include grain seeds, such as corn, wheat, barley, rice, sorghum, rye, etc. Leguminous plants include beans and peas. Beans include guar, locust bean, fenugreek, soybean, garden beans, cowpea, mungbean, lima bean, fava bean, lentils, chickpea, etc.

The term "extract or portion thereof" refers to any part of the plant. "Portion" generally refers to a specific tissue or organ such as a seed or root, whereas an "extract" typically involves the disruption of cell walls and possibly the partial purification of the resulting material. Naturally, the "extract or portion thereof" will comprise at least one LC-PUFA. Extracts can be prepared using standard techniques of the art.

Transgenic plants, as defined in the context of the present invention include plants and their progeny which have been genetically modified using recombinant techniques. This would generally be to cause or enhance production of at least one protein/enzyme defined herein in the desired plant or plant organ. Transgenic plant parts include all parts and cells of said plants such as, for example, cultured tissues, callus, protoplasts. Transformed plants contain genetic material that they did not contain prior to the transformation. The genetic material is preferably stably integrated into the genome of the plant. The introduced genetic material may comprise sequences that naturally occur in the same species but in a rearranged order or in a different arrangement of elements, for example an antisense sequence. Such plants are included herein in "transgenic plants". A "non-transgenic plant" is one which has not been genetically modified with the introduction of genetic material by recombinant DNA techniques. In a preferred embodiment, the transgenic plants are homozygous for each and every gene that has been introduced (transgene) so that their progeny do not segregate for the desired phenotype.

Several techniques exist for introducing foreign genetic material into a plant cell. Such techniques include acceleration of genetic material coated onto microparticle* directly into cells (see, for example, U.S. Pat. No. 4,945,050 and U.S. Pat. No. 5,141,131). Plants may be transformed using *Agrobacterium* technology (see, for example, U.S. Pat. No. 5,177,010, U.S. Pat. No. 5,104,310, U.S. Pat. No. 5,004,863, U.S. Pat. No. 5,159,135). Electroporation technology has also been used to transform plants (see, for example, WO 87/06614, U.S. Pat. Nos. 5,472,869, 5,384,253, WO 92/09696 and WO 93/21335). In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during development and/or differentiation using appropriate techniques described herein.

A number of vectors suitable for stable transfection of plant cells or for the establishment of transgenic plants have been described in, e.g., Pouwels et al. Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of plant promoters include, but are not limited to ribulose-1,6-bisphosphate carboxylase small subunit, beta-conglycinin promoter, phaseolin promoter, high molecular weight glutenin (HMW-GS) promoters, starch biosynthetic gene promoters, ADH promoter, heat-shock promoters and tissue specific promoters. Promoters may also contain certain enhancer sequence elements that may improve the transcription efficiency. Typical enhancers include but are not limited to Adh-intron I and Adh-intron 6.

Constitutive promoters direct continuous gene expression in all cells types and at all times (e.g., actin, ubiquitin. CaMV 35S). Tissue specific promoters are responsible for gene expression in specific cell or tissue types, such as the leaves or seeds (e.g., zein, oleosin, napin. ACP, globulin and the like) and these promoters may also be used. Promoters may also be active during a certain stage of the plants' development as well as active in plant tissues and organs. Examples of such promoters include but are not limited to pollen-specific, embryo specific, corn silk specific, cotton fibre specific, root specific, seed endosperm specific promoters and the like.

In a particularly preferred embodiment, the promoter directs expression in tissues and organs in which lipid and oil biosynthesis take place, particularly in seed cells such as endosperm cells and cells of the developing embryo. Promoters which are suitable are the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumin B4 promoter (Baumlein et al., 1992), and promoters which lead to the seed-specific expression in monocots such as maize, barley, wheat, rye, rice and the like. Notable promoters which are suitable are the barley Ipt2 or Ipt1 gene promoter (WO 95/15389 and WO 95/23230) or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998) and US 20030159173.

Under certain circumstances it may be desirable to use an inducible promoter. An inducible promoter is responsible for expression of genes in response to a specific signal, such as: physical stimulus (heat shock genes); light (RUBP carboxylase); hormone (Em); metabolites; and stress. Other desirable transcription and translation elements that function in plants may be used.

In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the cauliflower mosaic virus (35S and 19S) and the like may be used.

It will be apparent that transgenic plants adapted for the production of LC-PUFA as described herein, in particular DHA, can either be eaten directly or used as a source for the extraction of essential fatty acids, of which DHA would be a constituent.

As used herein, "germination" refers to the emergence of the root tip from the seed coat after imbibition. "Germination rate" refers to the percentage of seeds in a population which have germinated over a period of time, for example 7 or 10 days, after imbibition. A population of seeds can be assessed daily over several days to determine the germination percentage over time.

With regard to seeds of the present invention, as used herein the term "germination rate which is substantially the same" means that the germination rate of the transgenic seeds is at least 60%, more preferably at least 80%, and even more preferably at least 90%, that of isogenic non-transgenic seeds. Gemination rates can be calculated using techniques known in the art.

With further regard to seeds of the present invention, as used herein the term "timing of germination of the seed is substantially the same" means that the timing of germination of the transgenic seeds is at least 60%, more preferably at least 80%, and even more preferably at least 90%, that of isogenic non-transgenic seeds. Timing of gemination can be calculated using techniques known in the art.

The present inventors have found that at least in some circumstances the production of LC-PUFA in recombinant plant cells is enhanced when the cells are homozygous for the transgene. As a result, it is preferred that the recombinant plant cell, preferably the transgenic plant, is homozygous for at least one desaturase and/or elongase gene. In one embodiment, the cells/plant are homozygous for the zebrafish Δ6/Δ5 desaturase and/or the *C. elegans* elongase.

Transgenic Non-Human Animals

Techniques for producing transgenic animals are well known in the art. A useful general textbook on this subject is Houdebine. Transgenic animals—Generation and Use (Harwood Academic, 1997).

Heterologous DNA can be introduced, for example, into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals.

Another method used to produce a transgenic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology. Using this method, fibroblasts from donor animals are stably transfected with a plasmid incorporating the coding sequences for a binding domain or binding partner of interest under the control of regulatory. Stable transfectants are then fused to enucleated oocytes, cultured and transferred into female recipients.

Feedstuffs

The present invention includes compositions which can be used as feedstuffs. For purposes of the present invention, "feedstuffs" include any food or preparation for human or animal consumption (including for enteral and/or parenteral consumption) which when taken into the body (a) serve to nourish or build up tissues or supply energy; and/or (b) maintain, restore or support adequate nutritional status or metabolic function. Feedstuffs of the invention include nutritional compositions for babies and/or young children.

Feedstuffs of the invention comprise, for example, a cell of the invention, a plant of the invention, the plant part of the invention, the seed of the invention, an extract of the invention, the product of the method of the invention, the product of the fermentation process of the invention, or a composition along with a suitable carrier(s). The term "carrier" is used in its broadest sense to encompass any component which may or may not have nutritional value. As the skilled addressee will appreciate, the carrier must be suitable for use (or used in a sufficiently low concentration) in a feedstuff such that it does not have deleterious effect on an organism which consumes the feedstuff.

The feedstuff of the present invention comprises an oil, fatty acid ester, or fatty acid produced directly or indirectly by use of the methods, cells or plants disclosed herein. The composition may either be in a solid or liquid form. Additionally, the composition may include edible macronutrients, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed search. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material or by de novo synthesis.

A feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

The genus *Saccharomyces* spp is used in both brewing of beer and wine making and also as an agent in baking, particularly bread. Yeast is a major constituent of vegetable extracts. Yeast is also used as an additive in animal feed. It will be apparent that genetically engineered yeast strains can be provided which are adapted to synthesise LC-PUFA as described herein. These yeast strains can then be used in food stuffs and in wine and beer making to provide products which have enhanced fatty acid content and in particular DHA content.

Additionally, LC-PUFA produced in accordance with the present invention or host cells transformed to contain and express the subject genes may also be used as animal food supplements to alter an animal's tissue or milk fatty acid composition to one more desirable for human or animal consumption. Examples of such animals include sheep, cattle, horses and the like.

Furthermore, feedstuffs of the invention can be used in aquaculture to increase the levels of LC-PUFA in fish for human or animal consumption.

In mammals, the so-called "Sprecher" pathway converts DPA to DHA by three reactions, independent of a Δ7 elongase, Δ4 desaturase, and a beta-oxidation step (Sprecher et al., 1995) (FIG. 1). Thus, in feedstuffs for mammal consumption, for example formulations for the consumption by human infants, it may only be necessary to provide DPA produced using the methods of the invention as the mammalian subject should be able to fulfill its nutritional needs for DHA by using the "Sprecher" pathway to convert DPA to DHA. As a result, in an embodiment of the present invention, a feedstuff described herein for mammalian consumption at least comprises DPA, wherein at least one enzymatic reaction in the production of DPA was performed by a recombinant enzyme in a cell.

Compositions

The present invention also encompasses compositions, particularly pharmaceutical compositions, comprising one or more of the fatty acids and/or resulting oils produced using the methods of the invention.

A pharmaceutical composition may comprise one or more of the LC-PUFA and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectable, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, LC-PUFA produced in accordance with the present invention can be tabletted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant LC-PUFA(s).

For intravenous administration, the PUFA produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of LC-PUFA is desirable. However, it will be appreciated that any amount of LC-PUFA will be beneficial to the subject.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The dosage of the composition to be administered to the patient may be determined by one of ordinary skill in the art and depends upon various factors such as weight of the patient, age of the patient, overall health of the patient, past history of the patient, immune status of the patient, etc.

Additionally, the compositions of the present invention may be utilized for cosmetic purposes. It may be added to pre-existing cosmetic compositions such that a mixture is formed or a LC-PUFA produced according to the subject invention may be used as the sole "active" ingredient in a cosmetic composition.

Medical, Veterinary, Agricultural and Aquacultural Uses

The present invention also includes the treatment of various disorders by use of the pharmaceutical and/or feedstuff compositions described herein. In particular, the compositions of the present invention may be used to treat restenosis after angioplasty. Furthermore, symptoms of inflammation, rheumatoid arthritis, asthma and psoriasis may also be treated with the compositions (including feedstuffs) of the invention. Evidence also indicates that LC-PUFA may be involved in calcium metabolism; thus, the compositions of the present invention may be utilized in the treatment or prevention of osteoporosis and of kidney or urinary tract stones.

Additionally, the compositions of the present invention may also be used in the treatment of cancer. Malignant cells have been shown to have altered fatty acid compositions. Addition of fatty acids has been shown to slow their growth, cause cell death and increase their susceptibility to chemotherapeutic agents. Moreover, the compositions of the present invention may also be useful for treating cachexia associated with cancer.

The compositions of the present invention may also be used to treat diabetes as altered fatty acid metabolism and composition have been demonstrated in diabetic animals.

Furthermore, the compositions of the present invention, comprising LC-PUFA produced either directly or indirectly through the use of the cells of the invention, may also be used in the treatment of eczema and in the reduction of blood pressure. Additionally, the compositions of the present invention may be used to inhibit platelet aggregation, to induce vasodilation, to reduce cholesterol levels, to inhibit proliferation of vessel wall smooth muscle and fibrous tissue, to reduce or to prevent gastrointestinal bleeding and other side effects of non-steroidal anti-inflammatory drugs (U.S. Pat. No. 4,666,701), to prevent or to treat endometriosis and premenstrual syndrome (U.S. Pat. No. 4,758,592), and to treat myalgic encephalomyelitis and chronic fatigue after viral infections (U.S. Pat. No. 5,116,871).

Further uses of the compositions of the present invention include, but are not limited to, use in the treatment or prevention of cardiac arrhythmia's, angioplasty, AIDS, multiple sclerosis, Crohn's disease, schizophrenia, foetal alcohol syndrome, attention deficient hyperactivity disorder, cystic fibrosis, phenylketonuria, unipolar depression, aggressive hostility, adrenoleukodystophy, coronary heart disease, hypertension, obesity, Alzheimer's disease, chronic obstructive pulmonary disease, ulcerative colitis or an ocular disease, as well as for maintenance of general health.

Furthermore, the above-described pharmaceutical and nutritional compositions may be utilized in connection with animals (i.e., domestic or non-domestic, including mammals, birds, reptiles, lizards, etc.), as well as humans, as animals experience many of the same needs and conditions as humans. For example, the oil or fatty acids of the present invention may be utilized in animal feed supplements, animal feed substitutes, animal vitamins or in animal topical ointments.

Compositions such as feedstuffs of the invention can also be used in aquaculture to increase the levels of LC-PUFA in fish for human or animal consumption.

Any amount of LC-PUFA will be beneficial to the subject. However, it is preferred that an "amount effective to treat" the condition of interest is administered to the subject. Such dosages to effectively treat a condition which would benefit from administration of a LC-PUFA are known those skilled in the art. As an example, a dose of at least 300 mg/day of LC-PUFA for at least a few weeks, more preferably longer would be suitable in many circumstances.

Antibodies

The invention also provides monoclonal and/or polyclonal antibodies which bind specifically to at least one polypeptide of the invention or a fragment thereof. Thus, the present invention further provides a process for the production of monoclonal or polyclonal antibodies to polypeptides of the invention.

The term "binds specifically" refers to the ability of the antibody to bind to at least one protein of the present invention but not other proteins present in a recombinant cell, particularly a recombinant plant cell, of the invention.

As used herein, the term "epitope" refers to a region of a protein of the invention which is bound by the antibody. An epitope can be administered to an animal to generate antibodies against the epitope, however, antibodies of the present invention preferably specifically bind the epitope region in the context of the entire protein.

If polyclonal antibodies are desired, a selected mammal (e.g., mouse, rabbit, goat, horse, etc.) is immunised with an immunogenic polypeptide. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies of the invention may be bound to a solid support and/or packaged into kits in a suitable container along with suitable reagents, controls, instructions and the like.

Preferably, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect proteins of the invention.

EXAMPLES

Example 1

Materials and Methods

Culturing *Pavlova salina*

*Pavlova salina* isolates including strain CS-49 from the CSIRO Collection of Living Microalgae was cultivated under standard culture conditions (http://www.marine.csiro.au/microalgae). A stock culture from the Collection was sub-cultured and scaled-up in a dilution of 1 in 10 over consecutive transfers in 1 L Erlenmeyer flasks and then into 10 L polycarbonate carboys. The culture medium was f/2, a modification of Guillard and Ryther's (1962) f medium containing half-strength nutrients, with a growth temperature of 20±1° C. Other culturing conditions included a light intensity of 100 µmol. photons PAR·$m^{-2}$·$s^{-1}$, 12:12 hour light:dark photoperiod, and bubbling with 1% $CO_2$ in air at a rate of 200 mL·$L^{-1}$·$min^{-}$.

Yeast Culturing and Feeding with Cursor Fact Acids

Plasmids were introduced into yeast by heat shock and transformants were selected on yeast minimal medium (YMM) plates containing 2% raffinose as the sole carbon source. Clonal inoculum cultures were established in liquid YMM with 2% raffinose as the sole carbon source. Experimental cultures in were inoculated from these, in YMM+1% NP-40, to an initial $OD_{600}$ of ~0.3. Cultures were grown at 30° C. with shaking (~60 rpm) until $OD_{600}$ was approximately 1.0. At this point galactose was added to a final concentration of 2% and precursor fatty acids were added to a final concentration of 0.5 mM. Cultures were incubated at 20° C. with shaking for a further 48 hours prior to harvesting by centrifugation. Cell pellets were washed with 1% NP-40, 0.5% NP-40 and water to remove any unincorporated fatty acids from the surface of the cells.

Gas Chromatography (GC) Analysis of Fatty Acids

Fatty Acid Preparation

Fatty acid methyl esters (FAME) were formed by transesterification of the centrifuged yeast pellet or *Arabidopsis* seeds by heating with MeOH—$CHCl_3$—HCl (10:1:1, v/v/v) at 90-100° C. for 2 h in a glass test tube fitted with a Teflon-lined screw-cap. FAME were extracted into hexane-dichloromethane (4:1, v/v) and analysed by GC and GC-MS.

Capillary Gas-Liquid Chromatography (GC)

FAME were analysed with Hewlett Packard (HP) 5890 GC or Agilent 6890 gas chromatograph fitted with HP 7673A or 6980 series automatic injectors respectively and a flame-ionization detector (FID). Injector and detector temperatures were 290° C. and 310° C. respectively. FAME samples were injected at 50° C. onto a non-polar cross-linked methyl-silicone fused-silica capillary column (HP-5; 50 m×0.32 mm i.d.; 0.17 µm film thickness.). After 1 min, the oven temperature was raised to 210° C. at 30° C. $min^{-1}$, then to a final temperature of 280° C. at 3° C. $min^{-1}$ where it was kept for 5 min. Helium was the carrier gas with a column head pressure of 65 KPa and the purge opened 2 min after injection. Identification of peaks was based on comparison of relative retention time data with standard FAME with confirmation using mass-spectrometry. For quantification Empower software (Waters) or Chemstation (Agilent) was used to integrate peak areas.

Gas Chromatography-Mass Spectrometry (GC-MS)

GC-MS was carried out on a Finnigan GCQ Plus GC-MS ion-trap fitted with on-column injection set at 4° C. Samples were injected using an AS2000 auto sampler onto a retention gap attached to an HP-5 Ultra 2 bonded-phase column (50 m×0.32 mm i.d.×0.17 µm film thickness). The initial temperature of 45° C. was held for 1 min, followed by temperature programming at 30° C.·$min^{-1}$ to 140° C. then at 3° C.·$min^{-1}$ to 310° C. where it was held for 12 min. Helium was used as the carrier gas. Mass spectrometer operating conditions were: electron impact energy 70 eV; emission current 250 µamp, transfer line 310° C.; source temperature 240° C.; scan rate 0.8 scans·$s^{-1}$ and mass range 40-650 Dalton. Mass spectra were acquired and processed with Xcalibur™ software.

Construction of *P. salina* cDNA Library mRNA, for the construction of a cDNA library, was isolated from *P. salina* cells using the following method. 2 g (wet weight) of *P. salina* cells were powdered using a mortar and pestle in liquid nitrogen and sprinkled slowly into a beaker containing 22 ml of extraction buffer that was being stirred constantly. To this, 5% insoluble polyvinylpyrrolidone, 90 mM 2-mercaptoethanol, and 10 mM dithiotheitol were added and the mixture stirred for a further 10 minutes prior to being transferred to a Corex™ tube. 18.4 ml of 3M ammonium acetate was added and mixed well. The sample was then centrifuged at 6000×g for 20 minutes at 4° C. The supernatant was transferred to a new tube and nucleic acid precipitated by the addition of 0.1 volume of 3M NaAc (pH 5.2) and 0.5 volume of cold isopropanol. After a 1 hour incubation at -20° C., the sample was centrifuged at 6000×g for 30 minutes in a swing rotor. The pellet was resuspended in 1 ml of water extracted with phenol/chloroform. The aqueous layer was transferred to a new tube and nucleic acids were precipitated once again by the addition of 0.1 volume 3M NaAc (pH 5.2) and 2.5 volume of ice cold ethanol. The pellet was resuspended in water, the concentration of nucleic acid determined and then mRNA was isolated using the Oligotex mRNA system (Qiagen).

First strand cDNA was synthesised using an oligo-dT primer supplied with the ZAP-cDNA synthesis kit (Stratagene—cat #200400) and the reverse transcriptase SuperscriptIII (Invitrogen). Double stranded cDNA was ligated to EcoRI/XhoI adaptors and from this a library was constructed using the ZAP-cDNA synthesis kit as described in the accompanying instruction manual (Stratagene—cat #200400). The titer of the primary library was 2.5×$10^5$ plaque forming units (pfu)/ml and that of the amplified library was 2.5×$10^9$ pfu/ml. The average insert size of cDNA inserts in the library was 1.3 kilobases and the percentage of recombinants in the library was 74%.

Example 2

Microalgae and Polyunsaturated Fatty Acid Contents Thereof

The CSIRO Collection of Living Microalgae

CSIRO established and maintained a Collection of Living Microalgae (CLM) containing over 800 strains from 140 genera representing the majority of marine and some freshwater microalgal classes (list of strains available downloadable from http://www.marine.csiro.au). Selected micro-heterotrophic strains were also maintained.

This collection is the largest and most diverse microalgal culture collection in Australia. The CLM focused on isolates from Australian waters—over 80% of the strains were isolated from diverse localities and climatic zones, from tropical northern Australia to the Australian Antarctic Territory, from oceanic, inshore coastal, estuarine, intertidal and freshwater environments. Additionally, emphasis has been placed on representation of different populations of a single species, usually by more than one strain. All strains in the culture collection were unialgal and the majority were clonal. A subset of strains were axenic. Another collection is the NIES-Collection (National Institute for Environmental Studies, Environment Agency) maintained in Japan.

Microalgae are known for their cosmopolitanism at the morphological species level, with very low endemicity being shown. However this morphological cosmopolitanism can hide a plethora of diversity at the intra-specific level. There have been a number of studies of genetic diversity on different microalgae using approaches such as interbreeding, isozymes, growth rates and a range of molecular techniques. The diversity identified by these studies ranges from large regional and global scales (Chinain et al., 1997) to between and within populations (Gallagher, 1980; Medlin et al., 1996; Botch et al., 1999a,b). Variation at the intra-specific level, between morphologically indistinguishable microalgae, can usually only be identified using strains isolated from the environment and cultured in the laboratory.

It is essential to have identifiable and stable genotypes within culture collections. While there are recorded instances of change or loss of particular characteristics in long term culture (Coleman, 1977), in general, culturing guarantees genetic continuity and stability of a particular strain. Cryopreservation strategies could also be used to limit the potential for genetic drift.

Microalgae and their Use in Aquaculture

Because of their chemical/nutritional composition including PUFAs, microalgae are utilized in aquaculture as live feeds for various marine organisms. Such microalgae must be of an appropriate size for ingestion and readily digested. They must have rapid growth rates, be amenable to mass culture, and also be stable in culture to fluctuations in temperature, light and nutrients as may occur in hatchery systems. Strains fulfilling these attributes and used widely in aquaculture include northern hemisphere strains such as *Isochrysis* sp. (T.ISO) CS-177, *Pavlova lutheri* CS-182, *Chaetoceros calcitrans* CS-178, *C. muelleri* CS-176, *Skeletonema costarum* CS-181, *Thalassiosira pseudonana* CS-173, *Tetraselmis suecica* CS-187 and *Nannochloropsis oculata* CS-189. Australian strains used include *Pavlova pinguis* CS-375, *Skeletonema* sp. CS-252, *Nannochloropsis* sp. CS-246, *Rhodomonas salina* CS-24 and *Navicula jeffreyi* CS-46. Biochemical assessment of over 50 strains of microalgae used (or of potential use) in aquaculture found that cells grown to late-logarithmic growth phase typically contained 30 to 40% protein, 10 to 20% lipid and 5 to 15% carbohydrate (Brown et al., 1997).

Lipid Composition Including PUFA Content of Microalgae

There is considerable interest in microalgae containing a high content of the nutritionally important long-chain polyunsaturated fatty acids (LC-PUFA), in particular EPA [eicosapentaenoic acid, $20:5(\omega3)$] and DHA [docosahexaenoic acid, $22:6(\omega3)$] as these are essential for the health of both humans and aquacultured animals. While these PUFA are available in fish oils, microalgae are the primary producers of EPA and DHA.

The lipid composition of a range of microalgae (46 strains) and particularly the proportion and content of important PUFA in the lipid of the microalgae were profiled. $C_{18}$-$C_{22}$ PUFA composition of microalgal strains from different algal classes varied considerably across the range of classes of phototrophic algae (Table 3, FIG. 2, see also Dunstan et. al., 1994, Volkman et al., 1989; Mansour et al., 1999a). Diatoms and eustigmatophytes were rich in EPA and produced small amounts of the less common PUFA, ARA [arachidonic acid, $20:4(\omega6)$] with negligible amounts of DHA. In addition, diatoms made unusual C16 PUFA such as $16:4(\omega1)$ and $16:3(\omega4)$. In contrast, dinoflagellates had high concentrations of DHA and moderate to high proportions of EPA and precursor $C_{18}$ PUFA [$18:5(\omega3)$ and $18:4(\omega3)$ SDA, stearidonic acid]. Prymnesiophytes also contained EPA and DHA, with EPA the dominant PUFA. Cryptomonads were a rich source of the $C_{18}$ PUFA $18:3(\omega3)$ (ALA $\alpha$-linolenic acid) and SDA, as well as EPA and DHA. Green algae (e.g. Chlorophytes such as *Dunaliella* spp. and *Chlorella* spp.) were relatively deficient in both C20 and C22 PUFA, although some species had small amounts of EPA (up to 3%) and typically contained abundant ALA and $18:2(\omega6)$, and were also able to make $16:4(\omega3)$. The biochemical or nutritional significance of uncommon $C_{16}$ PUFA [e.g. $16:4(\omega3)$, $16:4(\omega1)$, $16:3(\omega4)$] and $C_{18}$ PUFA (e.g. $18:5(\omega3)$ and STA] is unclear. However there is current interest in $C_{18}$ PUFA such as SDA that are now being increasingly recognized as precursors for the beneficial EPA and DHA, unlike ALA which has only limited conversion to EPA and DHA.

New strains of Australian thraustochytrids were isolated. When examined, these thraustochytrids showed great morphological diversity from single cells to clusters of cells, complex reticulate forms and motile stages. Thruastochytrids are a group of single cell organisms that produce both high oil and LC-PUFA content. They were initially thought to be primitive fungi, although more recently have been assigned to the subclass Thraustochytridae (Chromista, Heterokonta), which aligns them more closely with other heterokont algae (e.g. diatoms and brown algae). Under culture, thraustochytrids can achieve considerably higher biomass yield (>20 g/L) than other microalgae. In addition, thraustochytrids can be grown in fermenters with an organic carbon source and therefore represent a highly attractive, renewable and contaminant-free, source of omega-3 oils.

TABLE 3

Distribution of selected PUFA and LC-PUFA in microalgae and other groups, and areas of application.

| Group | Genus/Species | PUFA | Application |
|---|---|---|---|
| Eustigmatophytes | *Nannochloropsis* | EPA | Aquaculture |
| Diatoms | *Chaetoceros* | | |
| Dinoflagellates | *Crypthecodinium cohnii* | DHA | Aquaculture, health supplements, infant formula |
| Thraustochytrids | *Schizochytrium* | | |
| Red algae | *Phorphyridium* | ARA | Aquaculture, infant formula |
| Thraustochytrids | undescribed species | | Pharmaceutical industry |
| Fungi | *Mortiella* | | (precursor to prostaglandins) |
| Blue green algae | *Spirulina* | GLA | health supplements |

Abbreviations: γ-linolenic acid, GLA, $18:3\omega6$; $20:5\omega3$, eicosapentaenoic acid, EPA, $20:5\omega3$; docosahexaenoic acid, DHA, $22:6\omega3$; arachidonic acid, ARA, $20:4\omega6$.

Representative fatty acid profiles for selected Australian thraustochytrids are shown in Table 4. Strain O was particularly attractive as it contained very high levels of DHA (61%). Other PUFA were present at less than 5% each. High DHA-containing thraustochytrids often also contained high proportions of $22:5\omega6$, docosapentaenoic acid (DPA), as was observed for strains A, C and H. DPA was only a minor component in strain O under the culture conditions employed, making this strain particularly interesting. Strain A contained both DHA (28%) and EPA (16%) as the main LC-PUFA. Strains C and H differed from the other strains with ARA (10-13%) also being present as a major LC-PUFA. A number of other LC-PUFA were present in the thraustochytrids including DPA(3) and 22:4ω6 and other components.

TABLE 4

Fatty acid composition (% of total) of thraustochytrid strains.

| Fatty acid | Percentage composition Strain | | | |
|---|---|---|---|---|
| | A | C | H | O |
| 16:0 | 18.0 | 16.4 | 13.5 | 22.1 |
| 20:4ω6 ARA | 4.0 | 10.5 | 13.4 | 0.7 |
| 20:5ω3 EPA | 15.8 | 7.7 | 5.2 | 4.1 |
| 22:5ω6 DPA(6) | 16.6 | 9.3 | 12.7 | 3.4 |
| 22:6ω3 DHA | 28.2 | 21.6 | 19.2 | 61.0 |

The microalgal and thraustochytrid isolates in the CLM that may be used for isolation of genes involved in the synthesis of LC-PUFA are of the genera or species as follows:

Class Bacillariophyceae (Diatoms)

*Attheya septentrionalis, Aulacoseira* sp., *Chaetoceros affinis, Chaetoceros calcitrans, Chaetoceros calcitrans* f. *pumilum, Chaetoceros* cf. *mitra, Chaetoceros* cf. *peruvianus, Chaetoceros* cf. *radians, Chaetoceros didymus, Chaetoceros difficile, Chaetoceros gracilis, Chaetoceros muelleri, Chaetoceros simplex, Chaetoceros socialis, Chaetoceros* sp., *Chaetoceros* cf. *minus, Chaetoceros* cf. *tenuissimus, Coscinodiscus wailesii*, other *Coscinodiscus* spp., *Dactyliosolen fragilissimus, Detonula pumila, Ditylum brightwellii, Eucampia zodiacus, Extubocellulus spinifera, Lauderia annulata, Leptocylindrus danicus, Melosira moniliformis, Melosira* sp., *Minidiscus trioculatus, Minutocellus polymorphus, Odontella aurita, Odontella mobiliensis, Odontella regia, Odontella rhombus, Odontella* sp., *Papiliocellulus simplex, Planktosphaerium* sp., *Proboscia alata, Rhizosolenia imbricata, Rhizosolenia setigera, Rhizosolenia* sp., *Skeletonema costatum, Skeletonema pseudocostatum, Skeletonema* sp., *Skeletonema tropicum*, other *Skeletonema* spp., *Stephanopyxis turris, Streptotheca* sp., *Streptotheca tamesis, Streptotheca* spp., *Striatella* sp., *Thalassiosira delicatula, Thalassiosira eccentrica, Thalassiosira mediterranea, Thalassiosira oceanica, Thalassiosira oestrupii, Thalassiosira profunda, Thalassiosira pseudonana, Thalassiosira rotula, Thalassiosira stellaris*, other *Thalassiosira* spp., *Achnanthes* cf. *amoena, Amphiprora* cf. *alata, Amphiprora hyalina, Amphora* spp., *Asterionella glacialis, Asterionellopsis glacialis, Biddulphia* sp., *Cocconeis* sp., *Cylindrotheca closterium, Cylindrotheca fusiformis, Delphineis* sp., *Diploneis* sp., *Entomoneis* sp., *Fallacia carpentariae, Grammatophora oceanica, Haslea ostrearia, Licmophora* sp., *Manguinea* sp., *Navicula* cf. *jeffreyi, Navicula jeffreyi*, other *Navicula* spp., *Nitzschia* cf. *bilobata, Nitzschia* cf. *constricta, Nitzschia* cf. *cylindrus, Nitzschia* cf. *frustulum, Nitzschia* cf *paleacea, Nitzschia closterium, Nitzschia fraudulenta, Nitzschia frustulum, Nitzschia* sp., *Phaeodactylum tricornutum, Pleurosigma delicatulum*, other *Pleurosigma* spp., *Pseudonitzschia australis, Pseudonitzschia delicatissima, Pseudonitzschia fraudulenta, Pseudonitzschia pseudodelicatissima, Pseudonitzschia pungens, Pseudonitzschia* sp., *Pseudostaurosira shiloi, Thalassionema nitzschioides*, or *Thalassiothrix heteromorpha*.

Class Chrysophyceae

*Chrysolepidomonas* cf. *marina, Hibberdia* spp., *Ochromonas danica, Pelagococcus subviridis, Phaeoplaca* spp., *Synura shagnicola* or other *Chrysophyte* spp.

Class Cryptophyceae

*Chroomonas placoidea, Chroomonas* sp., *Geminigera cryophila, Hemiselmis simplex, Hemiselmis* sp., *Rhodomonas baltica, Rhodomonas maculata, Rhodomonas salina, Rhodomonas* sp. or other *Cryptomonad* spp.

Class Dinophyceae (Dinoflagellates)

*Alexandrium affine, Alexandrium catenella, Alexandrium margalefi, Alexandrium minutum, Alexandrium protogonyaulax, Alexandrium tamarense, Amphidinium carterae, Amphidinium* cf *britannicum, Amphidinium klebsii, Amphidinium* sp., *Amphidinium steinii, Amylax tricantha, Cryptothecodinium cohnii, Ensiculifera* sp., *Fragilidium* spp., *Gambierdiscus toxicus, Gymnodinium catenatum, Gymnodinium galathaneum, Gymnodinium galatheanum, Gymnodinium nolleri, Gymnodinium sanguineum*, or other *Gymnodinium* spp., *Gyrodinium pulchellum*, or other *Gyrodinium* spp., *Heterocapsa niei, Heterocapsa rotundata, Katodinium* cf. *rotundatum, Kryptoperidinium foliaceum, Peridinium balticum, Prorocentrum gracile, Prorocentrum mexicanum, Prorocentrum micans, Protoceratium reticulatum, Pyrodinium bahamense, Scrippsiella* cf. *precaria*, or other *Scrippsiella* spp. *Symbiodinium microadriaticum*, or *Woloszynskia* sp.

Class Euglenophyceae

*Euglena gracilis.*

Class Prasinophyceae

*Pycnococcus* sp., *Mantoniella squamata, Micrornonas pusilla, Nephroselmis minuta, Nephroselmis pynformes, Nephroselmis rotunda, Nephroselmis* spp., or other *Prasinophyte* spp., *Pseudoscourfieldia marina, Pycnococcus provasolii, Pyramimonas cordata, Pyramimonas gelidicola, Pyramimonas grossii, Pyramimonas oltmansii, Pyramimonas propulsa*, other *Pyramimonas* spp., *Tetraselmis antarctica, Tetraselmis chuii, Tetraselmis* sp., *Tetraselmis suecica*, or other *Tetraselmis* spp.

Class Prymnesiophyceae

*Chrysochromulina acantha, Chrysochromulina apheles, Chrysochromulina brevifilum, Chrysochromulina camella, Chrysochromulina hirta, Chrysochromulina kappa, Chrysochromulina minor, Chrysochromulina pienaar, Chrysochromulina simplex, Chrysochromulina* sp., *Chrysochromulina spinifera, Chrysochromulina strobilus*, and other *Chrysophyte* spp., *Chrysotila lamellosa, Cricosphaera carterae, Crystallolithus hyalinus, Diacronema vlkianum, Dicrateria inornata, Dicrateria* sp., *Emiliania huxleyi, Gephyrocapsa oceanica, Imantonia rotunda*, and other *Isochrysis* spp., *Ochrosphaera neapolitana, Pavlova* cf. *pinguis, Pavlova gyrans, Pavlova lutheri, Pavlova pinguis, Pavlova salina, Pavlova* sp., *Phaeocystis* cf. *pouchetii, Phaeocystis globosa, Phaeocystis pouchetii*, other *Phaeocystis* spp., *Pleurochrysis aff. carterae, Prymnesium parvum, Prymnesium patelliferum*, other *Prymnesium* spp., or *Pseudoisochrysis paradoxa.*

Class Raphidophyceae

*Chattonella antiqua*, other *Chattonella* spp., *Fibrocapsa japonica*, other *Fibrocapsa* spp., *Heterosigma akashiwo, Heterosigma carterae*, or other *Heterosigma* spp.

Class Thraustochytridae

*Schizochytrium* spp., *Thraustochytrium aureum, Thraustochytrium roseum*, or other *Thraustochytrium* spp.

Class Eustigmatophytae as a Source of Genes for EPA Production:

*Eustigmatos vischeri, Monodus subterraneus, Nannochloropsis oculata, Nannochloropsis salina, Vischeria hel-* vetica, *Vischeria punctata, Chloridella neglecta, Chloridella simplex, Chlorobotrys regularis, Ellipsoidon parvum, Ellipsoidon solitare, Eustigmatos magnus, Eustigmatos polyphem, Goniochloris sculpta, Monodus subterraneus, Monodus unipapilla, Nannochloropsis gaditana, Nannochloropsis granulata, Nannochloropsis limnetica, Pseudocharaciopsis, ovalis, Pseudocharaciopsis texensis, Pseudostaurastrum limneticum*, or *Vischeria stellata*

Example 3

Isolation of Zebrafish Δ5/6 Desaturase and Functional Characterization in Yeast

As well as microalgae, some other organisms have the capacity to synthesise LC-PUFA from precursors such as α-linolenic acid (18:3, ALA) (see FIG. 1) and some of the genes responsible for such synthesis have been isolated (see Sayanova and Napier, 2004). The genes involved in omega-3 $C_{20}$+PUFA biosynthesis have been cloned from various organisms including algae, fungi, mosses, plants, nematodes and mammals. Based on the current understanding of genes involved in the synthesis of omega-3 $C_{20}$+PUFA, synthesis of EPA in plants would require the transfer of genes encoding at least two desaturases and one PUFA elongase. The synthesis of DHA from EPA in plants would require the additional transfer of a further desaturase and a further elongase (Sayanova and Napier, 2004). These enzymes are: for the synthesis of EPA, the sequential activities of a Δ6 desaturase, Δ6 elongase and a Δ5 desaturase is required. Based on an alternative pathway operative in some algae, EPA may also be synthesised by the sequential activities of a Δ9 elongase, a Δ8 desaturase and a Δ5 desaturase (Wallis and Browse, 1999; Qi et al., 2002). For the further conversion of EPA to DHA in plants, a further transfer of a Δ5 elongase and Δ4 desaturase will be required (Sayanova and Napier, 2004).

Hastings et al. (2001) isolated a gene encoding a Δ5/Δ6 bifunctional desaturase from zebra fish (*Dania rerio*) and showed that, when expressed in yeast, the desaturase was able to catalyse the synthesis of both Δ6 (GLA and SDA) and Δ5 (20:4 and EPA) fatty acids. The desaturase was therefore able to act on both ω6 and ω3 substrates.

Isolation of the Zebrafish Δ5/Δ6 Desaturase

RNA was extracted using the RNAeasy system according to the manufacturers instructions (Qiagen) from freshly dissected zebrafish livers. Based on the published sequence (Hastings et al. 2001), primers, sense, 5'-CCCAAGCTTAC-TATGGGTGGCGGAGGACAGC-3' (SEQ ID NO:39) and antisense 5'-CCGCTGGAGTTATTTGTTGAGATACGC-3' (SEQ ID NO:40) at the 5' and 3' extremities of the zebrafish Δ5/6 ORF were designed and used in a one-step reverse transcription-PCR (RT-PCR, Promega) with the extracted RNA and using buffer conditions as recommended by the manufacturer. A single amplicon of size 1335 bp was obtained, ligated into pGEM-T easy (Promega) and the sequence confirmed as identical to that published.

A fragment containing the entire coding region (SEQ ID NO:38) was excised and ligated into the yeast shuttle vector pYES2 (Invitrogen). The vector pYES2 carried the URA3 gene, which allowed selection for yeast transformants based on uracil prototrophy. The inserted coding region was under the control of the inducible GAL1 promoter and polyadenylation signal of pYES2. The resultant plasmid was designated pYES2-zfΔ5/6, for introduction and expression in yeast (*Saccharomyces cerevisiae*).

Expression of Zebrafish Δ5/Δ6 Desaturase in Yeast

The gene construct pYES2-zfΔ5/6 was introduced into yeast strain S288. Yeast was a good host for analysing heterologous potential LC-PUFA biosynthesis genes including desaturases and elongases for several reasons. It was easily transformed. It synthesised no LC-PUFA of its own and therefore any new PUFA made was easily detectable without any background problems. Furthermore, yeast cells readily incorporated fatty acids from growth media into cellular lipids, thereby allowing the presentation of appropriate precursors to transformed cells containing genes encoding new enzymes, allowing for confirmation of their enzymatic activities.

Biochemical Analyses

Yeast cells transformed with pYES2-zfΔ5/6 were grown in YMM medium and induced by the addition of galactose. The fatty acids 18:3ω3 (ALA, 0.5 mM) or 20:4ω3 (ETA, 0.5 mM) were added to the medium as described above. After 48 hours incubation, the cells were harvested and fatty acid analysis carried out by capillary gas-liquid chromatography (GC) as described in Example 1. The analysis showed that 18:4ω3 (1.9% of total fatty acid) was formed from 18:3ω3 and 20:5ω3 (0.24% of fatty acids) from 20:4ω3, demonstrating Δ6 desaturase activity and Δ5 desaturase activity, respectively. These data are summarized in Table 5 and confirm the results of Hastings et al (2001).

Example 4

Isolation of *C. elegans* Elongase and Functional Characterization in Yeast

Cloning of *C. elegans* Elongase Gene

Beaudoin and colleagues isolated a gene encoding an ELO-type fatty acid elongase from the nematode *Caenorhabditis elegans* (Beaudoin et al., 2000) and this gene was isolated as follows. Oligonucleotide primers having the sequences 5'-GCGGGTACCATGGCTCAGCATCCGCTC-3' (SEQ ID NO:41) (sense orientation) and 5'-GCGGGATC-CTTAGTTGTTCTTCTTCTT-3' (SEQ ID NO:42) (antisense orientation) were designed and synthesized, based on the 5' and 3' ends of the elongase coding region. These primers were used in a PCR reaction to amplify the 867 basepair coding region from a *C. elegans* N2 mixed-stage gene library, using an annealing temperature of 58° C. and an extension time of 1 minute. The PCR amplification was carried out for 30 cycles. The amplification product was inserted into the vector pGEM™ T-easy (Promega) and the nucleotide sequence confirmed (SEQ ID NO:37). An EcoRI/BamHI fragment including the entire coding region was excised and inserted into the EcoRI/BglII sites of pSEC-TRP (Stratagene), generating pSEC-Ceelo, for introduction and expression in yeast. pSEC-TRP contains the TRP1 gene, which allowed for the selection of transformants in yeast by tryptophan prototrophy, and the GAL1 promoter for expression of the chimeric gene in an inducible fashion in the presence of galactose in the growth medium.

TABLE 5

Enzymatic activities in yeast and *Arabidopsis*

| Clone | Precursor PUFA | Synthesised PUFA | % (of total FA) | Observed activity |
|---|---|---|---|---|
| pYES2-zfΔ5/6 | 18:3ω3 | 18:4ω3 | 1.9 | Δ6 desaturase |
| pYES2-zfΔ5/6 | 20:4ω3 | 20:5ω3 | 0.24 | Δ5 desaturase |
| pYES2zfΔ5/6, pSEC-Ceelo | 18:3ω3 | 18:4ω3 | 0.82 | Δ6 desaturase |
| | | 20:3ω3 | 0.20 | Δ9 elongase |

TABLE 5-continued

Enzymatic activities in yeast and *Arabidopsis*

| Clone | Precursor PUFA | Synthesised PUFA | % (of total FA) | Observed activity |
|---|---|---|---|---|
| | | 20:4ω3 | 0.02 | Δ6 elongase NOT |
| pYES2-psΔ8 | 18:3ω3 | 18:4ω3 | — | Δ6 desaturase |
| pYES2-psΔ8 | 20:3ω3 | 20:4ω3 | 0.12 | Δ8 desaturase |
| pYES2-psELO1 | 18:2ω6 | 20:2ω6 | — | |
| pYES2-psELO1 | 18:3ω3 | | | |
| pYES2-psELO1 | 20:3ω3 | 22:3ω3 | — | |
| pYES2-psELO1 | 20:4ω3 | 22:4ω3 | — | |
| pYES2-psELO1 | 20:5ω3 | 22:5ω3 | 0.82 | Δ5 elongase |
| pYES-psELO2 | 18:2ω6 | 20:2ω6 | 0.12 | Δ9 elongase |
| pYES-psELO2 | 18:3ω3 | 20:3ω3 | 0.20 | Δ9 elongase |
| pYES-psELO2 | 20:3ω3 | 22:3ω3 | — | |
| pYES-psELO2 | 20:4ω3 | 22:4ω3 | — | |
| pYES-psELO2 | 20:5ω3 | 22:5ω3 | — | |
| *Arabidopsis* + zfΔ5/6 & Ceelo (plant #1) | — | 18:3ω6 | 0.32 | Δ5/6 desaturase, Δ5/6/9 elongase |
| | — | 18:4ω3 | 1.1 | |
| | — | 20:4ω6 | 1.1 | |
| | — | 20:5ω3 | 2.1 | |
| | — | 20:3ω6 | 1.1 | |
| | — | 20:4ω3 | 0.40 | |
| | — | 20:2ω6 | 3.2 | |
| | — | 20:3ω3 | TR | |
| | — | 22:4ω6 | 0.06 | |
| | — | 22:5ω3 | 0.13 | |
| | — | 22:3ω6 | 0.03 | |

TR, trace, not accurately determined.

Functional Characterization of *C. elegans* Elongase Gene in Yeast

Yeast strain S288 was transformed, using the method described in Example 1, with both vectors pYES2-zfΔ5/6 and pSEC-Ceelo simultaneously and double transformants were selected on YMM medium that lacked tryptophan and uracil. The transformants grew well on both minimal and enriched media, in contrast to transformants of strain S288 carrying pSEC-Ceelo alone, in the absence of pYES2-zfΔ5/6, which grew quite poorly. Double transformants were grown in YMM medium and induced by the addition of galactose. The fatty acid 18:3ω3 (ALA, 0.5 mM) was added to the medium and, after 48 hours incubation, cells were harvested and fatty acid analysis carried out by capillary gas-liquid chromatography (GC) as described in Example 1. The analysis showed that 18:4ω3 (0.82% of total fatty acid) and 20:3ω3 (0.20%) were formed from 18:3ω3, and 20:4ω3 (0.02% of fatty acids) from either of those, demonstrating the concerted action of an elongase activity in addition to the Δ6 desaturase activity and Δ5 desaturase activity of the zebrafish desaturase (Table 5). The concerted action of a bifunctional Δ5/6 desaturase gene and an elongase gene has not been reported previously. In particular, the use of a bifunctional enzyme, if showing the same activities in plant cells, would reduce the number of genes that would need to be introduced and expressed. This also has not been reported previously.

Example 5

Coordinate Expression of Fatty Acid Desaturase and Elongase in Plants

Genetic Construct for Co-Expression of the Zebrafish Δ6/Δ5 Desaturase and *C. elegans* Elongase in Plant Cells Beaudoin and colleagues (2000) showed that the *C. elegans* Δ6 elongase protein, when expressed in yeast, could elongate the C18 Δ6 desaturated fatty acids GLA and SDA, i.e. that it had Δ6 elongase activity on C18 substrates. They also showed that the protein did not have Δ5 elongase activity on a C20 substrate in yeast. We tested, therefore, whether this elongase would be able to elongate the Δ6 desaturated fatty acids GLA and SDA in *Arabidopsis* seed. *Arabidopsis thaliana* seed have been shown to contain both omega-6 (18:2, LA) and omega-3 (18:3, ALA) fatty acids (Singh et al, 2001). The presence of 18:3 in particular makes *Arabidopsis* seed an excellent system to study the expression of genes that could lead to the synthesis of omega-3 $C_{20}$+PUFA like EPA and DHA.

The test for elongase activity in *Arabidopsis* required the coordinate expression of a Δ6 desaturase in the seed to first form GLA or SDA. We chose to express the elongase gene in conjunction with the zebrafish desaturase gene described above. There were no previous reports of the expression of the zebra fish Δ6/Δ5 desaturase and *C. elegans* elongase genes in plant cells, either individually or together.

Seed-specific co-expression of the zebra fish Δ6/Δ5 desaturase and *C. elegans* elongase genes was achieved by placing the genes independently under the control of a −309 napin promoter fragment, designated Fp1 (Stalberg et al., 1993). For plant transformation, the genes were inserted into the binary vector pWvec8 that comprised an enhanced hygromycin resistance gene as selectable marker (Wang et al., 1997). To achieve this, the *C. elegans* elongase coding region from Example 4 was inserted as a blunt-end fragment between the Fp1 and Nos 3' polyadenylation/terminator fragment in the binary vector pWvec8, forming pCeloPWvec8. The zebrafish Δ5/Δ6 desaturase coding region from Example 3 was initially inserted as a blunt end fragment between the Fp1 and Nos 3' terminator sequences and this expression cassette assembled between the HindIII and ApaI cloning sites of the pBluescript cloning vector (Stratagene). Subsequently, the entire vector containing the desaturase expression cassette was inserted into the HindIII site of pCeloPWvec8, forming pZebdesatCeloPWvec8. The construct, shown schematically in FIG. 3, was introduced into *Agrobacterium* strain AGL1 (Valvekens et al., 1988) by electroporation prior to transformation into *Arabidopsis thaliana*, ecotype Columbia. The construct was also designated the "DO" construct, and plants obtained by transformation with this construct were indicated by the prefix "DO".

Plant Transformation and Analysis

Plant transformation was carried out using the floral dipping method (Clough and Bent, 1998). Seeds (T1 seeds) from the treated plants (T0 plants) were plated out on hygromycin (20 mg/l) selective media and transformed plants selected and transferred to soil to establish T1 plants. One hygromycin resistant plant was recovered from a first screen and established in soil. The transformation experiment was repeated and 24 further confirmed T1 transgenic plants were recovered and established in soil. Most of these T1 plants were expected to be heterozygous for the introduced transgenes.

T2 seed from the 25 transgenic plants were collected at maturity and analysed for fatty acid composition. As summarised in Table 6, seed of untransformed *Arabidopsis* (Columbia ecotype) contained significant amounts of both the ω6 and ω3, C18 fatty acid precursors LA and ALA but did not contain any Δ6-desaturated C18 (18:3ω6 or 18:4ω3), ω6-desaturated C20 PUFA or ω3-desaturated C20 PUFA. In contrast, fatty acids of the seed oil of the transformed plants comprising the zebra fish Δ5/Δ6 desaturase and *C. elegans* elongase gene constructs contained 18:3ω6, 18:4ω3 and a whole series of ω6-

TABLE 6

Fatty acid composition in transgenic seed (% of the total fatty acid in seed oil).

| Plant number | Fatty acid | | | | | | | | | | |
|---|---|---|---|---|---|---|---|---|---|---|---|
| | GLA 18:3ω6 | SDA 18:4ω3 | ARA 20:4ω6 | EPA 20:5ω3 | DGLA 20:3ω6 | ETA 20:4ω3 | EDA 20:2ω6 | ETrA 20:3ω3 | 22:4ω6 | DPA 22:5ω3 | 22:3ω6 |
| Wt | — | — | — | — | — | — | — | — | — | — | — |
| DO1 | 0.32 | 1.10 | 1.10 | 2.10 | 1.10 | 0.40 | 3.20 | TR | 0.06 | 0.13 | 0.03 |
| DO2 | 0.20 | 0.70 | 0.60 | 1.20 | 0.80 | 0.40 | 1.60 | — | 0.10 | TR | — |
| DO3 | 0.20 | 0.50 | 0.40 | 0.80 | 0.60 | 0.30 | 1.90 | — | TR | TR | — |
| DO4 | 0.30 | 0.90 | 0.80 | 1.30 | 1.10 | 0.50 | 1.90 | — | — | 0.10 | — |
| DO5 | 0.10 | 0.50 | 0.20 | 0.40 | 0.40 | — | 0.30 | — | TR | TR | — |
| DO6 | 0.30 | 1.00 | 1.00 | 1.70 | 1.20 | 0.50 | 2.50 | — | 0.10 | 0.10 | — |
| DO7 | 0.10 | 0.40 | 0.40 | 0.70 | 0.70 | 0.30 | 1.60 | — | TR | TR | — |
| DO8 | 0.30 | 1.20 | 1.10 | 2.10 | 1.40 | 0.60 | 2.80 | — | 0.10 | 0.10 | — |
| DO9 | 0.30 | 1.30 | 0.90 | 2.20 | 1.30 | 0.60 | 3.10 | — | 0.10 | 0.10 | — |
| DO10 | 0.10 | 0.40 | 0.30 | 0.70 | 0.50 | 0.30 | 0.10 | — | TR | TR | — |
| DO11 | 0.30 | 1.00 | 1.40 | 2.30 | 1.50 | 0.60 | 3.20 | — | 0.10 | 0.20 | — |
| DO12 | 0.40 | 1.40 | 1.10 | 1.90 | 1.20 | 0.60 | 2.30 | — | 0.10 | 0.10 | — |
| DO13 | 0.20 | 0.60 | 0.60 | 0.90 | 0.80 | 0.40 | 0.40 | — | TR | 0.10 | — |
| DO14 | 0.30 | 1.00 | 0.70 | 1.70 | 1.10 | 0.60 | 2.50 | — | TR | TR | — |
| DO15 | 0.30 | 1.30 | 1.00 | 2.30 | 1.50 | 0.60 | 2.60 | — | 0.10 | 0.10 | — |
| DO17 | 0.20 | 0.40 | 0.40 | 0.70 | 0.70 | 0.30 | 1.80 | — | TR | TR | — |
| DO18 | 0.20 | 0.60 | 0.50 | 0.90 | 0.80 | 0.40 | 1.70 | — | TR | TR | — |
| DO19 | 0.20 | 0.40 | 0.40 | 0.80 | 0.70 | 0.30 | 2.00 | — | TR | 0.10 | — |
| DO20 | 0.30 | 1.00 | 0.50 | 0.90 | 0.70 | 0.30 | 1.60 | — | TR | TR | — |
| DO21 | 0.30 | 1.20 | 0.90 | 2.00 | 1.30 | 0.60 | 2.50 | — | — | 0.10 | — |
| DO22 | 0.30 | 0.90 | 0.70 | 1.20 | 1.00 | 0.40 | 0.30 | — | TR | TR | — |
| DO23 | — | — | — | — | 0.10 | 0.10 | 1.80 | — | — | — | — |
| DO24 | 0.30 | 1.10 | 0.70 | 1.50 | 1.10 | 0.50 | 2.90 | — | TR | 0.10 | — |
| DO25 | 0.10 | 0.50 | 0.30 | 0.70 | 0.50 | 0.20 | 1.60 | — | TR | 0.10 | — |

Wt = untransformed *Arabidopsis* (Columbia). TR indicates less than 0.05%. Dash (—) indicates not detected.

and ω3-C20 PUFA. These resulted from the sequential action of the desaturase and elongase enzymes on the respective C18 precursors. Most importantly and unexpectedly, the transgenic seed contained both 20:5ω3 (EPA), reaching at least 2.3% of the total fatty acid in the seedoil, and 22:5ω3 (DPA), reaching at least 0.2% of this omega-3 LC-PUFA in the fatty acid of the seedoil. The total C20 fatty acids produced in the transgenic seed oil reached at least 9.0%. The total ω3 fatty acids produced that were a product of Δ6 desaturation (i.e. downstream of 18:3ω3 (ALA), calculated as the sum of the percentages for 18:4ω3 (SDA), 20:4ω3 (ETA), 20:5ω3 (EPA) and 22:5ω3 (DPA)) reached at least 4.2%. These levels represent a conversion efficiency of ALA, which is present in seed oil of the wild-type *Arabidopsis* plants used for the transformation at a level of about 13-15%, to ω3 products through a Δ6 desaturation step of at least 28%. Stated otherwise, the ratio of ALA products to ALA (products:ALA) in the seed oil was at least 1:3.6. Of significance here. *Arabidopsis* has a relatively low amount of ALA in its seed oil compared to some commercial oilseed crops.

The T2 lines described above included lines that were homozygous for the transgenes as well as heterozygotes. To distinguish homozygotes and heterozygotes for lines expressing the transgenes at the highest levels, T2 plants were established from the T2 seed for the 5 lines containing the highest EPA levels, using selection on MS medium containing hygromycin (15 mg/L) to determine the presence of the transgenes. For example, the T2 seed was used from the T1 plant designated DO11, containing 2.3% EPA and showing a 3:1 segregation ratio of resistant to susceptible progeny on the hygromycin medium, indicating that DO11 contained the transgenes at a single genetic locus. Homozygous lines were identified. For example, T2 progeny plant DO11-5 was homozygous as shown by the uniformly hygromycin resistance in its T3 progeny. Other T2 plants were heterozygous for the hygromycin marker.

The fatty acid profiles of T3 seed lots from DO11-5 and other T2 progeny of DO11 were analysed and the data are presented in Table 7. As expected, the EPA contents reflected segregation of the DO construct. The levels of EPA in the fatty acid of the seedoil obtained from the T3 lines were in three groups: negligible (nulls for the DO construct), in the range 1.6-2.3% (heterozygotes for the DO construct) and reaching at least 3.1% (homozygotes for the DO construct). The levels obtained were higher in homozygotes than heterozygotes, indicating a gene dosage effect. T3 seed from the DO11-5 plant synthesized a total of 9.6% new ω3 and ω6 PUFAs, including 3.2% EPA, 1.6% ARA, 0.1% DPA, 0.6% SDA and 1.8% GLA (Table 7). This level of EPA synthesis in seed was four fold higher than the 0.8% level previously achieved in linseed

TABLE 7

Fatty acid composition in transgenic seed (% of the total fatty acid in seed oil).

| Fatty acid | Wildtype | DO11-5 | DO11-6 | DO11-7 | DO11-8 | DO11-10 | DO11-11 | DO11-12 |
|---|---|---|---|---|---|---|---|---|
| 14:0 | 0.3 | 0.0 | 0.1 | 0.1 | 0.1 | 0.1 | 0.0 | 0.1 |
| 15:0 | 0.0 | 0.0 | 0.2 | 0.2 | 0.2 | 0.1 | 0.0 | 0.1 |
| 16:1ω7 | 0.5 | 0.4 | 0.6 | 0.7 | 0.6 | 0.5 | 0.4 | 0.6 |
| 16:0 | 8.1 | 7.1 | 7.9 | 7.8 | 7.6 | 7.0 | 7.1 | 7.8 |
| 17:1ω8 | 0.0 | 0.0 | 0.0 | 0.1 | 0.1 | 0.1 | 0.0 | 0.1 |

TABLE 7-continued

Fatty acid composition in transgenic seed (% of the total fatty acid in seed oil).

| | | | | | | | | | |
|---|---|---|---|---|---|---|---|---|---|
| 17:0 | | 0.3 | 0.1 | 0.0 | 0.1 | 0.1 | 0.1 | 0.0 | 0.1 |
| 18:3ω6 | GLA | 0.0 | 0.6 | 0.0 | 0.0 | 0.0 | 0.3 | 0.3 | 0.0 |
| 18:4ω3 | SDA | 0.0 | 1.8 | 0.0 | 0.0 | 0.0 | 1.0 | 1.1 | 0.0 |
| 18:2ω6 | LA | 26.6 | 25.8 | 29.8 | 28.6 | 28.8 | 25.6 | 25.4 | 28.6 |
| 18:1ω9 | | 17.9 | 18.7 | 15.6 | 19.6 | 18.2 | 22.0 | 18.6 | 18.6 |
| 18:1ω7/ 18:3ω3 | ALA | 16.0 | 11.5 | 15.3 | 14.7 | 15.9 | 10.6 | 11.6 | 14.5 |
| 18:0 | | 3.4 | 4.2 | 2.9 | 2.7 | 2.8 | 3.5 | 3.9 | 2.8 |
| 19:0 | | 0.0 | 0.0 | 0.0 | 0.0 | 0.0 | 0.0 | 0.0 | 0.0 |
| 20:4ω6 | ARA | 0.0 | 1.6 | 0.0 | 0.0 | 0.0 | 0.9 | 0.9 | 0.0 |
| 20:5ω3 | EPA | 0.0 | 3.2 | 0.0 | 0.1 | 0.0 | 1.6 | 2.1 | 0.0 |
| 20:3ω6 | DGLA | 0.0 | 1.9 | 0.0 | 0.0 | 0.0 | 1.2 | 1.5 | 0.0 |
| 20:4ω3 | ETA | 0.0 | 0.4 | 0.0 | 0.0 | 0.0 | 0.4 | 0.6 | 0.0 |
| 20:2ω6 | | 0.0 | 3.4 | 0.2 | 0.1 | 0.2 | 2.2 | 3.1 | 0.1 |
| 20:1ω9/ ω11 | | 17.4 | 10.9 | 17.8 | 18.1 | 17.3 | 14.8 | 12.5 | 18.2 |
| 20:1ω7 | | 1.9 | 2.7 | 2.2 | 1.9 | 2.2 | 2.2 | 2.3 | 2.0 |
| 20:0 | | 1.8 | 1.8 | 2.1 | 1.8 | 2.0 | 2.0 | 2.0 | 2.0 |
| 22:4ω6 | | 0.0 | 0.0 | 0.0 | 0.0 | 0.0 | 0.1 | 0.0 | 0.0 |
| 22:5ω3 | DPA | 0.0 | 0.1 | 0.0 | 0.0 | 0.0 | 0.1 | 0.1 | 0.0 |
| 22:1ω11/ ω13 | | 0.0 | 0.0 | 0.0 | 0.0 | 0.0 | 0.0 | 0.0 | 0.0 |
| 22:1ω9 | | 1.3 | 0.8 | 1.9 | 1.7 | 1.7 | 1.5 | 1.1 | 1.7 |
| 22:1ω7 | | 0.0 | 0.0 | 0.2 | 0.1 | 0.2 | 0.1 | 0.0 | 0.1 |
| 22:0 | | 0.2 | 0.3 | 0.3 | 0.3 | 0.3 | 0.3 | 0.4 | 0.3 |
| 24:1ω9 | | 0.6 | 0.4 | 0.2 | 0.2 | 0.3 | 0.2 | 0.2 | 0.2 |
| 24:1ω7 | | 0.0 | 0.2 | 0.0 | 0.0 | 0.0 | 0.0 | 0.0 | 0.0 |
| 24:0 | | 0.0 | 0.2 | 0.2 | 0.2 | 0.2 | 0.2 | 0.2 | 0.2 |

| Fatty acid | | | DO11-13 | DO11-16 | DO11-18 | DO11-19 | DO11-20 | DO11-21 |
|---|---|---|---|---|---|---|---|---|
| 14:0 | | | 0.1 | 0.1 | 0.1 | 0.1 | 0.1 | 0.1 |
| 15:0 | | | 0.1 | 0.1 | 0.1 | 0.1 | 0.2 | 0.1 |
| 16:1ω7 | | | 0.5 | 0.6 | 0.4 | 0.4 | 0.7 | 0.5 |
| 16:0 | | | 7.7 | 7.6 | 6.8 | 6.7 | 7.6 | 7.3 |
| 17:1ω8 | | | 0.1 | 0.0 | 0.1 | 0.1 | 0.0 | 0.1 |
| 17:0 | | | 0.1 | 0.1 | 0.1 | 0.1 | 0.0 | 0.1 |
| 18:3ω6 | GLA | | 0.4 | 0.0 | 0.2 | 0.3 | 0.0 | 0.4 |
| 18:4ω3 | SDA | | 1.3 | 0.0 | 0.7 | 1.1 | 0.0 | 1.2 |
| 18:2ω6 | LA | | 25.6 | 29.0 | 25.7 | 25.2 | 29.4 | 27.3 |
| 18:1ω9 | | | 20.4 | 15.5 | 20.1 | 19.8 | 16.6 | 14.8 |
| 18:1ω7/ 18:3ω3 | ALA | | 11.1 | 16.0 | 13.7 | 13.6 | 14.8 | 13.1 |
| 18:0 | | | 3.9 | 2.9 | 3.3 | 3.4 | 2.9 | 3.7 |
| 19:0 | | | 0.1 | 0.0 | 0.1 | 0.1 | 0.0 | 0.1 |
| 20:4ω6 | ARA | | 1.3 | 0.0 | 0.4 | 0.8 | 0.0 | 1.3 |
| 20:5ω3 | EPA | | 2.1 | 0.0 | 1.1 | 1.8 | 0.0 | 2.3 |
| 20:3ω6 | DGLA | | 1.4 | 0.0 | 0.7 | 1.0 | 0.0 | 1.5 |
| 20:4ω3 | ETA | | 0.2 | 0.0 | 0.3 | 0.4 | 0.0 | 0.5 |
| 20:2ω6 | | | 2.4 | 0.2 | 1.7 | 2.1 | 0.1 | 2.8 |
| 20:1ω9/ ω11 | | | 13.2 | 18.0 | 15.4 | 14.0 | 18.6 | 12.4 |
| 20:1ω7 | | | 2.0 | 2.3 | 2.2 | 2.2 | 2.3 | 2.7 |
| 20:0 | | | 1.9 | 2.2 | 2.0 | 2.0 | 2.3 | 2.1 |
| 22:4ω6 | | | 0.1 | 0.0 | 0.0 | 0.0 | 0.0 | 0.1 |
| 22:5ω3 | DPA | | 0.1 | 0.0 | 0.1 | 0.1 | 0.0 | 0.2 |
| 22:1ω11/ ω13 | | | 0.0 | 0.0 | 0.0 | 0.0 | 0.0 | 0.0 |
| 22:1ω9 | | | 1.1 | 2.0 | 1.6 | 1.4 | 2.1 | 1.5 |
| 22:1ω7 | | | 0.0 | 0.2 | 0.1 | 0.1 | 0.2 | 0.2 |
| 22:0 | | | 0.3 | 0.4 | 0.3 | 0.3 | 0.4 | 0.4 |
| 24:1ω9 | | | 0.2 | 0.3 | 0.2 | 0.2 | 0.2 | 0.3 |
| 24:1ω7 | | | 0.0 | 0.0 | 0.0 | 0.0 | 0.0 | 0.0 |
| 24:0 | | | 0.2 | 0.2 | 0.2 | 0.2 | 0.2 | 0.3 |

Wild-type here refers to untransformed *Arabidopsis thaliana*, ecotype Columbia (Abbadi et al., 2004). Considering also that the level of ALA precursor for EPA synthesis in *Arabidopsis* seed was less than a third of that present in linseed, it appeared that the LC-PUFA pathway as described above which included a desaturase that was capable of using an acyl-CoA substrate, was operating with significantly greater efficiency than the acyl-PC dependent desaturase pathway expressed in linseed.

The relative efficiencies of the individual enzymatic steps encoded by the EPA construct can be assessed by examining the percentage conversion of substrate fatty acid to product fatty acids (including subsequent derivatives) in DO11-5. The zebra-fish Δ5/Δ6 desaturase exhibited strong Δ5 desaturation, with 89% of 20:4ω3 being converted to EPA and DPA, and 45% of 20:3ω6 being converted to ARA, consistent with the previously reported preference of this enzyme for ω3 PUFA over ω6 PUFA substrates (Hastings et al., 2001). In comparison, Δ6-desaturation occurred at significantly lower levels, with 32% of ALA and 14% LA being converted to Δ6-desaturated PUFA. Given that previous studies in yeast showed this enzyme to actually have higher Δ6-desaturase activity than Δ5-desaturase activity, the lower Δ6-desaturation levels achieved in *Arabidopsis* seeds could be reflect a limited availability of ALA and LA substrates in the acyl-CoA pool (Singh et al., in press). The Δ6-elongase operated highly efficiently, with 86% of GLA and 67% of SDA being elongated, suggesting that this enzyme may have a slight preference for elongation of ω6-PUFA substrate.

The germination ability of the T2 (segregating) and T3 seed (homozygous population) was assessed on MS medium and on soil. Seed from the EPA and DPA containing lines DO11 and DO11-5 showed the same timing and frequency of germination as wild-type seed, and the T2 and T3 plants did not have any apparent abnormal morphological features. Plant growth rates in vitro or in soil and the quantities of seed obtained from the plants were also unaffected. Including the germination of the T1 seed from which plant DO11 was obtained, the normal germination of seed of the DO11 line was thus observed over three generations. In addition, normal germination rates and timing were also observed for the other EPA and DPA containing seed. This feature was both important and not predictable, as higher plants do not naturally produce EPA or DPA and their seed therefore has never previously contained these LC-PUFA. Germination requires the catabolism of stored seed oils and use for growth and as an energy supply. The observed normal germination rates showed that plant seed were able to carry out these processes using EPA and DPA, and that these compounds were not toxic.

It has been reported that a Δ4 desaturase encoded by a gene isolated from *Thraustochytrium* spp and expressed in *Brassica juncea* leaves was able to convert exogenously supplied DPA to DHA (Qiu et al., 2001). DPA produced in the plant seed described herein can serve as a precursor for DHA production. This conversion of DPA to DHA may be achieved in plant cells by the introduction of a Δ4 desaturase gene into the DPA producing plant cells (Example 11).

Discussion

The presence of 22:5ω3 in the *Arabidopsis* seed oil implied that the *C. elegans* elongase gene not only had Δ6 elongase activity, but also Δ5 elongase activity in plant cells. This result was most surprising given that the gene had been demonstrated to lack Δ5 elongase activity in yeast. Furthermore, this demonstrated that only two genes could be used for the synthesis of DPA from ALA in plant cells. The synthesis of DPA in a higher plant has not previously been reported. Furthermore, the conversion efficiency of ALA to its ω3 products in seed, including EPA. DPA or both, of at least 28% was striking.

Synthesis of LC-PUFA such as EPA and DHA in cells such as plant cells by the Δ6 desaturation pathway required the sequential action of PUFA desaturases and elongases. The required desaturases in one pathway had Δ6, Δ5 and Δ4 desaturating activity, in that order, and the required PUFA elongases had elongating activity on Δ6 and Δ5 substrates. This conventional pathway operates in algae, mosses, fungi, diatoms, nematodes and some freshwater fish (Sayanova and Napier, 2004). The PUFA desaturases from algae, fungi, mosses and worms are selective for desaturation of fatty acids esterified to the sn-2 position of phosphatidylcholine (PC) while the PUFA elongases act on fatty acids in the form of acyl-CoA substrates represented in the acyl-CoA pool of tissues. In contrast, vertebrate Δ6 desaturases have been shown to be able to desaturate acyl-CoA substrates (Domergue et al., 2003a).

Attempts to reconstitute LC-PUFA pathways in plant cells and other cells have to take into account the different sites of action and substrate requirements of the desaturases and elongase enzymes. For example, PUFA elongases are membrane bound, and perhaps even integral membrane proteins, which use acyl-CoAs which are present as a distinct pool in the endoplasmic reticulum (ER). This acyl-CoA pool is physiologically separated from the PC component of the ER, hence for a PUFA fatty acid to be sequentially desaturated and elongated it has to be transferred between PC and acyl-CoA pools in the ER. Therefore, earlier reported attempts to constitute LC-PUFA biosynthesis in yeast using desaturases and elongase from lower and higher plants, fungi and worms, have been inefficient, at best. In addition, the constituted pathways have led to the synthesis of only C20 PUFA such as ARA and EPA. There is no previous report of the synthesis C22 PUFA such as DPA and DHA in yeast (Beaudoin et al., 2000, Domergue et al., 2003a).

The strategy described above of using a vertebrate desaturase, in this example a Δ5/Δ6 desaturase from zebra fish, with a Δ6 PUFA elongase from *C. elegans* had the advantage that both the desaturase and the elongase have activity on acyl-CoA substrates in the acyl-CoA pool. This may explain why this strategy was more efficient in the synthesis of LC-PUFA. Furthermore, using a bifunctional desaturase displaying dual Δ5/Δ6 desaturase activities allowed the synthesis of EPA by the action of only 2 genes instead of the 3 genes used by other researchers (Beaudoin et al., 2000, Domergue et al., 2003a). The use of a bifunctional Δ5/Δ6 elongase in plant cells also allowed the formation of DPA from ALA by the insertion of only three genes (one elongase and two desaturases) or, as exemplified, of only two genes (bifunctional elongase and bifunctional desaturase). Both of these aspects were surprising and unexpected.

Biochemical evidence suggests that the fatty acid elongation consists of 4 steps: condensation, reduction, dehydration and a second reduction. Two groups of condensing enzymes have been identified so far. The first are involved in the synthesis of saturated and monosaturated fatty acids (C18-22). These are the FAE-like enzymes and do not appear to have a role in LC-PUFA biosynthesis. The other class of elongases identified belong to the ELO family of elongases named after the ELO gene family whose activities are required for the synthesis of the very long-chain fatty acids of sphingolipids in yeast. Apparent paralogs of the ELO-type elongases isolated from LC-PUFA synthesizing organisms like algae, mosses, fungi and nematodes have been shown to be involved in the elongation and synthesis of LC-PUFA. It has been shown that only the expression of the condensing component of the elongase is required for the elongation of the respective acyl chain. Thus the introduced condensing component of the elongase is able to successfully recruit the reduction and dehydration activities from the transgenic host to carry out successful acyl elongations. Thus far, successful elongations of C16 and C18 PUFA have been demonstrated in yeast by the heterologous expression of ELO type elongases. In this regard, the *C. elegans* elongase used as described above was unable to elongate C20 PUFA when expressed in yeast (Beaudoin et al, 2000). Our demonstration that the *C. elegans* elongase, when expressed in plants, was able to elongate the C20:5 fatty acid EPA as evidenced by the production of DPA in *Arabidopsis* seed was a novel and unexpected result. One explanation as to why the *C. elegans* elongase was able to elongate C20 PUFA in plants, but not in yeast, might reside in its ability to interact successfully with the other components of the elongation machinery of plants to bind and act on C20 substrates.

This example showed that an ELO-type elongase from a non-vertebrate organism was able to elongate C20 PUFA in plant cells. Leonard et al. (2002) reported that an ELO-type elongase gene isolated from humans, when expressed in yeast, was able to elongate EPA to DPA but in a non-selective fashion.

Example 6

Isolation of a Δ8 Desaturase Gene from *P. salina* and Functional Characterization in Yeast Microalgae are the only organisms which have been reported to contain Δ8 desaturases, aside from the Δ8 sphingolipid desaturases in higher plants that are not involved in LC-PUFA biosynthesis. A gene encoding a Δ8 desaturase has been isolated from *Euglena gracilis* (Wallis and Browse, 1999). The existence of a Δ5 desaturase in *Isochrysis galbana* may be presumed because it contains a Δ9 elongase (Qi et al., 2002), the product of which, 20:3n-3, is the precursor for a Δ8 desaturase (see FIG. 1). The fatty acid profiles of microalgae alone, however, do not provide sufficient basis for identifying which microalgae will contain Δ8 desaturase genes since multiple pathways may operate to produce the LC-PUFA.
Isolation of a Δ5 Desaturase Gene Fragment An alignment of Δ6 desaturase amino acid sequences with those from the following Genbank accession numbers, AF465283, AF007561, AAC15586 identified the consensus amino acid sequence blocks DHPGGS (SEQ ID NO:43), WWKDKHN (SEQ ID NO:44) and QIEHHLF (SEQ ID NO:45) corresponding to amino acid positions 204-210 and 394-400, respectively, of AF465283. DHPGSS corresponded to the "cytochrome b5 domain" block that had been identified previously (Mitchell and Martin, 1995). WWKDKHN was a consensus block that had not previously been identified or used to design degenerate primers for the isolation of desaturase genes. The QIEHHLF block, or variants thereof, corresponded to a required histidine-containing motif that was conserved in desaturases. It had been identified and used before as the "third His box" to design degenerate oligonucleotides for desaturase gene isolation (Michaelson et al., 1998). This combination of blocks had not been used previously to isolate desaturase genes.

Based on the second and third conserved amino acid blocks, the degenerate primers 5'-TGGTGGAARCAYAAR-CAYAAY-3' (SEQ ID NO:46) and 5'-GCGAGGGATCCA-AGGRAANARRTGRTGYTC-3' (SEQ ID NO:47) were synthesised. Genomic DNA from *P. salina* was isolated using the DNAeasy system (Qiagen). PCR amplifications were carried out in reaction volumes of 20 μL using 20 pmol of each primer, 200 ng of *P. salina* genomic DNA and Hotstar Taq DNA polymerase (Qiagen) with buffer and nucleotide components as specified. The cycling conditions were: 1 cycle of 95° C. for 15 minutes; 5 cycles of 95° C. 1 min; 38° C., 1 min; 72° C., 1 min; followed by 35 cycles of 95° C., 35 sec; 52° C., 30 sec; 72° C., 1 min; and finishing with 1 cycle of 72° C., 10 min. A 515 basepair amplicon was generated, ligated into pGEM-T easy (Promega), sequenced and used as a probe to screen a *P. salina* cDNA library.
Isolation of a cDNA Encoding a Δ8 Desaturase from *P. salina*

A *P. salina* cDNA library in λ-bacteriophage was constructed using the Zap-cDNA Synthesis Kit (Stratagene) (see Example 1). The library was plated out at a concentration of ~50,000 plaques per plate and lifts taken with Hybond N+ membrane and treated using standard methods (Ausubel et al., 1988, supra). The 515 bp desaturase fragment, generated by PCR, was radio-labelled with $^{32}$P-dCTP and used to probe the lifts under the following high stringency conditions: Overnight hybridisation at 65° C. in 6×SSC with shaking, a 5 minute wash with 2×SSC/0.1% SDS followed by two 10 minute washes with 0.2×SSC/0.1% SDS.

Fifteen primary library plates (150 mm) were screened for hybridization to the labeled 515 bp fragment. Forty strongly hybridizing plaques were identified and ten of these were carried through to a secondary screen. Plasmids from five secondary plaques hybridizing to the 515 bp probe were excised with ExAssist Helper phage according to the suppliers protocol (Stratagene). The nucleotide sequences of the inserts were obtained using the ABI Prism Big Dye Terminator kit (PE Applied Biosystems). The nucleotide sequences were identical where they overlapped, indicating that all five inserts were from the same gene. One of the five inserts was shown to contain the entire coding region, shown below to be from a Δ8 desaturase gene. This sequence is provided as SEQ ID NO:6.

The full-length amino acid sequence (SEQ ID NO:1) revealed that the isolated cDNA encoded a putative Δ6 or Δ8 desaturase, based on BLAST analysis. These two types of desaturases are very similar at the amino acid level and it was therefore not possible to predict on sequence alone which activity was encoded. The maximum degree of identity between the *P. salina* desaturase and other desaturases (BLASTX) was 27-30%, while analysis using the GAP program which allows the insertions of "gaps" in the alignment showed that the maximum overall amino acid identity over the entire coding regions of the *P. salina* desaturase and AAD45877 from *Euglena gracilis* was 45%. A Pileup diagram of other sequences similar to the *Pavlova salina* desaturase is provided in FIG. 4.

The entire coding region of this clone, contained within an EcoRI/XhoI fragment, was inserted into pYES2 (Invitrogen), generating pYES2-psΔ8, for introduction and functional characterisation in yeast. Cells of yeast strain S288 were transformed with pYES2-psΔ8 as described in Example 1, and transformants were selected on medium without uracil. The yeast cells containing pYES2-psΔ8 were grown in culture and then induced by galactose. After the addition of 18:3ω3 or 20:3ω3 (0.5 mM) to the culture medium and 48 hours of further culturing at 30° C., the fatty acids in cellular lipids were analysed as described in Example 1. When 18:3ω3 (Δ9, 12, 15) was added to the medium, no 18:4ω3 (Δ6, 9, 12, 15) was detected. However, when 20:3ω3 (Δ11, 14,17) was added to the medium, the presence of 20:4ω3 (Δ8,11,14,17) in the cellular lipid of the yeast transformants was detected (0.12%). It was concluded the transgene encoded a polypeptide having Δ8 but not Δ6 desaturase activity in yeast cells.

Isolation of a gene encoding a Δ8 fatty acid desaturase that does not also have Δ6 desaturase activity has not been reported previously. The only previously reported gene encoding a Δ8 desaturase that was isolated (from *Euglena gracilis*) was able to catalyse the desaturation of both 18:3ω3 and 20:3ω3 (Wallis and Browse, 1999). Moreover, expression of a gene encoding a Δ8 desaturase has not previously been reported in higher plants.

As shown in FIG. 1, expression of a Δ8 desaturase in concert with a Δ9 elongase (for example the gene encoding ELO2—see below) and a Δ5 desaturase (for example, the zebrafish Δ5/Δ6 gene or an equivalent gene from *P. salina* or other microalgae) would cause the synthesis of EPA in plants.

Aside from providing an alternative route for the production of EPA in cells, the strategy of using a Δ9 elongase in combination with the Δ8 desaturase may provide an advantage in that the elongation, which occurs on fatty acids coupled to CoA, precedes the desaturation, which occurs on fatty acids coupled to PC, thereby ensuring the availability of the newly elongated C20 PUFA on PC for subsequent desaturations by Δ8 and Δ5 desaturases, leading possibly to a more efficient synthesis of EPA. That is, the order of reactions—an elongation followed by two desaturations—will reduce the number of substrate linking switches that need to occur. The increased specificity provided by the *P. salina* Δ8 desaturase is a further advantage.

Example 7

Isolation of *P. salina* ELO1 and ELO2 Fatty Acid Elongases

ELO-type PUFA elongases from organisms such as nematodes, fungi and mosses have been identified on the basis of EST or genome sequencing strategies. A gene encoding a Δ9 elongase with activity on 18:30 (ALA) was isolated from *Isochrysis galbana* using a PCR approach with degenerate primers, and shown to have activity in yeast cells that were supplied with exogenous 18:2ω6 (LA) or 18:3ω3 (ALA), forming C20 fatty acids 20:2ω6 and 20:3ω3 respectively. The coding region of the gene IgASE1 encoded a protein of 263 amino acids with a predicted molecular weight of about 30 kDa and with limited homology (up to 27% identity) to other elongating proteins.

Isolation of Elongase Gene Fragments from *P. salina*

Based on multiple amino acid sequence alignments for fatty acid elongases the consensus amino acid blocks FLHXYH (SEQ ID NO:48) and MYXYYF (SEQ ID NO:49) were identified and the corresponding degenerate primers 5'-CAGGATCCTTYYTNCATNNNTAYCA-3' (SEQ ID NO:50) (sense) and 5'-GATCTAGARAARTAR-TANNNRTACAT-3' (SEQ ID NO:51) (antisense) were synthesised. Primers designed to the motif FLHXYH or their use in combination with the MYXYYF primer have not previously been described. These primers were used in PCR amplification reactions in reaction volumes of 20 µL with 20 pmol of each primer, 200 ng of *P. salina* genomic DNA and Hotstar Taq DNA polymerase (Qiagen) with buffer and nucleotide components as specified by the supplier. The reactions were cycled as follows: 1 cycle of 95° C. for 15 minutes, 5 cycles of 95° C., 1 min, 38° C., 1 min, 72° C., 1 min, 35 cycles of 95° C., 35 sec, 52° C., 30 sec, 72° C., 1 min, 1 cycle of 72° C., 10 min. Fragments of approximately 150 bp were generated and ligated into pGEM-Teasy for sequence analysis.

Of the 35 clones isolated, two clones had nucleotide or amino acid sequence with similarity to known elongases. These were designated Elo1 and Elo2. Both gene fragments were radio-labelled with $^{32}$P-dCTP and used to probe the *P. salina* cDNA library under the following high stringency conditions: overnight hybridisation at 65° C. in 6×SSC with shaking, 5 minute wash with 2×SSC/0.1% SDS followed by two 10 minute washes with 0.2×SSC/0.1% SDS. Ten primary library plates (150 mm) were screened using the Elo1 or Elo2 probes. Elo1 hybridized strongly to several plaques on each plate, whilst Elo2 hybridised to only three plaques in the ten plates screened. All Elo1-hybridising plaques were picked from a single plate and carried through to a secondary screen, whilst all three Elo2-hybridising plaques were carried through to a secondary screen. Each secondary plaque was then used as a PCR template using the forward and reverse primers flanking the multiple cloning site in the pBluescript phagemid and the PCR products electrophoresed on a 1% TAE gel. Following electrophoresis, the gel was blotted onto a Hybond N+ membrane and the membrane hybridised overnight with $^{32}$P-labelled Elo1 and Elo2 probes. Six of the amplified Elo1 secondary plaques and one of the amplified Elo2 secondary plaques hybridised to the Elo1/2 probe (FIG. 5).

Two classes of elongase-like sequences were identified in the *P. salina* cDNA library on the basis of their hybdridisation to the Elo1 and Elo2 probes. Phagemids that hybridised strongly to either labelled fragment were excised with ExAssist Helper phage (Stratagene), and sequenced using the ABI Prism Big Dye Terminator kit (PE Applied Biosystems). All of the 5 inserts hybridizing to the Elo1 probe were shown to be from the same gene. Similarly DNA sequencing of the 2 inserts hybridising to the Elo2 probe showed them to be from the same gene. The cDNA sequence of the Elo1 clone is provided as SEQ ID NO:8, and the encoded protein as SEQ ID NO:2, whereas the cDNA sequence of the Elo2 clone is provided as SEQ ID NO:10, and the encoded proteins as SEQ ID NO:3, SEQ ID NO:85 and SEQ ID NO:86 using three possible start methionines).

A comparison was performed of the Elo1 and Elo2 and other known PUFA elongases from the database using the PILEUP software (NCBI), and is shown in FIG. 6.

The Elo1 cDNA was 1234 nucleotides long and had a open reading frame encoding a protein of 302 amino acid residues. According to the PILEUP analysis, Elo1 clustered with other Elo-type sequences associated with the elongation of PUFA including Δ6 desaturated fatty acids (FIG. 6). The Elo1 protein showed the greatest degree of identity (33%) to an elongase from the moss, *P. patens* (Accession No. AF428243) across the entire coding regions. The Elo1 protein also displayed a conserved amino acids motifs found in all other Elo-type elongases.

The Elo2 cDNA was 1246 nucleotides long and had an open reading frame encoding a protein of 304 amino acid residues. According to PILEUP analysis, Elo2 clustered with other Elo-type sequences associated with the elongation of PUFA, including those with activity on Δ6 or Δ9 PUFA (FIG. 6). Elo2 was on the same sub-branch as the Δ9 elongase isolated from *Isochrysis galbana* (AX571775). Elo2 displayed 31% identity to the *Isochrysis* gene across its entire coding region. The Elo2 ORF also displayed a conserved amino acid motif found in all other Elo-type elongases.

Example 8

Functional Characterization of Δ5 Fatty Acid Elongase in Yeast and Plant Cells

Yeast

The entire coding region of the *P. salina* Elo1 gene was ligated into pYES2, generating pYES2-psELO1, for characterisation in yeast. This genetic construct was introduced into yeast strains and tested for activity by growth in media containing exogenous fatty acids as listed in the Table 8. Yeast cells containing pYES2-psELO1 were able to convert 20:5ω3 into 22:5ω3, confirming Δ5 elongase activity on C20 substrate. The conversion ratio of 7% indicated high activity for this substrate. The same yeast cells converted 18:4ω3 (Δ6,9,12,15) to 20:4ω3 and 18:3ω6 (Δ6,9,12) to 20:3ω6, demonstrating that the elongase also had Δ6 elongase activity in yeast cells, but at approximately 10-fold lower conversion rates (Table 8). This indicated that the Elo1 gene encodes a specific or selective Δ5 elongase in yeast cells. This represents the first report of a specific Δ5 elongase, namely an enzyme that has a greater Δ5 elongase activity when compared to Δ6 elongase activity. This molecule is also the first Δ5 elongase isolated from an algael source. This enzyme is critical in the conversion of EPA to DPA (FIG. 1).

Plants

The Δ5 elongase, Elo1 isolated from *Pavlova* is expressed in plants to confirm its ability to function in plants. Firstly, a plant expression construct is made for constitutive expression of Elo1. For this purpose, the Elo1 sequence is placed under the control of the 35S promoter in the plant binary vector pBI121 (Clontech). This construct is introduced into *Arabidopsis* using the floral dip method described above. Analysis of leaf lipids is used to determine the specificity of fatty acids elongated by the Elo1 sequence. In another approach, co expression of the Elo1 construct with the zebra fish Δ5/Δ6 desaturase/*C. elegans* elongase construct and the Δ4 desaturase isolated from *Pavlova*, results in DHA synthesis from ALA in *Arabidopsis* seed, demonstrating the use of the Δ5 elongase in producing DHA in cells. In a further approach, the Elo1 gene may be co-expressed with Δ6-desaturase and Δ5 desaturase genes, or a Δ6/Δ5 bifunctional desaturase gene, to produce DPA from ALA in cells, particularly plant cells. In an alternative approach, the Δ5 elongase and Δ4 elongase genes are used in combination with the PKS genes of *Shewanella* which produce EPA (Takeyama et al., 1997), in plants, for the synthesis of DHA.

TABLE 8

Conversion of fatty acids in yeast cells transformed with genetic constructs expressing Elo1 or Elo2.

| Clone | Fatty acid precursor/ (% of total FA) | Fatty acid formed/ (% of total FA) | Conversion ratio (%) |
|---|---|---|---|
| pYES2-psELO1 | 20:5n-3/3% | 22:5n-3/0.21% | 7% |
| pYES2-psELO1 | 18:4n-3/16.9% | 20:4n-3/0.15% | 0.89% |
| pYES2-psELO1 | 18:3n-6/19.8% | 20:3n-6/0.14% | 0.71% |
| pYES2-psELO2 | 20:5n-3/2.3% | 22:5n-3/tr | — |
| pYES2-psELO2 | 18:4n-3/32.5% | 20:4n-3/0.38% | 1.2% |
| pYES2-psELO2 | 18:3n-6/12.9% | 20:3n-6/0.08% | 0.62% |
| pYES2-psELO2 | 18:2n-6/30.3% | 20:2n-6/0.12% | 0.40% |
| pYES2-psELO2 | 18:3n-3/42.9% | 18:3n-3/0.20% | 0.47% | tr: trace amounts (<0.02%) detected.

Example 9

Functional Characterization of Δ9 Fatty Acid Elongase in Yeast and Plant Cells

Expression in Yeast Cells

The entire coding region of the *P. salina* Elo2 gene encoding a protein of 304 amino acids (SEQ ID NO:3) was ligated into pYES2, generating pYES2-psELO2, for characterisation in yeast. This genetic construct was introduced into yeast strains and tested for activity by growth in media containing exogenous fatty acids. Yeast cells containing pYES2-psELO2 were able to convert 18:2ω6 into 20:2ω6 (0.12% of total fatty acids) and 18:3ω3 into 20:3ω3 (0.20%), confirming Δ9 elongase activity on C18 substrates (Table 8). These cells were also able to convert 18:3ω6 into 20:3ω6 and 18:4ω3 into 20:4ω3, confirming Δ6 elongase activity on C18 substrates in yeast. However, since the 18:3ω6 and 18:4ω3 substrates also have a desaturation in the Δ9 position, it could be that the Elo2 enzyme is specific for Δ9-desaturated fatty acids, irrespective of whether they have a Δ6 desaturation as well. The cells were able to convert 20:5ω3 into the 22:5 product DPA. This is the first report of a Δ9 elongase that also has Δ6 elongase activity from a non-vertebrate source, in particular from a fungal or algal source.

As the coding region contained three possible ATG start codons corresponding to methionine (Met) amino acids at positions 1, 11 (SEQ ID NO:85) and 29 (SEQ ID NO:86) of SEQ ID NO:3, the possibility that polypeptides beginning at amino acid positions 11 or 29 would also be active was tested. Using 5' oligonucleotide (sense) primers corresponding to the nucleotide sequences of these regions, PCR amplification of the coding regions was performed, and the resultant products digested with EcoRI. The fragments are cloned into pYES2 to form pYES2-psELO2-11 and pYES2-psELO2-29. Both plasmids are shown to encode active Δ9-elongase enzymes in yeast. The three polypeptides may also be expressed in *Synechococcus* or other cells such as plant cells to demonstrate activity.

Expression in Plant Cells

The Δ9 elongase gene, Elo2, isolated from *Pavlova* was expressed in plants to confirm its ability to function in plants. Firstly, a plant expression construct is made for constitutive expression of Elo2. For this purpose, the Elo2 coding sequence from amino acid position 1 of SEQ ID NO:3 was placed under the control of the 35S promoter in the plant binary vector pBI121 (Clontech). This construct is introduced into *Arabidopsis* using the floral dip method described above. Analysis of leaf lipids indicates the specificity of fatty acids that are elongated by the Elo2 sequence.

Co-Expression of Δ9 Elongase and Δ8-Desaturase Genes in Transformed Cells

The *P. salina* Δ8-desaturase and Δ9-elongase were cloned into a single binary vector, each under the control of the constitutive 35S promoter and nos terminator. In this gene construct, pBI121 containing the Δ8-desaturase sequence was cut with HindIII and ClaI (blunt-ended) to release a fragment containing the 35S promoter and the Δ8-desaturase gene, which was then ligated to the HindIII+SacI (blunt ended) cut pXZP143/Δ9-elongase vector to result in the intermediate pJRP013. This intermediate was then opened with HindIII and ligated to a pWvec8/Δ9-elongase binary vector (also HindIII-opened) to result in the construct pJRP014, which contains both genes between the left and right T-DNA borders, together with a hygromycin selectable marker gene suitable for plant transformation.

This double-gene construct was then used to transform tobacco using a standard *Agrobacterium*-mediated transformation technique. Following introduction of the construct into *Agrobacterium* strain AGLI, a single transformed colony was used to inoculate 20 mL of LB media and incubated with shaking for 48 hours at 28° C. The cells were pelleted (1000 g for 10 minutes), the supernatant discarded, and the pellet resuspended in 20 mL of sterile MS media. This was step was then repeated before 10 ml of this Agrobacterial solution was added to freshly cut (1 cm squares) tobacco leaves from cultivar W38. After gentle mixing, the tobacco leaf pieces and *Agrobacterium* solution were allowed to stand at room temperature for 10 min. The leaf pieces were transferred to MS plates, sealed, and incubated (co-cultivation) for 2 days at 24° C. Transformed cells were selected on medium containing hygromycin, and shoots regenerated. These shoots were then cut off and transferred to MS-rooting media pots for root growth, and eventually transferred to soil. Both leaf and seed lipids from these plants are analysed for the presence of 20:2ω6, 20:3ω6, 20:3ω3 and 20:4ω3 fatty acids, demonstrating the co-expression of the two genes.

Discussion

Biochemical evidence suggests that the fatty acid elongation consists of 4 steps: condensation, reduction, dehydration and a second reduction, and the reaction is catalysed by a complex of four proteins, the first of which catalyses the condensation step and is commonly called the elongase. There are 2 groups of condensing enzymes identified so far. The first are involved in the synthesis of saturated and monounsaturated fatty acids (C18-22). These are the FAE-like enzymes and do not play any role in LC-PUFA biosynthesis. The other class of elongases identified belong to the ELO family of elongases named after the ELO gene family whose activities are required for the synthesis of very LC fatty acids of sphingolipids in yeast. Apparent paralogs of the ELO-type elongases isolated from LC-PUFA synthesizing organisms like algae, mosses, fungi and nematodes have been shown to be involved in the elongation and synthesis of LC-PUFA. It has been shown that only the expression of the condensing component of the elongase is required for the elongation of the respective acyl chain. Thus the introduced condensing component of the elongase is able to successfully recruit the reduction and dehydration activities from the transgenic host to carry out successful acyl elongations. This was also true for the P. saliva Δ9-elongase.

Example 10

Isolation of a Gene Encoding a Δ4-Desaturase from P. salina

The final step in the aerobic pathway of DHA synthesis in organisms other than vertebrates, such as microorganisms, lower plants including algae, mosses, fungi, and possibly lower animals, is catalysed by a Δ4-desaturase that introduces a double bond into the carbon chain of the fatty acid at the Δ4 position. Genes encoding such an enzyme have been isolated from the algae Euglena and Pavlova and from Thraustochytrium, using different approaches. For example, Δ4-desaturase genes from Pavlova lutheri and Euglena gracilis were isolated by random sequencing of cloned ESTs (EST approach, Meyer et al., 2003; Tonon et al., 2003), and a Δ4-desaturase gene from Thraustochytrium sp. ATCC21685 was isolated by RT-PCR using primers corresponding to a cytochrome $b_5$ HPGG domain and histidine box III region (Qiu et al., 2001). The cloned Δ4-desaturase genes encoded front-end desaturases whose members are characterised by the presence of an N-terminal cytochrome $b_5$-like domain (Napier et al., 1999; Sayanova and Napier, 2004).

Isolation of a Gene Fragment from a Δ4-Desaturase Gene from P. salina

Comparison of known moss and microalgae Δ4-desaturases revealed several conserved motifs including a HPGG (SEQ ID NO:52) motif within a cytochrome $b_5$-like domain and three histidine box motifs that are presumed to be required for activity. Novel degenerate PCR primers PavD4Des-F3 (5'-AGCACGACGSSARCCACGGCG-3') (SEQ ID NO:53) and PavD4Des-R3 (5'-GTGGTGCAY-CABCACGTGCT-3') (SEQ ID NO:54) corresponding to the conserved amino acid sequence of histidine box I and complementary to a nucleotide sequence encoding the amino acid sequence of histidine box II, respectively, were designed as to amplify the corresponding region of P. salina desaturase genes, particularly a Δ4-desaturase gene. The use of degenerate PCR primers corresponding to histidine box I and histidine box II regions of Δ4-desaturase has not been reported previously.

PCR amplification reactions using these primers were carried out using P. salina first strand cDNA as template with cycling of 95° C., 5 min for 1 cycle, 94° C. 30 sec, 57° C. 30 sec, 72° C. 30 sec for 35 cycles, and 72° C. 5 min for 1 cycles. The PCR products were cloned into pGEM-T-easy (Promega) vectors, and nucleotide sequences were determined with an ABI3730 automatic sequencer using a reverse primer from the pGEM-Teasy vector. Among 14 clones sequenced, three clones showed homology to Δ4-desaturase genes. Two of these three clones are truncated at one primer end. The nucleotide sequence of the cDNA insert of the third, clone 1803, is provided as SEQ ID NO:11.

The amino acid sequence encoded by SEQ ID NO:11 was used to search the NCBI protein sequence database using the BLASTX software. The results indicated that this sequence was homologous to known Δ4-desaturases. The amino acid sequence of the P. salina gene fragment showed 65%, 49%, 46% and 46% identity to that of Δ4-desaturases of P. lutheri, Thraustochytrium sp. ATCC21685. Thraustochytrium aureum and Euglena gracilis respectively.

Isolation of a Full-Length Δ4-Desaturase Gene

The insert from clone 1803 was excised, and used as probe to isolate full-length cDNAs corresponding to the putative Δ4-desaturase gene fragment. About 750,000 pfu of the P. salina cDNA library were screened at high stringency. The hybridization was performed at 60° C. overnight and washing was done with 2×SSC/0.1% SDS 30 min at 65° C. then with 0.2×SSC/0.1% SDS 30 min at 65° C. Eighteen hybridising clones were isolated and secondary screening with six clones was performed under the same hybridization conditions. Single plaques from secondary screening of these six clones were isolated. Plasmids from five single plaques were excised and the nucleotide sequences of the inserts determined with an ABI 3730 automatic sequencer with reverse and forward primers from the vector. Sequencing results showed that four clones each contained Δ4-desaturase cDNA of approximately 1.7 kb in length, each with the same coding sequence and each apparently full-length. They differed slightly in the length of the 5' and 3' UTRs even though they contained identical protein coding regions. The cDNA sequence of the longest P. salina M-desaturase cDNA is provided as SEQ ID NO:13, and the encoded protein as SEQ ID NO:4.

The full-length cDNA was 1687 nucleotides long and had a coding region encoding 447 amino acids. The Pavlova salina Δ4-desaturase showed all the conserved motifs typical of 'front-end desaturases' including the N-terminal cytochrome $b_5$-like domain and three conserved histidine-rich motifs. Comparison of the nucleotide and amino acid sequences with other Δ4-desaturase genes showed that the greatest extent of homology was for the P. lutheri Δ4-desaturase (Accession No. AY332747), which was 69.4% identical in nucleotide sequence over the protein coding region, and 67.2% identical in amino acid sequence.

Demonstration of Enzyme Activity of Pavlova salina Δ4-Desaturase Gene

A DNA fragment including the Pavlova salina Δ4-desaturase cDNA coding region was excised as an EcoRI-SalI cDNA fragment and inserted into the pYES2 yeast expression vector using the EcoRI and XhoI sites. The resulted plasmid was transformed into yeast cells. The transformants were grown in YMM medium and the gene induced by the addition of galactose, in the presence of added (exogenous) ω6 and ω3 fatty acids in order to demonstrate enzyme activity and the range of substrates that could be acted upon by the expressed gene. The fatty acids 22:5ω3 (DPA, 1.0 mM), 20:4n-3 (ETA, 1.0 mM), 22:4ω6 (DTAG, 1.0 mM) and 20:4ω6 (ARA, 1.0 mM) were each added separately to the medium. After 72 hours incubation, the cells were harvested and fatty acid analysis carried out by capillary gas-liquid chromatography (GC) as described in Example 1. The data obtained are shown in Table 9.

TABLE 9

Yeast PUFA feeding showing activity of delta-4 desaturase gene.

| Fatty acid composition | Exogenous fatty acid added to growth medium | |
|---|---|---|
| (% of total fatty acid) | 22:4ω6 | 22:5ω3 |
| 14:0 | 0.63 | 0.35 |
| 15:0 | 0.06 | 0.06 |
| 16:1ω7c | 43.45 | 40.52 |
| 16:1ω5 | 0.20 | 0.13 |
| 16:0 | 18.06 | 15.42 |
| 17:1ω8 | 0.08 | 0.09 |
| 17:0 | 0.08 | — |
| 18:1ω9 | 26.73 | 30.07 |
| 18:1ω7 (major) & 18:3ω3 | 1.43 | 1.61 |
| 18:1ω5c | 0.02 | tr |
| 18:0 | 7.25 | 8.87 |
| 20:5ω3 | 0.40 | 0.62 |
| 20:1ω9/ω11 | 0.03 | tr |
| 20:0 | 0.08 | 0.09 |
| 22:5ω6 | 0.03 | 0.00 |
| 22:6ω3 | — | 0.04 |
| 22:4ω6 | 0.97 | — |
| 22:5ω3 | 0.00 | 1.66 |
| 22:0 | 0.06 | 0.06 |
| 24:1ω7 | 0.31 | 0.37 |
| 24:0 | 0.12 | 0.04 |
| Sum | 100.00% | 100.00% |

This showed that the cloned gene encoded a Δ4-desaturase which was able to desaturate both C22:4ω6 (3.0% conversion to 22:5ω6) and C22:5ω3 (2.4% conversion to 22:6ω3) at the Δ4 position. The enzyme did not show any Δ5 desaturation activity when the yeast transformants were fed C20:3ω6 or C20:4ω3.

Example 11

Expression of *P. salina* Δ4-Desaturase Gene in Plant Cells and Production of DHA To demonstrate activity of the Δ4-desaturase gene in plant cells, the coding region may be expressed either separately to allow the conversion of DPA to DHA, or in the context of other LC-PUFA synthesis genes such as, for example, a Δ5-elongase gene for the conversion of EPA to DHA. For expression as a separate gene, the Δ4-desaturase coding region may be excised as a BamHI-SalI fragment and inserted between a seed-specific promoter and a polyadenylation/transcription termination sequence, such as, for example, in vector pGNAP (Lee et al., 1998), so that it is expressed under the control of the seed specific promoter. The expression cassette may then be inserted into a binary vector and introduced into plant cells. The plant material used for the transformation may be either untransformed plants or transformed plants containing a construct which expressed the zebrafish Δ5/Δ6-dual desaturase gene and *C. elegans* elongase gene each under the control of a seed specific promoter (Example 5). Transgenic *Arabidopsis* containing the latter, dual-gene construct had successfully produced EPA and DPA in seeds, and the combination with the Δ4-desaturase gene would allow the conversion of the DPA to DHA in the plant cells, as demonstrated below.

To demonstrate co-expression of a Δ5-elongase gene with the Δ4-desaturase gene in recombinant cells, particularly plant cells, and allow the production of DHA, the Δ4-desaturase and the Δ5-elongase genes from *P. salina* (Example 8) were combined in a binary vector as follows. Both coding regions were placed under the control of seed-specific (napin) promoters and nos3' terminators, and the binary vector construct had a kanamycin resistance gene as a selectable marker for selection in plant cells. The coding region of the Δ5-elongase gene was excised from its cDNA clone as a PstI-SacII fragment and inserted into an intermediate plasmid (pXZP143) between the promoter and terminator, resulting in plasmid pXZP144. The coding region of the Δ4-desaturase gene was excised from its cDNA clone as a BamHI-SalI fragment and inserted into plasmid pXZP143 between the promoter and nos 3' transcription terminator, resulting in plasmid pXZP150. These two expression cassettes were combined in one vector by inserting the HindIII-ApaI fragment from pXZP144 (containing promoter-Elo1-nos3') between the StuI and ApaI sites of pXZP150, resulting in plasmid pXZP191. The HindIII-StuI fragment from pXZP191 containing both expression cassettes was then cloned into the binary vector pXZP330, a derivative of pBI121, resulting in plant expression vector pXZP355. This vector is shown schematically in FIG. 7.

Plant Transformation

The Δ5-elongase and the Δ4-desaturase genes on pXZP355 were introduced by the *Agrobacterium*-mediated floral dip transformation method into the *Arabidopsis* plants designated DO11 (Example 5) which were already transgenic for the zebrafish Δ5/Δ6 bifunctional desaturase and the *C. elegans* Δ5/Δ6 bifunctional elongase genes. Since those transgenes were linked to a hygromycin resistance gene as a selectable marker gene, the secondary transformation with pXZP355 used a kanamycin resistance selection, thus distinguishing the two sets of transgenes. Five transgenic plants are obtained, designated "DW" plants. Since the DO11 plants were segregating for the zebrafish Δ5/Δ6 bifunctional desaturase and the *C. elegans* Δ5/Δ6 bifunctional elongase genes, some of the transformed plants were expected to be heterozygous for these genes, while others were expected to be homozygous. Seed (T2 seed) of the five transformed plants were analysed and shown to contain up to at least 0.1% DPA and up to at least 0.5% DHA in the seed oils. Data are presented for two lines in Table 10. Analysis, by mass spectrometry (GC-MS), of the fatty acids in the peaks identified as EPA and DHA from the GC analysis proved that they were indeed EPA and DHA (FIG. 8).

The fatty acid analysis of the T2 seedoil demonstrated that significant conversion of EPA to DHA had occurred in the DW2 and DW5 lines, having 0.2% and 0.5% DHA, respectively. Examination of the enzyme efficiencies in plant DW5 containing the higher level of DHA showed that 17% of the EPA produced in its seed was elongated to DPA by the *P. salina* Δ5-elongase, and greater than 80% of this DPA was converted to DHA by the *P. salina* Δ4-desaturase. Since the Δ5-elongase and Δ4-desaturase genes were segregating in the T2 seed, the fatty acid composition data represented an average of pooled null, heterozygous and homozygous genotypes for these genes. It is expected that levels of DHA in progeny lines of DW5 will be greater in seed that is uniformly homozygous for these genes.

TABLE 10

Fatty acid composition (% of total fatty acids) of seed oils from *Arabidopsis thaliana* (ecotype Columbia) and derivatives carrying EPA and DHA gene constructs - EPA, DPA and DHA synthesis in transgenic seed.

| | | DO11 + DHA construct | | | |
|---|---|---|---|---|---|
| | Wild type | DW2 | DW5 | | |
| Fatty acid | Columbia | Total | Total | TAG | PL |
| Usual fatty acids | | | | | |
| 16:0 | 7.2 | 6.7 | 6.1 | 5.5 | 12.5 |
| 18:0 | 2.9 | 3.8 | 4.4 | 4.3 | 4.5 |
| $18:1\Delta^9$ | 20.0 | 20.6 | 16.6 | 18.9 | 13.7 |
| $18:2\Delta^{9,12}$ (LA) | 27.5 | 26.0 | 25.9 | 25.5 | 33.1 |
| $18:3\Delta^{9,12,15}$ (ALA) | 15.1 | 13.2 | 15.0 | 13.6 | 15.1 |
| 20.0 | 2.2 | 2.1 | 1.8 | 1.9 | 0.6 |
| $20:1\Delta^{11}$ | 19.8 | 14.8 | 10.5 | 10.5 | 3.2 |
| $20:1\Delta^{13}$ | 2.2 | 3.0 | 4.2 | 4.8 | 1.4 |
| $20:2\Delta^{11,14}$ | 0.1 | 1.7 | 3.5 | 3.8 | 3.7 |
| $22:1\Delta^{13}$ | 1.5 | 1.4 | 1.0 | 0.3 | 0.4 |
| Other minor | 1.5 | 2.9 | 2.7 | 2.4 | 3.8 |
| Total | 100.0 | 96.0 | 91.7 | 91.5 | 92.0 |
| New ω6-PUFA | | | | | |
| $18:3\Delta^{6,9,12}$ (GLA) | 0 | 0.2 | 0.4 | 0.4 | 0.2 |
| $20:3\Delta^{8,11,14}$ | 0 | 0.8 | 1.5 | 1.5 | 1.7 |
| $20:4\Delta^{5,8,11,14}$ (ARA) | 0 | 0.4 | 1.0 | 1.1 | 1.2 |
| $22:4\Delta^{7,10,13,16}$ | 0 | 0 | 0 | 0 | 0.2 |
| $22:5\Delta^{4,7,10,13,16}$ | 0 | 0 | 0.1 | 0.1 | 0.1 |
| Total | 0 | 1.4 | 3.0 | 3.1 | 3.4 |
| New ω3-PUFA | | | | | |
| $18:4\Delta^{6,9,12,15}$ (SDA) | 0 | 0.7 | 1.5 | 1.6 | 0.5 |
| $20:4\Delta^{8,11,14,17}$ | 0 | 0.5 | 0.8 | 0.7 | 0.9 |
| $20:5\Delta^{5,8,11,14,17}$ (EPA) | 0 | 1.1 | 2.4 | 2.5 | 2.3 |
| $22:5\Delta^{7,10,13,16,19}$ (DPA) | 0 | 0.1 | 0.1 | 0.2 | 0.7 |
| $22:6\Delta^{4,7,10,13,16,19}$ (DHA) | 0 | 0.2 | 0.5 | 0.4 | 0.2 |
| Total | 0 | 2.6 | 5.3 | 5.4 | 4.6 |
| Total fatty acids | 100.0 | 100.0 | 100.0 | 100.0 | 100.0 |
| Total MUFA[a] | 41.3 | 36.8 | 28.1 | 29.7 | 17.3 |
| Total $C_{18}$-PUFA[b] | 42.6 | 39.2 | 40.9 | 39.1 | 48.2 |
| Total new PUFA[c] | 0 | 4.0 | 8.3 | 8.5 | 8.0 |

[a]Total of $18:1\Delta^9$ and derived LC-MUFA (=$18:1\Delta^9 + 20:1\Delta^{11} + 22:1\Delta^{13}$)
[b]18:2 + 18:3
[c]Total of all new ω6 and ω3-PUFA Germination of 50 T2 seed from each of DW2 and DW5 on hygromycin-containing medium showed that the DW5 T1 plant was homozygous (50/50) for the Δ5/Δ6 bifunctional desaturase and Δ5/Δ6 bifunctional elongase genes, while the DW2 seed segregating in a 3:1 ration (resistant: susceptible) for these genes and DW2 was therefore heterozygous. This was consistent with the higher levels of EPA observed in DW5 seed compared to DW2 seed, and explained the increased level of DHA produced in the seed homozygous for these transgenes. This further demonstrated the desirability of seed that are homozygous for the trait.

We also noted the consequences of LC-PUFA synthesis on the overall fatty acid profile in these seed. Although we observed accumulation of new ω6 and ω3 PUFA (i.e. products of Δ6-desaturation) at levels of greater than 8% in DW5 seed, these seed had levels of the precursor fatty acids LA and ALA that were almost the same as in the wild-type seed. Rather than depleting LA and ALA, the levels of monounsaturated fatty acid $C18:1\Delta^9$ and its elongated derivatives (20:$1\Delta^{11}$ and 22:$1\Delta^{13}$) were significantly reduced. Thus it appeared that conversion of $C_{18}$-PUFA to LC-PUFA resulted in increased conversion of 18:1 to LA and ALA, and a corresponding reduction in 18:1 available for elongation.

The plant expression vector pXZP355 containing the Δ4-desaturase and the Δ5-elongase genes was also used to introduce the genes into plants of the homozygous line DO11-5, and 20 transgenic T1 plants were obtained. The levels of DHA and DPA in T2 seed from these plants were similar to those observed in seed from DW5. Reductions in the levels of the monounsaturated fatty acids were also observed in these seed.

Fractionation of the total seed lipids of DW5 seed revealed them to be comprised of 89% TAG and 11% polar lipids (largely made up phospholipids). Furthermore, fatty acid analysis of the TAG fraction from DW5 seed showed that the newly synthesised EPA and DHA were being incorporated into the seed oil and that the proportion of EPA and DHA in the fatty acid composition of the total seed lipid essentially reflected that of the TAG fraction (Table 10).

Example 12

Isolation of Homologous Genes from Other Sources

Homologs of the desaturase and elongase genes such as the *P. salina* genes described herein may be readily detected in other microalgae or other sources by hybridization to labelled probes derived from the genes, particularly to parts or all of the coding regions, for example by Southern blot hybridization or dot-blot hybridisation methods. The homologous genes may be isolated from genomic or cDNA libraries of such organisms, or by PCR amplification using primers corresponding to conserved regions. Similarly, homologs of vertebrate desaturases with high affinity for Acyl-CoA and/or freshwater fish bifunctional desaturases can be isolated by similar means using probes to the zebrafish Δ5/Δ6 desaturase.

Dot Blot Hebridisations

Genomic DNA from six microalgae species was isolated using a DNAeasy kit (Qiagen) using the suppliers instructions, and used in dot blot hybridization analyses for identification of homologous genes involved in LC-PUFA synthesis in these species. This also allowed evaluation of the sequence divergence of such genes compared to those isolated from *Pavlova salina*. The species of microalga examined in this analysis were from the genera *Melosira*, *Rhodomonas*, *Heterosigma*, *Nannochloropsis*, *Heterocapsa* and *Tetraselmis*. They were identified according to Hasle, G. R. & Syvertsen, E. E. 1996 Dinoflagellates. In: Tomas, C. R. (ed.) Identifying Marine Phytoplankton. Academic Press, San Diego, Calif. pp 531-532. These microalga were included in the analysis on the basis of the presence of EPA, DHA, or both when cultured in vitro (Example 2).

Genomic DNA (approximately 100 μg) isolated from each of the microalga was spotted onto strips of Hybond N+ membrane (Amersham). After air drying, each membrane strip was placed on a layer of 3 MM filter paper saturated with 0.4 M NaOH for 20 min, for denaturation of the DNA, and then rinsed briefly in 2×SSC solution. The membrane strips were air dried and the DNA cross linked to the membranes under UV light. Probes labeled with $^{32}P$ nucleotides and consisting of the coding regions without the untranslated regions of a number of *Pavlova*-derived genes, including the Δ8, Δ5 and Δ4 desaturases and Δ9 and Δ5 elongases, were prepared and hybridized to each membrane strip/DNA dot blot. The membranes were hybridized with each probe overnight in a buffer containing 50 mM Tris-HCl, pH7.5, 1M NaCl, 50% formamide, 10×Denhardt's solution, 10% dextran sulfate, 1% SDS, 0.1% sodium pyrophosphate, and 0.1 mg/ml herring sperm DNA, at 42° C., then washed three times in a solution containing 2×SSC, 0.5% SDS at 50° C. for 15 min each (low stringency wash in this experiment) or for a high stringency wash in 0.2×SSC, 0.5% SDS at 65° C. for 20 minutes each.

It is well understood that the stringency of the washing conditions employed in DNA blot/hybridizations can reveal useful information regarding the sequence relatedness of genes. Thus hybridizations maintained when subjected to a high stringency wash indicate a high level of sequence relatedness (e.g. 80% or greater nucleotide identity over at least 100-200 nucleotides), while hybridizations maintained only during low stringency washes indicate a relatively lower degree of DNA conservation between genes (e.g. 60% or greater nucleotide identity over at least 200 nucleotides).

The hybridized dot blots were exposed to BioMax X-ray film (Kodak), and the autoradiograms are shown in FIG. 9. The autoradiograms reveal the presence of homologs to the *P. salina* LC-PUFA genes in these species, and moreover reveal a range of homologies based on the different levels of hybridization seen under the high and low stringency conditions. It appeared that some of the microalgal species examined have LC-PUFA genes that may differ substantially from the genes in *P. salina*, while others are more related in sequence. For example, genes from *Tetraseimis* sp appeared to be highly similar to the Δ4- and Δ5-desaturases and the Δ5 elongase from *Pavlova salina* on the basis of the strength of hybridizations. In contrast, all of the LC-PUFA genes identified in *Melosira* sp appeared to have lower degrees of similarity to the *P. salina* genes.

Isolation of an LC-PUFA Elongase Gene from *Heterocapsa* sp.

*Heterocapsa* spp. such as *Heterocapsa niei* in the CSIRO collection (Example 2) are dinoflagellates that were identified as producers of LC-PUFA including EPA and DHA. To exemplify the isolation of LC-PUFA synthesis genes from these dinoflagellates, DNA was purified from cells of a *Heterocapsa niei* strain originally isolated in Port Hacking, NSW, Australia in 1977. DNA was isolated using a DNAeasy kit (Qiagen) using the suppliers instructions. Based on published multiple amino acid sequence alignments for fatty acid elongases (Qi et al., 2002; Parker-Barnes et al., 2000), the consensus amino acid blocks FLHXYH (SEQ ID NO:48) and MYXYYF (SEQ ID NO:49) were identified and corresponding degenerate primers encoding these sequences 5'-CAG-GATCCTTYYTNCATNNNTAYCA-3' (SEQ ID NO:50) (sense) or complementary to these sequences 5'-GATCTA-GARAARTARTANNNRTACAT-3' (SEQ ID NO:51) (antisense) were synthesised. PCR amplification reactions were carried out in reaction volumes of 20 μL with 20 pmol of each primer, 200 ng of *Heterocapsa* sp. genomic DNA and Hotstar Taq DNA polymerase (Qiagen) with buffer and nucleotide components as specified by the supplier. The reactions were cycled as follows: 1 cycle of 95° C. for 15 minutes, 5 cycles of 95° C., 1 min, 38° C., 1 min, 72° C., 1 min, 35 cycles of 95° C., 35 sec, 52° C., 30 sec, 72° C., 1 min, 1 cycle of 72° C., 10 min. Fragments of approximately 350 bp were generated and ligated into pGEM-Teasy for sequence analysis.

Of eight clones isolated, two identical clones had nucleotide and encoded amino acid sequences with similarity to regions of known elongases. These were designated Het350Elo, and the nucleotide and amino acid sequences are provided as SEQ ID NO:79 and SEQ ID NO:80 respectively. BLAST analysis and the presence of an in-frame stop codon suggested the presence of an intron between approximate positions 33 and 211.

The best matches to the amino acid sequence were animal elongase sequences, see for example Meyer et al. (2004), indicating that the isolated *Heterocapsa* gene sequence was probably involved in elongation of C18 and C20 fatty acid substrates.

Full-length clones of the elongase can readily be isolated by screening a *Heterocapsa* cDNA library or by 5'- and 3' RACE techniques, well known in the art.

Construction of *Melosira* sp. cDNA Library and EST Sequencing mRNA, for the construction of a cDNA library, was isolated from *Melosira* sp. cells using the following method. 2 g (wet weight) of *Melosira* sp. cells were powdered using a mortar and pestle in liquid nitrogen and sprinkled slowly into a beaker containing 22 ml of extraction buffer that was being stirred constantly. To this, 5% insoluble polyvinylpyrrolidone, 90 mM 2-mercaptoethanol, and 10 mM dithiotheitol were added and the mixture stirred for a further 10 minutes prior to being transferred to a Corex™ tube. 18.4 ml of 3M ammonium acetate was added and mixed well. The sample was then centrifuged at 6000×g for 20 minutes at 4° C. The supernatant was transferred to a new tube and nucleic acid precipitated by the addition of 0.1 volume of 3M NaAc (pH 5.2) and 0.5 volume of cold isopropanol. After 1 hour incubation at −20° C., the sample was centrifuged at 6000×g for 30 minutes in a swing-out rotor. The pellet was resuspended in ml of water and extracted with phenol/chloroform. The aqueous layer was transferred to a new tube and nucleic acids were precipitated once again by the addition of 0.1 volume 3M NaAc (pH 5.2) and 2.5 volume of ice cold ethanol. The pellet was resuspended in water, the concentration of nucleic acid determined and then mRNA was isolated using the Oligotex mRNA system (Qiagen).

First strand cDNA was synthesised using an oligo(dT) linker-primer supplied with the ZAP-cDNA synthesis kit (Stratagene—cat #200400) and the reverse transcriptase SuperscriptIII (Invitrogen). Double stranded cDNA was ligated to EcoRI adaptors and from this a library was constructed using the ZAP-cDNA synthesis kit as described in the accompanying instruction manual (Stratagene—cat #200400). A primary library of $1.4 \times 10^6$ plaque forming units (pfu) was obtained. The average insert size of cDNA inserts in the library was 0.9 kilobases based on 47 random plaques and the percentage of recombinants in the library was 99%.

Single pass nucleotide sequencing of 8684 expressed sequence tags (ESTs) was performed with SK primer (5'-CGCTCTAGAACTAGTGGATC-3') (SEQ ID NO:87) using the ABI BigDye system. Sequences of 6750 ESTs were longer than 400 nucleotides, showing the inserts were at least this size. ESTs showing homology to several fatty acid desaturases and one PUFA elongase were identified by BlastX analysis.

The amino acid sequence (partial) (SEQ ID NO:88) encoded by the cDNA clone Mm301461 showed 75% identity to *Thalassiosira pseudonana* fatty acid elongase 1 (Accession No. AY591337). The nucleotide sequence of EST clone Mm301461 is provided as SEQ ID NO:89. The high degree of identity to a known elongase makes it highly likely that Mm301461 encodes a *Melosira* fatty acid elongase. RACE techniques can readily be utilized to isolate the full-length clone encoding the elongase.

Example 13

Isolation of FAE-Like Elongase Gene Fragment from *P. salina*

Random cDNA clones from the *P. salina* cDNA library were sequenced by an EST approach. In an initial round of sequencing, 73 clones were sequenced. One clone, designated 11.B1, was identified as encoding a protein (partial sequence) having sequence similarity with known beta ketoacyl synthase-like fatty acid elongases, based on BLASTX analysis. The nucleotide sequence of 11.B1 from the 3' end is provided as (SEQ ID NO:55).

These plant elongases are different to the ELO class elongase in that they are known to be involved in the elongation of C16 to C18 fatty acids and also the elongation of very-long-chain saturated and monounsaturated fatty acids. Clone 11.B1, represents the first non-higher plant gene in this class isolated.

Example 14

Isolation of a Gene Encoding a Δ5-Desaturase from *P. salina*

Isolation of a Gene Fragment from a Δ5-Desaturase Gene from *P. salina*

In order to isolate a Δ5-desaturase gene from *P. salina*, oligonucleotides were designed for a conserved region of desaturases. The oligonucleotides designated d5A and d5B shown below were made corresponding to a short DNA sequence from a Δ5-desaturase gene from *Pavlova lutheri*. Oligo d5A: 5'-TGGGTTGAGTACTCGGCCAACCACAC-GACCAACTGCGCGCCCTCGTGGTGGT GCGACTG-GTGGATGTCTTACCTCAACTACCAGATC-GAGCATCATCTGT-3' (nucleotides 115-214 of International patent application published as WO03078639-A2, FIG. 4*a*) (SEQ ID NO:56) and oligo d5B: 5'-ATAGTG-CAGCCCGTGCTTCTCGAAGAGCGCCT-TGACGCGCGGCGCGATCGTC GGGTGGCGGAATTGCGGCATGGACGG-GAACAGATGATGCTCGATCTGG-3' (corresponding to the complement of nucleotides 195-294 of WO03078639-A2, FIG. 4*a*) (SEQ ID NO:57). These oligonucleotides were annealed and extended in a PCR reaction. The PCR product from was inserted into pGEM-T Easy vector and the nucleotide sequence confirmed.

The cloned fragment was labelled and used as a hybridization probe for screening of a *Pavlova salina* cDNA library under moderately high stringency conditions, hybridizing at 55° C. overnight with an SSC hybridization solution and washing the blots at 60° C. with 2×SSC/0.1% SDS three times each for 10 minutes. From screening of about 500,000 plaques, 60 plaques were isolated which gave at least a weak hybridization signal. Among 13 clones that were sequenced, one clone designated p1918 contained a partial-length cDNA encoding an amino acid sequence with homology to known Δ5-desaturase genes. For example, the amino acid sequence was 53% identical to amino acid residues 210-430 from the C-terminal region of a *Thraustochytrium* Δ5-desaturase gene (Accession No. AF489588).

Isolation of a Full-Length Δ5-Desaturase Gene

The partial-length sequence in p1918 was used to design a pair of sequence specific primers, which were then used in PCR screening of the 60 isolated plaques mentioned above. Nineteen of the 60 were positive, having the same or similar cDNA sequence. One of the clones that showed a strong hybridization signal using the partial-length sequence as a probe was used to determine the full-length sequence provided as SEQ ID NO:58, and the amino acid sequence (425 amino acids in length) encoded thereby is provided as SEQ ID NO:60.

The amino acid sequence was used to search the NCBI protein sequence database using the BLASTX software. The results indicated that this sequence was homologous to known Δ5-desaturases. The amino acid sequence of the *P. salina* protein showed 81% identity to a *P. lutheri* sequence of undefined activity in WO03/078639-A2, and 50% identity to a Δ5-desaturase from *Thraustochytrium* (Accession No. AF489588). The *Pavlova salina* Δ5-desaturase showed all the conserved motifs typical of 'front-end desaturases' including the N-terminal cytochrome $b_5$-like domain and three conserved histidine-rich motifs.

Co-Expression of Δ9 Elongase, Δ8-Desaturase and Δ5-Desaturase Genes in Transformed Cells Co-expression of the Δ5-desaturase gene together with the Δ9 elongase gene (Elo2, Example 7) and the Δ8-desaturase gene (Example 6) was achieved in cells as follows. The plant expression vector pXZP354 containing the three genes, each from *P. salina*, and each expressed from the seed specific napin promoter was constructed. The *P. salina* Δ8-desaturase coding region from the cDNA clone (above) was first inserted as a BamHI-NcoI fragment into pXZP143 between the seed specific napin promoter and Nos terminator, resulting in plasmid pXZP46. The *P. salina* Δ9-elongase gene was likewise inserted, as a PstI-XhoI fragment from its cDNA clone, into pXZP143 resulting in plasmid pXZP143-Elo2. The *P. salina* Δ5-desaturase gene was also inserted, as a PstI-BssHII fragment from its cDNA clone, into pXZP143, resulting in plasmid pXZP147. Then, the HindIII-ApaI fragment containing the Δ9-elongase expression cassette from pXZP143-Elo2 was inserted into pXZP146 downstream of the Δ8-desaturase expression cassette, resulting in plasmid pXZP148. The HindIII-ApaI fragment containing the Δ5-desaturase expression cassette from pXZP147 was inserted into pXZP148 downstream of Δ8-desaturase and Δ9-elongase expression cassettes, resulting in plasmid pXZP149. Then, as a final step, the HindIII-ApaI fragment containing the three genes from pXZP149 was inserted into a derivative of the binary vector pART27, containing a hygromycin resistance gene selection marker, resulting in plant expression plasmid pXZP354.

Plasmid pXZP354 was introduced into *Arabidopsis* by the *Agrobacterium*-mediated floral dip method, either in the simultaneous presence or the absence of expression plasmid pXZP355 (Example 11) containing the *P. salina* Δ5-elongase and Δ4-desaturase genes. Co-transformation of the vectors could be achieved since they contained different selectable marker genes. In the latter case, the transgenic plants (designated "DR" plants) were selected using hygromycin as selective agent, while in the former case, the plants ("DU" plants) were selected with both hygromycin and kanamycin.

Twenty-one DR plants (T1 plants) were obtained. Fatty acid analysis of seedoil from T2 seed from ten of these plants showed the presence of low levels of 20:2ω (EDA), 20:3ω6 (DGLA) and 20:4ω6 (ARA), including up to 0.4% ARA. Fatty acid analysis of seedoil from T2 seed from seven DU plants showed similar levels of these fatty acids. From the relative ratios of these fatty acids, it was concluded that the Δ5-desaturase and Δ8-desaturase genes were functioning efficiently in seed transformed with pXZP354 but that the activity of the Δ9 elongase gene was suboptimal. It is likely that shortening of the coding region at the N-terminal end, to initiate translation at amino acid position 11 or 29 of SEQ ID NO:3 (Example 9) (see SEQ ID NO's 85 and 86) will improve the level of activity of the Δ9 elongase gene. Expression of one or two of the genes from seed-specific promoters other than the napin promoter, so they are not all expressed from the napin promoter, is also expected to improve the expression level of the Δ9 elongase gene.

Example 15

Isolation of a Gene Encoding a Δ6-Desaturase from *Echium plantagineum*

Some plant species such as evening primrose (*Oenothera biennis*), common borage (*Borago officinalis*), blackcurrant (*Ribes nigrum*), and some *Echium* species belonging to the Boragenacae family contain the ω6- and ω3-esaturated C18 fatty acids, γ-linolenic acid (18:3ω6, GLA) and stearidonic acid (18:4ω3, SDA) in their leaf lipids and seed TAGs (Gull-Guerrero et al., 2000). GLA and SDA are recognized as beneficial fatty acids in human nutrition. The first step in the synthesis of LC-PUFA is a Δ6-desaturation. GLA is synthesized by a Δ6-desaturase that introduces a double bond into the Δ6-position of LA. The same enzyme is also able to introduce a double bond into Δ6-position of ALA, producing SDA. Δ6-Desaturase genes have been cloned from members of the Boraginaceae, like borage (Sayanova et al., 1997) and two *Echium* species (Garcia-Maroto et al., 2002).

*Echium plantagineum* is a winter annual native to Mediterranean Europe and North Africa. Its seed oil is unusual in that it has a unique ratio of ω3 and ω6 fatty acids and contains high amounts of GLA (9.2%) and SDA (12.9%) (Guil-Guerrero et al., 2000), suggesting the presence of Δ6-desaturase activity involved in desaturation of both ω3 and ω6 fatty acids in seeds of this plant.

Cloning of *E. platangineum* EplD6Des Gene

Degenerate primers with built-in XbaI or SacI restriction sites corresponding to N- and C-termini amino acid sequences MANAIKKY (SEQ ID NO: 61) and EALNTHG (SEQ ID NO: 62) of known *Echium pitardii* and *Echium gentianoides* (Garcia-Maroto et al., 2002) Δ6-desaturases were used for RT-PCR amplification of Δ6-desaturase sequences from *E. platangineum* using a proofreading DNA polymerase Pfu Turbo® (Stratagene). The 1.35 kb PCR amplification product was inserted into pBluescript SK(+) at the XbaI and SacI sites to generate plasmid pXZP106. The nucleotide sequence of the insert was determined (SEQ ID NO:63). It comprised an open reading frame encoding a polypeptide of 438 amino acid residues (SEQ ID NO:64) which had a high degree of homology with other reported Δ6- and Δ8-desaturases from *E. gentianoides* (SEQ ID NO:65), *E. pitardii* (SEQ ID NO:66), *Borago officinalis* (SEQ ID NO:67 and 68). *Helianthus annuus* (SEQ ID NO:69) and *Arabidopsis thaliana* (SEQ ID NO:70 and SEQ ID NO:71) (FIG. 10). It has a cytochrome $b_5$ domain at the N-terminus, including the HPGG (SEQ ID NO:72) motif in the heme-binding region, as reported for other Δ6- and Δ8-desaturases (Sayanova et al. 1997; Napier et al. 1999). In addition, the *E. plantagineum* Δ6 desaturase contains three conserved histidine boxes, including the third histidine box containing the signature QXXHH (SEQ ID NO:73) motif present in majority of the 'front-end' desaturases (FIG. 10) (Napier et al., 1999). Cluster analysis including representative members of Δ6 and Δ8 desaturases showed a clear grouping of the cloned gene with other Δ6 desaturases especially those from *Echium* species.

Heterologous Expression of *E. plantagineum* Δ6-DESATURASE Gene in Yeast

Expression experiments in yeast were carried out to confirm that the cloned *E. plantagineum* gene encoded a Δ6-desaturase enzyme. The gene fragment was inserted as an XbaI-SacI fragment into the SmaI-SacI sites of the yeast expression vector pSOS (Stratagene) containing the constitutive ADH1 promoter, resulting in plasmid pXZP271. This was transformed into yeast strain S288Cα by a heat shock method and transformant colonies selected by plating on minimal media plates. For the analysis of enzyme activity, 2 mL yeast clonal cultures were grown to an $O.D._{600}$ of 1.0 in yeast minimal medium in the presence of 0.1% NP-40 at 30° C. with shaking. Precursor free-fatty acids, either linoleic or linolenic acid as 25 mM stocks in ethanol, were added so that the final concentration of fatty acid was 0.5 mM. The cultures were transferred to 20° C. and grown for 2-3 days with shaking. Yeast cells were harvested by repeated centrifugation and washing first with 0.1% NP-40, then 0.05% NP-40 and finally with water. Fatty acids were extracted and analyzed. The peak identities of fatty acids were confirmed by GC-MS.

The transgenic yeast cells expressing the *Echium* EplD6Des were able to convert LA and ALA to GLA and SDA, respectively. Around 2.9% of LA was converted to GLA and 2.3% of ALA was converted to SDA, confirming the Δ6-desaturase activity encoded by the cloned gene.

Functional Expression of *E. platangineum* Δ6-Desaturase Gene in Transgenic Tobacco In order to demonstrate that the EplD6Des gene could confer the synthesis of Δ6 desaturated fatty acids in transgenic plants, the gene was expressed in tobacco plants. To do this, the gene fragment was excised from pXZP106 as an XbaI-SacI fragment and cloned into the plant expression vector pBI121 (Clonetech) at the XbaI and SacI sites under the control of a constitutive 35S CaMV promoter, to generate plant expression plasmid pXZP341. This was introduced into *Agrobacterium tumefaciens* AGL1, and used for transformation of tobacco W38 plant tissue, by selection with kanamycin.

Northern blot hybridization analysis of transformed plants was carried out to detect expression of the introduced gene, and total fatty acids present in leaf lipids of wild-type tobacco W38 and transformed tobacco plants were analysed as described above. Untransformed plants contained appreciable amounts of LA (21% of total fatty acids) and ALA (37% of total fatty acids) in leaf lipids. As expected, neither GLA nor SDA, products of Δ6-desaturation, were detected in the untransformed leaf. Furthermore, transgenic tobacco plants transformed with the pBI121 vector had similar leaf fatty acid composition to the untransformed W38 plants. In contrast, leaves of transgenic tobacco plants expressing the EplD6Des gene showed the presence of additional peaks with retention times corresponding to GLA and SDA. The identity of the GLA and SDA peaks were confirmed by GC-MS. Notably, leaf fatty acids of plants expressing the EplD6Des gene consistently contained approximately a two-fold higher concentration of GLA than SDA even when the total Δ6-desaturated fatty acids amounted up to 30% of total fatty acids in their leaf lipids (Table 11).

TABLE 11

Fatty acid composition in lipid from transgenic tobacco leaves (%).

| Plant | 16:0 | 18:0 | 18:1 | 18:2 | GLA | 18:3 | SDA | Total Δ6-desaturate products |
|---|---|---|---|---|---|---|---|---|
| W38 | 21.78 | 5.50 | 2.44 | 21.21 | — | 37.62 | — | — |
| ET27-1 | 20.33 | 1.98 | 1.25 | 10.23 | 10.22 | 41.10 | 6.35 | 16.57 |
| ET27-2 | 18.03 | 1.79 | 1.58 | 14.42 | 1.47 | 53.85 | 0.48 | 1.95 |
| ET27-4 | 19.87 | 1.90 | 1.35 | 7.60 | 20.68 | 29.38 | 9.38 | 30.07 |
| ET27-5 | 15.43 | 2.38 | 3.24 | 11.00 | 0.84 | 49.60 | 0.51 | 1.35 |
| ET27-6 | 19.85 | 2.05 | 1.35 | 11.12 | 4.54 | 50.45 | 2.19 | 6.73 |
| ET27-8 | 19.87 | 2.86 | 2.55 | 11.71 | 17.02 | 27.76 | 7.76 | 24.78 |

TABLE 11-continued

Fatty acid composition in lipid from transgenic tobacco leaves (%).

| Plant | 16:0 | 18:0 | 18:1 | 18:2 | GLA | 18:3 | SDA | Total Δ6-desaturate products |
|---|---|---|---|---|---|---|---|---|
| ET27-11 | 17.78 | 3.40 | 2.24 | 12.62 | 1.11 | 51.56 | 0.21 | 1.32 |
| ET27-12 | 16.84 | 2.16 | 1.75 | 13.49 | 2.71 | 50.80 | 1.15 | 3.86 |

Northern analysis of multiple independent transgenic tobacco lines showed variable levels of the EplD6Des transcript which generally correlated with the levels of Δ6-desaturated products synthesized in the plants. For example, transgenic plant ET27-2 which contained low levels of the EplD6Des transcript synthesised only 1.95% of its total leaf lipids as Δ6-desaturated fatty acids. On the other hand, transgenic plant ET27-4 contained significantly higher levels of EplD6Des transcript and also had a much higher proportion (30%) of Δ6-desaturated fatty acids in its leaf lipids.

Analysis of the individual tobacco plants showed that, without exception, GLA was present at a higher concentration than SDA even though a higher concentration of ALA than LA was present in untransformed plants. In contrast, expression of EplD6Des in yeast had resulted in approximately equivalent levels of conversion of LA into GLA and ALA into SDA. Echium plantagineum seeds, on the other hand, contain higher levels of SDA than GLA. EplD6Des probably carries out its desaturation in vivo in Echium plantagineum seeds on LA and ALA esterified to phosphatidyl choline (PC) (Jones and Harwood 1980). In the tobacco leaf assay, the enzyme is most likely desaturating LA and ALA esterified to the chloroplast lipid monogalactosyldiacylglycerol (MGDG) (Browse and Slack, 1981). In the yeast assay, free fatty acid precursors LA and ALA added to the medium most likely enter the acyl-CoA pool and are available to be acted upon by EplD6Des in this form.

Functional Expression of E. platangineum Δ6-Desaturase Gene in Transgenic Seed

To show seed-specific expression of the Echium Δ6-desaturase gene, the coding region was inserted into the seed-specific expression cassette as follows. An NcoI-SacI fragment including the Δ6-desaturase coding region was inserted into pXZP6, a pBluescriptSK derivative containing a Nos terminator, resulting in plasmid pXZP157. The SmaI-ApaI fragment containing the coding region and terminator EplD6Des-NosT was cloned into pWVec8-Fp1 downstream of the Fp1 prompter, resulting in plasmid pXZP345. The plasmid pXZP345 was used for transforming wild type Arabidopsis plants, ecotype Columbia, and transgenic plants selected by hygromycin B selection. The transgenic plants transformed with this gene were designated "DP" plants.

Fatty acid composition analysis of the seed oil from T2 seed from eleven T1 plants transformed with the construct showed the presence of GLA and SDA in all of the lines, with levels of Δ6-desaturation products reaching to at least 11% (Table 12). This demonstrated the efficient Δ6-desaturation of LA and ALA in the seed.

TABLE 12

Fatty acid composition in transgenic Arabiclopsis seeds expressing Δ6-desaturase from Echium.

| Plant Columbia | Fatty acid (%) | | | | | | | | | Total Δ6-desaturation products (%) |
|---|---|---|---|---|---|---|---|---|---|---|
| | 16:0 | 18:0 | $18:1^{\Delta 9}$ | $18:2^{\Delta 9,12}$ (LA) | $18:3^{\Delta 6,9,12}$ (GLA) | $18:3^{\Delta 9,12,15}$ (ALA) | $18:4^{\Delta 6,9,12,15}$ (SDA) | 20:0 | 20:1 | |
| DP-2 | 8.0 | 2.8 | 22.9 | 27.3 | 2.5 | 11.3 | 0.7 | 1.6 | 15.8 | 3.2 |
| DP-3 | 7.8 | 2.7 | 20.6 | 25.9 | 3.0 | 12.1 | 0.8 | 1.7 | 17.8 | 3.8 |
| DP-4 | 7.8 | 2.8 | 20.4 | 28.5 | 1.2 | 13.7 | 0.4 | 1.7 | 16.1 | 1.5 |
| DP-5 | 8.2 | 3.2 | 17.4 | 29.3 | 1.2 | 14.2 | 0.3 | 2.1 | 15.6 | 1.6 |
| DP-7 | 8.2 | 2.9 | 18.4 | 26.7 | 5.0 | 12.7 | 1.4 | 1.7 | 15.2 | 6.4 |
| DP-11 | 9.0 | 3.5 | 17.8 | 28.4 | 3.0 | 13.4 | 0.9 | 2.1 | 13.9 | 3.8 |
| DP-12 | 8.6 | 3.0 | 18.9 | 27.8 | 3.3 | 12.6 | 1.0 | 1.8 | 15.4 | 4.3 |
| DP-13 | 8.7 | 2.9 | 14.4 | 27.3 | 8.5 | 13.7 | 2.6 | 1.7 | 12.4 | 11.1 |
| DP-14 | 9.3 | 2.9 | 14.2 | 32.3 | 2.1 | 15.4 | 0.7 | 1.8 | 12.8 | 2.8 |
| DP-15 | 8.2 | 2.9 | 17.8 | 30.1 | 0.3 | 15.3 | 0.2 | 1.9 | 15.5 | 0.5 |
| DP-16 | 8.0 | 2.8 | 19.5 | 29.2 | 2.7 | 13.1 | 0.8 | 1.7 | 14.2 | 3.5 |

Example 16

Mutagenesis of E. platangineum EplD6Des Gene

To determine whether variability could be introduced into the Δ6-desaturase gene and yet retain desaturase activity, the E. platangineum Δ6-desaturase cDNA was randomly mutated by PCR using Taq polymerase and EPD6DesF1 and EPD6DesR1 primers in the presence of dITP as described by Zhou and Christie (1997). The PCR products were cloned as XbaI-SacI fragments in pBluescript SK(+) at XbaI and SacI sites, and sequences of randomly selected clones determined. Random variants with amino acid residue changes were chosen to clone as XbaI-SacI fragments into pBI121 and the enzyme activities of proteins expressed from these variants characterized in transgenic tobacco leaves as described above for the wild-type gene.

FIG. 11A represents the activity of the EplD6Des sequence variants when expressed in tobacco plants. The variants could be divided into two broad classes in terms of their ability to carry out Δ6-desaturation. Mutations represented as empty diamonds showed substantial reductions in the Δ6-desaturation activity while mutations denoted as solid diamonds had little or no effect on the activity of the encoded Δ6-desaturase enzyme. FIG. 11B represents the quantitative effect that a selection of mutations in the EplD6Des gene had on the Δ6-desaturase activity. An L14P mutation in the cytochrome $b_5$ domain and an S301P mutation between histidine box II and histidine box III of EplD6Des caused substantial reductions in their Δ6-desaturase activities, resulting in a 3- to 5-fold reduction in total Δ6-desaturated fatty acids when compared to the wild-type enzyme in W38 plants. Surprisingly, significant activity was retained for each. In contrast, most of the variants examined, as exemplified by the S205N mutation, had no effect on the Δ6-desaturation activity of EplD6Des gene.

Example 17

Comparison of acyl-CoA and acyl-PC Substrate Dependent Desaturases for Production of LC-PUFA in Cells As described above, the synthesis of LC-PUFA such as EPA and DHA in cells by the conventional Δ6 desaturation pathway requires the sequential action of PUFA desaturases and elongases, shown schematically in FIG. 12 part A. This conventional pathway operates in algae, mosses, fungi, diatoms, nematodes and some freshwater fish (Sayanova and Napier, 2004). The PUFA desaturases from algae, fungi, mosses and worms are selective for desaturation of fatty acids esterified to the sn-2 position of phosphatidylcholine (PC) while the PUFA elongases act on fatty acids in the form of acyl-CoA substrates represented in the acyl-CoA pool in the endoplasmic reticulum (ER), which is physiologically separated from the PC component of the ER. Therefore, sequentially desaturation and elongation reactions on a fatty acid substrate requires that the fatty acid is transferred between the acyl-PC and acyl-CoA pools in the ER. This requires acyltransferases that are able to accommodate LC-PUFA substrates. This "substrate switching" requirement may account for the low efficiency observed in earlier reported attempts to re-constitute LC-PUFA biosynthesis (Beaudoin et al., 2000, Domergue et al., 2003a). The alternative Δ5 desaturation pathway (FIG. 12 part B) suffers from the same disadvantage of requiring "substrate switching".

As described in Example 5, the strategy of using a vertebrate desaturase which was able to desaturate acyl-CoA substrates, provided relatively efficient production of LC-PUFA in plant cells including in seed. In Example 5, the combination of a Δ5/Δ6 desaturase from zebra fish with a Δ6 elongase from C. elegans had the advantage that both the desaturase and the elongase enzymes had activity on acyl-CoA substrates in the acyl-CoA pool. This may explain why this strategy was more efficient in the synthesis of LC-PUFA. To provide a direct comparison of the relative efficiencies of using an acyl-CoA substrate-dependent desaturase compared to an acyl-PC substrate-dependent desaturase, we conducted the following experiment. This compared the use of the Echium Δ6 desaturase (Example 15) and the P. salina Δ5 desaturase (Example 14), both of which are thought to use acyl-PC substrates, with the zebrafish Δ6/Δ5 desaturase which uses an acyl-CoA substrate (Example 5).

A construct was prepared containing two acyl-PC dependent desaturases, namely the Echium Δ6 desaturase and P. salina Δ5 desaturase, in combination with the C. elegans Δ6 elongase. The Echium Δ6 desaturase gene on an NcoI-SacI fragment was inserted into pXZP143 (Example 15) resulting in pXZP192. The C. elegans Δ6 elongase gene (Fp1-CeElo-NosT expression cassette) on the HindIII-ApaI fragment of pCeloPWVec8 (Example 5) was inserted into the StuI-ApaI sites of pXZP147 (Example 14) to make pXZP193. The HindIII-ApaI fragment of pXZP193 containing both genes (Fp1-PsD5Des-NosT and Fp1-CeElo-NosT) was inserted into the ApaI-StuI sites of pXZP192, resulting in plasmid pXZP194 containing the three expression cassettes. The XbaI-ApaI fragment from pXZP194 was inserted in a pWvec8 derivative, resulting in pXZP357.

The plasmid pXZP357 was used to transform plants of wild-type Arabidopsis ecotype Columbia by Agrobacterium-mediated floral dip method, and six transgenic plants were obtained after hygromycin B (20 mg/L) selection. The transgenic T1 plants were designated "DT" plants. The hygromycin resistant transformed plants were transferred into soil and self-fertilised. The T2 seed were harvested and the seed fatty acid composition of two lines, DT1 and DT2, was analysed. The seed fatty acids of DT1 and DT2 contained low levels of 18:3ω6 and 18:4ω4 (0.9 and 0.8% of GLA, 0.3% and 0.1% of SDA, respectively, Table 13). In addition, both DT1 and DT2 seed also contained 0.3% and 0.1% of the 20:4ω6 (ARA). However, there was no apparent synthesis of the ω3 fatty acid EPA in either of the T2 seed lines, which probably reflected the greater desaturation ability of the Echium Δ6 desaturase on the ω6 substrate LA compared to the ω3 substrate ALA (Example 15).

TABLE 13

Fatty acid composition of seed-oil from T2 seed of DT1 and DT2. Fatty acid values are % of total fatty acids.

| Fatty acid | Control | DT1 | DT2 |
|---|---|---|---|
| 16:0 | 7.2 | 6.5 | 6.5 |
| 18:0 | 2.9 | 3.6 | 3.3 |
| 18:1ω9 | 20.0 | 23.2 | 22.3 |
| 18:2ω6 | 27.5 | 23.6 | 24.4 |
| 18:3ω3 | 15.1 | 15.4 | 16.1 |
| 20:0 | 2.2 | 2.0 | 1.9 |
| 20:1ω9/ω11 | 19.9 | 19.4 | 19.5 |
| 20:1ω7 | 2.2 | 3.4 | 3.0 |
| 20:2ω6 | 0.1 | 0.0 | 0.0 |
| 22:1ω7 | 0.0 | 0.0 | 0.0 |
| Other minor | 2.8 | 1.5 | 1.9 |
| Total | 100.0 | 98.6 | 98.9 |
| New ω6-PUFA | | | |
| 18:3ω6 | 0.0 | 0.9 | 0.8 |
| 20:3ω6 | 0.0 | 0.0 | 0.0 |
| 20:4ω6 | 0.0 | 0.3 | 0.1 |
| Total New ω3-PUFA | 0.0 | 1.2 | 0.9 |
| 18:4ω3 | 0.0 | 0.3 | 0.2 |
| 20:4ω3 | 0.0 | 0.0 | 0.0 |
| 20:5ω3 | 0.0 | 0.0 | 0.0 |
| Total | 0.0 | 0.3 | 0.2 |
| Total fatty acids | 100.0 | 100.0 | 100.0 |

This data was in clear contrast to Example 5, above, where expression of the acyl-CoA dependent desaturase from zebrafish in combination with a Δ6 elongase resulted in the production of at least 1.1% ARA and 2.3% EPA in T2 seed fatty acids. Thus it would appear that acyl-PC dependent desaturases were less effective than acyl-CoA dependent desaturases in driving the synthesis of LC-PUFA in plants cells.

Example 18

Expression of LC-PUFA Genes in Synechococcus

Synechococcus spp. (Bacteria; Cyanobacteria; Chroococcales; Synechococcus species for example Synechococcus elongatus, also known as Synechocystis spp.) are unicellular, photosynthetic, marine or freshwater bacteria in the order cyanobacteria that utilize chlorophyll a in the light-harvesting apparatus. The species include important primary producers in the marine environment. One distinct biochemical feature of Synechococcus is the presence of phycoerythrin, an orange fluorescent compound that can be detected at an excitation wavelength of 540 nm, and which can be used to identify Synechococcus. Members of the marine synechococccus group are closely related at the level of 16s rRNA. They are obligately marine and have elevated growth requirements for $Na^+$, $Cl^-$, $Mg^{2+}$, and $Ca^{2+}$, but can be grown readily in both natural and artificial seawater liquid media as well as on plates (Waterbury et al. 1988). Since they have a rapid heterotrophic or autotrophic growth rate, contain fatty acid precursors such as LA and ALA, and are relatively simple to transform, they are suitable for functional studies involving LC-PUFA synthesis genes, or for production of LC-PUFA in fermenter type production systems. Strains such as Synechococcus sp. strain WH8102, PCC7002 (7002, marine), or PCC7942 (freshwater) can be grown easily and are amenable to biochemical and genetic manipulation (Carr, N. G., and N. H. Mann. 1994. The oceanic cyanobacterial picoplankton, p. 27-48. In D. A. Bryant (ed.), the Molecular biology of cyanobacteria. Kluwer Academic publishers, Boston). For example, Synechococcus has been used as a heterologous expression system for desaturases (Domergue 2003b).

Wildtype Synechococcus 7002 Fatty Acid Profile and Growth Rates

To show that cyanobacterium Synechococcus 7002 was a suitable host for the transformation of fatty acid synthesis genes and that this expression system could be used to rapidly test the functions and specificities of fatty acid synthesis genes, the growth of the wildtype strain 7002 was first analysed at 22° C., 25° C. and 30° C. and the resultant fatty acid profiles analysed by gas chromatography for growth at 22° C. and 30° C. (Table 14).

the chromosome of Synechococcus strains such as strain 7002. This vector contained the Synechococcus 7002 sul2 gene in a pBluescript plasmid backbone, which provided an ampicillin gene as a selectable marker and allowed bacterial replication in species such as E. coli. The vector was engineered to contain a plat promoter from E. coli fused to a downstream multiple cloning site, with the two elements inserted approximately in the centre of the sul2 gene. The sul2 gene in Synechococcus encodes a low affinity sulfate which is not essential under normal growth conditions. Any gene other than sul2, preferably a non-essential gene, could have been chosen for incorporation in the recombination vector.

The sul2 gene was amplified from Synechococcus 7002 genomic DNA using gene-specific primers, based on the near-identical sequence in strain PCC6803 (Genbank Accession No. NC_000911, nucleotides 2902831 to 2904501) and inserted into the vector pGEM-T. The plac promoter from pBluescript was amplified using the primers 5'-gctacgc-ccggggatcctcgaggctggcgcaacgcaattaatgtga-3' (SEQ ID NO:81) (sense) and 5'-cacaggaaacagcttgacatcgattac-cggcaattgtacggcggccgctacggatatcctcgctcgagctcgcccgggg tagct-3' (SEQ ED NO:82) (antisense), which also introduced a number of restriction sites at the ends of the promoter sequence. The amplified fragment was then digested with SmaI and ligated to the large PvuII fragment of pBluescript including the beta-lactamase gene. This intermediate vector was then digested with EcoRV and SacI and ligated to the HpaI to SacI fragment (designated sul2b) of the sul2 gene. The resultant plasmid was digested with BamHI, treated with DNA polymerase I (Klenow fragment) to fill in the ends, and ligated to the SmaI to HpaI fragment (designated sul2a) of the sul2 gene. Excess restriction sites were then removed from

TABLE 14

Synechococcus 7002 wildtype fatty acid profiles at 22° C. and 30° C. growth temperatures (% of total fatty acid).

| Temp | Myristic | Palmitic | Palmitoleic | Stearic | Oleic | 18:1iso | Linoleic | GLA | Linolenic |
|---|---|---|---|---|---|---|---|---|---|
| 22° C. | 0.79 | 42.5 | 10.6 | 0.92 | 8.4 | 1.5 | 7.5 | 0.54 | 27.1 |
| 30° C. | 0.76 | 47.1 | 10.9 | 0.67 | 17.0 | 0.34 | 20.4 | | 2.9 |

Growth at 30° C. was much more rapid than at 22° C., with intermediate rates at 25° C. (FIG. 13). The cells were found to contain both linoleic (LA, 18:2 ω6) and linolenic (ALA, 18:3 ω3) acids which could be used as precursors for LC-PUFA synthesis. Although some of the preferred precursor ALA was produced at the 30° C., higher levels were obtained at 22° C. Tests were also carried out to determine whether cells could be grown at 30° C., followed by reducing the incubation temperature to 22° C. after sufficient biomass had been achieved, to see if this would result in a shift to higher production of linolenic acid (FIG. 14). In this experiment, levels of ALA obtained were greater than 5%. In further experiments, 25° C. was used as the preferred temperature for strain 7002, providing adequate growth rates and suitable precursor fatty acid profile.

Transformation Strategy

Both replicative plasmid vectors and non-replicative homologous recombination vectors have been used previously to transform various cyanobacterial species, including Synechococcus 7002 (Williams and Szalay, 1983; Ikeda et al., 2002; Akiyama et al., 1998a). The recombination vectors may be preferred in certain applications, and have been used to inactivate a gene, rather than create an expression strain.

A recombination vector was constructed that was suitable for introduction of one or more fatty acid synthesis genes into this vector by digestion with SacI and SpeI, blunting the ends with T4 DNA polymerase, and religation. Finally, a multiple cloning site was introduced downstream of the plac promoter by digesting the vector with ClaI and NotI, and ligating in a ClaI to NotI fragment from pBluescript, generating the recombination vector which was designated pJRP3.2.

Various genes related to LC-PUFA synthesis were adapted by PCR methods to include flanking restriction sites as well as ribosome binding site (RBS) sequences that were suitable for expression in the prokaryote, Synechococcus. For example, the Echium plantagineum Δ6-desaturase (Example 15) was amplified with the primers 5'-AGCACATCGATGAAG-GAGATATACCCatggctaatgcaatcaagaa-3' (SEQ ID NO:83) (sense) and 5'-ACGATGCGGCCGCTCAACCATGAGTAT-TAAGAGCTT-3' (SEQ ID NO:84) (antisense).

The amplified product was digested with ClaI and NotI and cloned into the ClaI to NotI sites of pJRP3.2. A selectable marker gene comprising a chloramphenicol acetyl transferase coding region (CAT) (catB3 gene, Accession No. AAC53634) downstream of a pbsA promoter (psbA-CAT) was inserted into the XhoI site of pJRP3.2, producing the vector pJRP3.3. The selectable marker gene was inserted within the sulB gene to enable easy selection for homologous recombination events after introduction of the recombination vector into Synechococcus.

Transformation of *Synechococcus* 7002 was achieved by mixing vector DNA with cells during the exponential phase of growth, during which DNA uptake occurred, as follows. Approximately 1 µg of the recombination vector DNA resuspended in 100 µL of 10 mM Tris-HCl was added to 900 µL of mid-log phase cells growing in BG-11 broth. The cells were incubated for 90 min at 30° C. and light intensity of 20 µmol photons·m$^{-2}$·s$^{-1}$. 250 µL aliquots were then added to 2 mL BG-11 broth, mixed with 2 mL molten agar (1.5%) and poured onto BG-11 agar plates containing 50 µg/mL chloramphenicol (Cm) for selection of recombinant cells. The plates were incubated for 10-14 days at the same temperature/light conditions before the Cm-resistant colonies were clearly visible. These colonies were then re-streaked several times onto fresh BG-11/Cm50 plates. After several rounds of restreaking on selective plates, liquid medium was inoculated with individual colonies and the cultures incubated at 25° C.

*Synechococcus* 7002 cells containing the *Echium* Δ6-desaturase gene inserted into the sulB gene via the recombination vector and expressed from the plac promoter are shown to produce GLA (18:3 Δ6,9,12) and SDA (18:4, Δ6,9,12,15) from endogenous linoleic acid (LA) and linolenic acid (ALA), respectively, as substrates.

Episomal vectors can also be used in *Synechococcus* rather than the integrative/recombinational vectors described above. *Synechococcus* species have native plasmids that have been adapted for use in transformation, for example pAQ-EX1, where a fragment of the native plasmid pAQ1 (Accession No. NC_005025) was fused with an *E. coli* plasmid to form a shuttle vector with both *E. coli* and *Synechococcus* origins of replication (Ikeda et al., 2002; Akiyama et al., 1998b).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abbadi, A. et al., (2001) Eur. J. Lipid. Sci. Technol. 103:106-113.
Abbadi, A., et al. (2004) Plant Cell 16:2734-2748.
Abbott et al., (1998) Science 282:2012-2018.
Agaba, M. et al., (2004) Marine Biotechnol (NY) 6:251-261.
Akiyama, H. et al. (1998a) DNA Res. 5:327-334.
Akiyama, H. et al. (1998b) DNA Res. 5:127-129.
Baumlein, H. et al., (1991) Mol. Gen. Genet. 225:459-467.
Baumlein, H. et al., (1992) Plant J. 2:233-239.
Beaudoin, F. et al., (2000) Proc. Natl. Acad. Sci U.S.A. 97:6421-6426.
Berberich, T. et al., (1998) Plant Mol. Biol. 36:297-306.
Bolch, C. J. et al., (1999a) J. Phycology 35:339-355.
Botch, C. J. et al., (1999b) J. Phycology 35:356-367.
Broun, P. et al., (1998) Plant J. 13:201-210.
Brown, M. R. et al., (1997) Aquaculture 151:315-331,
Browse. J. A. and Slack. C. R. (1981) FEBS Letters 131:111-114.
Chinain, M. et al., (1997) J. Phycology 33:36-43.
Cho, H. P. et al., (1999a) J. Biol. Chem. 274:471-477.
Cho, H. P. et al., (19996) J. Biol Chem 274:37335-37339.
Clough, S. J. and Bent, A. F. (1998) Plant J. 16:735-43.
Coleman, A. W. (1977) Am. J. Bot, 64:361-368.
Domergue, F. et al., (2002) Eur. J. Biochem. 269:4105-4113.
Domergue, F. et al., (2003a) J. Biol. Chem. 278:35115-35126.
Domergue, F. et al., (2003b) Plant Physiol. 131:1648-1660.
Drexler, H. et al., (2003) J. Plant Physiol. 160:779-802.
Dunstan, G. A. et al., (1994) Phytochemistry 35:155-161.
Gallagher, J. C. (1980) J. Phycology 16:464-474.
Garcia-Maroto, F. et al., (2002) Lipids 37:417-426.
Girke, T. et al., (1998) Plant J. 15:39-48.
Guil-Guerrero, J. L. et al., (2000). Phytochemistry 53:451-456.
Haseloff, J. and Gerlach, W. L. (1988) Nature 334:585-591.
Hastings, N. et al., (2001) Proc. Natl. Acad. Sci. U.S.A. 98:14304-14309.
Hong, H. et al., (2002) Lipids 37:863-868.
Hong, H. et al., (2002a) Lipids 37:863-868.
Horiguchi, G. et al., (1998) Plant Cell Physiol. 39:540-544.
Huang, Y. S. et al., (1999) Lipids 34:649-659.
Ikeda, K. et al. (2002) World J. Microbiol. Biotech. 18:55-56.
Inagaki, K. et al., (2002) Biosci Biotechnol Biochem 66:613-621.
Jones, A. V. and Harwood, J. L (1980) Biochem J. 190:851-854.
Kajikawa, M. et al., (2004) Plant Mol Biol 54:335-52.
Knutzon, D. S. et al., (1998) J. Biol Chem. 273:29360-6.
Lee, M. et al., (1998) Science 280:915-918.
Leonard, A. E. et al., (2000) Biochem. J. 347:719-724.
Leonard, A. E. et al., (2000b) Biochem. J. 350:765-770.
Leonard, A. E. et al., (2002) Lipids 37:733-740.
Lo, J. et al., (2003) Genome Res. 13:455-466.
Mansour, M. P. et al., (1999a) J. Phycol. 35:710-720.
Medlin, L. K. et al., (1996) J. Marine Systems 9:13-31.
Metz, J. G. et al., (2001) Science 293:290-293.
Meyer, A. et al., (2003) Biochemistry 42:9779-9788.
Meyer, A. et al., (2004) Lipid Res 45:1899-1909.
Michaelson. L. V. et al., (1998a) J. Biol. Chem. 273:19055-19059.
Michaelson, L. V. et al., (1998b) FEBS Lett. 439:215-218.
Mitchell, A. G. and Martin, C. E. (1995) J. Biol. Chem. 270:29766-29772.
Morita, N. et al., (2000) Biochem. Soc. Trans. 28:872-879.
Napier, J. A. et al., (1998) Biochem J. 330:611-614.
Napier, J. A et. al., (1999) Trends in Plant Sci 4:2-4.
Napier, J. A. et al., (1999) Curr. Op. Plant Biol. 2:123-127,
Needleman, S. B. and Wunsch, C. D. (1970) J. Mol. Biol. 48:443-453.
Parker-Barnes, J. F. et al., (2000) Proc Natl Acad Sci USA 97:8284-8289.
Pereira, S. L. et al., (2004) Biochem. J. 378:665-671.
Perriman, R. et al., (1992) Gene 113:157-163.
Qi, B. et al., (2002) FEBS Lett. 510:159-165.
Qiu, X. et al., (2001) J. Biol. Chem. 276:31561-31566.
Reddy, A. S. et al., (1993) Plant Mol. Biol. 22:293-300.
Saito, T. et al., (2000) Eur. J. Biochem. 267:1813-1818.
Sakuradani, E. et al., (1999) Gene 238:445-453.
Sayanova, O. V. et al., (1997) Proc. Natl. Acad. Sci. U.S.A. 94:4211-4216.
Sayanova, O. V. et al., (1999) Plant Physiol. 121:641-646.
Sayanova, O. V. et al., (2003) FEBS Lett. 542:100-104.

Sayanova, O. V. and Napier, J. A. (2004) Phytochemistry 65:147-158.
Shippy, R. et al., (1999) Mol. Biotech. 12:117-129.
Simopoulos, A. P. (2000) Poultry Science 79:961-970.
Singh, S. et al., (2001) Planta 212:872-879.
Smith, N. A. et al., (2000) Nature 407:319-320.
Sperling, P. et al., (2000) Eur. J. Biochem. 267:3801-3811.
Sperling, P. and Heinz, E. (2001) Eur. J. Lipid Sci. Technol 103:158-180,
Sprecher, H. et al., (1995) J. Lipid Res. 36:2471-2477.
Spychalla, P. J. et al., (1997) Proc. Natl. Acad. Sci. U.S.A. 94:1142-1147.
Stalberg, K. et al., (1993) Plant. Mol. Biol. 23:671-683.
Takeyama, H. et al., (1997) Microbiology 143:2725-2731.
Tanaka, M. et al., (1999) Biotechnol. Lett. 21:939-945.
Tonon, T. et al., (2003) FEBS Lett. 553:440-444.
Trautwein, E. A. (2001) Eur. J. Lipid Sci. Technol. 103:45-55.
Tvrdik, P. (2000) J. Cell Biol. 149:707-718.
Valvekens, D. et al., (1988) Proc. Natl. Acad. Sci. USA. 85:5536-5540.
Volkman, J. K. et al., (1989) J. Exp. Mar. Biol. Ecol. 128:219-240.
Wallis, J. G. and Browse, J. (1999) Arch. Biochem. Biophys. 365:307-316.
Wang, M. B. et al., (1997) J. Gen. Breed. 51:325-334.
Waterbury, J. B. et al. (1988) Methods Enzymol. 167:100-105.
Waterhouse, P. M. et al., (1998) Proc. Natl. Acad. Sci. USA 95:13959-13964.
Watts, J. L. and Browse, J. (1999b) Arch Biochem Biophys 362:175-182.
Williams, J. G. and Szalay, A. A. (1983) Gene 24:37-51,
Whitney, H. M. et al., (2003). Planta 217:983-992.
Yazawa, K. (1996) Lipids 31:S297-S300.
Yu, R. et al., (2000) Lipids 35:1061-1064.
Zank, T. K. et al., (2000) Plant J. 31:255-268.
Zank, T. K. et al., (2002) Plant J. 31:255-268.
Zhang, Q. et al., (2004) FEBS Lett. 556:81-85.
Zhou, X. R. and Christie, P. J. (1997) J Bacterial 179:5835-5842.

The invention claimed is:

1. A process for producing oil containing eicosapentaenoic acid and docosapentaenoic acid, comprising the steps of obtaining a transgenic seed of an oilseed plant which comprises eicosapentaenoic acid and docosapentaenoic acid in an esterified form as part of triglycerides, and a microalgal fatty acid desaturase, wherein the total fatty acid of the transgenic seed comprises at least 2.5% ω3 C20 fatty acids (w/w) and wherein the docosapentaenoic acid is present at a level based on a conversion ratio of eicosapentaenoic acid to docosapentaenoic acid of at least 5% (w/w), and extracting oil from the transgenic seed so as to thereby produce the oil.

2. The process of claim 1, wherein the step of extracting the oil comprises crushing the seed.

3. The process of claim 1, wherein the total fatty acid of the seed comprises at least 9% C20 fatty acids (w/w).

4. The process of claim 1, wherein the total fatty acid of the seed comprises at least 1.5% eicosapentaenoic acid and at least 0.13% docosapentaenoic acid (w/w).

5. The process of claim 1, wherein the total fatty acid of the seed comprises at least 2.1% eicosapentaenoic acid and less than 0.1% eicosatrienoic acid (w/w).

6. The process of claim 1, wherein at least 25% (w/w) of the eicosapentaenoic acid and docosapentaenoic acid of the seed is incorporated into triacylglycerols in the seed.

7. The process of claim 1, wherein at least 50% (w/w) of the eicosapentaenoic acid and docosapentaenoic acid of the seed is incorporated into triacylglycerols in the seed.

8. The process of claim 1, wherein the oil comprises at least 50% triacylglycerols.

9. The process of claim 1, wherein the total fatty acid of the seed comprises at least 7.9% C20 fatty acids (w/w).

10. The process of claim 9, wherein the total fatty acid of the seed comprises at least 10.2% C20 fatty acids (w/w).

11. The process of claim 10, wherein the total fatty acid of the seed comprises at least 1.5% eicosapentaenoic acid and at least 0.13% docosapentaenoic acid (w/w).

12. The process of claim 10, wherein at least 50% (w/w) of the eicosapentaenoic acid and docosapentaenoic acid of the seed is incorporated into triacylglycerols in the seed.

13. The process of claim 1, wherein the docosapentaenoic acid is present at a level based on a conversion ratio of eicosapentaenoic acid to docosapentaenoic acid of at least 7% (w/w).

14. The process of claim 13, wherein the total fatty acid of the seed comprises at least 1.5% eicosapentaenoic acid and at least 0.13% docosapentaenoic acid (w/w).

15. The process of claim 13, wherein at least 50% (w/w) of the eicosapentaenoic acid and docosapentaenoic acid of the seed is incorporated into triacylglycerols in the seed.

16. The process of claim 13, wherein the docosapentaenoic acid is present at a level based on a conversion ratio of eicosapentaenoic acid to docosapentaenoic acid of at least 10% (w/w).

17. The process of claim 16, wherein the total fatty acid of the seed comprises at least 1.5% eicosapentaenoic acid and at least 0.13% docosapentaenoic acid (w/w).

18. The process of claim 16, wherein at least 50% (w/w) of the eicosapentaenoic acid and docosapentaenoic acid of the seed is incorporated into triacylglycerols in the seed.

19. The process of claim 1, wherein the transgenic seed is a transgenic canola seed.

20. The process of claim 4, wherein the transgenic seed is a transgenic canola seed.

\* \* \* \* \*

SEQUENCE LISTING

<160> NUMBER OF SEQ ID NOS: 89

<210> SEQ ID NO 1
<211> LENGTH: 427
<212> TYPE: PRT
<213> ORGANISM: Pavlova salina

<400> SEQUENCE: 1

Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
    210                 215                 220

-continued

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
            245                 250                 255

Gln Tyr Tyr Tyr Val Pro Val Met Ala Ile Leu Asp Leu Tyr Trp Arg
        260                 265                 270

Leu Glu Ser Ile Ala Tyr Val Ala Met Arg Leu Pro Lys Met Leu Pro
    275                 280                 285

Gln Ala Leu Ala Leu Val Ala His Tyr Ala Ile Val Ala Trp Val Phe
290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                405                 410                 415

Asn Ile Arg Ala Leu Ala Phe Glu His Leu Leu
            420                 425

<210> SEQ ID NO 2
<211> LENGTH: 302
<212> TYPE: PRT
<213> ORGANISM: Pavlova salina

<400> SEQUENCE: 2

Met Lys Ala Ala Ala Gly Lys Val Gln Gln Glu Ala Glu Arg Leu Thr
1               5                   10                  15

Ala Gly Leu Trp Leu Pro Met Met Leu Ala Ala Gly Tyr Leu Leu Val
            20                  25                  30

Leu Ser Ala Asn Arg Ala Ser Phe Tyr Glu Asn Ile Asn Asn Glu Lys
        35                  40                  45

Gly Ala Tyr Ser Thr Ser Trp Phe Ser Leu Pro Cys Val Met Thr Ala
    50                  55                  60

Val Tyr Leu Gly Gly Val Phe Gly Leu Thr Lys Tyr Phe Glu Gly Arg
65                  70                  75                  80

Lys Pro Met Gln Gly Leu Lys Asp Tyr Met Phe Thr Tyr Asn Leu Tyr
                85                  90                  95

Gln Val Ile Ile Asn Val Trp Cys Ile Ala Ala Phe Val Glu Val
            100                 105                 110

Arg Arg Ala Gly Met Ser Ala Val Gly Asn Lys Val Asp Leu Gly Pro
        115                 120                 125

Asn Ser Phe Arg Leu Gly Phe Val Thr Trp Val His Tyr Asn Asn Lys
    130                 135                 140

Tyr Val Glu Leu Leu Asp Thr Leu Trp Met Val Leu Arg Lys Lys Thr
145                 150                 155                 160

Gln Gln Val Ser Phe Leu His Val Tyr His His Val Leu Leu Ile Trp
                165                 170                 175

```
Ala Trp Phe Cys Val Val Lys Phe Cys Asn Gly Gly Asp Ala Tyr Phe
            180                 185                 190

Gly Gly Met Leu Asn Ser Ile Ile His Val Met Met Tyr Ser Tyr Tyr
        195                 200                 205

Thr Met Ala Leu Leu Gly Trp Ser Cys Pro Trp Lys Arg Tyr Leu Thr
    210                 215                 220

Gln Ala Gln Leu Val Gln Phe Cys Ile Cys Leu Ala His Ala Thr Trp
225                 230                 235                 240

Ala Ala Ala Thr Gly Val Tyr Pro Phe His Ile Cys Leu Val Glu Ile
                245                 250                 255

Trp Val Met Val Ser Met Leu Tyr Leu Phe Thr Lys Phe Tyr Asn Ser
                260                 265                 270

Ala Tyr Lys Gly Ala Ala Lys Gly Ala Ala Ala Ser Ser Asn Gly Ala
        275                 280                 285

Ala Ala Pro Ser Gly Ala Lys Pro Lys Ser Ile Lys Ala Asn
    290                 295                 300

<210> SEQ ID NO 3
<211> LENGTH: 304
<212> TYPE: PRT
<213> ORGANISM: Pavlova salina

<400> SEQUENCE: 3

Met Gly Pro Leu Ser Thr Leu Leu Ala Trp Met Pro Thr Trp Gly Glu
1               5                   10                  15

Phe Val Ala Gly Leu Thr Tyr Val Glu Arg Gln Gln Met Ser Glu Glu
                20                  25                  30

Leu Val Arg Ala Asn Lys Leu Pro Leu Ser Leu Ile Pro Glu Val Asp
            35                  40                  45

Phe Phe Thr Ile Ala Ser Val Tyr Val Gly Asp His Trp Arg Ile Pro
        50                  55                  60

Phe Thr Ala Ile Ser Ala Tyr Leu Val Leu Ile Thr Leu Gly Pro Gln
65                  70                  75                  80

Leu Met Ala Arg Arg Pro Pro Leu Pro Ile Asn Thr Leu Ala Cys Leu
                85                  90                  95

Trp Asn Phe Ala Leu Ser Leu Phe Ser Phe Val Gly Met Ile Val Thr
            100                 105                 110

Trp Thr Thr Ile Gly Glu Arg Leu Trp Lys Asn Gly Ile Glu Asp Thr
        115                 120                 125

Val Cys Gly His Pro Ile Phe Met Gly Tyr Gly Trp Ile Gly Tyr Val
    130                 135                 140

Met Leu Ala Phe Ile Trp Ser Lys Leu Phe Glu Leu Ile Asp Thr Val
145                 150                 155                 160

Phe Leu Val Ala Lys Lys Ala Asp Val Ile Phe Leu His Trp Tyr His
                165                 170                 175

His Val Thr Val Leu Leu Tyr Cys Trp His Ser Tyr Ala Val Arg Ile
            180                 185                 190

Pro Ser Gly Ile Trp Phe Ala Ala Met Asn Tyr Phe Val His Ala Ile
        195                 200                 205

Met Tyr Ala Tyr Phe Gly Met Thr Gln Ile Gly Pro Arg Gln Arg Lys
    210                 215                 220

Leu Val Arg Pro Tyr Ala Arg Leu Ile Thr Thr Phe Gln Leu Ser Gln
225                 230                 235                 240

Met Gly Val Gly Leu Ala Val Asn Gly Leu Ile Ile Arg Tyr Pro Ser
                245                 250                 255
```

```
Ile Gly His His Cys His Ser Asn Lys Thr Asn Thr Ile Leu Ser Trp
            260                 265                 270

Ile Met Tyr Ala Ser Tyr Phe Val Leu Phe Ala Ala Leu Tyr Val Lys
        275                 280                 285

Asn Tyr Ile Phe Ser Lys Leu Lys Ser Pro Lys Arg Lys Lys Val Glu
    290                 295                 300

<210> SEQ ID NO 4
<211> LENGTH: 447
<212> TYPE: PRT
<213> ORGANISM: Pavlova salina

<400> SEQUENCE: 4

Met Pro Pro Ser Ala Ala Lys Gln Met Gly Ala Ser Thr Gly Val His
1               5                   10                  15

Ala Gly Val Thr Asp Ser Ser Ala Phe Thr Arg Lys Asp Val Ala Asp
            20                  25                  30

Arg Pro Asp Leu Thr Ile Val Gly Asp Ser Val Tyr Asp Ala Lys Ala
        35                  40                  45

Phe Arg Ser Glu His Pro Gly Gly Ala His Phe Val Ser Leu Phe Gly
    50                  55                  60

Gly Arg Asp Ala Thr Glu Ala Phe Met Glu Tyr His Arg Arg Ala Trp
65                  70                  75                  80

Pro Lys Ser Arg Met Ser Arg Phe His Val Gly Ser Leu Ala Ser Thr
                85                  90                  95

Glu Glu Pro Val Ala Ala Asp Glu Gly Tyr Leu Gln Leu Cys Ala Arg
            100                 105                 110

Ile Ala Lys Met Val Pro Ser Val Ser Ser Gly Phe Ala Pro Ala Ser
        115                 120                 125

Tyr Trp Val Lys Ala Gly Leu Ile Leu Gly Ser Ala Ile Ala Leu Glu
    130                 135                 140

Ala Tyr Met Leu Tyr Ala Gly Lys Arg Leu Leu Pro Ser Ile Val Leu
145                 150                 155                 160

Gly Trp Leu Phe Ala Leu Ile Gly Leu Asn Ile Gln His Asp Ala Asn
                165                 170                 175

His Gly Ala Leu Ser Lys Ser Ala Ser Val Asn Leu Ala Leu Gly Leu
            180                 185                 190

Cys Gln Asp Trp Ile Gly Gly Ser Met Ile Leu Trp Leu Gln Glu His
        195                 200                 205

Val Val Met His His Leu His Thr Asn Asp Val Asp Lys Asp Pro Asp
    210                 215                 220

Gln Lys Ala His Gly Ala Leu Arg Leu Lys Pro Thr Asp Ala Trp Ser
225                 230                 235                 240

Pro Met His Trp Leu Gln His Leu Tyr Leu Leu Pro Gly Glu Thr Met
                245                 250                 255

Tyr Ala Phe Lys Leu Leu Phe Leu Asp Ile Ser Glu Leu Val Met Trp
            260                 265                 270

Arg Trp Glu Gly Glu Pro Ile Ser Lys Leu Ala Gly Tyr Leu Phe Met
        275                 280                 285

Pro Ser Leu Leu Leu Lys Leu Thr Phe Trp Ala Arg Phe Val Ala Leu
    290                 295                 300

Pro Leu Tyr Leu Ala Pro Ser Val His Thr Ala Val Cys Ile Ala Ala
305                 310                 315                 320

Thr Val Met Thr Gly Ser Phe Tyr Leu Ala Phe Phe Phe Phe Ile Ser
                325                 330                 335
```

```
His Asn Phe Glu Gly Val Ala Ser Val Gly Pro Asp Gly Ser Ile Thr
                340                 345                 350

Ser Met Thr Arg Gly Ala Ser Phe Leu Lys Arg Gln Ala Glu Thr Ser
        355                 360                 365

Ser Asn Val Gly Gly Pro Leu Leu Ala Thr Leu Asn Gly Gly Leu Asn
370                 375                 380

Tyr Gln Ile Glu His His Leu Phe Pro Arg Val His His Gly Phe Tyr
385                 390                 395                 400

Pro Arg Leu Ala Pro Leu Val Lys Ala Glu Leu Glu Ala Arg Gly Ile
            405                 410                 415

Glu Tyr Lys His Tyr Pro Thr Ile Trp Ser Asn Leu Ala Ser Thr Leu
        420                 425                 430

Arg His Met Tyr Ala Leu Gly Arg Arg Pro Arg Ser Lys Ala Glu
        435                 440                 445

<210> SEQ ID NO 5
<211> LENGTH: 1235
<212> TYPE: DNA
<213> ORGANISM: Pavlova salina

<400> SEQUENCE: 5
atgggacgcg gcggagacag cagtgggcag gcgcatccgg cggcggagct ggcggtcccg      60
agcgaccgcg cggaggtgag caacgctgac agcaaagcgc tgcacatcgt gctgtatggc     120
aagcgcgtgg atgtgaccaa gttccaacgc acgcacccgg tggtagcaa ggtcttccgg      180 atcttccagg accgcgatgc gacggagcag ttcgagtcct accactcgaa gcgcgcgatc     240
aagatgatgg agggcatgct caagaagtct gaggatgctc ccgccgacac gcccttgccc     300
tcccagtcac cgatggggaa ggacttcaag gcgatgatcg agcggcacgt tgcagcgggt     360
tactacgatc catgcccgct cgatgagctg ttcaagctca gcctcgtgct cctcccgacc     420
tttgcgggca tgtacatgct caaggcgggc gtcggctccc cgctctgcgg cgccctcatg     480
gtgagctttg ctggtacct cgatggctgg ctcgcgcacg actatctgca ccactccgtc      540
ttcaaggggt ccgtcgcacg caccgtcggg tggaacaacg cggcgggcta cttcctcggc     600
ttcgtgcagg ggtatgcggt cgagtggtgg cgcgcgcggc ataacacgca ccacgtgtgc     660
accaatgagg acggctcgga ccccgacatc aaaacggcgc cgctgctcat atacgtcgcc    720
aacaagccga gcatcgccaa cgcctgaac gccttccagc gctaccagca gtactactat      780
gtgccggtga tggcaatcct cgacctgtac tggcggctcg agtcgatcgc ctacgtcgcg     840
atgcgcctgc cgaagatgct gccgcaggcc ctcgcactcg tcgcgcacta cgccatcgtc     900
gcgtgggtct ttgcgggcaa ctaccacctg ctcccgctcg tgacggttct gcgcgggttt     960
ggcactggga tcaccgtttt cgcgacgcac tacggtgagg acattctcga cgcggaccag    1020
gtgcgtcaca tgacgctcgt cgagcagacg gcactcacct cgcgcaacat ctcgggcggc    1080
tggctcgtga acgtgctcac cggcttcatc tcactgcaga cggagcacca cctgttcccg    1140
atgatgccaa ccggcaacct catgactatc cagcccgagg tgcgcgcctt cttcaagaag    1200
cacggacttg agtaccgcga gggcaacctc attga                                1235

<210> SEQ ID NO 6
<211> LENGTH: 1700
<212> TYPE: DNA
<213> ORGANISM: Pavlova salina

<400> SEQUENCE: 6
ggcacgaggc agctggccgc cgtcgagaga acgccagggg ggtcatggga cgcggcggag       60
```

```
acagcagtgg gcaggcgcat ccggcggcgg agctggcggt cccgagcgac cgcgcggagg    120
tgagcaacgc tgacagcaaa gcgctgcaca tcgtgctgta tggcaagcgc gtggatgtga    180
ccaagttcca acgcacgcac ccgggtggta gcaaggtctt ccggatcttc caggaccgcg    240
atgcgacgga gcagttcgag tcctaccact cgaagcgcgc gatcaagatg atggagggca    300
tgctcaagaa gtctgaggat gctcccgccg cacgcccttt gcctcccag tcaccgatgg     360 ggaaggactt caaggcgatg atcgagcggc acgttgcagc gggttactac gatccatgcc    420
cgctcgatga gctgttcaag ctcagcctcg tgctcctccc gacctttgcg ggcatgtaca    480
tgctcaaggc gggcgtcggc tccccgctct gcggcgccct catggtgagc tttggctggt    540
acctcgatgg ctggctcgcg cacgactatc tgcaccactc cgtcttcaag gggtccgtcg    600
cacgcaccgt cgggtggaac aacgcggcgg gctacttcct cggcttcgtg caggggtatg    660
cggtcgagtg gtggcgcgcg cggcataaca cgcaccacgt gtgcaccaat gaggacggct    720
cggaccccga catcaaaacg cgccgctgc tcatatacgt gcgcaacaag ccgagcatcg     780
ccaagcgcct gaacgccttc cagcgctacc agcagtacta ctatgtgccg gtgatggcaa    840
tcctcgacct gtactggcgg ctcgagtcga tcgcctacgt cgcgatgcgc ctgccgaaga    900
tgctgccgca ggccctcgca ctcgtcgcgc actacgccat cgtcgcgtgg gtctttgcgg    960
gcaactacca cctgctcccg ctcgtgacgg ttctgcgcgg gtttggcact gggatcaccg   1020
ttttcgcgac gcactacggt gaggacattc tcgacgcgga ccaggtgcgt cacatgacgc   1080
tcgtcgagca gacggcactc acctcgcgca acatctcggg cggctggctc gtgaacgtgc   1140
tcaccggctt catctcactg cagacggagc accacctgtt cccgatgatg ccaaccggca   1200
acctcatgac tatccagccc gaggtgcgcg ccttcttcaa gaagcacgga cttgagtacc   1260
gcgagggcaa cctcattgag tgcgtgcggc agaacatccg tgcgcttgca ttcgagcacc   1320
tgctttgagc gctctccgct tccaaggggcg ggatcggcgc atccgttggt gctgcggcac  1380
caacgcttcc gctctcgagc gcagatgttg gttgcatcac gcatcacacc caccccagc    1440 cggatcaccc agctcccgat gcttggcgta cctagccgcg tcctcccagc atgcactgca   1500
actcattcac cacctgctac agtttcggcc taatccatgg cccgactgct tgccgccttg   1560
cacaccgacg agtacgccga ctcggtccaa tgcctcggcg taatctgctg gcgtgctgcg   1620
gcactgtgat tcattcattg atcgcacagt tcacagcatg ttcgctgaca caacgtttgc   1680
tgacctcata gacagtagaa                                                1700
```

<210> SEQ ID NO 7
<211> LENGTH: 909
<212> TYPE: DNA
<213> ORGANISM: Pavlova salina

<400> SEQUENCE: 7

```
atgaaagctg cggcaggcaa ggtgcagcag gaggcggagc gcctcacggc gggcctctgg     60
ctgccgatga tgcttgcggc cggttatctg ctggttctct ctgcaaaccg cgcgagcttc    120
tacgagaaca tcaacaacga gaagggcgcc tactcgacgt cgtggttctc gctgccgtgc    180
gtcatgacgg ctgtgtacct gggcggtgtg tttggcttga ccaagtactt tgagggtcgc    240
aagccgatgc agggcctgaa ggattacatg tttacgtaca acctgtacca ggtgatcatc    300
aacgtgtggt gcatcgcggc tttcgtcgtg gaggtgaggc gcgcgggcat gagcgcggtg    360
ggcaacaagg tcgacctcgg ccccaactcc ttcaggctcg gctttgtgac gtgggtgcac    420
tacaacaaca gtacgtcga gctgctcgac acgctgtgga tggtgctgcg caagaagacg    480
```

| | |
|---|---|
| cagcaggtct ccttcctgca cgtgtaccac cacgtgctgc tcatctgggc gtggttctgc | 540 |
| gtagtcaaat tctgcaacgg cggcgacgcc tactttggcg gcatgctcaa ctcgatcatc | 600 |
| cacgtgatga tgtactcgta ctacacgatg gcgctgctcg gctggagttg tccatggaag | 660 |
| cgatacctca ctcaggcgca gctcgtgcag ttctgcattt gcctcgcgca cgcgacgtgg | 720 |
| gcggccgcga cgggcgtgta ccccttccac atttgcctcg tcgagatctg ggtgatggtg | 780 |
| tcgatgctgt acctgttcac caagttctac aactctgcgt acaagggcgc agcaaagggc | 840 |
| gcagcagcga gcagcaacgg tgcggcggcg ccgagcggag ccaagcctaa gagcatcaag | 900 |
| gccaactga | 909 |

<210> SEQ ID NO 8
<211> LENGTH: 1216
<212> TYPE: DNA
<213> ORGANISM: Pavlova salina

<400> SEQUENCE: 8

| | |
|---|---|
| gaattcggca cgaggtcttc ttccagctgt ggtcgtcatg aaagctgcgg caggcaaggt | 60 |
| gcagcaggag gcggagcgcc tcacggcggg cctctggctg ccgatgatgc ttgcggccgg | 120 |
| ttatctgctg gttctctctg caaaccgcgc gagcttctac gagaacatca acaacgagaa | 180 |
| gggcgcctac tcgacgtcgt ggttctcgct gccgtgcgtc atgacggctg tgtacctggg | 240 |
| cggtgtgttt ggcttgacca agtactttga gggtcgcaag ccgatgcagg gcctgaagga | 300 |
| ttacatgttt acgtacaacc tgtaccaggt gatcatcaac gtgtggtgca tcgcggcttt | 360 |
| cgtcgtggag gtgaggcgcg cgggcatgag cgcggtgggc aacaaggtcg acctcggccc | 420 |
| caactccttc aggctcggct ttgtgacgtg ggtgcactac aacaacaagt acgtcgagct | 480 |
| gctcgacacg ctgtggatgg tgctgcgcaa gaagacgcag caggtctcct tcctgcacgt | 540 |
| gtaccaccac gtgctgctca tctgggcgtg gttctgcgta gtcaaattct gcaacggcgg | 600 |
| cgacgcctac tttggcggca tgctcaactc gatcatccac gtgatgatgt actcgtacta | 660 |
| cacgatggcg ctgctcggct ggagttgtcc atggaagcga tacctcactc aggcgcagct | 720 |
| cgtgcagttc tgcatttgcc tcgcgcacgc gacgtgggcg gccgcgacgg gcgtgtaccc | 780 |
| cttccacatt tgcctcgtcg agatctgggt gatggtgtcg atgctgtacc tgttcaccaa | 840 |
| gttctacaac tctgcgtaca agggcgcagc aaagggcgca gcagcgagca gcaacggtgc | 900 |
| ggcggcgccg agcggagcca agcctaagag catcaaggcc aactgaggcc tggcacgcgg | 960 |
| gcgaggccgc ggcacgccgc gcagttccgg tcggcgcaac gtcgcggctg cgccgcgcta | 1020 |
| cgcaccacgc aggcagtggt tcaggtggcg aagtgtgcag cctgtctgtc gcctgcacac | 1080 |
| ccattgattg gtcccgctcg cgctactctg cgcactgcca agtcgccaag acctgtacgt | 1140 |
| gtatgatctg actgataccg catacggatg tcccgtatgc gacgactgcc atacgtgctg | 1200 |
| cacacgttgt ccaacc | 1216 |

<210> SEQ ID NO 9
<211> LENGTH: 915
<212> TYPE: DNA
<213> ORGANISM: Pavlova salina

<400> SEQUENCE: 9

| | |
|---|---|
| atggggccgt tgagcacgct gctagcgtgg atgcccacct ggggcgagtt tgtcgccggg | 60 |
| ctgacctatg tcgagcgcca gcagatgtca gaggagctcg tgcgcgcaaa taagctcccg | 120 |
| ctgtcgctca tcccggaggt ggacttcttc acgatcgcgt cagtctacgt gggcgaccat | 180 |

-continued

```
tggcggatcc cattcacggc catctcggct tatctggtct tgatcacgct cgggccgcag     240
ctcatggcca ggcggccgcc attgccaatc aacaccttgg cgtgcctctg gaatttcgcg     300
ctgtcgctct ttagttttgt cggcatgatt gttacgtgga cgaccatcgg cgagcgcctg     360
tggaaaaatg gtatcgagga cacagtgtgc ggccatccga tattcatggg gtacggctgg     420
atcggatatg ttatgcttgc cttcatctgg tcgaagctct tcgagctgat cgacaccgta     480
ttcctcgtcg cgaagaaggc cgacgtcatc ttcctgcact ggtaccacca cgtgacggtg     540
ctgctatact gctggcattc gtacgctgtt cgtatcccgt ccggcatctg gtttgccgcg     600
atgaattatt tcgtacacgc catcatgtac gcctactttg gcatgacaca gattgggccg     660
aggcagcgca agctcgtgcg accgtacgca cggctcatca ccacgttcca gctgtcgcag     720
atgggcgtcg gtctggccgt caatggcctt atcatccgct acccgtcgat aggccatcat     780
tgccactcga acaagacgaa caccattttg agctggatca tgtacgcgag ctactttgtg     840
cttttcgccg cactatacgt gaagaactac atcttctcca agctgaagtc gcccaagagg     900
aagaaggtgg aatga                                                      915
```

<210> SEQ ID NO 10
<211> LENGTH: 1219
<212> TYPE: DNA
<213> ORGANISM: Pavlova salina

<400> SEQUENCE: 10

```
gaattcggca cgaggtgcag ccttgagcct tacgcaggcc gactcgcccg tggctagcac      60
gcagcgcgcc aaccccatg gggccgttga gcacgctgct agcgtggatg cccacctggg     120
gcgagtttgt cgccgggctg acctatgtcg agcgccagca gatgtcagag gagctcgtgc     180
gcgcaaataa gctcccgctg tcgctcatcc cggaggtgga cttcttcacg atcgcgtcag     240
tctacgtggg cgaccattgg cggatcccat tcacggccat ctcggcttat ctggtcttga     300
tcacgctcgg gccgcagctc atggccaggc ggccgccatt gccaatcaac accttggcgt     360
gcctctggaa tttcgcgctg tcgctcttta gttttgtcgg catgattgtt acgtggacga     420
ccatcggcga gcgcctgtgg aaaaatggta tcgaggacac agtgtgcggc catccgatat     480
tcatggggta cggctggatc ggatatgtta tgcttgcctt catctggtcg aagctcttcg     540
agctgatcga caccgtattc ctcgtcgcga agaaggccga cgtcatcttc ctgcactggt     600
accaccacgt gacggtgctg ctatactgct ggcattcgta cgctgttcgt atcccgtccg     660
gcatctggtt tgccgcgatg aattatttcg tacacgccat catgtacgcc tactttggca     720
tgacacagat tgggccgagg cagcgcaagc tcgtgcgacc gtacgcacgg ctcatcacca     780
cgttccagct gtcgcagatg ggcgtcggtc tggccgtcaa tggccttatc atccgctacc     840
cgtcgatagg ccatcattgc cactcgaaca agacgaacac cattttgagc tggatcatgt     900
acgcgagcta ctttgtgctt ttcgccgcac tatacgtgaa gaactacatc ttctccaagc     960
tgaagtcgcc caagaggaag aaggtggaat gattgactcg agctcgtgtt ccgccatct    1020 gtcattttac ggctcctcct gatgcggacg gcagctctga tctttgccac aggaccgatg    1080
acggccgatg gtgtctggtt ccagctggct ctgtcattcg cggctcatgg gcacccgggt    1140
gggagcacca gctgtcagac cggactcgat gagatagcgg tgacagacgg accgtgacca    1200
cgagtctcat catctgttg                                                 1219
```

<210> SEQ ID NO 11
<211> LENGTH: 125

```
<212> TYPE: DNA
<213> ORGANISM: Pavlova salina

<400> SEQUENCE: 11
agcacgacgg gaaccacggc gcgctctcca agtcggcctc ggtcaacctg gcgctcgggt    60
tgtgccagca ctggatcggc gggagcatga tcctctggct gcaggagcac gtgatgatgc   120
accac                                                              125

<210> SEQ ID NO 12
<211> LENGTH: 1344
<212> TYPE: DNA
<213> ORGANISM: Pavlova salina

<400> SEQUENCE: 12
atgcctccga gcgcggcgaa gcagatgggc gcgagcacgg gcgtgcatgc gggcgtcaca    60
gattcgtcgg ccttcacgcg caaggatgtc gccgacaggc cggacctcac gatcgtgggt   120
gacagcgtgt acgatgcgaa ggcgttccgc tccgagcatc cgggtggcgc gcactttgtg   180
tcgctgttcg gcgggcgcga tgccacggag gcgttcatgg agtaccaccg gcgcgcctgg   240
cccaagtcgc gcatgtcgcg cttccacgtc ggctctctgg catcgaccga ggagcccgtc   300
gccgccgatg agggctacct ccagctgtgc gctcgcatcg ccaagatggt gccgtcggtc   360
agcagcgggt tcgcgccggc gtcgtactgg gtgaaggccg gctgatcct cggctccgcg   420 atcgcgctcg aggcgtacat gctgtacgcg ggcaagcgcc tgctcccgtc gatcgtgctc   480
gggtggctgt ttgcgctgat tggcctgaac atccagcacg atgccaacca cggcgcgctc   540
tccaagtcgg cctcggtcaa cctggcgctc gggttgtgcc aggactggat cggcgggagc   600
atgatcctct ggctgcagga gcacgttgtc atgcaccact gcacaccaa cgacgttgac   660 aaggacccgg accagaaggc gcacggcgcc ctgcggctca gccgaccga cgcgtggagc   720 ccgatgcact ggctgcagca cctctacctg ctgcctgggg agacgatgta cgccttcaag   780
ctgctgtttc tcgacatcag cgagctggtg atgtggcggt gggagggcga gcccatcagc   840
aagctggccg ggtacctctt catgcccctg ctgctcctca agctcacctt ctgggcgcgc   900
tttgtcgcgc tgccgctgta cctcgcgccc agcgtgcaca cggcggtgtg catcgcggcg   960
acggtaatga cggggagctt ctacctcgcc ttcttcttct tcatctcgca caacttcgag  1020
ggcgtggcga gcgtcggacc ggacggcagc atcaccagca tgacgcgcgg cgcatccttc  1080
ctcaagcggc aggccgagac ctcgtccaac gtgggcggcc gctgctcgc cacgctcaac  1140 ggcggcctca actaccaaat cgagcaccac ctcttcccca gggtgcacca cggcttctac  1200
cctcgcctcg cgccgttggt caaggcggag ctcgaggcgc gcggcattga gtacaagcac  1260
taccccacca tatggagcaa cctggcatcc acgctgaggc acatgtacgc gctcggccgc  1320
aggccgcgca gcaaggcgga gtga                                        1344

<210> SEQ ID NO 13
<211> LENGTH: 1687
<212> TYPE: DNA
<213> ORGANISM: Pavlova salina

<400> SEQUENCE: 13
ctcctgtgag accgcgttgc gccagcgcaa ggaccgacct gcacgcgcga tgcctccgag    60
cgcggcgaag cagatgggcg cgagcacggg cgtgcatgcg gcgtcacag attcgtcggc   120 cttcacgcgc aaggatgtcg ccgacaggcc ggacctcacg atcgtgggtg acagcgtgta   180
cgatgcgaag gcgttccgct ccgagcatcc gggtggcgcg cactttgtgt cgctgttcgg   240
```

```
cgggcgcgat gccacggagg cgttcatgga gtaccaccgg cgcgcctggc ccaagtcgcg    300
catgtcgcgc ttccacgtcg gctctctggc atcgaccgag gagcccgtcg ccgccgatga    360
gggctacctc cagctgtgcg ctcgcatcgc caagatggtg ccgtcggtca gcagcgggtt    420
cgcgccggcg tcgtactggg tgaaggccgg gctgatcctc ggctccgcga tcgcgctcga    480
ggcgtacatg ctgtacgcgg gcaagcgcct gctcccgtcg atcgtgctcg ggtggctgtt    540
tgcgctgatt ggcctgaaca tccagcacga tgccaaccac ggcgcgctct ccaagtcggc    600
ctcggtcaac ctggcgctcg ggttgtgcca ggactggatc ggcgggagca tgatcctctg    660
gctgcaggag cacgttgtca tgcaccactt gcacaccaac gacgttgaca aggacccgga    720
ccagaaggcg cacggcgccc tgcggctcaa gccgaccgac gcgtggagcc cgatgcactg    780
gctgcagcac ctctacctgc tgcctgggga cgatgtac gccttcaagc tgctgtttct    840
cgacatcagc gagctggtga tgtggcggtg ggagggcgag cccatcagca agctggccgg    900
gtacctcttc atgccctcgc tgctcctcaa gctcaccttc tgggcgcgct ttgtcgcgct    960
gccgctgtac ctcgcgccca gcgtgcacac ggcggtgtgc atcgcggcga cggtaatgac   1020
ggggagcttc tacctcgcct tcttcttctt catctcgcac aacttcgagg gcgtggcgag   1080
cgtcggaccg gacggcagca tcaccagcat gacgcgcggc gcatccttcc tcaagcggca   1140
ggccgagacc tcgtccaacg tgggcggccc gctgctcgcc acgctcaacg gcggcctcaa   1200
ctaccaaatc gagcaccacc tcttccccag ggtgcaccac ggcttctacc ctcgcctcgc   1260
gccgttggtc aaggcggagc tcgaggcgcg cggcattgag tacaagcact accccaccat   1320
atggagcaac ctggcatcca cgctgaggca catgtacgcg ctcggccgca ggccgcgcag   1380
caaggcggag tgacgagcct cccaatcggc tgcccaggct gctggcagct tgggtcgacc   1440
atcggcatcg actcggcgac gccgacgcca gccgtggtcg cacaaacggc tcggcgttgg   1500
ttcttcggct accgcgccgg aaccggggca cgcacctgac tcggtgacga ttgcggtcgc   1560
accagcagaa gcgctcaccc ccgcccccgc tcggatcggg cggcatagag catacatcta   1620
gcgcgttctt actatatgcc actgtgtaga ctagtcttct agcgccggaa aatctgctat   1680
caacaat                                                              1687
```

<210> SEQ ID NO 14
<211> LENGTH: 288
<212> TYPE: PRT
<213> ORGANISM: Caenorhabditis elegans

<400> SEQUENCE: 14

```
Met Ala Gln His Pro Leu Val Gln Arg Leu Leu Asp Val Lys Phe Asp
1               5                   10                  15

Thr Lys Arg Phe Val Ala Ile Ala Thr His Gly Pro Lys Asn Phe Pro
            20                  25                  30

Asp Ala Glu Gly Arg Lys Phe Phe Ala Asp His Phe Asp Val Thr Ile
        35                  40                  45

Gln Ala Ser Ile Leu Tyr Met Val Val Phe Gly Thr Lys Trp Phe
    50                  55                  60

Met Arg Asn Arg Gln Pro Phe Gln Leu Thr Ile Pro Leu Asn Ile Trp
65                  70                  75                  80

Asn Phe Ile Leu Ala Ala Phe Ser Ile Ala Gly Ala Val Lys Met Thr
                85                  90                  95

Pro Glu Phe Gly Thr Ile Ala Asn Lys Gly Ile Val Ala Ser Tyr
            100                 105                 110
```

```
Cys Lys Val Phe Asp Phe Thr Lys Gly Glu Asn Gly Tyr Trp Val Trp
            115                 120                 125

Leu Phe Met Ala Ser Lys Leu Phe Glu Leu Val Asp Thr Ile Phe Leu
        130                 135                 140

Val Leu Arg Lys Arg Pro Leu Met Phe Leu His Trp Tyr His His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val His Ala Phe Met Tyr
                180                 185                 190

Ser Tyr Tyr Phe Leu Arg Ser Met Lys Ile Arg Val Pro Gly Phe Ile
                195                 200                 205

Ala Gln Ala Ile Thr Ser Leu Gln Ile Val Gln Phe Ile Ile Ser Cys
        210                 215                 220

Ala Val Leu Ala His Leu Gly Tyr Leu Met His Phe Thr Asn Ala Asn
225                 230                 235                 240

Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
                260                 265                 270

Arg Gly Gly Lys Asp Lys Tyr Lys Ala Val Pro Lys Lys Lys Asn Asn
                275                 280                 285

<210> SEQ ID NO 15
<211> LENGTH: 444
<212> TYPE: PRT
<213> ORGANISM: Danio rerio

<400> SEQUENCE: 15

Met Gly Gly Gly Gly Gln Gln Thr Asp Arg Ile Thr Asp Thr Asn Gly
1               5                   10                  15

Arg Phe Ser Ser Tyr Thr Trp Glu Glu Val Gln Lys His Thr Lys His
                20                  25                  30

Gly Asp Gln Trp Val Val Val Glu Arg Lys Val Tyr Asn Val Ser Gln
            35                  40                  45

Trp Val Lys Arg His Pro Gly Gly Leu Arg Ile Leu Gly His Tyr Ala
    50                  55                  60

Gly Glu Asp Ala Thr Glu Ala Phe Thr Ala Phe His Pro Asn Leu Gln
65                  70                  75                  80

Leu Val Arg Lys Tyr Leu Lys Pro Leu Leu Ile Gly Glu Leu Glu Ala
                85                  90                  95

Ser Glu Pro Ser Gln Asp Arg Gln Lys Asn Ala Ala Leu Val Glu Asp
                100                 105                 110

Phe Arg Ala Leu Arg Glu Arg Leu Glu Ala Glu Gly Cys Phe Lys Thr
            115                 120                 125

Gln Pro Leu Phe Phe Ala Leu His Leu Gly His Ile Leu Leu Leu Glu
        130                 135                 140

Ala Ile Ala Phe Met Met Val Trp Tyr Phe Gly Thr Gly Trp Ile Asn
145                 150                 155                 160

Thr Leu Ile Val Ala Val Ile Leu Ala Thr Ala Gln Ser Gln Ala Gly
                165                 170                 175

Trp Leu Gln His Asp Phe Gly His Leu Ser Val Phe Lys Thr Ser Gly
                180                 185                 190

Met Asn His Leu Val His Lys Phe Val Ile Gly His Leu Lys Gly Ala
                195                 200                 205
```

```
Ser Ala Gly Trp Trp Asn His Arg His Phe Gln His His Ala Lys Pro
    210                 215                 220

Asn Ile Phe Lys Lys Asp Pro Asp Val Asn Met Leu Asn Ala Phe Val
225                 230                 235                 240

Val Gly Asn Val Gln Pro Val Glu Tyr Gly Val Lys Lys Ile Lys His
                245                 250                 255

Leu Pro Tyr Asn His Gln His Lys Tyr Phe Phe Ile Gly Pro Pro
            260                 265                 270

Leu Leu Ile Pro Val Tyr Phe Gln Phe Gln Ile Phe His Asn Met Ile
        275                 280                 285

Ser His Gly Met Trp Val Asp Leu Leu Trp Cys Ile Ser Tyr Tyr Val
    290                 295                 300

Arg Tyr Phe Leu Cys Tyr Thr Gln Phe Tyr Gly Val Phe Trp Ala Ile
305                 310                 315                 320

Ile Leu Phe Asn Phe Val Arg Phe Met Glu Ser His Trp Phe Val Trp
                325                 330                 335

Val Thr Gln Met Ser His Ile Pro Met Asn Ile Asp Tyr Glu Lys Asn
            340                 345                 350

Gln Asp Trp Leu Ser Met Gln Leu Val Ala Thr Cys Asn Ile Glu Gln
        355                 360                 365

Ser Ala Phe Asn Asp Trp Phe Ser Gly His Leu Asn Phe Gln Ile Glu
    370                 375                 380

His His Leu Phe Pro Thr Val Pro Arg His Asn Tyr Trp Arg Ala Ala
385                 390                 395                 400

Pro Arg Val Arg Ala Leu Cys Glu Lys Tyr Gly Val Lys Tyr Gln Glu
                405                 410                 415

Lys Thr Leu Tyr Gly Ala Phe Ala Asp Ile Ile Arg Ser Leu Glu Lys
            420                 425                 430

Ser Gly Glu Leu Trp Leu Asp Ala Tyr Leu Asn Lys
        435                 440

<210> SEQ ID NO 16
<211> LENGTH: 444
<212> TYPE: PRT
<213> ORGANISM: Homo sapiens

<400> SEQUENCE: 16

Met Ala Pro Asp Pro Leu Ala Ala Glu Thr Ala Ala Gln Gly Leu Thr
1               5                   10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140
```

```
Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
            165                 170                 175

Leu Gln His Asp Phe Gly His Leu Ser Val Phe Ser Thr Ser Lys Trp
        180                 185                 190

Asn His Leu Leu His His Phe Val Ile Gly His Leu Lys Gly Ala Pro
    195                 200                 205

Ala Ser Trp Trp Asn His Met His Phe Gln His His Ala Lys Pro Asn
210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Asn Tyr
            245                 250                 255

Met Pro Tyr Asn His Gln His Lys Tyr Phe Phe Leu Ile Gly Pro Pro
        260                 265                 270

Ala Leu Leu Pro Leu Tyr Phe Gln Trp Tyr Ile Phe Tyr Phe Val Ile
    275                 280                 285

Gln Arg Lys Lys Trp Val Asp Leu Ala Trp Met Ile Thr Phe Tyr Val
290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
            325                 330                 335

Val Thr Gln Met Asn His Ile Pro Met His Ile Asp His Asp Arg Asn
        340                 345                 350

Met Asp Trp Val Ser Thr Gln Leu Gln Ala Thr Cys Asn Val His Lys
    355                 360                 365

Ser Ala Phe Asn Asp Trp Phe Ser Gly His Leu Asn Phe Gln Ile Glu
370                 375                 380

His His Leu Phe Pro Thr Met Pro Arg His Asn Tyr His Lys Val Ala
385                 390                 395                 400

Pro Leu Val Gln Ser Leu Cys Ala Lys His Gly Ile Glu Tyr Gln Ser
            405                 410                 415

Lys Pro Leu Leu Ser Ala Phe Ala Asp Ile Ile His Ser Leu Lys Glu
        420                 425                 430

Ser Gly Gln Leu Trp Leu Asp Ala Tyr Leu His Gln
            435                 440

<210> SEQ ID NO 17
<211> LENGTH: 456
<212> TYPE: PRT
<213> ORGANISM: Pythium irregulare

<400> SEQUENCE: 17

Met Gly Thr Asp Gln Gly Lys Thr Phe Thr Trp Gln Glu Val Ala Lys
1               5                   10                  15

His Asn Thr Ala Lys Ser Ala Trp Val Ile Ile Arg Gly Glu Val Tyr
            20                  25                  30

Asp Val Thr Glu Trp Ala Asp Lys His Pro Gly Gly Ser Glu Leu Ile
        35                  40                  45

Val Leu His Ser Gly Arg Glu Cys Thr Asp Thr Phe Tyr Ser Tyr His
    50                  55                  60

Pro Phe Ser Asn Arg Ala Asp Lys Ile Leu Ala Lys Tyr Lys Ile Gly
65                  70                  75                  80
```

```
Lys Leu Val Gly Gly Tyr Glu Phe Pro Val Phe Lys Pro Asp Ser Gly
                85                  90                  95

Phe Tyr Lys Glu Cys Ser Arg Val Ala Glu Tyr Phe Lys Thr Asn
            100                 105                 110

Asn Leu Asp Pro Lys Ala Ala Phe Ala Gly Leu Trp Arg Met Val Phe
            115                 120                 125

Val Phe Ala Val Ala Ala Leu Ala Tyr Met Gly Met Asn Glu Leu Ile
130                 135                 140

Pro Gly Asn Val Tyr Ala Gln Tyr Ala Trp Gly Val Phe Gly Val
145                 150                 155                 160

Phe Gln Ala Leu Pro Leu Leu His Val Met His Asp Ser Ser His Ala
                165                 170                 175

Ala Cys Ser Ser Pro Ala Met Trp Gln Ile Ile Gly Arg Gly Val
                180                 185                 190

Met Asp Trp Phe Ala Gly Ala Ser Met Val Ser Trp Leu Asn Gln His
                195                 200                 205

Val Val Gly His His Ile Tyr Thr Asn Val Ala Gly Ala Asp Pro Asp
        210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                245                 250                 255

Tyr Gly Val Leu Gly Leu Lys Phe Arg Ile Gln Asp Val Phe Glu Thr
                260                 265                 270

Phe Val Ser Leu Thr Asn Gly Pro Val Arg Val Asn Pro His Pro Val
                275                 280                 285

Ser Asp Trp Val Gln Met Ile Phe Ala Lys Ala Phe Trp Thr Phe Tyr
290                 295                 300

Arg Ile Tyr Ile Pro Leu Val Trp Leu Lys Ile Thr Pro Ser Thr Phe
305                 310                 315                 320

Trp Gly Val Phe Phe Leu Ala Glu Phe Thr Thr Gly Trp Tyr Leu Ala
                325                 330                 335

Phe Asn Phe Gln Val Ser His Val Ser Thr Glu Cys Glu Tyr Pro Cys
            340                 345                 350

Gly Asp Ala Pro Ser Ala Glu Val Gly Asp Glu Trp Ala Ile Ser Gln
            355                 360                 365

Val Lys Ser Ser Val Asp Tyr Ala His Gly Ser Pro Leu Ala Ala Phe
370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Asp Val
            405                 410                 415

Cys Lys Lys Tyr Asn Ile Lys Tyr Thr Val Leu Pro Thr Phe Thr Glu
            420                 425                 430

Ala Leu Leu Ala His Phe Lys His Leu Lys Asn Met Gly Glu Leu Gly
            435                 440                 445

Lys Pro Val Glu Ile His Met Gly
450                 455

<210> SEQ ID NO 18
<211> LENGTH: 439
<212> TYPE: PRT
<213> ORGANISM: Thraustochytrium sp.

<400> SEQUENCE: 18
```

-continued

```
Met Gly Lys Gly Ser Glu Gly Arg Ser Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430
```

Ala Asp Thr Lys Lys Gln Asp
        435

<210> SEQ ID NO 19
<211> LENGTH: 446
<212> TYPE: PRT
<213> ORGANISM: Mortierella alpina

<400> SEQUENCE: 19

Met Gly Thr Asp Gln Gly Lys Thr Phe Thr Trp Glu Glu Leu Ala Ala
1               5                   10                  15

His Asn Thr Lys Gly Asp Leu Phe Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Val Phe Pro Glu Pro Thr Val Phe His
                85                  90                  95

Lys Thr Ile Lys Thr Arg Val Glu Gly Tyr Phe Thr Asp Arg Asp Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Phe Glu Pro Asp Val Arg Arg Ile Lys Pro Asn Gln Lys Trp
225                 230                 235                 240

Phe Val Asn His Ile Asn Gln Asp Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
        370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
            405                 410                 415

Val Pro Tyr Leu Val Lys Asp Thr Phe Trp Gln Ala Phe Ala Ser His
        420                 425                 430

Leu Glu His Leu Arg Val Leu Gly Leu Arg Pro Lys Glu Glu
        435                 440                 445

<210> SEQ ID NO 20
<211> LENGTH: 447
<212> TYPE: PRT
<213> ORGANISM: Caenorhabditis elegans

<400> SEQUENCE: 20

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Ile Pro Asp Ile Lys
65                  70                  75                  80

Asp Asp Pro Ile Lys Gly Ile Asp Asp Val Asn Met Gly Thr Phe Asn
            85                  90                  95

Ile Ser Glu Lys Arg Ser Ala Gln Ile Asn Lys Ser Phe Thr Asp Leu
        100                 105                 110

Arg Met Arg Val Arg Ala Glu Gly Leu Met Asp Gly Ser Pro Leu Phe
    115                 120                 125

Tyr Ile Arg Lys Ile Leu Glu Thr Ile Phe Thr Ile Leu Phe Ala Phe
130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
            165                 170                 175

Gln Leu Phe Lys Asn Arg Tyr Tyr Asn Asp Leu Ala Ser Tyr Phe Val
        180                 185                 190

Gly Asn Phe Leu Gln Gly Phe Ser Ser Gly Gly Trp Lys Glu Gln His
    195                 200                 205

Asn Val His His Ala Ala Thr Asn Val Val Gly Arg Asp Gly Asp Leu
210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
            245                 250                 255

Trp Thr Phe Met Leu Pro Phe Leu Arg Leu Ser Trp Leu Leu Gln Ser
        260                 265                 270

Ile Ile Phe Val Ser Gln Met Pro Thr His Tyr Tyr Asp Tyr Tyr Arg
    275                 280                 285

Asn Thr Ala Ile Tyr Glu Gln Val Gly Leu Ser Leu His Trp Ala Trp
290                 295                 300

```
Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Ser His Val
            325                 330                 335

Val Thr Phe Asn His Tyr Ser Val Glu Lys Phe Ala Leu Ser Ser Asn
            340                 345                 350

Ile Met Ser Asn Tyr Ala Cys Leu Gln Ile Met Thr Thr Arg Asn Met
            355                 360                 365

Arg Pro Gly Arg Phe Ile Asp Trp Leu Trp Gly Gly Leu Asn Tyr Gln
            370                 375                 380

Ile Glu His His Leu Phe Pro Thr Met Pro Arg His Asn Leu Asn Thr
385                 390                 395                 400

Val Met Pro Leu Val Lys Glu Phe Ala Ala Ala Asn Gly Leu Pro Tyr
                405                 410                 415

Met Val Asp Asp Tyr Phe Thr Gly Phe Trp Leu Glu Ile Glu Gln Phe
            420                 425                 430

Arg Asn Ile Ala Asn Val Ala Ala Lys Leu Thr Lys Lys Ile Ala
            435                 440                 445

<210> SEQ ID NO 21
<211> LENGTH: 444
<212> TYPE: PRT
<213> ORGANISM: Homo sapiens

<400> SEQUENCE: 21

Met Gly Lys Gly Gly Asn Gln Gly Glu Gly Ala Ala Glu Arg Glu Val
1               5                   10                  15

Ser Val Pro Thr Phe Ser Trp Glu Glu Ile Gln Lys His Asn Leu Arg
            20                  25                  30

Thr Asp Arg Trp Leu Val Ile Asp Arg Lys Val Tyr Asn Ile Thr Lys
        35                  40                  45

Trp Ser Ile Gln His Pro Gly Gly Gln Arg Val Ile Gly His Tyr Ala
    50                  55                  60

Gly Glu Asp Ala Thr Asp Ala Phe Arg Ala Phe His Pro Asp Leu Glu
65                  70                  75                  80

Phe Val Gly Lys Phe Leu Lys Pro Leu Leu Ile Gly Glu Leu Ala Pro
                85                  90                  95

Glu Glu Pro Ser Gln Asp His Gly Lys Asn Ser Lys Ile Thr Glu Asp
            100                 105                 110

Phe Arg Ala Leu Arg Lys Thr Ala Glu Asp Met Asn Leu Phe Lys Thr
        115                 120                 125

Asn His Val Phe Phe Leu Leu Leu Leu Ala His Ile Ile Ala Leu Glu
130                 135                 140

Ser Ile Ala Trp Phe Thr Val Phe Tyr Phe Gly Asn Gly Trp Ile Pro
145                 150                 155                 160

Thr Leu Ile Thr Ala Phe Val Leu Ala Thr Ser Gln Ala Gln Ala Gly
                165                 170                 175

Trp Leu Gln His Asp Tyr Gly His Leu Ser Val Tyr Arg Lys Pro Lys
            180                 185                 190

Trp Asn His Leu Val His Lys Phe Val Ile Gly His Leu Lys Gly Ala
        195                 200                 205

Ser Ala Asn Trp Trp Asn His Arg His Phe Gln His His Ala Lys Pro
    210                 215                 220

Asn Ile Phe His Lys Asp Pro Asp Val Asn Met Leu His Val Phe Val
225                 230                 235                 240
```

Leu Gly Glu Trp Gln Pro Ile Glu Tyr Gly Lys Lys Leu Lys Tyr
             245                 250                 255

Leu Pro Tyr Asn His Gln His Glu Tyr Phe Leu Ile Gly Pro Pro
             260                 265                 270

Leu Leu Ile Pro Met Tyr Phe Gln Tyr Gln Ile Ile Met Thr Met Ile
             275                 280                 285

Val His Lys Asn Trp Val Asp Leu Ala Trp Ala Val Ser Tyr Ile
             290                 295                 300

Arg Phe Phe Ile Thr Tyr Ile Pro Phe Tyr Gly Ile Leu Gly Ala Leu
305                 310                 315                 320

Leu Phe Leu Asn Phe Ile Arg Phe Leu Glu Ser His Trp Phe Val Trp
             325                 330                 335

Val Thr Gln Met Asn His Ile Val Met Glu Ile Asp Gln Glu Ala Tyr
             340                 345                 350

Arg Asp Trp Phe Ser Ser Gln Leu Thr Ala Thr Cys Asn Val Glu Gln
             355                 360                 365

Ser Phe Phe Asn Asp Trp Phe Ser Gly His Leu Asn Phe Gln Ile Glu
             370                 375                 380

His His Leu Phe Pro Thr Met Pro Arg His Asn Leu His Lys Ile Ala
385                 390                 395                 400

Pro Leu Val Lys Ser Leu Cys Ala Lys His Gly Ile Glu Tyr Gln Glu
                 405                 410                 415

Lys Pro Leu Leu Arg Ala Leu Leu Asp Ile Ile Arg Ser Leu Lys Lys
                 420                 425                 430

Ser Gly Lys Leu Trp Leu Asp Ala Tyr Leu His Lys
             435                 440

<210> SEQ ID NO 22
<211> LENGTH: 444
<212> TYPE: PRT
<213> ORGANISM: Mus musculus

<400> SEQUENCE: 22

Met Gly Lys Gly Gly Asn Gln Gly Glu Gly Ser Thr Glu Arg Gln Ala
1               5                   10                  15

Pro Met Pro Thr Phe Arg Trp Glu Glu Ile Gln Lys His Asn Leu Arg
             20                  25                  30

Thr Asp Arg Trp Leu Val Ile Asp Arg Lys Val Tyr Asn Val Thr Lys
         35                  40                  45

Trp Ser Gln Arg His Pro Gly Gly His Arg Val Ile Gly His Tyr Ser
     50                  55                  60

Gly Glu Asp Ala Thr Asp Ala Phe Arg Ala Phe His Leu Asp Leu Asp
65                  70                  75                  80

Phe Val Gly Lys Phe Leu Lys Pro Leu Leu Ile Gly Glu Leu Ala Pro
                 85                  90                  95

Glu Glu Pro Ser Leu Asp Arg Gly Lys Ser Ser Gln Ile Thr Glu Asp
             100                 105                 110

Phe Arg Ala Leu Lys Lys Thr Ala Glu Asp Met Asn Leu Phe Lys Thr
         115                 120                 125

Asn His Leu Phe Phe Phe Leu Leu Leu Ser His Ile Ile Val Met Glu
     130                 135                 140

Ser Leu Ala Trp Phe Ile Leu Ser Tyr Phe Gly Thr Gly Trp Ile Pro
145                 150                 155                 160

Thr Leu Val Thr Ala Phe Val Leu Ala Thr Ser Gln Ala Gln Ala Gly
                 165                 170                 175

```
Trp Leu Gln His Asp Tyr Gly His Leu Ser Val Tyr Lys Lys Ser Ile
            180                 185                 190

Trp Asn His Val Val His Lys Phe Val Ile Gly His Leu Lys Gly Ala
        195                 200                 205

Ser Ala Asn Trp Trp Asn Arg His Phe Gln His Ala Lys Pro
210                 215                 220

Asn Ile Phe His Lys Asp Pro Asp Ile Lys Ser Leu His Val Phe Val
225                 230                 235                 240

Leu Gly Glu Trp Gln Pro Leu Glu Tyr Gly Lys Lys Leu Lys Tyr
            245                 250                 255

Leu Pro Tyr Asn His Gln His Glu Tyr Phe Phe Leu Ile Gly Pro Pro
            260                 265                 270

Leu Leu Ile Pro Met Tyr Phe Gln Tyr Gln Ile Ile Met Thr Met Ile
            275                 280                 285

Ser Arg Arg Asp Trp Val Asp Leu Ala Trp Ala Ile Ser Tyr Tyr Met
290                 295                 300

Arg Phe Phe Tyr Thr Tyr Ile Pro Phe Tyr Gly Ile Leu Gly Ala Leu
305                 310                 315                 320

Val Phe Leu Asn Phe Ile Arg Phe Leu Glu Ser His Trp Phe Val Trp
            325                 330                 335

Val Thr Gln Met Asn His Leu Val Met Glu Ile Asp Leu Asp His Tyr
            340                 345                 350

Arg Asp Trp Phe Ser Ser Gln Leu Ala Ala Thr Cys Asn Val Glu Gln
            355                 360                 365

Ser Phe Phe Asn Asp Trp Phe Ser Gly His Leu Asn Phe Gln Ile Glu
            370                 375                 380

His His Leu Phe Pro Thr Met Pro Arg His Asn Leu His Lys Ile Ala
385                 390                 395                 400

Pro Leu Val Lys Ser Leu Cys Ala Lys His Gly Ile Glu Tyr Gln Glu
            405                 410                 415

Lys Pro Leu Leu Arg Ala Leu Ile Asp Ile Val Ser Ser Leu Lys Lys
            420                 425                 430

Ser Gly Glu Leu Trp Leu Asp Ala Tyr Leu His Lys
            435                 440

<210> SEQ ID NO 23
<211> LENGTH: 459
<212> TYPE: PRT
<213> ORGANISM: Pythium irregulare

<400> SEQUENCE: 23

Met Val Asp Leu Lys Pro Gly Val Lys Arg Leu Val Ser Trp Lys Glu
1               5                   10                  15

Ile Arg Glu His Ala Thr Pro Ala Thr Ala Trp Ile Val Ile His His
            20                  25                  30

Lys Val Tyr Asp Ile Ser Lys Trp Asp Ser His Pro Gly Gly Ser Val
        35                  40                  45

Met Leu Thr Gln Ala Gly Glu Asp Ala Thr Asp Ala Phe Ala Val Phe
    50                  55                  60

His Pro Ser Ser Ala Leu Lys Leu Leu Glu Gln Phe Tyr Val Gly Asp
65                  70                  75                  80

Val Asp Glu Thr Ser Lys Ala Glu Ile Glu Gly Glu Pro Ala Ser Asp
            85                  90                  95

Glu Glu Arg Ala Arg Arg Glu Arg Ile Asn Glu Phe Ile Ala Ser Tyr
            100                 105                 110
```

```
Arg Arg Leu Arg Val Lys Val Lys Gly Met Gly Leu Tyr Asp Ala Ser
        115                 120                 125

Ala Leu Tyr Tyr Ala Trp Lys Leu Val Ser Thr Phe Gly Ile Ala Val
        130                 135                 140

Leu Ser Met Ala Ile Cys Phe Phe Asn Ser Phe Ala Met Tyr Met
145                 150                 155                 160

Val Ala Gly Val Ile Met Gly Leu Phe Tyr Gln Gln Ser Gly Trp Leu
                165                 170                 175

Ala His Asp Phe Leu His Asn Gln Val Cys Glu Asn Arg Thr Leu Gly
            180                 185                 190

Asn Leu Ile Gly Cys Leu Val Gly Asn Ala Trp Gln Gly Phe Ser Val
        195                 200                 205

Gln Trp Trp Lys Asn Lys His Asn Leu His His Ala Val Pro Asn Leu
        210                 215                 220

His Ser Ala Lys Asp Glu Gly Phe Ile Gly Asp Pro Asp Ile Asp Thr
225                 230                 235                 240

Met Pro Leu Leu Ala Trp Ser Lys Glu Met Ala Arg Lys Ala Phe Glu
                245                 250                 255

Ser Ala His Gly Pro Phe Phe Ile Arg Asn Gln Ala Phe Leu Tyr Phe
            260                 265                 270

Pro Leu Leu Leu Ala Arg Leu Ser Trp Leu Ala Gln Ser Phe Phe
        275                 280                 285

Tyr Val Phe Thr Glu Phe Ser Phe Gly Ile Phe Asp Lys Val Glu Phe
        290                 295                 300

Asp Gly Pro Glu Lys Ala Gly Leu Ile Val His Tyr Ile Trp Gln Leu
305                 310                 315                 320

Ala Ile Pro Tyr Phe Cys Asn Met Ser Leu Phe Glu Gly Val Ala Tyr
                325                 330                 335

Phe Leu Met Gly Gln Ala Ser Cys Gly Leu Leu Leu Ala Leu Val Phe
            340                 345                 350

Ser Ile Gly His Asn Gly Met Ser Val Tyr Glu Arg Glu Thr Lys Pro
        355                 360                 365

Asp Phe Trp Gln Leu Gln Val Thr Thr Thr Arg Asn Ile Arg Ala Ser
        370                 375                 380

Val Phe Met Asp Trp Phe Thr Gly Gly Leu Asn Tyr Gln Ile Asp His
385                 390                 395                 400

His Leu Phe Pro Leu Val Pro Arg His Asn Leu Pro Lys Val Asn Val
                405                 410                 415

Leu Ile Lys Ser Leu Cys Lys Glu Phe Asp Ile Pro Phe His Glu Thr
            420                 425                 430

Gly Phe Trp Glu Gly Ile Tyr Glu Val Val Asp His Leu Ala Asp Ile
        435                 440                 445

Ser Lys Glu Phe Ile Thr Glu Phe Pro Ala Met
        450                 455

<210> SEQ ID NO 24
<211> LENGTH: 448
<212> TYPE: PRT
<213> ORGANISM: Borago officinalis

<400> SEQUENCE: 24

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30
```

```
Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
        50                  55                  60

Pro Ala Ser Thr Trp Lys Asn Leu Asp Lys Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
                100                 105                 110

Met Phe Ala Thr Leu Cys Phe Ile Ala Met Leu Phe Ala Met Ser Val
                115                 120                 125

Tyr Gly Val Leu Phe Cys Glu Gly Val Leu Val His Leu Phe Ser Gly
        130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
                180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
        210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
                260                 265                 270

Leu Leu Thr Lys Arg Asn Val Ser Tyr Arg Ala Gln Glu Leu Leu Gly
        275                 280                 285

Cys Leu Val Phe Ser Ile Trp Tyr Pro Leu Leu Val Ser Cys Leu Pro
        290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
                340                 345                 350

Gly Thr Leu Asp Ile Ser Cys Pro Pro Trp Met Asp Trp Phe His Gly
        355                 360                 365

Gly Leu Gln Phe Gln Ile Glu His His Leu Phe Pro Lys Met Pro Arg
        370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
        420                 425                 430

Lys Pro Leu Pro Lys Asn Leu Val Trp Glu Ala Leu His Thr His Gly
        435                 440                 445
```

<210> SEQ ID NO 25
<211> LENGTH: 446
<212> TYPE: PRT
<213> ORGANISM: Anemone leveillei

<400> SEQUENCE: 25

```
Met Ala Glu Lys Arg Arg Ser Ile Ser Ser Asp Asp Leu Arg Ser His
1               5                   10                  15

Asn Lys Pro Gly Asp Val Trp Ile Ser Ile Gln Gly Lys Ile Tyr Asp
            20                  25                  30

Val Thr Glu Trp Gly Lys Asp His Pro Gly Gly Glu Gly Pro Leu Leu
        35                  40                  45

Asn Leu Ala Gly Gln Asp Val Thr Asp Ala Phe Val Ala Phe His Pro
    50                  55                  60

Gly Ser Ala Trp Lys Asn Leu Asp Lys Phe His Ile Gly Tyr Leu Gln
65                  70                  75                  80

Asp Tyr Val Val Ser Asp Val Ser Lys Asp Tyr Arg Lys Leu Val Ser
                85                  90                  95

Glu Phe Ser Lys Ala Gly Leu Tyr Glu Lys Lys Gly His Gly His Leu
            100                 105                 110

Ile Arg Leu Leu Val Met Ser Leu Val Phe Ile Ala Ser Val Ser Gly
        115                 120                 125

Val Val Leu Ser Asp Lys Thr Ser Val His Val Gly Ser Ala Val Leu
    130                 135                 140

Leu Ala Val Ile Trp Met Gln Phe Gly Phe Ile Gly His Asp Ser Gly
145                 150                 155                 160

His Tyr Asn Ile Met Thr Ser Pro Glu Leu Asn Arg Tyr Met Gln Ile
                165                 170                 175

Phe Ser Val Asn Val Val Ser Gly Val Ser Val Gly Trp Trp Lys Arg
            180                 185                 190

Tyr His Asn Ala His His Ile Ala Val Asn Ser Leu Glu Tyr Asp Pro
        195                 200                 205

Asp Leu Gln Tyr Val Pro Phe Leu Val Val Ser Thr Ala Ile Phe Asp
    210                 215                 220

Ser Leu Thr Ser His Phe Tyr Arg Lys Lys Met Thr Phe Asp Ala Val
225                 230                 235                 240

Ala Arg Phe Leu Val Ser Phe Gln His Trp Thr Phe Tyr Pro Leu Met
                245                 250                 255

Ala Ile Gly Arg Val Ser Phe Leu Ala Gln Ser Ile Gly Val Leu Leu
            260                 265                 270

Ser Lys Lys Pro Leu Pro Asp Arg His Leu Glu Trp Phe Gly Leu Val
        275                 280                 285

Val Phe Trp Ala Trp Tyr Ser Leu Leu Ile Ser Cys Leu Pro Asn Trp
    290                 295                 300

Trp Glu Arg Val Ile Phe Ile Ala Val Asn Phe Ala Val Thr Gly Ile
305                 310                 315                 320

Gln His Val Gln Phe Cys Leu Asn His Tyr Ser Ala Gln Thr Tyr Ile
                325                 330                 335

Gly Ala Pro Cys Ala Asn Asp Trp Phe Glu Lys Gln Thr Lys Gly Ser
            340                 345                 350

Ile Asp Ile Ser Cys Ser Pro Trp Thr Asp Trp Phe His Gly Gly Leu
        355                 360                 365

Gln Phe Gln Ile Glu His His Leu Phe Pro Arg Met Pro Arg Cys Asn
    370                 375                 380

Leu Arg Lys Ile Ser Pro Phe Val Lys Glu Leu Cys Arg Lys His Asn
```

```
                385                 390                 395                 400
Leu Val Tyr Thr Ser Val Ser Phe Phe Glu Gly Asn Arg Arg Thr Leu
                    405                 410                 415
Ala Thr Leu Lys Asn Ala Ala Leu Lys Ala Arg Asp Leu Thr Ser Pro
                    420                 425                 430
Ile Pro Lys Asn Leu Val Trp Glu Ala Val His Thr His Gly
                    435                 440                 445

<210> SEQ ID NO 26
<211> LENGTH: 520
<212> TYPE: PRT
<213> ORGANISM: Ceratodon purpureus

<400> SEQUENCE: 26

Met Val Ser Gln Gly Gly Gly Leu Ser Gln Gly Ser Ile Glu Glu Asn
 1               5                  10                  15
Ile Asp Val Glu His Leu Ala Thr Met Pro Leu Val Ser Asp Phe Leu
                20                  25                  30
Asn Val Leu Gly Thr Thr Leu Gly Gln Trp Ser Leu Ser Thr Thr Phe
                35                  40                  45
Ala Phe Lys Arg Leu Thr Thr Lys Lys His Ser Ser Asp Ile Ser Val
 50                  55                  60
Glu Ala Gln Lys Glu Ser Val Ala Arg Gly Pro Val Glu Asn Ile Ser
 65                  70                  75                  80
Gln Ser Val Ala Gln Pro Ile Arg Arg Arg Trp Val Gln Asp Lys Lys
                 85                  90                  95
Pro Val Thr Tyr Ser Leu Lys Asp Val Ala Ser His Asp Met Pro Gln
                100                 105                 110
Asp Cys Trp Ile Ile Lys Glu Lys Val Tyr Asp Val Ser Thr Phe
                115                 120                 125
Ala Glu Gln His Pro Gly Gly Thr Val Ile Asn Thr Tyr Phe Gly Arg
                130                 135                 140
Asp Ala Thr Asp Val Phe Ser Thr Phe His Ala Ser Thr Ser Trp Lys
145                 150                 155                 160
Ile Leu Gln Asn Phe Tyr Ile Gly Asn Leu Val Arg Glu Glu Pro Thr
                165                 170                 175
Leu Glu Leu Leu Lys Glu Tyr Arg Glu Leu Arg Ala Leu Phe Leu Arg
                180                 185                 190
Glu Gln Leu Phe Lys Ser Ser Lys Ser Tyr Tyr Leu Phe Lys Thr Leu
                195                 200                 205
Ile Asn Val Ser Ile Val Ala Thr Ser Ile Ala Ile Ile Ser Leu Tyr
                210                 215                 220
Lys Ser Tyr Arg Ala Val Leu Leu Ser Ala Ser Leu Met Gly Leu Phe
225                 230                 235                 240
Ile Gln Gln Cys Gly Trp Leu Ser His Asp Phe Leu His His Gln Val
                245                 250                 255
Phe Glu Thr Arg Trp Leu Asn Asp Val Val Gly Tyr Val Val Gly Asn
                260                 265                 270
Val Val Leu Gly Phe Ser Val Ser Trp Trp Lys Thr Lys His Asn Leu
                275                 280                 285
His His Ala Ala Pro Asn Glu Cys Asp Gln Lys Tyr Thr Pro Ile Asp
                290                 295                 300
Glu Asp Ile Asp Thr Leu Pro Ile Ile Ala Trp Ser Lys Asp Leu Leu
305                 310                 315                 320
Ala Thr Val Glu Ser Lys Thr Met Leu Arg Val Leu Gln Tyr Gln His
```

```
                    325                 330                 335
Leu Phe Phe Leu Val Leu Leu Thr Phe Ala Arg Ala Ser Trp Leu Phe
            340                 345                 350

Trp Ser Ala Ala Phe Thr Leu Arg Pro Glu Leu Thr Leu Gly Glu Lys
        355                 360                 365

Leu Leu Glu Arg Gly Thr Met Ala Leu His Tyr Ile Trp Phe Asn Ser
    370                 375                 380

Val Ala Phe Tyr Leu Leu Pro Gly Trp Lys Pro Val Val Trp Met Val
385                 390                 395                 400

Val Ser Glu Leu Met Ser Gly Phe Leu Leu Gly Tyr Val Phe Val Leu
                405                 410                 415

Ser His Asn Gly Met Glu Val Tyr Asn Thr Ser Lys Asp Phe Val Asn
            420                 425                 430

Ala Gln Ile Ala Ser Thr Arg Asp Ile Lys Ala Gly Val Phe Asn Asp
        435                 440                 445

Trp Phe Thr Gly Gly Leu Asn Arg Gln Ile Glu His His Leu Phe Pro
    450                 455                 460

Thr Met Pro Arg His Asn Leu Asn Lys Ile Ser Pro His Val Glu Thr
465                 470                 475                 480

Leu Cys Lys Lys His Gly Leu Val Tyr Glu Asp Val Ser Met Ala Ser
                485                 490                 495

Gly Thr Tyr Arg Val Leu Lys Thr Leu Lys Asp Val Ala Asp Ala Ala
            500                 505                 510

Ser His Gln Gln Leu Ala Ala Ser
        515                 520

<210> SEQ ID NO 27
<211> LENGTH: 525
<212> TYPE: PRT
<213> ORGANISM: Physcomitrella patens

<400> SEQUENCE: 27

Met Val Phe Ala Gly Gly Leu Gln Gln Gly Ser Leu Glu Glu Asn
1               5                   10                  15

Ile Asp Val Glu His Ile Ala Ser Met Ser Leu Phe Ser Asp Phe Phe
            20                  25                  30

Ser Tyr Val Ser Ser Thr Val Gly Ser Trp Ser Val His Ser Ile Gln
        35                  40                  45

Pro Leu Lys Arg Leu Thr Ser Lys Lys Arg Val Ser Glu Ser Ala Ala
    50                  55                  60

Val Gln Cys Ile Ser Ala Glu Val Gln Arg Asn Ser Ser Thr Gln Gly
65                  70                  75                  80

Thr Ala Glu Ala Leu Ala Glu Ser Val Val Lys Pro Thr Arg Arg Arg
                85                  90                  95

Ser Ser Gln Trp Lys Lys Ser Thr His Pro Leu Ser Glu Val Ala Val
            100                 105                 110

His Asn Lys Pro Ser Asp Cys Trp Ile Val Lys Asn Lys Val Tyr
        115                 120                 125

Asp Val Ser Asn Phe Ala Asp Glu His Pro Gly Gly Ser Val Ile Ser
    130                 135                 140

Thr Tyr Phe Gly Arg Asp Gly Thr Asp Val Phe Ser Ser Phe His Ala
145                 150                 155                 160

Ala Ser Thr Trp Lys Ile Leu Gln Asp Phe Tyr Ile Gly Asp Val Glu
                165                 170                 175

Arg Val Glu Pro Thr Pro Glu Leu Leu Lys Asp Phe Arg Glu Met Arg
```

```
                    180                 185                 190
Ala Leu Phe Leu Arg Glu Gln Leu Phe Lys Ser Ser Lys Leu Tyr Tyr
            195                 200                 205

Val Met Lys Leu Leu Thr Asn Val Ala Ile Phe Ala Ala Ser Ile Ala
            210                 215                 220

Ile Ile Cys Trp Ser Lys Thr Ile Ser Ala Val Leu Ala Ser Ala Cys
225                 230                 235                 240

Met Met Ala Leu Cys Phe Gln Gln Cys Gly Trp Leu Ser His Asp Phe
                245                 250                 255

Leu His Asn Gln Val Phe Glu Thr Arg Trp Leu Asn Glu Val Val Gly
            260                 265                 270

Tyr Val Ile Gly Asn Ala Val Leu Gly Phe Ser Thr Gly Trp Trp Lys
            275                 280                 285

Glu Lys His Asn Leu His His Ala Ala Pro Asn Glu Cys Asp Gln Thr
            290                 295                 300

Tyr Gln Pro Ile Asp Glu Asp Ile Asp Thr Leu Pro Leu Ile Ala Trp
305                 310                 315                 320

Ser Lys Asp Ile Leu Ala Thr Val Glu Asn Lys Thr Phe Leu Arg Ile
                325                 330                 335

Leu Gln Tyr Gln His Leu Phe Phe Met Gly Leu Leu Phe Phe Ala Arg
            340                 345                 350

Gly Ser Trp Leu Phe Trp Ser Trp Arg Tyr Thr Ser Thr Ala Val Leu
            355                 360                 365

Ser Pro Val Asp Arg Leu Leu Glu Lys Gly Thr Val Leu Phe His Tyr
            370                 375                 380

Phe Trp Phe Val Gly Thr Ala Cys Tyr Leu Leu Pro Gly Trp Lys Pro
385                 390                 395                 400

Leu Val Trp Met Ala Val Thr Glu Leu Met Ser Gly Met Leu Leu Gly
                405                 410                 415

Phe Val Phe Val Leu Ser His Asn Gly Met Glu Val Tyr Asn Ser Ser
            420                 425                 430

Lys Glu Phe Val Ser Ala Gln Ile Val Ser Thr Arg Asp Ile Lys Gly
            435                 440                 445

Asn Ile Phe Asn Asp Trp Phe Thr Gly Gly Leu Asn Arg Gln Ile Glu
450                 455                 460

His His Leu Phe Pro Thr Met Pro Arg His Asn Leu Asn Lys Ile Ala
465                 470                 475                 480

Pro Arg Val Glu Val Phe Cys Lys Lys His Gly Leu Val Tyr Glu Asp
                485                 490                 495

Val Ser Ile Ala Thr Gly Thr Cys Lys Val Leu Lys Ala Leu Lys Glu
            500                 505                 510

Val Ala Glu Ala Ala Ala Glu Gln His Ala Thr Thr Ser
            515                 520                 525

<210> SEQ ID NO 28
<211> LENGTH: 457
<212> TYPE: PRT
<213> ORGANISM: Mortierella alpina

<400> SEQUENCE: 28

Met Ala Ala Ala Pro Ser Val Arg Thr Phe Thr Arg Ala Glu Ile Leu
1               5                   10                  15

Asn Ala Glu Ala Leu Asn Glu Gly Lys Lys Asp Ala Glu Ala Pro Phe
                20                  25                  30

Leu Met Ile Ile Asp Asn Lys Val Tyr Asp Val Arg Glu Phe Val Pro
```

-continued

```
                  35                  40                  45
Asp His Pro Gly Gly Ser Val Ile Leu Thr His Val Gly Lys Asp Gly
 50                  55                  60

Thr Asp Val Phe Asp Thr Phe His Pro Glu Ala Ala Trp Glu Thr Leu
 65                  70                  75                  80

Ala Asn Phe Tyr Val Gly Asp Ile Asp Glu Ser Asp Arg Ala Ile Lys
                     85                  90                  95

Asn Asp Asp Phe Ala Ala Glu Val Arg Lys Leu Arg Thr Leu Phe Gln
                100                 105                 110

Ser Leu Gly Tyr Tyr Asp Ser Ser Lys Ala Tyr Tyr Ala Phe Lys Val
                115                 120                 125

Ser Phe Asn Leu Cys Ile Trp Gly Leu Ser Thr Phe Ile Val Ala Lys
                130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
                180                 185                 190

Leu Gly Gly Val Cys Gln Gly Phe Ser Ser Ser Trp Trp Lys Asp Lys
                195                 200                 205

His Asn Thr His His Ala Ala Pro Asn Val His Gly Glu Asp Pro Asp
                210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
                260                 265                 270

Arg Leu Ser Trp Cys Leu Gln Ser Ile Met Phe Val Leu Pro Asn Gly
                275                 280                 285

Gln Ala His Lys Pro Ser Gly Ala Arg Val Pro Ile Ser Leu Val Glu
                290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Ile Val Tyr Phe Leu Val Ser
                325                 330                 335

Gln Ala Val Cys Gly Asn Leu Leu Ala Ile Val Phe Ser Leu Asn His
                340                 345                 350

Asn Gly Met Pro Val Ile Ser Lys Glu Glu Ala Val Asp Met Asp Phe
                355                 360                 365

Phe Thr Lys Gln Ile Ile Thr Gly Arg Asp Val His Pro Gly Leu Phe
                370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Gly Val Arg Tyr His Thr Thr Gly Met
                420                 425                 430

Ile Glu Gly Thr Ala Glu Val Phe Ser Arg Leu Asn Glu Val Ser Lys
                435                 440                 445

Ala Ala Ser Lys Met Gly Lys Ala Gln
                450                 455
```

<210> SEQ ID NO 29
<211> LENGTH: 443
<212> TYPE: PRT
<213> ORGANISM: Caenorhabditis elegans

<400> SEQUENCE: 29

```
Met Val Val Asp Lys Asn Ala Ser Gly Leu Arg Met Lys Val Asp Gly
1               5                   10                  15

Lys Trp Leu Tyr Leu Ser Glu Glu Leu Val Lys His Pro Gly Gly
            20                  25                  30

Ala Val Ile Glu Gln Tyr Arg Asn Ser Asp Ala Thr His Ile Phe His
            35                  40                  45

Ala Phe His Glu Gly Ser Ser Gln Ala Tyr Lys Gln Leu Asp Leu Leu
        50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Glu Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys His Asn Thr His
        195                 200                 205

His Ala Ala Thr Asn Val Ile Asp His Asp Gly Asp Ile Asp Leu Ala
    210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285

Asn Ala Phe Trp Glu Gln Ala Thr Ile Val Gly His Trp Ala Trp Val
    290                 295                 300

Phe Tyr Gln Leu Phe Leu Pro Thr Trp Pro Leu Arg Val Ala Tyr
305                 310                 315                 320

Phe Ile Ile Ser Gln Met Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
    370                 375                 380
```

```
Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
            405                 410                 415

Val Asp Asp Tyr Phe Asp Gly Tyr Ala Met Asn Leu Gln Gln Leu Lys
        420                 425                 430

Asn Met Ala Glu His Ile Gln Ala Lys Ala Ala
        435                 440

<210> SEQ ID NO 30
<211> LENGTH: 299
<212> TYPE: PRT
<213> ORGANISM: Homo sapiens

<400> SEQUENCE: 30

Met Glu His Phe Asp Ala Ser Leu Ser Thr Tyr Phe Lys Ala Leu Leu
1               5                   10                  15

Gly Pro Arg Asp Thr Arg Val Lys Gly Trp Phe Leu Leu Asp Asn Tyr
            20                  25                  30

Ile Pro Thr Phe Ile Cys Ser Val Ile Tyr Leu Leu Ile Val Trp Leu
        35                  40                  45

Gly Pro Lys Tyr Met Arg Asn Lys Gln Pro Phe Ser Cys Arg Gly Ile
50                  55                  60

Leu Val Val Tyr Asn Leu Gly Leu Thr Leu Leu Ser Leu Tyr Met Phe
65                  70                  75                  80

Cys Glu Leu Val Thr Gly Val Trp Glu Gly Lys Tyr Asn Phe Phe Cys
                85                  90                  95

Gln Gly Thr Arg Thr Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
    130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Val Pro Ser Met
            180                 185                 190

Arg Pro Tyr Leu Trp Trp Lys Lys Tyr Ile Thr Gln Gly Gln Leu Leu
        195                 200                 205

Gln Phe Val Leu Thr Ile Ile Gln Thr Ser Cys Gly Val Ile Trp Pro
    210                 215                 220

Cys Thr Phe Pro Leu Gly Trp Leu Tyr Phe Gln Ile Gly Tyr Met Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Asp His Gln Asn Gly
            260                 265                 270

Ser Met Ala Ala Val Asn Gly His Thr Asn Ser Phe Ser Pro Leu Glu
        275                 280                 285

Asn Asn Val Lys Pro Arg Lys Leu Arg Lys Asp
        290                 295

<210> SEQ ID NO 31
<211> LENGTH: 290
```

```
<212> TYPE: PRT
<213> ORGANISM: Physcomitrella patens

<400> SEQUENCE: 31

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 32
<211> LENGTH: 318
<212> TYPE: PRT
<213> ORGANISM: Mortierella alpina

<400> SEQUENCE: 32

Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
```

```
                50                  55                  60
Leu Ala Arg Glu Leu Pro Leu Met Asn Pro Phe His Val Leu Ile
 65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
                100                 105                 110

Cys Leu Val Ser Ile Ser Ala Tyr Met Cys Gly Gly Ile Leu Tyr Glu
                115                 120                 125

Ala Tyr Gln Ala Asn Tyr Gly Leu Phe Glu Asn Ala Ala Asp His Thr
                130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
                180                 185                 190

Thr Ile Trp Trp Leu Val Thr Phe Val Ala Pro Asn Gly Glu Ala Tyr
                195                 200                 205

Phe Ser Ala Ala Leu Asn Ser Phe Ile His Val Ile Met Tyr Gly Tyr
                210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
                260                 265                 270

Pro Phe Phe Ile Thr Ala Leu Leu Trp Phe Tyr Met Trp Thr Met Leu
                275                 280                 285

Gly Leu Phe Tyr Asn Phe Tyr Arg Lys Asn Ala Lys Leu Ala Lys Gln
                290                 295                 300

Ala Lys Ala Asp Ala Ala Lys Glu Lys Ala Arg Lys Leu Gln
305                 310                 315

<210> SEQ ID NO 33
<211> LENGTH: 519
<212> TYPE: PRT
<213> ORGANISM: Thraustochytrium sp.

<400> SEQUENCE: 33

Met Thr Val Gly Tyr Asp Glu Glu Ile Pro Phe Glu Gln Val Arg Ala
  1               5                  10                  15

His Asn Lys Pro Asp Asp Ala Trp Cys Ala Ile His Gly His Val Tyr
                 20                  25                  30

Asp Val Thr Lys Phe Ala Ser Val His Pro Gly Gly Asp Ile Ile Leu
                 35                  40                  45

Leu Ala Ala Gly Lys Glu Ala Thr Val Leu Tyr Glu Thr Tyr His Val
                 50                  55                  60

Arg Gly Val Ser Asp Ala Val Leu Arg Lys Tyr Arg Ile Gly Lys Leu
 65                  70                  75                  80

Pro Asp Gly Gln Gly Gly Ala Asn Glu Lys Glu Lys Arg Thr Leu Ser
                 85                  90                  95

Gly Leu Ser Ser Ala Ser Tyr Tyr Thr Trp Asn Ser Asp Phe Tyr Arg
                100                 105                 110

Val Met Arg Glu Arg Val Val Ala Arg Leu Lys Glu Arg Gly Lys Ala
```

```
                  115                 120                 125
Arg Arg Gly Gly Tyr Glu Leu Trp Ile Lys Ala Phe Leu Leu Val
130                 135                 140
Gly Phe Trp Ser Ser Leu Tyr Trp Met Cys Thr Leu Asp Pro Ser Phe
145                 150                 155                 160
Gly Ala Ile Leu Ala Ala Met Ser Leu Gly Val Phe Ala Ala Phe Val
                165                 170                 175
Gly Thr Cys Ile Gln His Asp Gly Asn His Gly Ala Phe Ala Gln Ser
                180                 185                 190
Arg Trp Val Asn Lys Val Ala Gly Trp Thr Leu Asp Met Ile Gly Ala
                195                 200                 205
Ser Gly Met Thr Trp Glu Phe Gln His Val Leu Gly His His Pro Tyr
210                 215                 220
Thr Asn Leu Ile Glu Glu Asn Gly Leu Gln Lys Val Ser Gly Lys
225                 230                 235                 240
Lys Met Asp Thr Lys Leu Ala Asp Gln Glu Ser Asp Pro Asp Val Phe
                245                 250                 255
Ser Thr Tyr Pro Met Met Arg Leu His Pro Trp His Gln Lys Arg Trp
                260                 265                 270
Tyr His Arg Phe Gln His Ile Tyr Gly Pro Phe Ile Phe Gly Phe Met
                275                 280                 285
Thr Ile Asn Lys Val Val Thr Gln Asp Val Gly Val Leu Arg Lys
                290                 295                 300
Arg Leu Phe Gln Ile Asp Ala Glu Cys Arg Tyr Ala Ser Pro Met Tyr
305                 310                 315                 320
Val Ala Arg Phe Trp Ile Met Lys Ala Leu Thr Val Leu Tyr Met Val
                325                 330                 335
Ala Leu Pro Cys Tyr Met Gln Gly Pro Trp His Gly Leu Lys Leu Phe
                340                 345                 350
Ala Ile Ala His Phe Thr Cys Gly Glu Val Leu Ala Thr Met Phe Ile
                355                 360                 365
Val Asn His Ile Ile Glu Gly Val Ser Tyr Ala Ser Lys Asp Ala Val
                370                 375                 380
Lys Gly Thr Met Ala Pro Pro Lys Thr Met His Gly Val Thr Pro Met
385                 390                 395                 400
Asn Asn Thr Arg Lys Glu Val Glu Ala Ala Ser Lys Ser Gly Ala
                405                 410                 415
Val Val Lys Ser Val Pro Leu Asp Asp Trp Ala Val Val Gln Cys Gln
                420                 425                 430
Thr Ser Val Asn Trp Ser Val Gly Ser Trp Phe Trp Asn His Phe Ser
                435                 440                 445
Gly Gly Leu Asn His Gln Ile Glu His His Leu Phe Pro Gly Leu Ser
                450                 455                 460
His Glu Thr Tyr Tyr His Ile Gln Asp Val Phe Gln Ser Thr Cys Ala
465                 470                 475                 480
Glu Tyr Gly Val Pro Tyr Gln His Glu Pro Ser Leu Trp Thr Ala Tyr
                485                 490                 495
Trp Lys Met Leu Glu His Leu Arg Gln Leu Gly Asn Glu Glu Thr His
                500                 505                 510
Glu Ser Trp Gln Arg Ala Ala
                515

<210> SEQ ID NO 34
<211> LENGTH: 541
```

```
<212> TYPE: PRT
<213> ORGANISM: Euglena gracilis

<400> SEQUENCE: 34

Met Leu Val Leu Phe Gly Asn Phe Tyr Val Lys Gln Tyr Ser Gln Lys
1               5                   10                  15

Asn Gly Lys Pro Glu Asn Gly Ala Thr Pro Glu Asn Gly Ala Lys Pro
            20                  25                  30

Gln Pro Cys Glu Asn Gly Thr Val Glu Lys Arg Glu Asn Asp Thr Ala
        35                  40                  45

Asn Val Arg Pro Thr Arg Pro Ala Gly Pro Pro Ala Thr Tyr Tyr
    50                  55                  60

Asp Ser Leu Ala Val Ser Gly Gln Gly Lys Glu Arg Leu Phe Thr Thr
65              70                  75                  80

Asp Glu Val Arg Arg His Ile Leu Pro Thr Asp Gly Trp Leu Thr Cys
                85                  90                  95

His Glu Gly Val Tyr Asp Val Thr Asp Phe Leu Ala Lys His Pro Gly
            100                 105                 110

Gly Gly Val Ile Thr Leu Gly Leu Gly Arg Asp Cys Thr Ile Leu Ile
        115                 120                 125

Glu Ser Tyr His Pro Ala Gly Arg Pro Asp Lys Val Met Glu Lys Tyr
    130                 135                 140

Arg Ile Gly Thr Leu Gln Asp Pro Lys Thr Phe Tyr Ala Trp Gly Glu
145                 150                 155                 160

Ser Asp Phe Tyr Pro Glu Leu Lys Arg Arg Ala Leu Ala Arg Leu Lys
                165                 170                 175

Glu Ala Gly Gln Ala Arg Arg Gly Leu Gly Val Lys Ala Leu Leu
            180                 185                 190

Val Leu Thr Leu Phe Phe Val Ser Trp Tyr Met Trp Val Ala His Lys
    195                 200                 205

Ser Phe Leu Trp Ala Ala Val Trp Gly Phe Ala Gly Ser His Val Gly
    210                 215                 220

Leu Ser Ile Gln His Asp Gly Asn His Gly Ala Phe Ser Arg Asn Thr
225                 230                 235                 240

Leu Val Asn Arg Leu Ala Gly Trp Gly Met Asp Leu Ile Gly Ala Ser
                245                 250                 255

Ser Thr Val Trp Glu Tyr Gln His Val Ile Gly His His Gln Tyr Thr
                260                 265                 270

Asn Leu Val Ser Asp Thr Leu Phe Ser Leu Pro Glu Asn Asp Pro Asp
            275                 280                 285

Val Phe Ser Ser Tyr Pro Leu Met Arg Met His Pro Asp Thr Ala Trp
    290                 295                 300

Gln Pro His His Arg Phe Gln His Leu Phe Ala Phe Pro Leu Phe Ala
305                 310                 315                 320

Leu Met Thr Ile Ser Lys Val Leu Thr Ser Asp Phe Ala Val Cys Leu
                325                 330                 335

Ser Met Lys Lys Gly Ser Ile Asp Cys Ser Ser Arg Leu Val Pro Leu
            340                 345                 350

Glu Gly Gln Leu Leu Phe Trp Gly Ala Lys Leu Ala Asn Phe Leu Leu
    355                 360                 365

Gln Ile Val Leu Pro Cys Tyr Leu His Gly Thr Ala Met Gly Leu Ala
    370                 375                 380

Leu Phe Ser Val Ala His Leu Val Ser Gly Glu Tyr Leu Ala Ile Cys
385                 390                 395                 400
```

```
Phe Ile Ile Asn His Ile Ser Glu Ser Cys Glu Phe Met Asn Thr Ser
                    405                 410                 415
Phe Gln Thr Ala Ala Arg Arg Thr Glu Met Leu Gln Ala Ala His Gln
                420                 425                 430
Ala Ala Glu Ala Lys Lys Val Lys Pro Thr Pro Pro Asn Asp Trp
            435                 440                 445
Ala Val Thr Gln Val Gln Cys Cys Val Asn Trp Arg Ser Gly Gly Val
            450                 455                 460
Leu Ala Asn His Leu Ser Gly Gly Leu Asn His Gln Ile Glu His His
465                 470                 475                 480
Leu Phe Pro Ser Ile Ser His Ala Asn Tyr Pro Thr Ile Ala Pro Val
                485                 490                 495
Val Lys Glu Val Cys Glu Glu Tyr Gly Leu Pro Tyr Lys Asn Tyr Val
                500                 505                 510
Thr Phe Trp Asp Ala Val Cys Gly Met Val Gln His Leu Arg Leu Met
                515                 520                 525
Gly Ala Pro Pro Val Pro Thr Asn Gly Asp Lys Lys Ser
                530                 535                 540

<210> SEQ ID NO 35
<211> LENGTH: 263
<212> TYPE: PRT
<213> ORGANISM: Isochrysis galbana

<400> SEQUENCE: 35

Met Ala Leu Ala Asn Asp Ala Gly Glu Arg Ile Trp Ala Ala Val Thr
1               5                   10                  15
Asp Pro Glu Ile Leu Ile Gly Thr Phe Ser Tyr Leu Leu Leu Lys Pro
                20                  25                  30
Leu Leu Arg Asn Ser Gly Leu Val Asp Glu Lys Lys Gly Ala Tyr Arg
            35                  40                  45
Thr Ser Met Ile Trp Tyr Asn Val Leu Leu Ala Leu Phe Ser Ala Leu
50                  55                  60
Ser Phe Tyr Val Thr Ala Thr Ala Leu Gly Trp Asp Tyr Gly Thr Gly
65                  70                  75                  80
Ala Trp Leu Arg Arg Gln Thr Gly Asp Thr Pro Gln Pro Leu Phe Gln
                85                  90                  95
Cys Pro Ser Pro Val Trp Asp Ser Lys Leu Phe Thr Trp Thr Ala Lys
                100                 105                 110
Ala Phe Tyr Tyr Ser Lys Tyr Val Glu Tyr Leu Asp Thr Ala Trp Leu
            115                 120                 125
Val Leu Lys Gly Lys Arg Val Ser Phe Leu Gln Ala Phe His His Phe
130                 135                 140
Gly Ala Pro Trp Asp Val Tyr Leu Gly Ile Arg Leu His Asn Glu Gly
145                 150                 155                 160
Val Trp Ile Phe Met Phe Phe Asn Ser Phe Ile His Thr Ile Met Tyr
                165                 170                 175
Thr Tyr Tyr Gly Leu Thr Ala Ala Gly Tyr Lys Phe Lys Ala Lys Pro
                180                 185                 190
Leu Ile Thr Ala Met Gln Ile Cys Gln Phe Val Gly Gly Phe Leu Leu
            195                 200                 205
Val Trp Asp Tyr Ile Asn Val Pro Cys Phe Asn Ser Asp Lys Gly Lys
210                 215                 220
Leu Phe Ser Trp Ala Phe Asn Tyr Ala Tyr Val Gly Ser Val Phe Leu
225                 230                 235                 240
```

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 36
<211> LENGTH: 419
<212> TYPE: PRT
<213> ORGANISM: Euglena gracilis

<400> SEQUENCE: 36

Met Lys Ser Lys Arg Gln Ala Leu Ser Pro Leu Gln Leu Met Glu Gln
1               5                   10                  15

Thr Tyr Asp Val Val Asn Phe His Pro Gly Gly Ala Glu Ile Ile Glu
            20                  25                  30

Asn Tyr Gln Gly Arg Asp Ala Thr Asp Ala Phe Met Val Met His Phe
        35                  40                  45

Gln Glu Ala Phe Asp Lys Leu Lys Arg Met Pro Lys Ile Asn Pro Ser
    50                  55                  60

Phe Glu Leu Pro Pro Gln Ala Ala Val Asn Glu Ala Gln Glu Asp Phe
65                  70                  75                  80

Arg Lys Leu Arg Glu Glu Leu Ile Ala Thr Gly Met Phe Asp Ala Ser
                85                  90                  95

Pro Leu Trp Tyr Ser Tyr Lys Ile Ser Thr Thr Leu Gly Leu Gly Val
            100                 105                 110

Leu Gly Tyr Phe Leu Met Val Gln Tyr Gln Met Tyr Phe Ile Gly Ala
        115                 120                 125

Val Leu Leu Gly Met His Tyr Gln Gln Met Gly Trp Leu Ser His Asp
    130                 135                 140

Ile Cys His His Gln Thr Phe Lys Asn Arg Asn Trp Asn Asn Leu Val
145                 150                 155                 160

Gly Leu Val Phe Gly Asn Gly Leu Gln Gly Phe Ser Val Thr Cys Trp
                165                 170                 175

Lys Asp Arg His Asn Ala His His Ser Ala Thr Asn Val Gln Gly His
            180                 185                 190

Asp Pro Asp Ile Asp Asn Leu Pro Pro Leu Ala Trp Ser Glu Asp Asp
        195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
        275                 280                 285

Ser Leu Leu Val Phe Phe Val Ser Glu Leu Val Gly Gly Phe Gly Ile
    290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gln Ile His Glu Thr
                325                 330                 335

Met Asn Ile Arg Arg Gly Ile Ile Thr Asp Trp Phe Pro Gly Gly Leu
            340                 345                 350

```
       Asn Tyr Gln Ile Glu His His Leu Trp Pro Thr Leu Pro Arg His Asn
           355                 360                 365

Leu Thr Ala Val Ser Tyr Gln Val Glu Gln Leu Cys Gln Lys His Asn
           370                 375                 380

Leu Pro Tyr Arg Asn Pro Leu Pro His Glu Gly Leu Val Ile Leu Leu
       385                 390                 395                 400

Arg Tyr Leu Ala Val Phe Ala Arg Met Ala Glu Lys Gln Pro Ala Gly
                       405                 410                 415

Lys Ala Leu

<210> SEQ ID NO 37
<211> LENGTH: 867
<212> TYPE: DNA
<213> ORGANISM: Caenorhabditis elegans

<400> SEQUENCE: 37
atggctcagc atccgctcgt tcaacggctt ctcgatgtca aattcgacac gaaacgattt      60
gtggctattg ctactcatgg gccaaagaat ttccctgacg cagaaggtcg caagttcttt     120
gctgatcact tgatgttac  tattcaggct tcaatcctgt acatggtcgt tgtgttcgga     180
acaaaatggt tcatgcgtaa tcgtcaacca ttccaattga ctattccact caacatctgg     240
aatttcatcc tcgccgcatt ttccatcgca ggagctgtca aaatgacccc agagttcttt     300
ggaaccattg ccaacaaagg aattgtcgca tcctactgca aagtgtttga tttcacgaaa     360
ggagagaatg gatactgggt gtggctcttc atggcttcca aacttttcga acttgttgac     420
accatcttct tggttctccg taaacgtcca ctcatgttcc ttcactggta tcaccatatt     480
ctcaccatga tctacgcctg gtactctcat ccattgaccc aggattcaa  cagatacgga     540 atttatctta actttgtcgt ccacgccttc atgtactctt actacttcct tcgctcgatg     600
aagattcgcg tgccaggatt catcgcccaa gctatcacat ctcttcaaat cgttcaattc     660
atcatctctt gcgccgttct tgctcatctt ggttatctca tgcacttcac caatgccaac     720
tgtgatttcg agccatcagt attcaagctc gcagttttca tggacacaac atacttggct     780
cttttcgtca acttcttcct ccaatcatat gttctccgcg aggaaaaga  caagtacaag     840 gcagtgccaa agaagaagaa caactaa                                         867

<210> SEQ ID NO 38
<211> LENGTH: 1335
<212> TYPE: DNA
<213> ORGANISM: Danio rerio

<400> SEQUENCE: 38
atgggtggcg aggacagca  gacagaccga atcaccgaca ccaacggcag attcagcagc       60
tacacctggg aggaggtgca gaaacacacc aaacatggag atcagtgggt ggtggtggag      120
aggaaggttt ataacgtcag ccagtgggtg aagagacacc ccggaggact gaggatcctc      180
ggacactatg ctggagaaga cgccacggag gcgttcactg cgtttcatcc aaaccttcag      240
ctggtgagga ataccctgaa gccgctgcta atcggagagc tggaggcgtc tgaacccagt      300
caggaccggc agaaaaacgc tgctctcgtg gaggatttcc gagccctgcg tgagcgtctg      360
gaggctgaag gctgttttaa aacgcagccg ctgttttttcg ctctgcattt gggccacatt      420
ctgctcctgg aggccatcgc tttcatgatg gtgtggatt  tcggcaccgg ttggatcaac      480 acgtcatcg  tcgctgttat tctggctact gcacagtcac aagctggatg gttgcagcat      540
gacttcggtc atctgtccgt gtttaaaacc tctggaatga atcatttggt gcacaaattt      600
```

```
gtcatcggac acctgaaggg agcgtctgcg ggctggtgga accatcggca cttccagcat    660
cacgctaaac ccaacatctt caagaaggac ccggacgtca acatgctgaa cgcctttgtg    720
gtgggaaacg tgcagcccgt ggagtatggc gttaagaaga tcaagcatct gccctacaac    780
catcagcaca agtacttctt cttcattggt cctcccctgc tcatcccagt gtatttccag    840
ttccaaatct ttcacaatat gatcagtcat ggcatgtggg tggacctgct gtggtgtatc    900
agctactacg tccgatactt cctttgttac acgcagttct acggcgtctt ttgggctatt    960
atcctcttta atttcgtcag gtttatggag agccactggt ttgtttgggt cacacagatg   1020
agccacatcc ccatgaacat tgactatgag aaaaatcagg actggctcag catgcagctg   1080
gtcgcgacct gtaacatcga gcagtctgcc ttcaacgact ggttcagcgg acacctcaac   1140
ttccagatcg agcatcatct ctttcccaca gtgcctcggc acaactactg gcgcgccgct   1200
ccacgggtgc gagcgttgtg tgagaaatac ggagtcaaat accaagagaa gaccttgtac   1260
ggagcatttg cggatatcat taggtctttg gagaaatctg gcgagctctg gctggatgcg   1320
tatctcaaca aataa                                                    1335

<210> SEQ ID NO 39
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 39
cccaagctta ctatgggtgg cggaggacag c                                    31

<210> SEQ ID NO 40
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 40
ccgctggagt tatttgttga gatacgc                                         27

<210> SEQ ID NO 41
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 41
gcgggtacca tggctcagca tccgctc                                         27

<210> SEQ ID NO 42
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 42
gcgggatcct tagttgttct tcttctt                                         27

<210> SEQ ID NO 43
<211> LENGTH: 6
<212> TYPE: PRT
<213> ORGANISM: Artificial sequence
<220> FEATURE:
```

<223> OTHER INFORMATION: Conserved region

<400> SEQUENCE: 43

Asp His Pro Gly Gly Ser
1               5

<210> SEQ ID NO 44
<211> LENGTH: 7
<212> TYPE: PRT
<213> ORGANISM: Artificial sequence
<220> FEATURE:
<223> OTHER INFORMATION: Conserved region

<400> SEQUENCE: 44

Trp Trp Lys Asp Lys His Asn
1               5

<210> SEQ ID NO 45
<211> LENGTH: 7
<212> TYPE: PRT
<213> ORGANISM: Artificial sequence
<220> FEATURE:
<223> OTHER INFORMATION: Conserved region

<400> SEQUENCE: 45

Gln Ile Glu His His Leu Phe
1               5

<210> SEQ ID NO 46
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 46
tggtggaarc ayaarcayaa y                                              21

<210> SEQ ID NO 47
<211> LENGTH: 30
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (19)..(19)
<223> OTHER INFORMATION: n = any nucleotide

<400> SEQUENCE: 47
gcgagggatc caaggraana rrtgrtgytc                                     30

<210> SEQ ID NO 48
<211> LENGTH: 6
<212> TYPE: PRT
<213> ORGANISM: Artificial sequence
<220> FEATURE:
<223> OTHER INFORMATION: Conserved region
<220> FEATURE:
<221> NAME/KEY: MISC_FEATURE
<222> LOCATION: (4)..(4)
<223> OTHER INFORMATION: X = any amino acid

<400> SEQUENCE: 48

Phe Leu His Xaa Tyr His
1               5

<210> SEQ ID NO 49

```
<211> LENGTH: 6
<212> TYPE: PRT
<213> ORGANISM: Artificial sequence
<220> FEATURE:
<223> OTHER INFORMATION: Conserved region
<220> FEATURE:
<221> NAME/KEY: MISC_FEATURE
<222> LOCATION: (3)..(3)
<223> OTHER INFORMATION: X = any amino acid

<400> SEQUENCE: 49

Met Tyr Xaa Tyr Tyr Phe
1               5

<210> SEQ ID NO 50
<211> LENGTH: 25
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (14)..(14)
<223> OTHER INFORMATION: n = any nucleotide
<220> FEATURE:
<221> NAME/KEY: misc_feature
<222> LOCATION: (18)..(18)
<223> OTHER INFORMATION: n = any nucleotide
<220> FEATURE:
<221> NAME/KEY: misc_feature
<222> LOCATION: (19)..(19)
<223> OTHER INFORMATION: n = any nucleotide
<220> FEATURE:
<221> NAME/KEY: misc_feature
<222> LOCATION: (20)..(20)
<223> OTHER INFORMATION: n = any nucleotide

<400> SEQUENCE: 50
caggatcctt yytncatnnn tayca                                          25

<210> SEQ ID NO 51
<211> LENGTH: 26
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (18)..(18)
<223> OTHER INFORMATION: n = any nucleotide
<220> FEATURE:
<221> NAME/KEY: misc_feature
<222> LOCATION: (19)..(19)
<223> OTHER INFORMATION: n = any nucleotide
<220> FEATURE:
<221> NAME/KEY: misc_feature
<222> LOCATION: (20)..(20)
<223> OTHER INFORMATION: n = any nucleotide

<400> SEQUENCE: 51
gatctagara artartannn rtacat                                         26

<210> SEQ ID NO 52
<211> LENGTH: 4
<212> TYPE: PRT
<213> ORGANISM: Artificial sequence
<220> FEATURE:
<223> OTHER INFORMATION: Conserved region

<400> SEQUENCE: 52

His Pro Gly Gly
1
```

<210> SEQ ID NO 53
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 53
agcacgacgs sarccacggc g                                              21

<210> SEQ ID NO 54
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 54
gtggtgcayc abcacgtgct                                                20

<210> SEQ ID NO 55
<211> LENGTH: 642
<212> TYPE: DNA
<213> ORGANISM: Pavlova salina
<220> FEATURE:
<221> NAME/KEY: misc_feature
<222> LOCATION: (13)..(13)
<223> OTHER INFORMATION: n = unknown
<220> FEATURE:
<221> NAME/KEY: misc_feature
<222> LOCATION: (39)..(39)
<223> OTHER INFORMATION: n = unknown
<220> FEATURE:
<221> NAME/KEY: misc_feature
<222> LOCATION: (51)..(51)
<223> OTHER INFORMATION: n = unknown
<220> FEATURE:
<221> NAME/KEY: misc_feature
<222> LOCATION: (77)..(77)
<223> OTHER INFORMATION: n = unknown
<220> FEATURE:
<221> NAME/KEY: misc_feature
<222> LOCATION: (302)..(302)
<223> OTHER INFORMATION: n = unknown
<220> FEATURE:
<221> NAME/KEY: misc_feature
<222> LOCATION: (639)..(639)
<223> OTHER INFORMATION: n = unknown

<400> SEQUENCE: 55
ggctgcgcaa ctnttggaag ggcgatcggt gcgggcctnt tcgttattac nccagctggc      60 gaaagggga tgtgctncaa ggcgattaag ttgggtaacg ccaggttttc ccagtcacga      120
cgttgtaaaa cgacggccag tgaattgtaa tacgactcac tatagggcga attgggtacc     180 gggcccccc tcgagaagtc gggtcgcatc ctgcggggcg acaagatctg gcagattggc     240
tttggcagtg ggttcaagtg caactcggcc gtgtggcagg cgaacaggag cgttgagcca    300
tntgagctcg actgacgagc tcggagctgc ggtacagaca ctgtcggcgg ctcgagaggg    360
ctgcgacttc agacgtgatc gggagattgt gcattggtgc gccgccgggc gcggcctgcc    420
gcccgggcgc tgcacgtcat cgtcagtagt cacggtcggc atcagcgccc ggcccgtggt    480
tggtacgtgg tagcgcaggc tgcgcagctg ccaacagccg ccgcccgagg tgggtggtgg    540
gactccgggt gtcagtcaca ctcagtggcg gccgccggca gtaggccgtg actctgccgt    600
ggcgttagta tcagtggcag tcagctgctg tcgtcaatnt tt                        642

<210> SEQ ID NO 56

```
<211> LENGTH: 100
<212> TYPE: DNA
<213> ORGANISM: Artificial Sequence
<220> FEATURE:
<223> OTHER INFORMATION: Oligonucleotide primer

<400> SEQUENCE: 56
tgggttgagt actcggccaa ccacacgacc aactgcgcgc cctcgtggtg gtgcgactgg      60
tggatgtctt acctcaacta ccagatcgag catcatctgt                          100

<210> SEQ ID NO 57
<211> LENGTH: 100
<212> TYPE: DNA
<213> ORGANISM: Artificial Sequence
<220> FEATURE:
<223> OTHER INFORMATION: Oligonucleotide primer

<400> SEQUENCE: 57
atagtgcagc ccgtgcttct cgaagagcgc cttgacgcgc ggcgcgatcg tcgggtggcg      60
gaattgcggc atggacggga acagatgatg ctcgatctgg                          100

<210> SEQ ID NO 58
<211> LENGTH: 1612
<212> TYPE: DNA
<213> ORGANISM: Pavlova salina

<400> SEQUENCE: 58
gccttctgga cgactgtcat gccgccgcgc gatagctact cgtacgccgc cccgccgtcg      60
gcccagctgc acgaggtcga taccccgcag gagcatgata agaaggagct cgtcatcggt     120
gaccgcgcgt acgacgtgac caactttgtg aagcgccacc cggtgggcaa gatcatcgca     180
taccaggttg gcacagatgc gacggacgcg tacaagcagt tccatgtgcg gtctgccaag     240
gcggacaaga tgctcaagtc gctgccttcg cgccccggtg caagggcta ctcgccccgc      300 cgcgctgacc tcattgccga cttccaggag ttcaccaagc agctggaggc ggagggcatg     360
tttgagccgt cgctgccgca cgtggcatac cgcctggcgg aggtgatcgc gatgcacgtg     420
gccggcgccg cgctcatctg gcacgggtac accttcgcgg gcattgccat gctcggcgtt     480
gtgcagggcc gctgcggctg gctcatgcac gagggcggcc actactcgct cacgggcaac     540
attgcttttg accgtgccat ccaagtcgcg tgctacggcc ttggctgcgg catgtcgggc     600
gcgtggtggc gcaaccagca caacaagcac cacgcgacgc cgcagaagtt gcagcacgac     660
gtcgacctcg acaccctccc gctcgtcgcc ttccacgagg ggatagccgc caaggtgaag     720
agccccgcga tgaaggcgtg gcttagtatg caggcgaagc tcttcgcgcc agtgaccacg     780
ctgctggtcg cgctgggctg gcagctgtac ctgcacccgc gccatatgct gcgcaccaag     840
cactacgacg agctcgcgat gctcggcatt cgctacggcc ttgtcggcta cctcgcggcg     900
aactacggcg cggggtacgt gctcgcgtgc tacctgctgt acgtgcagct cggcgccatg     960
tacatcttct gcaactttgc cgtgtcgcac acacacctgc cggttgtcga gcctaacgag    1020
cacgcaacgt gggtggagta cgccgcgaac cacacgacca actgctcgcc ctcgtggtgg    1080
tgcgactggt ggatgtcgta cctcaactac cagatcgagc accacctcta cccgtccatg    1140
ccgcagttcc gccaccccga gattgcgccg ggggtgaagc agctcttcga gaagcacggc    1200
ctgcactacg acgtgcgtgg ctacttcgag gccatggcgg acacgtttgc caaccttgac    1260
aacgtcgcgc acgcgccgga gaagaagatg cagtgagcgc gcgagtgagc aacgccaagc    1320
gtccaccgcg gagtcgcccg tggtcctcct gccgatcgcg gcctgtctct ccagctgaca    1380
```

-continued

```
tctctgctttt gcttgcccat gatcgacgtc gcctccctct ctctccacac gatgtgcctg    1440
acgaatgacc tgcgggataa tcagcgctcg catgcccatg ccagcgccaa tggcagctgc    1500
tgcggcagcc gccaagtggt aatccatgac acgctgctcc acgacgcgca cgccttccat    1560
cttgacaatc agcatggacg tagcatcatc agttcagtga ctaattcctt tc            1612
```

<210> SEQ ID NO 59
<211> LENGTH: 1278
<212> TYPE: DNA
<213> ORGANISM: Pavlova salina

<400> SEQUENCE: 59

```
atgccgccgc gcgatagcta ctcgtacgcc gccccgccgt cggcccagct gcacgaggtc     60
gataccccgc aggagcatga taagaaggag ctcgtcatcg gtgaccgcgc gtacgacgtg    120
accaactttg tgaagcgcca cccgggtggc aagatcatcg cataccaggt tggcacagat    180
gcgacggacg cgtacaagca gttccatgtg cggtctgcca aggcggacaa gatgctcaag    240
tcgctgcctt cgcgcccggt gcacaagggc tactcgcccc gccgcgctga cctcattgcc    300
gacttccagg agttcaccaa gcagctggag cggagggca tgtttgagcc gtcgctgccg    360
cacgtggcat accgcctggc ggaggtgatc gcgatgcacg tggccggcgc cgcgctcatc    420
tggcacgggt acaccttcgc gggcattgcc atgctcggcg ttgtgcaggg cgctgcggc     480 tggctcatgc acgagggcgg ccactactcg ctcacgggca cattgctttt tgaccgtgcc    540
atccaagtcg cgtgctacgg ccttggctgc ggcatgtcgg gcgcgtggtg gcgcaaccag    600
cacaacaagc accacgcgac gccgcagaag ttgcagcacg acgtcgacct cgacaccctc    660
ccgctcgtcg ccttccacga gcggatagcc gccaaggtga gagccccgc gatgaaggcg    720 tggcttagta tgcaggcgaa gctcttcgcg ccagtgacca cgctgctggt cgcgctgggc    780
tggcagctgt acctgcaccc cgcgccatatg ctgcgcacca gcactacga cgagctcgcg    840 atgctcggca ttcgctacgg ccttgtcggc tacctcgcgg cgaactacgg cgcggggtac    900
gtgctcgcgt gctacctgct gtacgtgcag ctcggcgcca tgtacatctt ctgcaacttt    960
gccgtgtcgc acacacacct gccggttgtc gagcctaacg agcacgcaac gtgggtggag   1020
tacgccgcga ccacacgac caactgctcg ccctcgtggt ggtgcgactg gtggatgtcg   1080
tacctcaact accagatcga gcaccactc taccgtcca tgccgcagtt ccgccacccg   1140
aagattgcgc gcgggtgaa gcagctcttc gagaagcacg gcctgcacta cgacgtgcgt   1200
ggctacttcg aggccatggc ggacacgttt gccaaccttg acaacgtcgc gcacgcgccg   1260
gagaagaaga tgcagtga                                                 1278
```

<210> SEQ ID NO 60
<211> LENGTH: 425
<212> TYPE: PRT
<213> ORGANISM: Pavlova salina

<400> SEQUENCE: 60

```
Met Pro Pro Arg Asp Ser Tyr Ser Tyr Ala Ala Pro Pro Ser Ala Gln
1               5                   10                  15

Leu His Glu Val Asp Thr Pro Gln Glu His Asp Lys Lys Glu Leu Val
            20                  25                  30

Ile Gly Asp Arg Ala Tyr Asp Val Thr Asn Phe Val Lys Arg His Pro
        35                  40                  45

Gly Gly Lys Ile Ile Ala Tyr Gln Val Gly Thr Asp Ala Thr Asp Ala
    50                  55                  60
```

```
Tyr Lys Gln Phe His Val Arg Ser Ala Lys Ala Asp Lys Met Leu Lys
 65                  70                  75                  80

Ser Leu Pro Ser Arg Pro Val His Lys Gly Tyr Ser Pro Arg Arg Ala
                 85                  90                  95

Asp Leu Ile Ala Asp Phe Gln Glu Phe Thr Lys Gln Leu Glu Ala Glu
            100                 105                 110

Gly Met Phe Glu Pro Ser Leu Pro His Val Ala Tyr Arg Leu Ala Glu
            115                 120                 125

Val Ile Ala Met His Val Ala Gly Ala Leu Ile Trp His Gly Tyr
        130                 135                 140

Thr Phe Ala Gly Ile Ala Met Leu Gly Val Val Gln Gly Arg Cys Gly
145                 150                 155                 160

Trp Leu Met His Glu Gly Gly His Tyr Ser Leu Thr Gly Asn Ile Ala
                165                 170                 175

Phe Asp Arg Ala Ile Gln Val Ala Cys Tyr Gly Leu Gly Cys Gly Met
            180                 185                 190

Ser Gly Ala Trp Trp Arg Asn Gln His Asn Lys His His Ala Thr Pro
            195                 200                 205

Gln Lys Leu Gln His Asp Val Asp Leu Asp Thr Leu Pro Leu Val Ala
    210                 215                 220

Phe His Glu Arg Ile Ala Ala Lys Val Lys Ser Pro Ala Met Lys Ala
225                 230                 235                 240

Trp Leu Ser Met Gln Ala Lys Leu Phe Ala Pro Val Thr Thr Leu Leu
                245                 250                 255

Val Ala Leu Gly Trp Gln Leu Tyr Leu His Pro Arg His Met Leu Arg
            260                 265                 270

Thr Lys His Tyr Asp Glu Leu Ala Met Leu Gly Ile Arg Tyr Gly Leu
        275                 280                 285

Val Gly Tyr Leu Ala Ala Asn Tyr Gly Ala Gly Tyr Val Leu Ala Cys
    290                 295                 300

Tyr Leu Leu Tyr Val Gln Leu Gly Ala Met Tyr Ile Phe Cys Asn Phe
305                 310                 315                 320

Ala Val Ser His Thr His Leu Pro Val Val Glu Pro Asn Glu His Ala
                325                 330                 335

Thr Trp Val Glu Tyr Ala Ala Asn His Thr Thr Asn Cys Ser Pro Ser
            340                 345                 350

Trp Trp Cys Asp Trp Trp Met Ser Tyr Leu Asn Tyr Gln Ile Glu His
            355                 360                 365

His Leu Tyr Pro Ser Met Pro Gln Phe Arg His Pro Lys Ile Ala Pro
    370                 375                 380

Arg Val Lys Gln Leu Phe Glu Lys His Gly Leu His Tyr Asp Val Arg
385                 390                 395                 400

Gly Tyr Phe Glu Ala Met Ala Asp Thr Phe Ala Asn Leu Asp Asn Val
                405                 410                 415

Ala His Ala Pro Glu Lys Lys Met Gln
            420                 425

<210> SEQ ID NO 61
<211> LENGTH: 8
<212> TYPE: PRT
<213> ORGANISM: Echium pitardii

<400> SEQUENCE: 61

Met Ala Asn Ala Ile Lys Lys Tyr
1               5
```

<210> SEQ ID NO 62
<211> LENGTH: 7
<212> TYPE: PRT
<213> ORGANISM: Echium pitardii

<400> SEQUENCE: 62

Glu Ala Leu Asn Thr His Gly
1               5

<210> SEQ ID NO 63
<211> LENGTH: 1347
<212> TYPE: DNA
<213> ORGANISM: Echium plantagineum

<400> SEQUENCE: 63

```
atggctaatg caatcaagaa gtacattact gcagaggagc tgaagaagca tgataaagca        60
ggggatctct ggatctccat tcaaggaaaa atctatgatg tttcagattg gttgaaggac       120
catccaggtg gaacttccc cttgctgagc cttgctggcc aagaggtaac tgatgcattt       180
gttgcatttc attctggtac aacttggaag cttcttgaaa aattcttcac tggttattac       240
cttaaagatt actctgtttc tgaggtgtcc aaagattaca ggaagcttgt gtttgagttt       300
aataaaatgg gcttgtttga caaaaagggt catattgttc ttgtgactgt cttgtttata       360
gctatgttgt ttggtatgag tgtttatggg gttttgtttt gtgagggtgt tttggtacat       420
ttgcttgctg gggggttgat gggttttgtc tggattcaga gtggttggat tggtcatgat       480
gctgggcatt atattgttat gcctgatgct aggcttaata agcttatggg tattgttgct       540
gccaattgtt tatctggaat aagcattggt tggtggaaat ggaaccataa tgcacatcac       600
attgcctgta atagcctcga ttacgacccg gatttgcagt acattccgtt tcttgttgtg       660
tcgtccaagt tgtttagctc gctcacctct catttctatg aaaagaaact gacatttgac       720
tctttatcga gattctttgt aagccatcag cattggacgt tttacccggt tatgtgtatg       780
gctagggtta atatgtttgt gcagtctctg ataatgttgt tgactaagcg aaatgtgttc       840
tatagaagtc aagaactgtt gggattggtg gtgttttgga tttggtaccc gttgcttgtt       900
tcttgcttgc ctaattgggg agaacgagta atgttcgttg ttgctagtct ctcggtgact       960
ggaatgcaac aagtgcagtt ctctttgaac catttctcgt cgagtgttta tgttggtcag      1020
cctaaaggga acgattggtt cgagaaacaa acatgtggga cgctcgacat ttcttgccct      1080
tcgtggatgg attggtttca tggtggattg caattccaag ttgagcatca tttgttccct      1140
aagctgccca gatgccacct tcggaaaatc tccccgttcg tgatggagtt atgcaagaag      1200
cataatttgt cttacaattg tgcatctttc tccgaggcca acaatatgac actcagaaca      1260
ttaagggaca cagcattgca agctcgcgat ttaaccaagc cgctccccaa gaatttggta      1320
tgggaagctc ttaatactca tggttga                                         1347
```

<210> SEQ ID NO 64
<211> LENGTH: 448
<212> TYPE: PRT
<213> ORGANISM: Echium plantagineum

<400> SEQUENCE: 64

Met Ala Asn Ala Ile Lys Lys Tyr Ile Thr Ala Glu Glu Leu Lys Lys
1               5                   10                  15

His Asp Lys Ala Gly Asp Leu Trp Ile Ser Ile Gln Gly Lys Ile Tyr
            20                  25                  30

Asp Val Ser Asp Trp Leu Lys Asp His Pro Gly Gly Asn Phe Pro Leu

```
                 35                  40                  45

Leu Ser Leu Ala Gly Gln Glu Val Thr Asp Ala Phe Val Ala Phe His
         50                  55                  60

Ser Gly Thr Thr Trp Lys Leu Leu Glu Lys Phe Phe Thr Gly Tyr Tyr
 65                  70                  75                  80

Leu Lys Asp Tyr Ser Val Ser Glu Val Ser Lys Asp Tyr Arg Lys Leu
                 85                  90                  95

Val Phe Glu Phe Asn Lys Met Gly Leu Phe Asp Lys Lys Gly His Ile
                100                 105                 110

Val Leu Val Thr Val Leu Phe Ile Ala Met Leu Phe Gly Met Ser Val
                115                 120                 125

Tyr Gly Val Leu Phe Cys Glu Gly Val Leu Val His Leu Leu Ala Gly
            130                 135                 140

Gly Leu Met Gly Phe Val Trp Ile Gln Ser Gly Trp Ile Gly His Asp
145                 150                 155                 160

Ala Gly His Tyr Ile Val Met Pro Asp Ala Arg Leu Asn Lys Leu Met
                    165                 170                 175

Gly Ile Val Ala Ala Asn Cys Leu Ser Gly Ile Ser Ile Gly Trp Trp
            180                 185                 190

Lys Trp Asn His Asn Ala His His Ile Ala Cys Asn Ser Leu Asp Tyr
                195                 200                 205

Asp Pro Asp Leu Gln Tyr Ile Pro Phe Leu Val Val Ser Ser Lys Leu
            210                 215                 220

Phe Ser Ser Leu Thr Ser His Phe Tyr Glu Lys Lys Leu Thr Phe Asp
225                 230                 235                 240

Ser Leu Ser Arg Phe Phe Val Ser His Gln His Trp Thr Phe Tyr Pro
                    245                 250                 255

Val Met Cys Met Ala Arg Val Asn Met Phe Val Gln Ser Leu Ile Met
            260                 265                 270

Leu Leu Thr Lys Arg Asn Val Phe Tyr Arg Ser Gln Glu Leu Leu Gly
                275                 280                 285

Leu Val Val Phe Trp Ile Trp Tyr Pro Leu Leu Val Ser Cys Leu Pro
            290                 295                 300

Asn Trp Gly Glu Arg Val Met Phe Val Val Ala Ser Leu Ser Val Thr
305                 310                 315                 320

Gly Met Gln Gln Val Gln Phe Ser Leu Asn His Phe Ser Ser Ser Val
                    325                 330                 335

Tyr Val Gly Gln Pro Lys Gly Asn Asp Trp Phe Glu Lys Gln Thr Cys
            340                 345                 350

Gly Thr Leu Asp Ile Ser Cys Pro Ser Trp Met Asp Trp Phe His Gly
                355                 360                 365

Gly Leu Gln Phe Gln Val Glu His His Leu Phe Pro Lys Leu Pro Arg
            370                 375                 380

Cys His Leu Arg Lys Ile Ser Pro Phe Val Met Glu Leu Cys Lys Lys
385                 390                 395                 400

His Asn Leu Ser Tyr Asn Cys Ala Ser Phe Ser Glu Ala Asn Asn Met
                    405                 410                 415

Thr Leu Arg Thr Leu Arg Asp Thr Ala Leu Gln Ala Arg Asp Leu Thr
            420                 425                 430

Lys Pro Leu Pro Lys Asn Leu Val Trp Glu Ala Leu Asn Thr His Gly
                435                 440                 445

<210> SEQ ID NO 65
<211> LENGTH: 448
```

```
<212> TYPE: PRT
<213> ORGANISM: Echium gentianoides

<400> SEQUENCE: 65
```

| | | | | | | | | | | | | | | |
|---|---|---|---|---|---|---|---|---|---|---|---|---|---|---|
| Met | Ala | Asn | Ala | Ile | Lys | Lys | Tyr | Ile | Thr | Ala | Glu | Glu | Leu | Lys | Lys |
| 1 | | | | 5 | | | | | 10 | | | | | 15 | |

His Asp Lys Glu Gly Asp Leu Trp Ile Ser Ile Gln Gly Lys Val Tyr
            20                  25                 30

Asp Val Ser Asp Trp Leu Lys Asp His Pro Gly Gly Lys Phe Pro Leu
        35                  40                 45

Leu Ser Leu Ala Gly Gln Glu Val Thr Asp Ala Phe Val Ala Phe His
50               55                 60

Ser Gly Ser Thr Trp Lys Phe Leu Asp Ser Phe Phe Thr Gly Tyr Tyr
65               70              75               80

Leu Lys Asp Tyr Ser Val Ser Glu Val Ser Lys Asp Tyr Arg Lys Leu
            85                  90               95

Val Phe Glu Phe Asn Lys Met Gly Leu Phe Asp Lys Lys Gly His Ile
            100              105            110

Val Leu Val Thr Val Leu Phe Ile Ala Met Met Phe Ala Met Ser Val
            115              120            125

Tyr Gly Val Leu Phe Cys Glu Gly Val Leu Val His Leu Leu Ala Gly
        130                135              140

Gly Leu Met Gly Phe Val Trp Ile Gln Ser Gly Trp Ile Gly His Asp
145              150              155            160

Ala Gly His Tyr Ile Val Met Pro Asn Pro Arg Leu Asn Lys Leu Met
            165              170            175

Gly Ile Val Ala Gly Asn Cys Leu Ser Gly Ile Ser Ile Gly Trp Trp
        180                185              190

Lys Trp Asn His Asn Ala His His Ile Ala Cys Asn Ser Leu Asp Tyr
            195              200            205

Asp Pro Asp Leu Gln Tyr Ile Pro Phe Leu Val Val Ser Ser Lys Leu
210              215              220

Phe Ser Ser Leu Thr Ser His Phe Tyr Glu Lys Lys Leu Thr Phe Asp
225              230              235            240

Ser Leu Ser Arg Phe Phe Val Ser His Gln His Trp Thr Phe Tyr Pro
            245              250            255

Val Met Cys Ser Ala Arg Val Asn Met Phe Val Gln Ser Leu Ile Met
        260                265              270

Leu Leu Thr Lys Arg Asn Val Phe Tyr Arg Ser Gln Glu Leu Leu Gly
            275              280            285

Leu Val Val Phe Trp Ile Trp Tyr Pro Leu Leu Val Ser Cys Leu Pro
        290                295              300

Asn Trp Gly Glu Arg Ile Met Phe Val Val Ala Ser Leu Ser Val Thr
305              310              315            320

Gly Met Gln Gln Val Gln Phe Ser Leu Asn His Phe Ser Ala Ser Val
            325              330            335

Tyr Val Gly Gln Pro Lys Gly Asn Asp Trp Phe Glu Lys Gln Thr Cys
        340                345            350

Gly Thr Leu Asp Ile Ser Cys Pro Ser Trp Met Asp Trp Phe His Gly
            355              360            365

Gly Leu Gln Phe Gln Val Glu His His Leu Phe Pro Lys Leu Pro Arg
        370                375              380

Cys His Leu Arg Lys Ile Ser Pro Phe Val Met Glu Leu Cys Lys Lys
385              390              395            400

```
His Asn Leu Ser Tyr Asn Cys Ala Ser Phe Ser Glu Ala Asn Glu Met
                405                 410                 415

Thr Leu Arg Thr Leu Arg Asp Thr Ala Leu Gln Ala Arg Asp Leu Thr
            420                 425                 430

Lys Pro Leu Pro Lys Asn Leu Val Trp Glu Ala Leu Asn Thr His Gly
            435                 440                 445

<210> SEQ ID NO 66
<211> LENGTH: 448
<212> TYPE: PRT
<213> ORGANISM: Echium pitardii

<400> SEQUENCE: 66

Met Ala Asn Ala Ile Lys Lys Tyr Ile Thr Ala Glu Glu Leu Lys Lys
1               5                   10                  15

His Asp Lys Glu Gly Asp Leu Trp Ile Ser Ile Gln Gly Lys Val Tyr
            20                  25                  30

Asp Val Ser Asp Trp Leu Lys Asp His Pro Gly Gly Lys Phe Pro Leu
        35                  40                  45

Leu Ser Leu Ala Gly Gln Glu Val Thr Asp Ala Phe Val Ala Phe His
    50                  55                  60

Ser Gly Ser Thr Trp Lys Leu Leu Asp Ser Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Asn Lys Met Gly Leu Phe Asp Lys Lys Gly His Ile
            100                 105                 110

Val Leu Val Thr Val Phe Phe Ile Ala Met Met Phe Ala Met Ser Val
        115                 120                 125

Tyr Gly Val Leu Phe Cys Glu Gly Val Leu Val His Leu Leu Ala Gly
    130                 135                 140

Gly Leu Met Gly Phe Val Trp Ile Gln Ser Gly Trp Ile Gly His Asp
145                 150                 155                 160

Ala Gly His Tyr Ile Val Met Pro Asn Pro Lys Leu Asn Lys Leu Met
                165                 170                 175

Gly Ile Val Ala Ser Asn Cys Leu Ser Gly Ile Ser Ile Gly Trp Trp
            180                 185                 190

Lys Trp Asn His Asn Ala His His Ile Ala Cys Asn Ser Leu Asp Tyr
        195                 200                 205

Asp Pro Asp Leu Gln Tyr Ile Pro Phe Leu Val Val Ser Ser Lys Leu
    210                 215                 220

Phe Ser Ser Leu Thr Ser His Phe Tyr Glu Lys Lys Leu Thr Phe Asp
225                 230                 235                 240

Ser Leu Ser Arg Phe Phe Val Ser His Gln His Trp Thr Phe Tyr Pro
                245                 250                 255

Val Met Cys Ser Ala Arg Val Asn Met Phe Val Gln Ser Leu Ile Met
            260                 265                 270

Leu Leu Thr Lys Arg Asn Val Phe Tyr Arg Ser Gln Glu Leu Leu Gly
        275                 280                 285

Leu Val Val Phe Trp Ile Trp Tyr Pro Leu Leu Val Ser Cys Leu Pro
    290                 295                 300

Asn Trp Gly Glu Arg Ile Met Phe Val Val Ala Ser Leu Ser Val Thr
305                 310                 315                 320

Gly Leu Gln Gln Val Gln Phe Ser Leu Asn His Phe Ala Ala Ser Val
                325                 330                 335
```

```
Tyr Val Gly Gln Pro Lys Gly Ile Asp Trp Phe Glu Lys Gln Thr Cys
            340                 345                 350

Gly Thr Leu Asp Ile Ser Cys Pro Ser Trp Met Asp Trp Phe His Gly
            355                 360                 365

Gly Leu Gln Phe Gln Val Glu His His Leu Phe Pro Lys Leu Pro Arg
            370                 375                 380

Cys His Leu Arg Lys Ile Ser Pro Phe Val Met Glu Leu Cys Lys Lys
385                 390                 395                 400

His Asn Leu Ser Tyr Asn Cys Ala Ser Phe Ser Gln Ala Asn Glu Met
                405                 410                 415

Thr Leu Arg Thr Leu Arg Asp Thr Ala Leu Gln Ala Arg Asp Leu Thr
            420                 425                 430

Lys Pro Leu Pro Lys Asn Leu Val Trp Glu Ala Leu Asn Thr His Gly
            435                 440                 445

<210> SEQ ID NO 67
<211> LENGTH: 448
<212> TYPE: PRT
<213> ORGANISM: Borago officinalis

<400> SEQUENCE: 67

Met Ala Ala Gln Ile Lys Lys Tyr Ile Thr Ser Asp Glu Leu Lys Asn
1               5                   10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Ser Ser Lys Phe
210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270
```

```
Leu Leu Thr Lys Arg Asn Val Ser Tyr Arg Ala His Glu Leu Leu Gly
        275                 280                 285

Cys Leu Val Phe Ser Ile Trp Tyr Pro Leu Leu Val Ser Cys Leu Pro
290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
                340                 345                 350

Gly Thr Leu Asp Ile Ser Cys Pro Pro Trp Met Asp Trp Phe His Gly
        355                 360                 365

Gly Leu Gln Phe Gln Ile Glu His His Leu Phe Pro Lys Met Pro Arg
    370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
                420                 425                 430

Lys Pro Leu Pro Lys Asn Leu Val Trp Glu Ala Leu His Thr His Gly
        435                 440                 445

<210> SEQ ID NO 68
<211> LENGTH: 446
<212> TYPE: PRT
<213> ORGANISM: Borago officinalis

<400> SEQUENCE: 68

Met Glu Gly Thr Lys Lys Tyr Ile Ser Val Gly Leu Glu Lys His
1               5                   10                  15

Asn Gln Leu Gly Asp Val Trp Ile Ser Ile Gly Lys Val Tyr Asn
                20                  25                  30

Val Thr Asp Trp Ile Lys Lys His Pro Gly Gly Asp Val Pro Ile Met
            35                  40                  45

Asn Leu Ala Gly Gln Asp Ala Thr Asp Ala Phe Ile Ala Tyr His Pro
50                  55                  60

Gly Thr Ala Trp Lys Asn Leu Glu Asn Leu Phe Thr Gly Tyr His Leu
65                  70                  75                  80

Glu Asp Tyr Leu Val Ser Glu Ile Ser Lys Asp Tyr Arg Lys Leu Ala
                85                  90                  95

Ser Glu Phe Ser Lys Ala Gly Leu Phe Glu Lys Lys Gly His Thr Val
                100                 105                 110

Ile Tyr Cys Leu Ser Phe Ile Ala Leu Leu Cys Gly Cys Val Tyr
            115                 120                 125

Gly Val Leu Cys Ser Asn Ser Leu Trp Val His Met Leu Ser Gly Ala
        130                 135                 140

Met Leu Gly Met Cys Phe Ile Gln Ala Ala Tyr Leu Gly His Asp Ser
145                 150                 155                 160

Gly His Tyr Thr Met Met Ser Ser Lys Gly Tyr Asn Lys Phe Ala Gln
                165                 170                 175

Val Leu Asn Gly Asn Cys Leu Thr Gly Ile Ser Ile Ala Trp Trp Lys
            180                 185                 190

Trp Thr His Asn Ala His His Ile Ala Cys Asn Ser Leu Asp Tyr Asp
        195                 200                 205
```

-continued

Pro Asp Leu Gln His Leu Pro Val Phe Ala Val Pro Ser Ser Phe Phe
    210                 215                 220

Lys Ser Leu Thr Ser Arg Phe Tyr Gly Arg Glu Leu Thr Phe Asp Gly
225                 230                 235                 240

Leu Ser Arg Phe Leu Val Ser Tyr Gln His Phe Thr Ile Tyr Leu Val
                245                 250                 255

Met Ile Phe Gly Arg Ile Asn Leu Tyr Val Gln Thr Phe Leu Leu Leu
            260                 265                 270

Phe Ser Thr Arg Lys Val Pro Asp Arg Ala Leu Asn Ile Ile Gly Ile
            275                 280                 285

Leu Val Tyr Trp Thr Trp Phe Pro Tyr Leu Val Ser Cys Leu Pro Asn
            290                 295                 300

Trp Asn Glu Arg Val Leu Phe Val Leu Thr Cys Phe Ser Val Thr Ala
305                 310                 315                 320

Leu Gln His Ile Gln Phe Thr Leu Asn His Phe Ala Ala Asp Val Tyr
                325                 330                 335

Val Gly Pro Pro Thr Gly Thr Asn Trp Phe Glu Lys Gln Ala Ala Gly
            340                 345                 350

Thr Ile Asp Ile Ser Cys Ser Ser Trp Met Asp Trp Phe Phe Gly Gly
            355                 360                 365

Leu Gln Phe Gln Leu Glu His His Leu Phe Pro Arg Met Pro Arg Cys
370                 375                 380

Gln Leu Arg Asn Ile Ser Pro Ile Val Gln Asp Tyr Cys Lys Lys His
385                 390                 395                 400

Asn Leu Pro Tyr Arg Ser Leu Ser Phe Phe Asp Ala Asn Val Ala Thr
                405                 410                 415

Ile Lys Thr Leu Arg Thr Ala Ala Leu Gln Ala Arg Asp Leu Thr Val
            420                 425                 430

Val Pro Gln Asn Leu Leu Trp Glu Ala Phe Asn Thr His Gly
            435                 440                 445

<210> SEQ ID NO 69
<211> LENGTH: 458
<212> TYPE: PRT
<213> ORGANISM: Helianthus annus

<400> SEQUENCE: 69

Met Val Ser Pro Ser Ile Glu Val Leu Asn Ser Ile Ala Asp Gly Lys
1               5                   10                  15

Lys Tyr Ile Thr Ser Lys Glu Leu Lys Lys His Asn Asn Pro Asn Asp
            20                  25                  30

Leu Trp Ile Ser Ile Leu Gly Lys Val Tyr Asn Val Thr Glu Trp Ala
        35                  40                  45

Lys Glu His Pro Gly Gly Asp Ala Pro Leu Ile Asn Leu Ala Gly Gln
50                  55                  60

Asp Val Thr Asp Ala Phe Ile Ala Phe His Pro Gly Thr Ala Trp Lys
65                  70                  75                  80

His Leu Asp Lys Leu Phe Thr Gly Tyr His Leu Lys Asp Tyr Gln Val
                85                  90                  95

Ser Asp Ile Ser Arg Asp Tyr Arg Lys Leu Ala Ser Glu Phe Ala Lys
            100                 105                 110

Ala Gly Met Phe Glu Lys Lys Gly His Gly Val Ile Tyr Ser Leu Cys
        115                 120                 125

Phe Val Ser Leu Leu Leu Ser Ala Cys Val Tyr Gly Val Leu Tyr Ser
    130                 135                 140

```
Gly Ser Phe Trp Ile His Met Leu Ser Gly Ala Ile Leu Gly Leu Ala
145                 150                 155                 160

Trp Met Gln Ile Ala Tyr Leu Gly His Asp Ala Gly His Tyr Gln Met
                165                 170                 175

Met Ala Thr Arg Gly Trp Asn Lys Phe Ala Gly Ile Phe Ile Gly Asn
            180                 185                 190

Cys Ile Thr Gly Ile Ser Ile Ala Trp Trp Lys Trp Thr His Asn Ala
        195                 200                 205

His His Ile Ala Cys Asn Ser Leu Asp Tyr Asp Pro Asp Leu Gln His
    210                 215                 220

Leu Pro Met Leu Ala Val Ser Ser Lys Leu Phe Asn Ser Ile Thr Ser
225                 230                 235                 240

Val Phe Tyr Gly Arg Gln Leu Thr Phe Asp Pro Leu Ala Arg Phe Phe
                245                 250                 255

Val Ser Tyr Gln His Tyr Leu Tyr Tyr Pro Ile Met Cys Val Ala Arg
                260                 265                 270

Val Asn Leu Tyr Leu Gln Thr Ile Leu Leu Leu Ile Ser Lys Arg Lys
            275                 280                 285

Ile Pro Asp Arg Gly Leu Asn Ile Leu Gly Thr Leu Ile Phe Trp Thr
        290                 295                 300

Trp Phe Pro Leu Leu Val Ser Arg Leu Pro Asn Trp Pro Glu Arg Val
305                 310                 315                 320

Ala Phe Val Leu Val Ser Phe Cys Val Thr Gly Ile Gln His Ile Gln
                325                 330                 335

Phe Thr Leu Asn His Phe Ser Gly Asp Val Tyr Val Gly Pro Pro Lys
            340                 345                 350

Gly Asp Asn Trp Phe Glu Lys Gln Thr Arg Gly Thr Ile Asp Ile Ala
        355                 360                 365

Cys Ser Ser Trp Met Asp Trp Phe Gly Gly Leu Gln Phe Gln Leu
    370                 375                 380

Glu His His Leu Phe Pro Arg Leu Pro Arg Cys His Leu Arg Ser Ile
385                 390                 395                 400

Ser Pro Ile Cys Arg Glu Leu Cys Lys Lys Tyr Asn Leu Pro Tyr Val
                405                 410                 415

Ser Leu Ser Phe Tyr Asp Ala Asn Val Thr Thr Leu Lys Thr Leu Arg
            420                 425                 430

Thr Ala Ala Leu Gln Ala Arg Asp Leu Thr Asn Pro Ala Pro Gln Asn
        435                 440                 445

Leu Ala Trp Glu Ala Phe Asn Thr His Gly
    450                 455

<210> SEQ ID NO 70
<211> LENGTH: 449
<212> TYPE: PRT
<213> ORGANISM: Arabidopsis thaliana

<400> SEQUENCE: 70

Met Ala Asp Gln Thr Lys Lys Arg Tyr Val Thr Ser Glu Asp Leu Lys
1               5                   10                  15

Lys His Asn Lys Pro Gly Asp Leu Trp Ile Ser Ile Gln Gly Lys Val
            20                  25                  30

Tyr Asp Val Ser Asp Trp Val Lys Ser His Pro Gly Gly Glu Ala Ala
        35                  40                  45

Ile Leu Asn Leu Ala Gly Gln Asp Val Thr Asp Ala Phe Ile Ala Tyr
    50                  55                  60
```

-continued

```
His Pro Gly Thr Ala Trp His His Leu Glu Lys Leu His Asn Gly Tyr
 65                  70                  75                  80

His Val Arg Asp His Val Ser Asp Val Ser Arg Asp Tyr Arg Arg
             85                  90                  95

Leu Ala Ala Glu Phe Ser Lys Arg Gly Leu Phe Asp Lys Lys Gly His
            100                 105                 110

Val Thr Leu Tyr Thr Leu Thr Cys Val Gly Val Met Leu Ala Ala Val
            115                 120                 125

Leu Tyr Gly Val Leu Ala Cys Thr Ser Ile Trp Ala His Leu Ile Ser
        130                 135                 140

Ala Val Leu Leu Gly Leu Leu Trp Ile Gln Ser Ala Tyr Val Gly His
145                 150                 155                 160

Asp Ser Gly His Tyr Thr Val Thr Ser Thr Lys Pro Cys Asn Lys Leu
                165                 170                 175

Ile Gln Leu Leu Ser Gly Asn Cys Leu Thr Gly Ile Ser Ile Ala Trp
            180                 185                 190

Trp Lys Trp Thr His Asn Ala His His Ile Ala Cys Asn Ser Leu Asp
        195                 200                 205

His Asp Pro Asp Leu Gln His Ile Pro Ile Phe Ala Val Ser Thr Lys
210                 215                 220

Phe Phe Asn Ser Met Thr Ser Arg Phe Tyr Gly Arg Lys Leu Thr Phe
225                 230                 235                 240

Asp Pro Leu Ala Arg Phe Leu Ile Ser Tyr Gln His Trp Thr Phe Tyr
                245                 250                 255

Pro Val Met Cys Val Gly Arg Ile Asn Leu Phe Ile Gln Thr Phe Leu
            260                 265                 270

Leu Leu Phe Ser Lys Arg His Val Pro Asp Arg Ala Leu Asn Ile Ala
        275                 280                 285

Gly Ile Leu Val Phe Trp Thr Trp Phe Pro Leu Leu Val Ser Phe Leu
290                 295                 300

Pro Asn Trp Gln Glu Arg Phe Ile Phe Val Phe Val Ser Phe Ala Val
305                 310                 315                 320

Thr Ala Ile Gln His Val Gln Phe Cys Leu Asn His Phe Ala Ala Asp
                325                 330                 335

Val Tyr Thr Gly Pro Pro Asn Gly Asn Asp Trp Phe Glu Lys Gln Thr
            340                 345                 350

Ala Gly Thr Leu Asp Ile Ser Cys Arg Ser Phe Met Asp Trp Phe Phe
        355                 360                 365

Gly Gly Leu Gln Phe Gln Leu Glu His His Leu Phe Pro Arg Leu Pro
370                 375                 380

Arg Cys His Leu Arg Thr Val Ser Pro Val Val Lys Glu Leu Cys Lys
385                 390                 395                 400

Lys His Asn Leu Pro Tyr Arg Ser Leu Ser Trp Trp Glu Ala Asn Val
                405                 410                 415

Trp Thr Ile Arg Thr Leu Lys Asn Ala Ala Ile Gln Ala Arg Asp Ala
            420                 425                 430

Thr Asn Pro Val Leu Lys Asn Leu Leu Trp Glu Ala Val Asn Thr His
        435                 440                 445

Gly

<210> SEQ ID NO 71
<211> LENGTH: 449
<212> TYPE: PRT
<213> ORGANISM: Arabidopsis thaliana
```

```
<400> SEQUENCE: 71

Met Ala Glu Glu Thr Glu Lys Lys Tyr Ile Thr Asn Glu Asp Leu Lys
1               5                   10                  15

Lys His Asn Lys Ser Gly Asp Leu Trp Ile Ala Ile Gln Gly Lys Val
            20                  25                  30

Tyr Asn Val Ser Asp Trp Ile Lys Thr His Pro Gly Gly Asp Thr Val
        35                  40                  45

Ile Leu Asn Leu Val Gly Gln Asp Val Thr Asp Ala Phe Ile Ala Phe
    50                  55                  60

His Pro Gly Thr Ala Trp His His Leu Asp His Leu Phe Thr Gly Tyr
65                  70                  75                  80

His Ile Arg Asp Phe Gln Val Ser Glu Val Ser Arg Asp Tyr Arg Arg
                85                  90                  95

Met Ala Ala Glu Phe Arg Lys Leu Gly Leu Phe Glu Asn Lys Gly His
            100                 105                 110

Val Thr Leu Tyr Thr Leu Ala Phe Val Ala Met Phe Leu Gly Val
        115                 120                 125

Leu Tyr Gly Val Leu Ala Cys Thr Ser Val Phe Ala His Gln Ile Ala
130                 135                 140

Ala Ala Leu Leu Gly Leu Leu Trp Ile Gln Ser Ala Tyr Ile Gly His
145                 150                 155                 160

Asp Ser Gly His Tyr Val Ile Met Ser Asn Lys Ser Tyr Asn Arg Phe
                165                 170                 175

Ala Gln Leu Leu Ser Gly Asn Cys Leu Thr Gly Ile Ser Ile Ala Trp
            180                 185                 190

Trp Lys Trp Thr His Asn Ala His His Leu Ala Cys Asn Ser Leu Asp
        195                 200                 205

Tyr Asp Pro Asp Leu Gln His Ile Pro Val Phe Ala Val Ser Thr Lys
    210                 215                 220

Phe Phe Ser Ser Leu Thr Ser Arg Phe Tyr Asp Arg Lys Leu Thr Phe
225                 230                 235                 240

Asp Pro Val Ala Arg Phe Leu Val Ser Tyr Gln His Phe Thr Tyr Tyr
                245                 250                 255

Pro Val Met Cys Phe Gly Arg Ile Asn Leu Phe Ile Gln Thr Phe Leu
            260                 265                 270

Leu Leu Phe Ser Lys Arg Glu Val Pro Asp Arg Ala Leu Asn Phe Ala
        275                 280                 285

Gly Ile Leu Val Phe Trp Thr Trp Phe Pro Leu Leu Val Ser Cys Leu
    290                 295                 300

Pro Asn Trp Pro Glu Arg Phe Phe Val Phe Thr Ser Phe Thr Val
305                 310                 315                 320

Thr Ala Leu Gln His Ile Gln Phe Thr Leu Asn His Phe Ala Ala Asp
                325                 330                 335

Val Tyr Val Gly Pro Pro Thr Gly Ser Asp Trp Phe Glu Lys Gln Ala
            340                 345                 350

Ala Gly Thr Ile Asp Ile Ser Cys Arg Ser Tyr Met Asp Trp Phe Phe
        355                 360                 365

Gly Gly Leu Gln Phe Gln Leu Glu His His Leu Phe Pro Arg Leu Pro
    370                 375                 380

Arg Cys His Leu Arg Lys Val Ser Pro Val Val Gln Glu Leu Cys Lys
385                 390                 395                 400

Lys His Asn Leu Pro Tyr Arg Ser Met Ser Trp Phe Glu Ala Asn Val
                405                 410                 415
```

```
Leu Thr Ile Asn Thr Leu Lys Thr Ala Ala Tyr Gln Ala Arg Asp Val
                420                 425                 430

Ala Asn Pro Val Val Lys Asn Leu Val Trp Glu Ala Leu Asn Thr His
            435                 440                 445

Gly

<210> SEQ ID NO 72
<211> LENGTH: 4
<212> TYPE: PRT
<213> ORGANISM: Artificial Sequence
<220> FEATURE:
<223> OTHER INFORMATION: Conserved motif

<400> SEQUENCE: 72

His Pro Gly Gly
1

<210> SEQ ID NO 73
<211> LENGTH: 5
<212> TYPE: PRT
<213> ORGANISM: Artificial Sequence
<220> FEATURE:
<223> OTHER INFORMATION: Conserved motif
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = any amino acid

<400> SEQUENCE: 73

Gln Xaa Xaa His His
1               5

<210> SEQ ID NO 74
<211> LENGTH: 271
<212> TYPE: PRT
<213> ORGANISM: Thraustochytrium sp.

<400> SEQUENCE: 74

Met Met Glu Pro Leu Asp Arg Tyr Arg Ala Leu Ala Glu Leu Ala Ala
1               5                   10                  15

Arg Tyr Ala Ser Ser Ala Ala Phe Lys Trp Gln Val Thr Tyr Asp Ala
                20                  25                  30

Lys Asp Ser Phe Val Gly Pro Leu Gly Ile Arg Glu Pro Leu Gly Leu
            35                  40                  45

Leu Val Gly Ser Val Val Leu Tyr Leu Ser Leu Ala Val Val Tyr
        50                  55                  60

Ala Leu Arg Asn Tyr Leu Gly Leu Met Ala Leu Arg Ser Val His
65              70                  75                  80

Asn Leu Gly Leu Cys Leu Phe Ser Gly Ala Val Trp Ile Tyr Thr Ser
                85                  90                  95

Tyr Leu Met Ile Gln Asp Gly His Phe Arg Ser Leu Glu Ala Ala Thr
            100                 105                 110

Cys Glu Pro Leu Lys His Pro His Phe Gln Leu Ile Ser Leu Leu Phe
        115                 120                 125

Ala Leu Ser Lys Ile Trp Glu Trp Phe Asp Thr Val Leu Leu Ile Val
    130                 135                 140

Lys Gly Asn Lys Leu Arg Phe Leu His Val Leu His Ala Thr Thr
145                 150                 155                 160
```

```
Phe Trp Leu Tyr Ala Ile Asp His Ile Phe Leu Ser Ser Ile Lys Tyr
                165                 170                 175

Gly Val Ala Val Asn Ala Phe Ile His Thr Val Met Tyr Ala His Tyr
            180                 185                 190

Phe Arg Pro Phe Pro Lys Gly Leu Arg Pro Leu Ile Thr Gln Leu Gln
        195                 200                 205

Ile Val Gln Phe Ile Phe Ser Ile Gly Ile His Thr Ala Ile Tyr Trp
    210                 215                 220

His Tyr Asp Cys Glu Pro Leu Val His Thr His Phe Trp Glu Tyr Val
225                 230                 235                 240

Thr Pro Tyr Leu Phe Val Val Pro Phe Leu Ile Leu Phe Phe Asn Phe
                245                 250                 255

Tyr Leu Gln Gln Tyr Val Leu Ala Pro Ala Lys Thr Lys Lys Ala
                260                 265                 270

<210> SEQ ID NO 75
<211> LENGTH: 266
<212> TYPE: PRT
<213> ORGANISM: Dabio rerio

<400> SEQUENCE: 75

Met Ser Val Leu Ala Leu Gln Glu Tyr Glu Phe Glu Arg Gln Phe Asn
1               5                   10                  15

Glu Asp Glu Ala Ile Arg Trp Met Gln Glu Asn Trp Lys Lys Ser Phe
            20                  25                  30

Leu Phe Ser Ala Leu Tyr Ala Ala Cys Ile Leu Gly Gly Arg His Val
        35                  40                  45

Met Lys Gln Arg Glu Lys Phe Glu Leu Arg Lys Pro Leu Val Leu Trp
    50                  55                  60

Ser Leu Thr Leu Ala Ala Phe Ser Ile Phe Gly Ala Ile Arg Thr Gly
65                  70                  75                  80

Gly Tyr Met Val Asn Ile Leu Met Thr Lys Gly Leu Lys Gln Ser Val
                85                  90                  95

Cys Asp Gln Ser Phe Tyr Asn Gly Pro Val Ser Lys Phe Trp Ala Tyr
            100                 105                 110

Ala Phe Val Leu Ser Lys Ala Pro Glu Leu Gly Asp Thr Leu Phe Ile
        115                 120                 125

Val Leu Arg Lys Gln Lys Leu Ile Phe Leu His Trp Tyr His His Ile
    130                 135                 140

Thr Val Leu Leu Tyr Ser Trp Tyr Ser Tyr Lys Asp Met Val Ala Gly
145                 150                 155                 160

Gly Gly Trp Phe Met Thr Met Asn Tyr Leu Val His Ala Val Met Tyr
                165                 170                 175

Ser Tyr Tyr Ala Leu Arg Ala Ala Gly Phe Lys Ile Ser Arg Lys Phe
            180                 185                 190

Ala Met Phe Ile Thr Leu Thr Gln Ile Thr Gln Met Val Met Gly Cys
        195                 200                 205

Val Val Asn Tyr Leu Val Tyr Leu Trp Met Gln Gln Gly Gln Glu Cys
    210                 215                 220

Pro Ser His Val Gln Asn Ile Val Trp Ser Ser Leu Met Tyr Leu Ser
225                 230                 235                 240

Tyr Phe Val Leu Phe Cys Gln Phe Phe Glu Ala Tyr Ile Thr Lys
                245                 250                 255

Arg Lys Ser Asn Ala Ala Lys Lys Ser Gln
                260                 265
```

<210> SEQ ID NO 76
<211> LENGTH: 320
<212> TYPE: PRT
<213> ORGANISM: Pavlova lutheri

<400> SEQUENCE: 76

```
His Glu Ala Ser Cys Arg Ile Arg His Glu Ala Ala Leu Trp Ser Trp
  1               5                  10                  15
Leu Pro Thr Tyr Asp Glu Phe Val Asp Gly Leu Ser Phe Val Asp Arg
                 20                  25                  30
Glu Lys Ile Gly Val His Met Val Asp Gln Gly Val Ile Thr Ser Ala
             35                  40                  45
Glu Trp Ala Ala Ile Ser Val Asp Lys His Met Ser Phe Phe Ser Asp
         50                  55                  60
Ala Ala Glu Phe Thr Gly Asp His Trp Ile Ile Pro Leu Val Ala Val
 65                  70                  75                  80
Ala Leu Tyr Leu Val Met Ile Val Gly Pro Met Ile Met Ala Asn
                 85                  90                  95
Arg Pro Pro Leu Pro Val Asn Gly Leu Ala Cys Ala Trp Asn Trp Phe
                100                 105                 110
Leu Ala Ala Phe Ser Thr Phe Gly Val Ala Cys Thr Trp His Cys Ile
            115                 120                 125
Phe Thr Arg Leu Arg Ser Arg Gly Phe Glu Ser Thr Thr Cys Gly Ser
        130                 135                 140
Ala Met Phe Met Ser Gln Gly Tyr Val Gly Leu Ala Met Leu Leu Phe
145                 150                 155                 160
Ile Tyr Ser Lys Leu Phe Glu Leu Ile Asp Thr Phe Phe Leu Ile Ala
                165                 170                 175
Lys Lys Ala Asp Val Ile Phe Leu His Trp Tyr His Val Thr Val
            180                 185                 190
Leu Leu Tyr Cys Trp His Ser His Ser Val Arg Ile Pro Ser Gly Ile
            195                 200                 205
Trp Phe Ala Ala Met Asn Tyr Phe Val His Ala Ile Met Tyr Ser Tyr
        210                 215                 220
Phe Ala Met Thr Gln Met Gly Pro Arg Tyr Arg Lys Leu Val Arg Pro
225                 230                 235                 240
Tyr Ala Arg Leu Ile Thr Thr Leu Gln Ile Ser Gln Met Phe Val Gly
                245                 250                 255
Leu Ile Val Asn Gly Ser Ile Ile Tyr Phe Thr Ser Leu Gly His Ala
                260                 265                 270
Cys Lys Ser Ser Lys Thr Asn Thr Ile Leu Ser Trp Leu Met Tyr Leu
            275                 280                 285
Ser Tyr Phe Val Leu Phe Gly Leu Leu Tyr Leu Arg Asn Tyr Ile Leu
        290                 295                 300
Gly Thr His Gly Lys Pro Ala Gly Lys Arg Ala Lys Gly Lys Ala Glu
305                 310                 315                 320
```

<210> SEQ ID NO 77
<211> LENGTH: 282
<212> TYPE: PRT
<213> ORGANISM: Danio rerio

<400> SEQUENCE: 77

```
Met Glu Thr Phe Ser His Arg Val Asn Ser Tyr Ile Asp Ser Trp Met
  1               5                  10                  15
Gly Pro Arg Asp Leu Arg Val Thr Gly Trp Phe Leu Leu Asp Asp Tyr
```

```
                    20                  25                  30
Ile Pro Thr Phe Ile Phe Thr Val Met Tyr Leu Leu Ile Val Trp Met
            35                  40                  45

Gly Pro Lys Tyr Met Lys Asn Arg Gln Ala Tyr Ser Cys Arg Ala Leu
        50                  55                  60

Leu Val Pro Tyr Asn Leu Cys Leu Thr Leu Leu Ser Leu Tyr Met Phe
65                  70                  75                  80

Tyr Glu Leu Val Met Ser Val Tyr Gln Gly Gly Tyr Asn Phe Phe Cys
                85                  90                  95

Gln Asn Thr His Ser Gly Gly Asp Ala Asp Asn Arg Met Met Asn Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Phe Leu His Val
        130                 135                 140

Tyr His His Ala Thr Met Leu Asn Ile Trp Trp Phe Val Met Asn Trp
145                 150                 155                 160

Val Pro Cys Gly His Ser Tyr Phe Gly Ala Thr Phe Asn Ser Phe Ile
            165                 170                 175

His Val Leu Met Tyr Ser Tyr Tyr Gly Leu Ser Ala Val Pro Ala Leu
                180                 185                 190

Arg Pro Tyr Leu Trp Trp Lys Lys Tyr Ile Thr Gln Gly Gln Leu Val
            195                 200                 205

Gln Phe Val Leu Thr Met Phe Gln Thr Ser Cys Ala Val Val Trp Pro
        210                 215                 220

Cys Gly Phe Pro Met Gly Trp Leu Tyr Phe Gln Ile Ser Tyr Met Val
225                 230                 235                 240

Thr Leu Ile Leu Leu Phe Ser Asn Phe Tyr Ile Gln Thr Tyr Lys Lys
                245                 250                 255

Arg Ser Gly Ser Val Asn Gly His Thr Asn Gly Val Met Ser Ser Glu
            260                 265                 270

Lys Ile Lys His Arg Lys Ala Arg Ala Asp
        275                 280

<210> SEQ ID NO 78
<211> LENGTH: 396
<212> TYPE: PRT
<213> ORGANISM: Pavlova lutheri

<400> SEQUENCE: 78

Arg Gly Leu Val Pro Asn Ser Ala Arg Gly Leu Arg Asp Asp Lys Asp
1               5                   10                  15

Asp Gly Ser Leu Ser Ala Thr Ser Asp Phe Phe Arg Ser Thr Ile Thr
            20                  25                  30

Asp Cys Gly Asn Phe Cys Asp Glu Ser Val Asp Phe Gln Met Lys Leu
        35                  40                  45

Phe Glu Arg Asn Gln Ile Ser Glu Arg Cys Tyr Phe Pro Pro Gly Ile
        50                  55                  60

Arg Ala Tyr Arg Lys Gly Glu Arg Asp Phe Asp Ser Met Ala Ala
65                  70                  75                  80

Ala Arg Lys Glu Phe Glu Thr Val Val Phe Thr Thr Asp Glu Leu
                85                  90                  95

Leu Ala Lys Thr Gly Val Lys Pro Arg Asp Ile Asp Ile Leu Val Val
            100                 105                 110

Asn Cys Ser Leu Phe Asn Pro Thr Pro Ser Leu Ala Ala Ile Val Ile
```

```
                    115                 120                 125
Asn His Tyr Gln Met Lys Asp Ser Val Gln Ser Tyr Ser Leu Gly Gly
130                 135                 140

Met Gly Cys Ser Ala Gly Leu Ile Ser Ile His Leu Ala Lys Asp Leu
145                 150                 155                 160

Leu Gln Val Tyr Pro Arg Lys Arg Ala Leu Val Ile Ser Thr Glu Asn
                165                 170                 175

Ile Thr Gln Asn Phe Tyr Gln Gly Asn Glu Lys Ser Met Leu Ile Ser
            180                 185                 190

Asn Thr Leu Phe Arg Met Gly Ala Ala Val Leu Leu Ser Gly Arg
        195                 200                 205

His Ala Asp Arg Arg Val Ala Lys Tyr Gln Leu Leu His Thr Val Arg
210                 215                 220

Thr His Lys Gly Ala Asp Pro Asp Ala Tyr Arg Cys Val Phe Gln Glu
225                 230                 235                 240

Glu Asp Lys Ala Gly His Val Gly Val Arg Leu Ser Lys Asp Val Met
                245                 250                 255

Glu Cys Ala Gly Ala Ala Met Lys Thr Asn Ile Ser Val Leu Ala Pro
            260                 265                 270

Leu Ile Leu Pro Val Ser Glu Gln Val Arg Phe Leu Ala Asn Tyr Val
        275                 280                 285

Ala Arg Lys Trp Leu Arg Met Lys Gly Val Lys Gly Tyr Val Pro Asp
    290                 295                 300

Phe Thr Thr Ala Val Gln His Phe Cys Ile His Thr Gly Gly Arg Ala
305                 310                 315                 320

Val Leu Asp Ala Leu Gln Ala Asn Leu Ser Leu Ser Asp Tyr Tyr Leu
                325                 330                 335

Glu Pro Ser Arg Tyr Ser Leu Trp Arg Trp Gly Asn Val Ser Ser Ala
            340                 345                 350

Ser Val Trp Tyr Glu Leu Asp Trp Leu Glu Lys Ser Gly Arg Ile Arg
        355                 360                 365

Arg Gly Asp Lys Val Trp Gln Ile Gly Phe Gly Ser Gly Phe Lys Cys
    370                 375                 380

Asn Ser Ala Val Trp Arg Ala Cys Arg Ala Met Pro
385                 390                 395

<210> SEQ ID NO 79
<211> LENGTH: 315
<212> TYPE: DNA
<213> ORGANISM: Heterocapsa niei

<400> SEQUENCE: 79
gattcaggat cctttttgca taggtaccac tccaccatgt ttccgatctg gtagggttgt      60
gtgcgtggtc cacgcctctt cacttggaca agtgccgtcg ggccaagtgc cgtcgggcca     120
agtgccgtcg ggccaaggaa agcactccag cgctcacaac cacctcaccc ccccctcccg     180 cccccccgctt cgttttcgct tgctttcagg tggatggggg cccgctgggt gcctggaggc     240
cagtcgtatt tttgtgcgac catcaattcc accgtgcatg ttgtcatgta cgcctattac     300
ttttctagat caatc                                                     315

<210> SEQ ID NO 80
<211> LENGTH: 100
<212> TYPE: PRT
<213> ORGANISM: Artificial Sequence
<220> FEATURE:
<223> OTHER INFORMATION: Protein encoded by SEQ ID NO:79 which comprises
``` a stop codon between residues 17 and 18 suggesting the presence of
an intron

<400> SEQUENCE: 80

Asp Ser Gly Ser Phe Leu His Arg Tyr His Ser Thr Met Phe Pro Ile
1               5                  10                  15

Trp Gly Cys Val Arg Gly Pro Arg Leu Phe Thr Trp Thr Ser Ala Val
            20                  25                  30

Gly Pro Ser Ala Val Gly Pro Ser Ala Val Gly Pro Arg Lys Ala Leu
        35                  40                  45

Gln Arg Ser Gln Pro Pro His Pro Pro Leu Pro Pro Pro Ala Ser Phe
    50                  55                  60

Ser Leu Ala Phe Arg Trp Met Gly Ala Arg Trp Val Pro Gly Gly Gln
65                  70                  75                  80

Ser Tyr Phe Cys Ala Thr Ile Asn Ser Thr Val His Val Val Met Tyr
                85                  90                  95

Ala Tyr Tyr Phe
            100

<210> SEQ ID NO 81
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 81
gctacgcccg gggatcctcg aggctggcgc aacgcaatta atgtga                46

<210> SEQ ID NO 82
<211> LENGTH: 84
<212> TYPE: DNA
<213> ORGANISM: Artificial Sequence
<220> FEATURE:
<223> OTHER INFORMATION: Oligonucleotide primer

<400> SEQUENCE: 82
cacaggaaac agcttgacat cgattaccgg caattgtacg gcggccgcta cggatatcct    60
cgctcgagct cgcccggggt agct                                          84

<210> SEQ ID NO 83
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 83
agcacatcga tgaaggagat atacccatgg ctaatgcaat caagaa                46

<210> SEQ ID NO 84
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 84
acgatgcggc cgctcaacca tgagtattaa gagctt                          36

<210> SEQ ID NO 85
<211> LENGTH: 294
<212> TYPE: PRT

-continued

<213> ORGANISM: Pavlova salina

<400> SEQUENCE: 85

Met Pro Thr Trp Gly Glu Phe Val Ala Gly Leu Thr Tyr Val Glu Arg
1               5                   10                  15

Gln Gln Met Ser Glu Glu Leu Val Arg Ala Asn Lys Leu Pro Leu Ser
            20                  25                  30

Leu Ile Pro Glu Val Asp Phe Phe Thr Ile Ala Ser Val Tyr Val Gly
        35                  40                  45

Asp His Trp Arg Ile Pro Phe Thr Ala Ile Ser Ala Tyr Leu Val Leu
    50                  55                  60

Ile Thr Leu Gly Pro Gln Leu Met Ala Arg Arg Pro Pro Leu Pro Ile
65                  70                  75                  80

Asn Thr Leu Ala Cys Leu Trp Asn Phe Ala Leu Ser Leu Phe Ser Phe
                85                  90                  95

Val Gly Met Ile Val Thr Trp Thr Thr Ile Gly Glu Arg Leu Trp Lys
            100                 105                 110

Asn Gly Ile Glu Asp Thr Val Cys Gly His Pro Ile Phe Met Gly Tyr
        115                 120                 125

Gly Trp Ile Gly Tyr Val Met Leu Ala Phe Ile Trp Ser Lys Leu Phe
    130                 135                 140

Glu Leu Ile Asp Thr Val Phe Leu Val Ala Lys Lys Ala Asp Val Ile
145                 150                 155                 160

Phe Leu His Trp Tyr His His Val Thr Val Leu Leu Tyr Cys Trp His
                165                 170                 175

Ser Tyr Ala Val Arg Ile Pro Ser Gly Ile Trp Phe Ala Ala Met Asn
            180                 185                 190

Tyr Phe Val His Ala Ile Met Tyr Ala Tyr Phe Gly Met Thr Gln Ile
        195                 200                 205

Gly Pro Arg Gln Arg Lys Leu Val Arg Pro Tyr Ala Arg Leu Ile Thr
    210                 215                 220

Thr Phe Gln Leu Ser Gln Met Gly Val Gly Leu Ala Val Asn Gly Leu
225                 230                 235                 240

Ile Ile Arg Tyr Pro Ser Ile Gly His His Cys His Ser Asn Lys Thr
                245                 250                 255

Asn Thr Ile Leu Ser Trp Ile Met Tyr Ala Ser Tyr Phe Val Leu Phe
            260                 265                 270

Ala Ala Leu Tyr Val Lys Asn Tyr Ile Phe Ser Lys Leu Lys Ser Pro
        275                 280                 285

Lys Arg Lys Lys Val Glu
    290

<210> SEQ ID NO 86
<211> LENGTH: 276
<212> TYPE: PRT
<213> ORGANISM: Pavlova salina

<400> SEQUENCE: 86

Met Ser Glu Glu Leu Val Arg Ala Asn Lys Leu Pro Leu Ser Leu Ile
1               5                   10                  15

Pro Glu Val Asp Phe Phe Thr Ile Ala Ser Val Tyr Val Gly Asp His
            20                  25                  30

Trp Arg Ile Pro Phe Thr Ala Ile Ser Ala Tyr Leu Val Leu Ile Thr
        35                  40                  45

Leu Gly Pro Gln Leu Met Ala Arg Arg Pro Pro Leu Pro Ile Asn Thr
    50                  55                  60

```
Leu Ala Cys Leu Trp Asn Phe Ala Leu Ser Leu Phe Ser Phe Val Gly
 65                  70                  75                  80

Met Ile Val Thr Trp Thr Thr Ile Gly Glu Arg Leu Trp Lys Asn Gly
                 85                  90                  95

Ile Glu Asp Thr Val Cys Gly His Pro Ile Phe Met Gly Tyr Gly Trp
            100                 105                 110

Ile Gly Tyr Val Met Leu Ala Phe Ile Trp Ser Lys Leu Phe Glu Leu
        115                 120                 125

Ile Asp Thr Val Phe Leu Val Ala Lys Lys Ala Asp Val Ile Phe Leu
    130                 135                 140

His Trp Tyr His His Val Thr Val Leu Leu Tyr Cys Trp His Ser Tyr
145                 150                 155                 160

Ala Val Arg Ile Pro Ser Gly Ile Trp Phe Ala Ala Met Asn Tyr Phe
                165                 170                 175

Val His Ala Ile Met Tyr Ala Tyr Phe Gly Met Thr Gln Ile Gly Pro
            180                 185                 190

Arg Gln Arg Lys Leu Val Arg Pro Tyr Ala Arg Leu Ile Thr Thr Phe
        195                 200                 205

Gln Leu Ser Gln Met Gly Val Gly Leu Ala Val Asn Gly Leu Ile Ile
    210                 215                 220

Arg Tyr Pro Ser Ile Gly His His Cys His Ser Asn Lys Thr Asn Thr
225                 230                 235                 240

Ile Leu Ser Trp Ile Met Tyr Ala Ser Tyr Phe Val Leu Phe Ala Ala
                245                 250                 255

Leu Tyr Val Lys Asn Tyr Ile Phe Ser Lys Leu Lys Ser Pro Lys Arg
            260                 265                 270

Lys Lys Val Glu
        275

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 87
cgctctagaa ctagtggatc                                              20

<210> SEQ ID NO 88
<211> LENGTH: 223
<212> TYPE: PRT
<213> ORGANISM: Melosira sp.

<400> SEQUENCE: 88

Thr Ile Phe Lys Ser Asn Ala Val Pro Ala Leu Asp Pro Tyr Pro Ile
 1               5                  10                  15

Lys Phe Val Tyr Asn Val Ser Gln Ile Met Met Cys Ala Tyr Met Thr
                20                  25                  30

Ile Glu Ala Gly Leu Val Ala Tyr Arg Ser Gly Tyr Thr Val Met Pro
            35                  40                  45

Cys Asn Asp Tyr Asn Thr Asn Asn Pro Pro Val Gly Asn Leu Leu Trp
        50                  55                  60

Leu Phe Tyr Ile Ser Lys Val Trp Asp Phe Trp Asp Thr Ile Phe Ile
 65                  70                  75                  80

Val Ile Gly Lys Lys Trp Lys Gln Leu Ser Phe Leu His Val Tyr His
                 85                  90                  95
```

```
His Thr Thr Ile Phe Leu Phe Tyr Trp Leu Asn Ser His Val Asn Tyr
            100                 105                 110

Asp Gly Asp Ile Tyr Leu Thr Ile Leu Leu Asn Gly Phe Ile His Thr
        115                 120                 125

Val Met Tyr Thr Tyr Tyr Phe Val Cys Met His Thr Lys Val Pro Glu
        130                 135                 140

Thr Gly Lys Ser Leu Pro Ile Trp Trp Lys Ser Ser Leu Thr Met Met
145                 150                 155                 160

Gln Met Ile Gln Phe Val Thr Met Met Ser Gln Ala Ser Tyr Leu Leu
                165                 170                 175

Val Thr Asn Cys Glu Lys Thr Ser Arg Gly Val Val Ile Ala Tyr Phe
            180                 185                 190

Val Tyr Ile Phe Thr Leu Leu Val Leu Phe Ala Gln Phe Phe Arg Ala
        195                 200                 205

Ser Tyr Met Lys Pro Lys Gly Lys Lys Ala Lys Met Lys Lys Val
        210                 215                 220

<210> SEQ ID NO 89
<211> LENGTH: 683
<212> TYPE: DNA
<213> ORGANISM: Melosira sp.

<400> SEQUENCE: 89
acgatcttca agtcaaacgc cgtccctgcc ctggatccat accccatcaa attcgtttac      60
aatgtgtccc agatcatgat gtgcgcgtac atgacgatcg aggcaggcct ggtggcctac     120
cgcagtggct atactgtcat gccatgcaac gactacaaca ccaacaaccc ccctgtcggg     180
aacctgctgt ggctgtttta catttccaaa gtttgggact tttgggacac catctttatc     240
gtgattggca aaaagtggaa gcagctgagc ttcttgcacg tgtaccacca caccaccatc     300
tttttgttct actggctcaa ctcgcatgtc aactacgacg gagatattta tctgacgatt     360
ctgttgaacg gcttcatcca caccgtcatg tacacttatt acttcgtttg catgcacacg     420
aaggtgcccg agactggaaa gtcgttgccc atttggtgga atccagtctc accatgatg     480 caaatgatcc aattcgtcac catgatgagc caggcttcgt acttgctcgt gacgaactgc     540
gaaaagacca gtcggggggt cgttattgcg tactttgtgt acattttcac tctactcgtc     600
ttatttgctc agttcttccg agcatcttac atgaagccca agggaaagaa ggcgaaaatg     660
aagaaggtat aagctgctgg cat                                              683
```